US012655121B2

(12) United States Patent
Wang et al.

(10) Patent No.: US 12,655,121 B2
(45) Date of Patent: Jun. 16, 2026

(54) COMPOUNDS WITH ALK INHIBITORY ACTIVITY AND PREPARATION METHOD AND USE THEREOF

(71) Applicant: CGENETECH (SUZHOU, CHINA) CO., LTD., Suzhou (CN)

(72) Inventors: Tong Wang, Suzhou (CN); Yong Zheng, Suzhou (CN); Yongsheng Wang, Suzhou (CN); Qin Lu, Suzhou (CN); Huiping Pan, Suzhou (CN); Qiang Yu, Suzhou (CN); Juping Ding, Suzhou (CN); Yan Hao, Suzhou (CN)

(73) Assignee: CGENETECH (SUZHOU, CHINA) CO., LTD., Suzhou (CN)

( * ) Notice: Subject to any disclaimer, the term of this patent is extended or adjusted under 35 U.S.C. 154(b) by 454 days.

(21) Appl. No.: 18/504,208

(22) Filed: Nov. 8, 2023

(65) Prior Publication Data

US 2024/0246927 A1 Jul. 25, 2024

Related U.S. Application Data

(63) Continuation of application No. PCT/CN2022/092109, filed on May 11, 2022.

(30) Foreign Application Priority Data

May 12, 2021 (CN) ........................ 202110515421.8

(51) Int. Cl.

| | |
|---|---|
| ***C07D 401/04*** | (2006.01) |
| ***A61K 31/454*** | (2006.01) |
| ***A61K 31/496*** | (2006.01) |
| ***A61K 31/5377*** | (2006.01) |
| ***C07D 209/58*** | (2006.01) |
| ***C07D 401/14*** | (2006.01) |

(52) U.S. Cl.

CPC .......... *C07D 401/04* (2013.01); *A61K 31/454* (2013.01); *A61K 31/496* (2013.01); *A61K 31/5377* (2013.01); *C07D 209/58* (2013.01); *C07D 401/14* (2013.01)

(58) Field of Classification Search

CPC ............................ A61K 31/454; C07D 401/14

See application file for complete search history.

(56) References Cited

FOREIGN PATENT DOCUMENTS

| | | | | |
|---|---|---|---|---|
| CN | 102459172 A | | 5/2012 | |
| CN | 104177342 A | | 12/2014 | |
| CN | 104230960 A | | 12/2014 | |
| CN | 104804016 A | | 7/2015 | |
| CN | 108559095 A | | 9/2018 | |
| JP | 4588121 B1 | * | 11/2010 | ............. A61P 35/02 |
| JP | 2018531993 A | | 11/2018 | |
| WO | 2010143664 A1 | | 12/2010 | |
| WO | 2017073706 A1 | | 5/2017 | |

OTHER PUBLICATIONS

Second Office Action in Corresponding Japanese Application No. 2023-568660, mailed Apr. 1, 2025; 6 pgs.

First Office Action and Search Report issued in Chinese Patent Application No. 202110515421.8; mailed May 27, 2023; 18 pgs.

* cited by examiner

*Primary Examiner* — Andrew D Kosar

*Assistant Examiner* — John D Mcanany

(74) *Attorney, Agent, or Firm* — HAUPTMAN HAM, LLP

(57) ABSTRACT

The present application relates to the technical field of pharmaceutical chemistry, and particularly relates to compounds with ALK inhibitory activity and preparation method and use thereof. The compounds with ALK inhibitory activity provided by the present application are ALK inhibitors for treating diseases responsive to the inhibition of ALK kinase, can be used for treating ALK-positive diseases, such as tumors and cancers, and have broad application prospects.

14 Claims, No Drawings

COMPOUNDS WITH ALK INHIBITORY ACTIVITY AND PREPARATION METHOD AND USE THEREOF

CROSS-REFERENCE TO RELATED APPLICATION

The present application is a Continuation of International Application No. PCT/CN2022/092109 filed May 11, 2022, which claims priority to Chinese patent application "COMPOUNDS WITH ALK INHIBITORY ACTIVITY AND PREPARATION METHOD AND USE THEREOF" with an application No. 202110515421.8, filed on May 12, 2021, the contents of which are incorporated herein by reference in their entireties.

TECHNICAL FIELD

The present application relates to the technical field of pharmaceutical chemistry, particularly to compounds with ALK inhibitory activity and preparation method and use thereof.

BACKGROUND ART

Anaplastic lymphoma kinase (ALK) is a receptor tyrosine kinase (RTK), belongs to an insulin receptor superfamily, and has high homology to leukocyte tyrosine kinase. In 1994, ALK is first found in large-cell lymphoma (ALCL) in a form of NPM1-ALK fusion gene. The ALK gene is located at human chromosome 2p23 and encodes polypetides of 1620 amino acids. After post-translational modification, a mature ALK protein of 200-220 kDa is generated. ALK is composed of an extracellular ligand-binding domain consisting of 1030 amino acids, a transemembrane domain and an intracellular tyrosine kinase domain. ALK is highly conserved in various species. ALK expressed in adult brain is considered as playing an important role in developments and functions of a nervous system. ALK is also expressed in small intestine, testicles, prostate, and colon, but it is not expressed in normal lymphatic tissues, lungs, and other tissues.

ALK can activate multiple intracellular signaling pathways, including phospholipase Cy, JAK kinase and signal transducer and activator of transcription-3 (STAT3), phosphatidylinositol 3-kinase (PI3K), mammalian target of rapamycin (mTOR) and mitogen-activated protein kinase (MAPK), etc., and participates in regulating cell growth, transformation and antiapoptosis. ALK genetic recombination, mutation, or amplification has been found in a variety of tumors. Up to now, 21 different genes have been found to translocate with ALK. Different ALK fusion proteins may cause activation of different signal pathways, leading to different proliferation rates, invasion and tumorigenicity of cancer cells.

So far, ALK fusion proteins, overexpression of ALK genes, and ALK gene mutations have been identified in a large number of human diseases, including tumors and cancers, such as melanoma, neuroblastoma, glioblastoma, rhabdomyosarcoma, astrocytoma, Ewing's sarcoma, retinoblastoma, anaplastic large cell lymphoma (ALCL), inflammatory myofibroblastoma (IMT), diffuse large B-cell lymphoma (DLBCL), non-small cell lung cancer (NSCLC), renal medullary carcinoma (RMC), renal cell carcinoma (RCC), breast cancer, colon cancer, ovarian serous carcinoma (SOC), and esophageal squamous cell carcinoma (ESCC).

Due to the relevance of ALK to tumors and cancers, the demand for ALK inhibitors for treating diseases responsive to ALK kinase inhibition will become increasingly urgent. In view of this, the present application provides compounds with ALK inhibitory activity and preparation method and use thereof.

SUMMARY OF THE INVENTION

On the basis of complying with common knowledge in the field, the above preferred conditions can be arbitrarily combined without exceeding the scope of the concept and protection of the present application.

In order to solve the above technical problem, the present application provides a compound shown in formula (I) or a pharmaceutically acceptable salt thereof:

Formula (I)

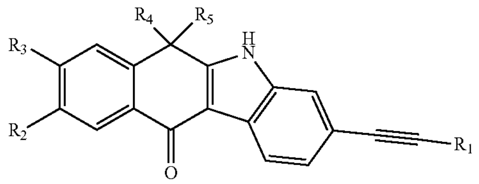

wherein, $R_1$ is selected from hydrogen, substituted or unsubstituted C1-C4 alkyl, C3-C6 cycloalkyl, substituted or unsubstituted aryl or heterocyclic aryl, and halogen;

$R_2$ is selected from hydrogen, substituted or unsubstituted C1-C4 alkyl, cyano, and halogen; the substituent of C1-C4 alkyl is selected from C3-C6 cycloalkyl, halogen, and cyano;

$R_3$ is selected from heterocyclic aryl, aryl, and substituted or unsubstituted 5-7 membered heterocycle, wherein the 5-7 membered heterocycle contains 1-3 heteroatoms that are each independently selected from N, P, O, and S;

In the present application, the heterocyclic aryl includes but is not limited to pyridyl, pyridazinyl, indolyl, azaindolyl, indozolyl, benzimidazolyl, benzofuranyl, thienyl, furanyl, imidazolyl, benzothienyl, benzoisoxazolyl, benzoxazolyl, benzopyrazolyl, benzothiazolyl, benzothiadiazolyl, benzotriazolyl, adenyl, isoxazolyl, oxazolyl, pyrazolyl, pyrrolyl, thiazolyl, thiadiazoly, triazolyl, pyrimidinyl, and pyrazinyl;

$R_4$ and $R_5$ are each independently selected from hydrogen, substituted or unsubstituted saturated C1-C4 alkyl, and substituted or unsubstituted unsaturated C1-C4 alkyl.

As a preferred technical solution, in the compound or a pharmaceutically acceptable salt thereof, $R_1$ is selected from hydrogen, substituted or unsubstituted C1-C4 alkyl, and C3-C6 cycloalkyl;

$R_2$ is selected from hydrogen, unsubstituted C1-C4 alkyl, cyano, and halogen;

$R_3$ is selected from substituted or unsubstituted 5-7 membered heterocycle, wherein the 5-7 membered heterocycle contains 1-3 heteroatoms that are each independently selected from N, P, O, and S;

$R_4$ and $R_5$ are each independently selected from hydrogen, and unsubstituted saturated C1-C4 alkyl.

As a preferred technical solution, in the compound or a pharmaceutically acceptable salt thereof, $R_1$ is selected from hydrogen, methyl, ethyl, propyl,

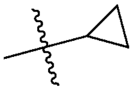,
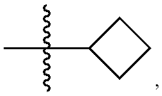, and
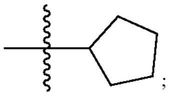;

$R_2$ is selected from methyl, ethyl, propyl, cyano, Cl, Br, and F;

$R_3$ is selected from substituted or unsubstituted 6-membered heterocycle, wherein the 6-membered heterocycle contains 1-3 heteroatoms of N;

$R_4$ and $R_5$ are each independently selected from hydrogen, methyl, ethyl, and propyl.

As a preferred technical solution, in the compound or a pharmaceutically acceptable salt thereof, $R_1$ is selected from hydrogen, methyl, and

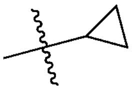;

$R_2$ is selected from methyl, ethyl, cyano, Cl, Br and F;

$R_3$ is selected from

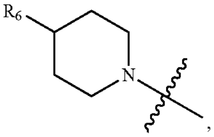,
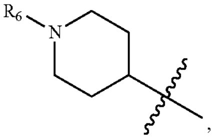, and
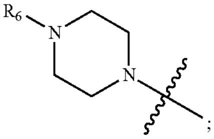;

$R_6$, $R_7$, and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R_4$ and $R_5$ are each independently selected from methyl.

As a preferred technical solution, in the compound or a pharmaceutically acceptable salt thereof, $R_6$, $R_7$, and $R_8$ are each independently selected from hydrogen, methyl, ethyl, cyano, dimethylamino, diethylamido,

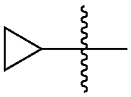,
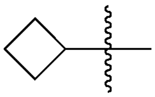,
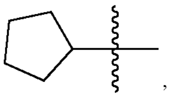,
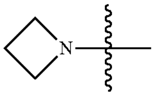,
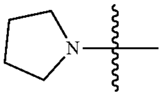,
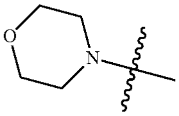,

-continued

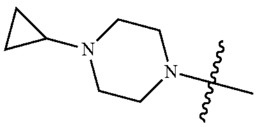,
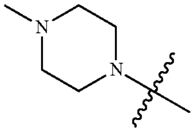, and
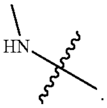.

As a preferred technical solution, in the compound or a pharmaceutically acceptable salt thereof, $R_1$ is selected from hydrogen and;

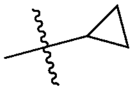;

$R_2$ is selected from ethyl, cyano, and C1;

$R_3$ is selected from

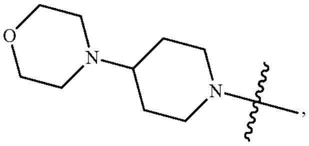,
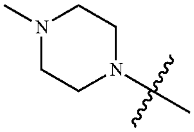,
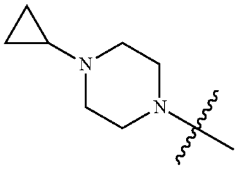,
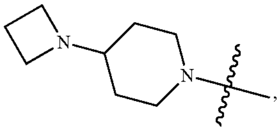,
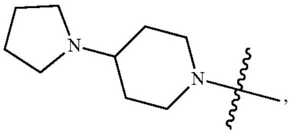,
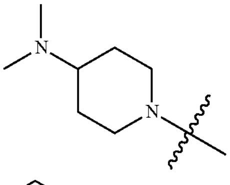,
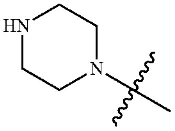,
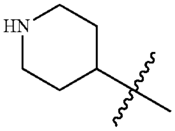,
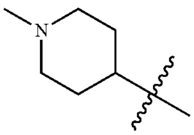,
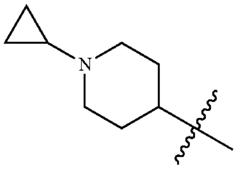,
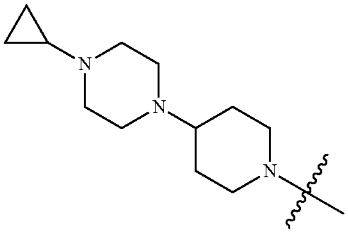, -continued
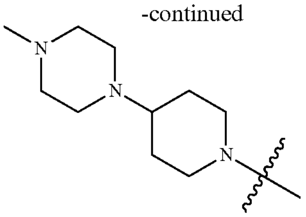
, and
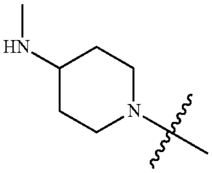
.
As a preferred technical solution, in the compound or pharmaceutically acceptable salt thereof, the compound shown in formula (I) is selected from:
E1
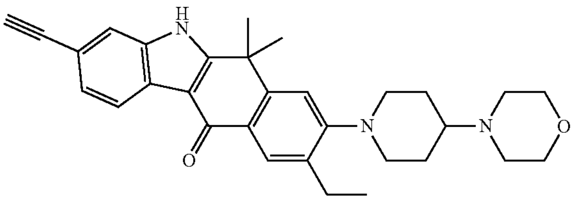
E2
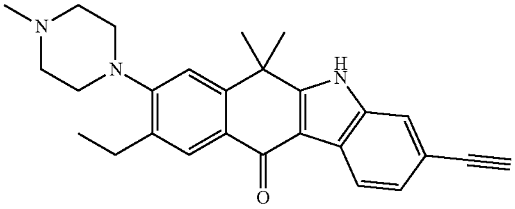
E3
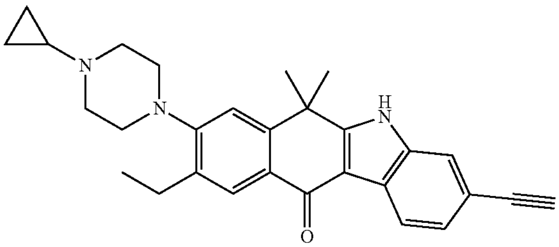
E4
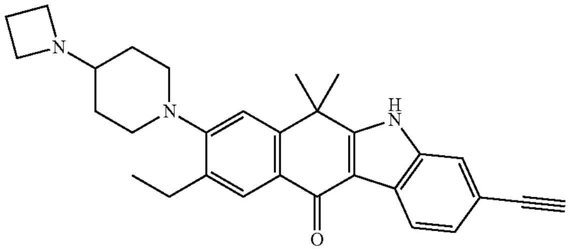
-continued
E5
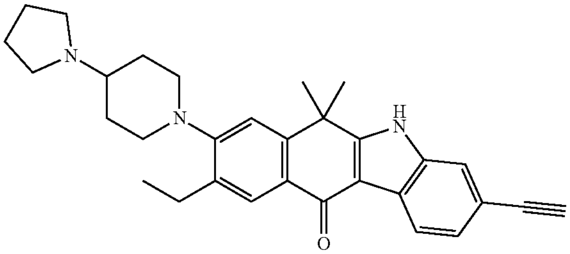
E6
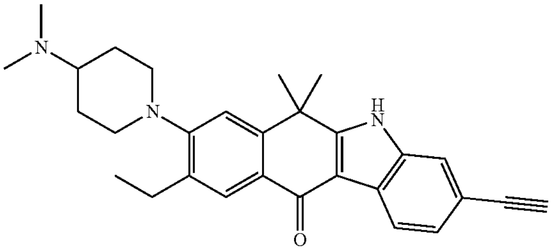
E7
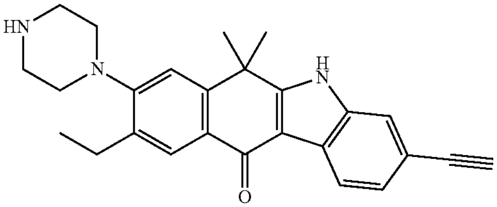
E8
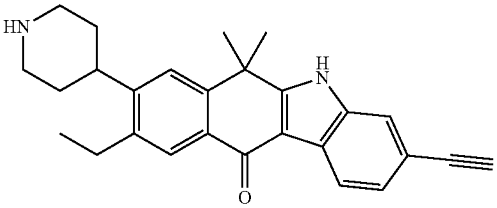
E9
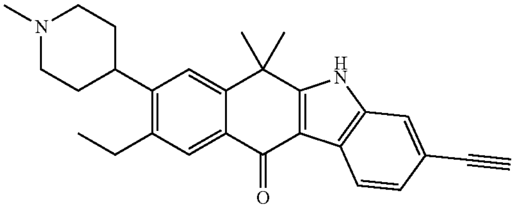
E10
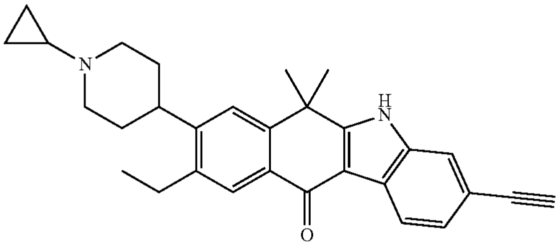

-continued
E11
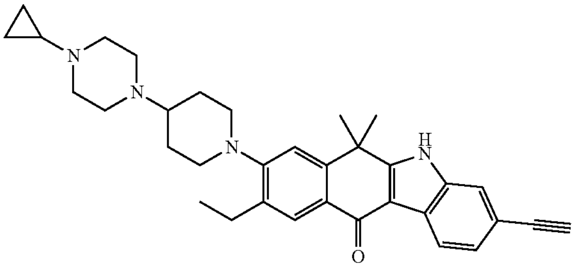
E12
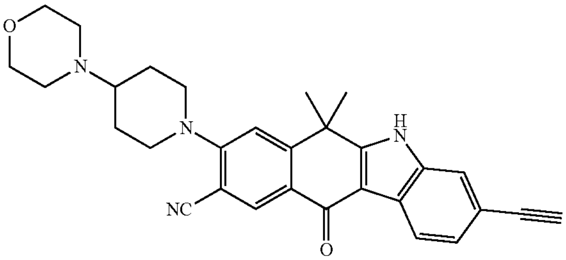
E13
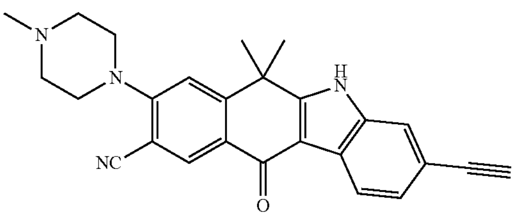
E14
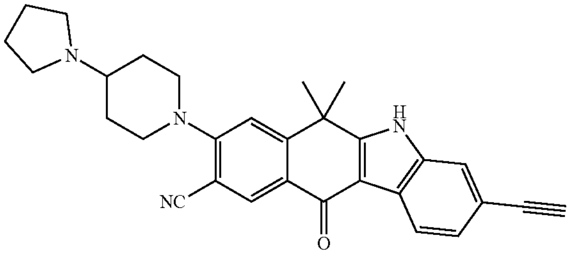
E15
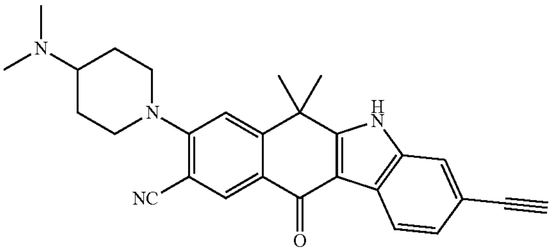
E16
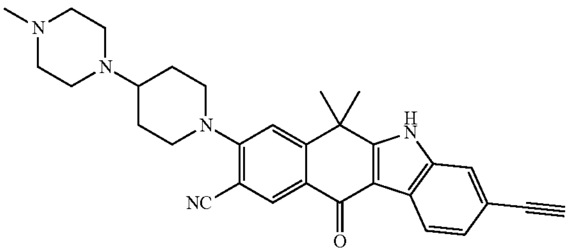
-continued
E17
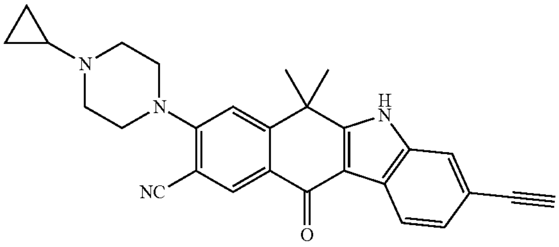
E18
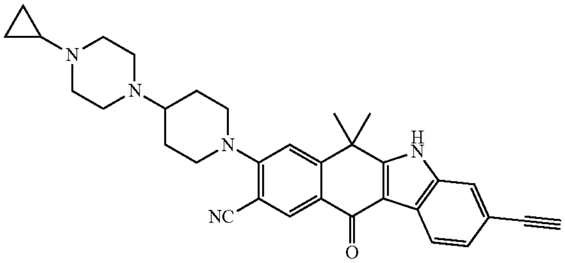
E19
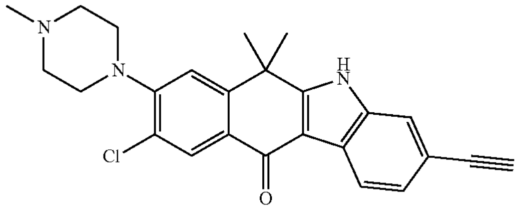
E20
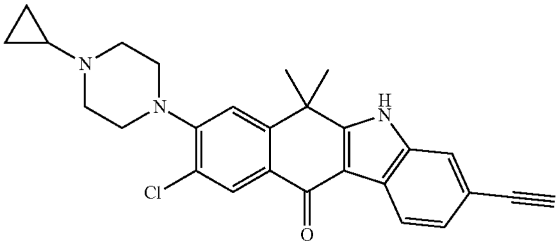
E21
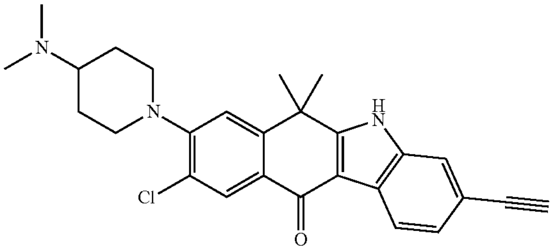
E22
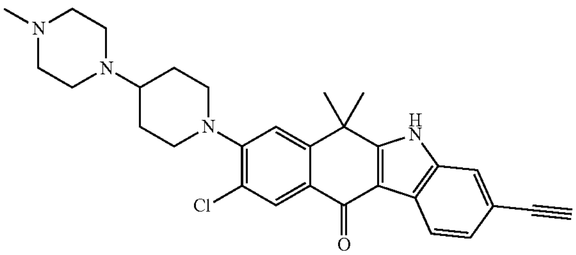

-continued

E23

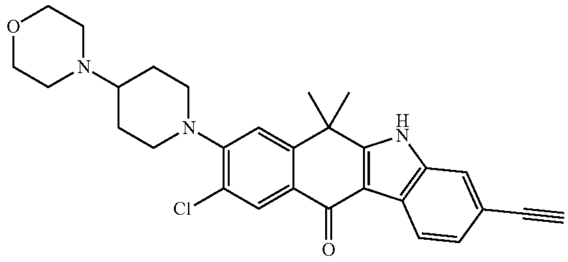

E24

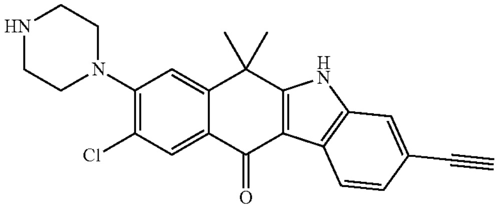

E25

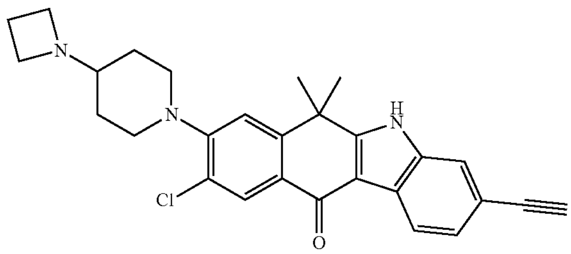

E26

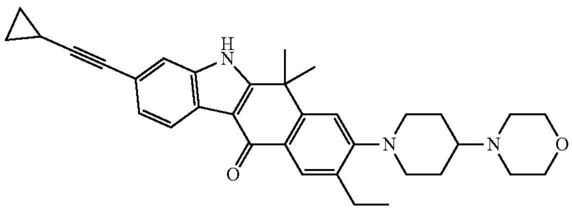

E27

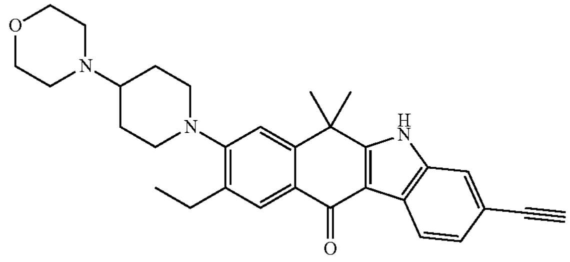

E28

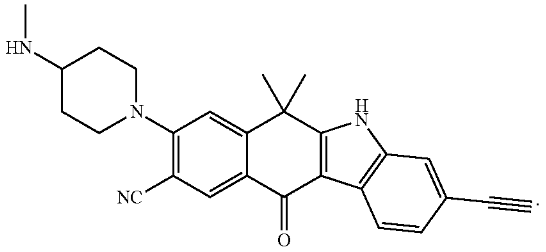

The second aspect of the present application provides a pharmaceutical composition, which comprises a therapeutically effective amount of the compound shown in formula (I) or a pharmaceutically acceptable salt thereof, and a medicinal carrier or excipient.

The third aspect of the present application provides use of the pharmaceutical composition in preparing a medicament for inhibiting ALK activity.

The fourth aspect of the present application provides use of the pharmaceutical composition for treating ALK-positive tumors or cancers.

The fifth aspect of the present application provides a method for preparing the compound or a pharmaceutically acceptable salt thereof, comprising at least the following steps: adding a carbonate into a solution of a compound shown in formula (II) in methanol, and stirring the mixture to conduct a reaction;

wherein the compound shown in formula (II) is represented by the following formula:

Formula (II)

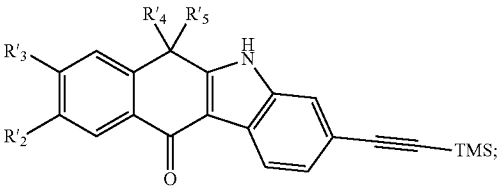

wherein, $R'_2$ is selected from ethyl, cyano, Cl, Br and F;

$R'_3$ is selected from

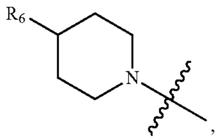

,

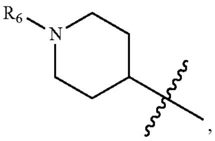

, and

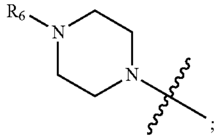

;

$R_6$, $R_7$ and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R_4$ and $R'_4$ represent the same group;

$R_5$ and $R'_5$ represent the same group.

The sixth aspect of the present application provides a method for preparing the compound or a pharmaceutically acceptable salt thereof, comprising at least the following steps: adding a compound shown in formula (III) and a carbonate into acetonitrile and methanol, and stirring the mixture to conduct a reaction;

wherein, the compound shown in formula (III) is represented by the following formula:

Formula (III)

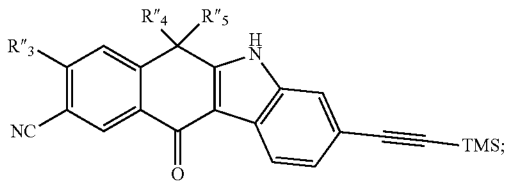

R"$_3$ is selected from

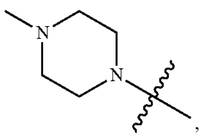
,
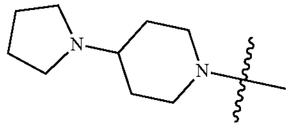
,
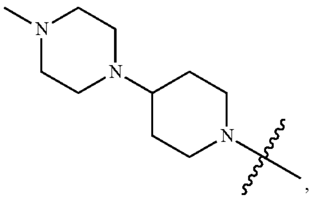
, and
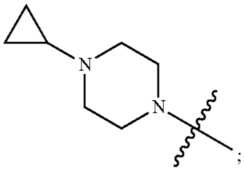
;

$R_4$ and R"$_4$ represent the same group;

$R_5$ and R"$_5$ represent the same group.

The seventh aspect of the present application provides a method for preparing the compound or a pharmaceutically acceptable salt thereof, comprising at least the following steps: adding tetrabutylammonium fluoride into a solution of a compound shown in formula (IV) in tetrahydrofuran, and stirring the mixture to conduct a reaction;

wherein the compound shown in formula (IV) is represented by the following formula:

Formula (IV)

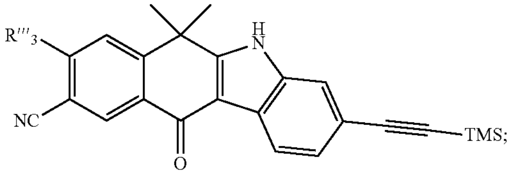

R'''$_3$ is selected from

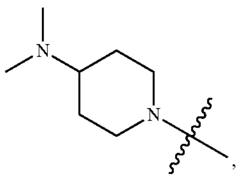
,

-continued

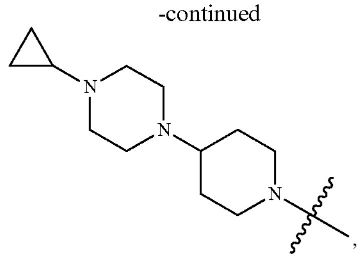
, and
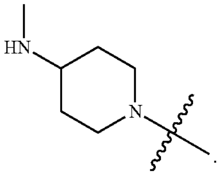
.

The eighth aspect of the present application provides a method for preparing the compound or a pharmaceutically acceptable salt thereof, comprising at least the following steps: adding tripotassium phosphate, 2-dicyclohexylphosphino-2,4,6-triisopropylbiphenyl, and tris(dibenzylideneacetone) dipalladium into a solution of a compound shown in formula (V) and alkyl alkyne in acetonitrile, and stirring the mixture to conduct a reaction in an inert atmosphere; wherein the compound shown in formula (V) is represented by the following formula:

Formula (V)

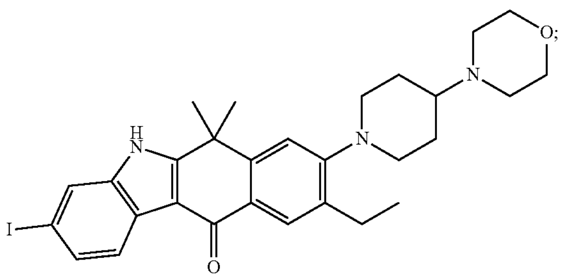

the alkyl alkyne is one selected from the group consisting of ethynyl cyclopropane, propyne, ethynyl cyclobutane, and butyne.

The compounds with ALK inhibitory activity and preparation method and use thereof provided by the present invention have the following several beneficial effects:

(1) the series of compounds provided in the present application exhibit superior ALK kinase inhibitory activity and ALK gene fusion cell proliferation inhibitory activity, which are significantly superior to the control compound;

(2) the ALK inhibitor provided in the present application can be used to treat ALK-positive diseases, such as anaplastic large cell lymphoma, diffuse large B-cell lymphoma, inflammatory myofibroblastoma, renal cell cancer, breast cancer, colon cancer, thyroid cancer, glioblastoma, and non-small cell lung cancer (especially brain metastatic non-small cell lung cancer), and recurrent ALK-positive non-small cell lung cancer caused by ALK mutation, overcomes the treatment resistance of marketed drugs, and has broad application prospects;

(3) the preparation method provided in the present application has no special reactions, is easy to operate and control in both the laboratory and industrial stages, is green and environmentally friendly, and has good safety.

DETAILED DESCRIPTION OF THE INVENTION

For the purpose of the detailed description below, it should be understood that various alternative changes and step sequences may be adopted in the present application, unless explicitly stated to the contrary. In addition, except in any operational example or otherwise indicated, all numbers indicating the amount of ingredients used, such as in the description and claims, should be understood to be modified by the term "about" in all cases. Therefore, unless indicated to the contrary, the numerical parameters described in the following description and accompanying claims are approximate values that vary based on the expected performance(s) to be obtained in the present application. At least, it is not an attempt to limit the application of the doctrine of equivalents to the scope of claims. Each numerical parameter should at least be interpreted according to the number of reported significant FIGURES and by applying ordinary rounding techniques.

The first aspect of the present application provides a compound shown in formula (I) or a pharmaceutically acceptable salt thereof:

Formula (I)

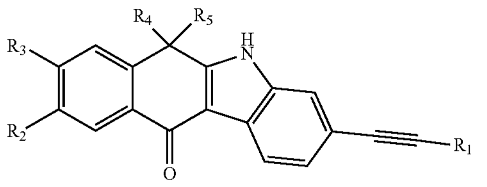

wherein, $R_1$ is selected from hydrogen, substituted or unsubstituted C1-C4 alkyl, C3-C6 cycloalkyl, substituted or unsubstituted aryl or heterocyclic aryl, and halogen;

$R_2$ is selected from hydrogen, substituted or unsubstituted C1-C4 alkyl, cyano, and halogen; the substituent of C1-C4 alkyl is selected from C3-C6 cycloalkyl, halogen, and cyano;

$R_3$ is selected from heterocyclic aryl, aryl, and substituted or unsubstituted 5-7 membered heterocycle, wherein the 5-7 membered heterocycle contains 1-3 heteroatoms that are each independently selected from N, P, O, and S; the heterocyclic aryl is selected from pyridyl, pyridazinyl, indolyl, azaindolyl, indozolyl, benzimidazolyl, benzofuranyl, thienyl, furanyl, imidazolyl, benzothienyl, benzoisoxazolyl, benzoxazolyl, benzopyrazolyl, benzothiazolyl, benzothiadiazolyl, benzotriazolyl, adenyl, isoxazolyl, oxazolyl, pyrazolyl, pyrrolyl, thiazolyl, thiadiazoly, triazolyl, pyrimidinyl, and pyrazinyl;

$R_4$ and $R_5$ are each independently selected from hydrogen, substituted or unsubstituted saturated C1-C4 alkyl, and substituted or unsubstituted unsaturated C1-C4 alkyl.

In some preferred embodiments, in the compound or a pharmaceutically acceptable salt thereof, $R_1$ is selected from hydrogen, substituted or unsubstituted C1-C4 alkyl, and C3-C6 cycloalkyl;

$R_2$ is selected from hydrogen, unsubstituted C1-C4 alkyl, cyano, and halogen;

$R_3$ is selected from substituted or unsubstituted 5-7 membered heterocycle, wherein the 5-7 membered heterocycle contains 1-3 heteroatoms that are each independently selected from N, P, O, and S;

$R_4$ and $R_5$ are each independently selected from hydrogen, and unsubstituted saturated C1-C4 alkyl.

In some preferred embodiments, in the compound or a pharmaceutically acceptable salt thereof, $R_1$ is selected from hydrogen, methyl, ethyl, propyl,

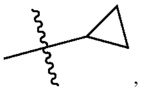 [SMILES: *C1CC1],
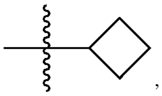, and
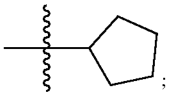;

$R_2$ is selected from methyl, ethyl, propyl, cyano, Cl, Br, and F;

$R_3$ is selected from substituted or unsubstituted 6-membered heterocycle, wherein the 6-membered heterocycle contains 1-3 heteroatoms of N;

$R_4$ and $R_5$ are each independently selected from hydrogen, methyl, ethyl, and propyl.

In some preferred embodiments, in the compound or a pharmaceutically acceptable salt thereof, $R_1$ is selected from hydrogen, methyl, and

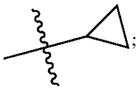;

$R_2$ is selected from methyl, ethyl, cyano, Cl, Br, and F;

$R_3$ is selected from

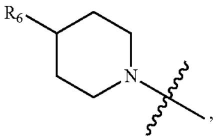,
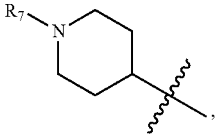, and
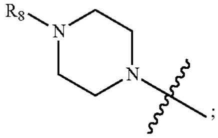;

$R_6$, $R_7$, and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R_4$ and $R_5$ are each independently selected from methyl.

In some preferred embodiments, in the compound or a pharmaceutically acceptable salt thereof, $R_6$, $R_7$ and $R_8$ are each independently selected from hydrogen, methyl, ethyl, cyano, dimethylamino, diethylamido,

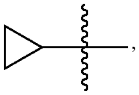,
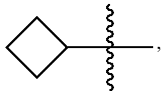,
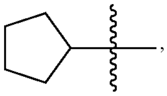,

-continued

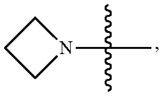,
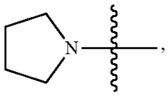,
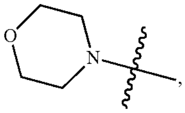,
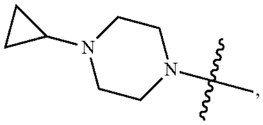,
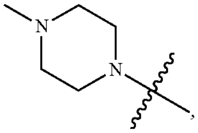, and
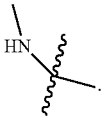.

In some preferred embodiments, in the compound or a pharmaceutically acceptable salt thereof, $R_1$ is selected from hydrogen, and

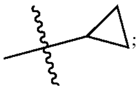 [SMILES: *C1CC1];

$R_2$ is selected from ethyl, cyano, and C1;

$R_3$ is selected from

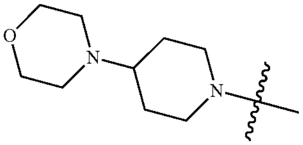,
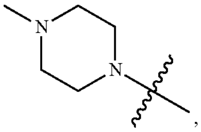,
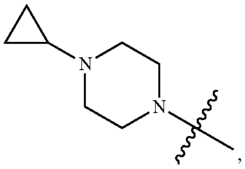,
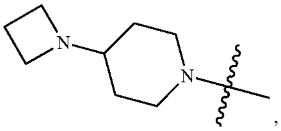,
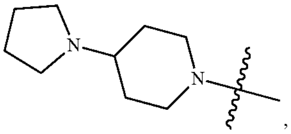,
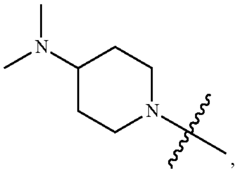,
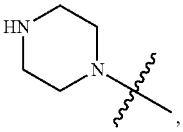,
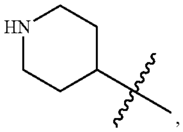,
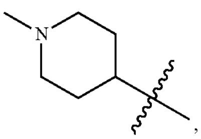,
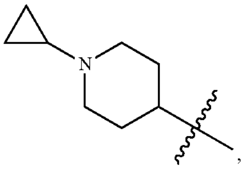, -continued

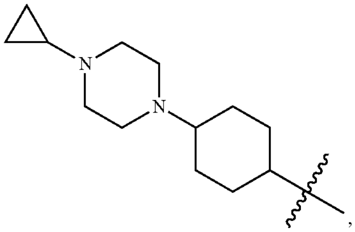,
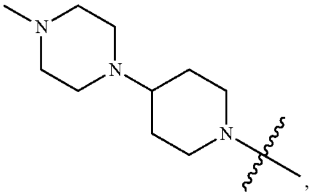, and
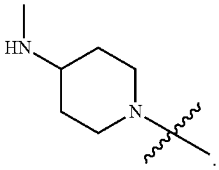.

In some preferred embodiments, in the compound or a pharmaceutically acceptable salt thereof, the compound shown in formula (I) is selected from:

E1

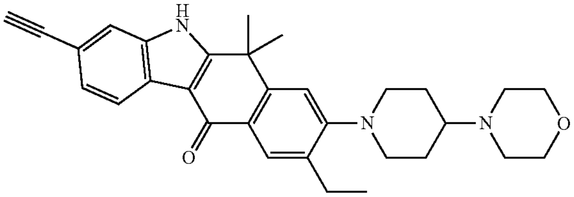

E2

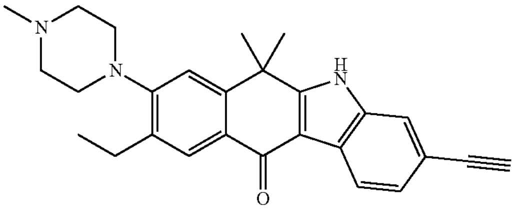

E3

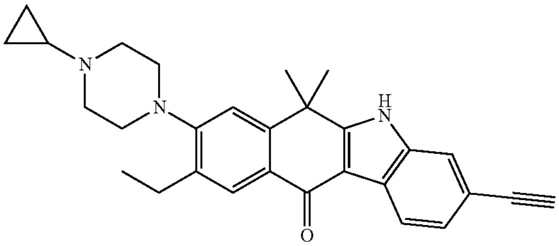

-continued
E4
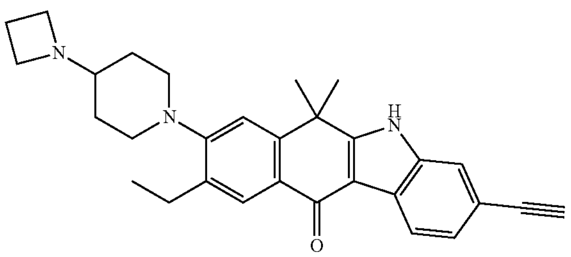
E5
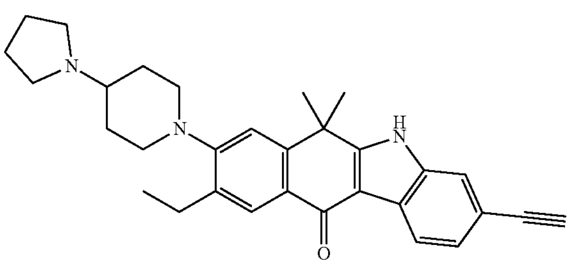
E6
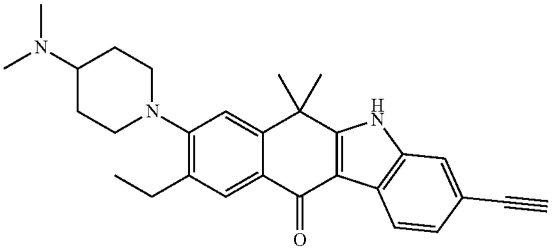
E7
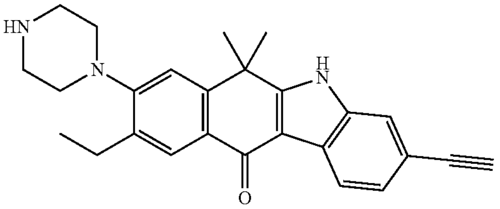
E8
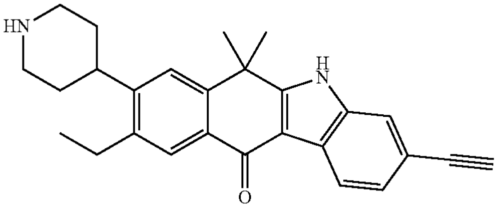
E9
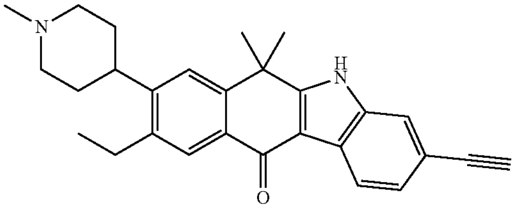
-continued
E10
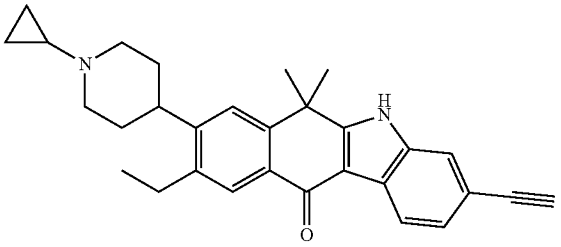
E11
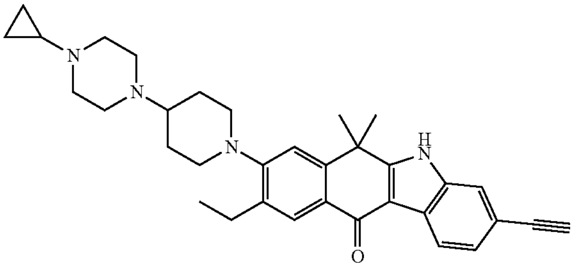
E12
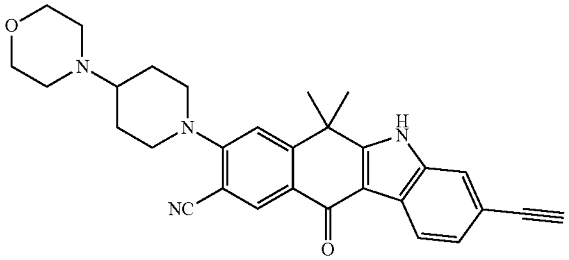
E13
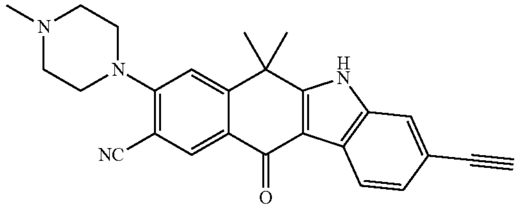
E14
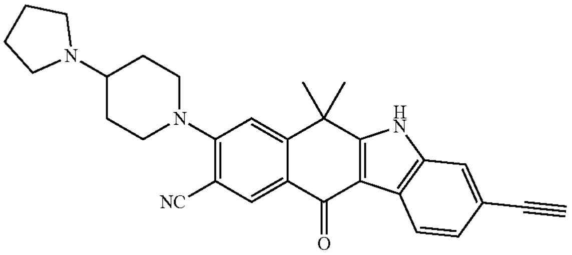
E15
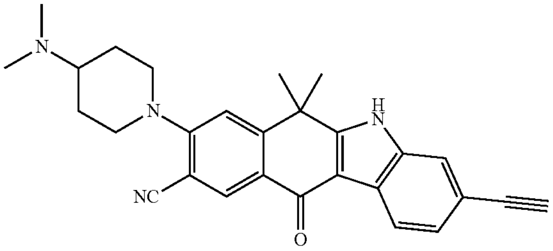

-continued
E16
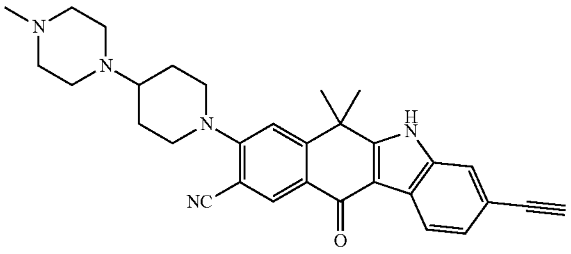
E17
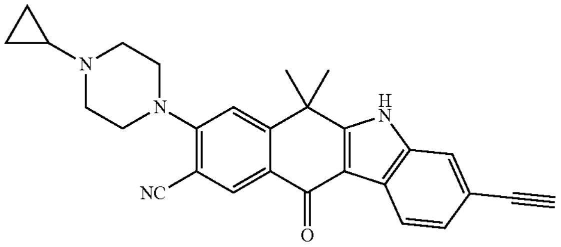
E18
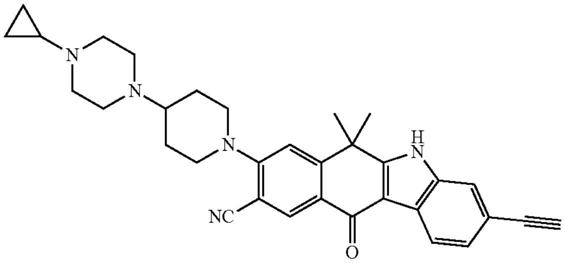
E19
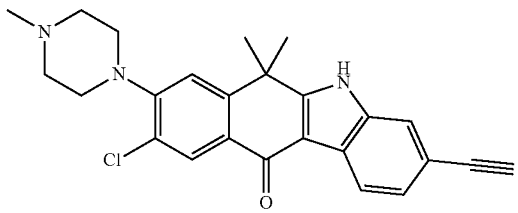
E20
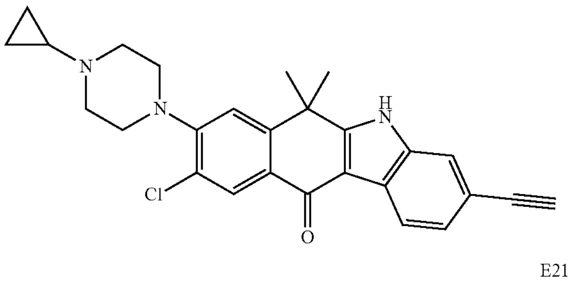
E21
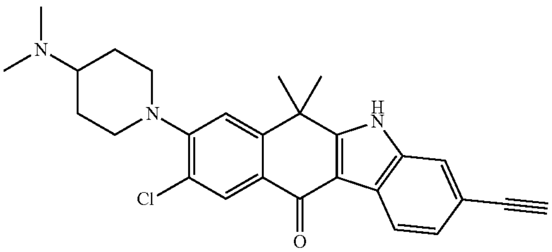
-continued
E22
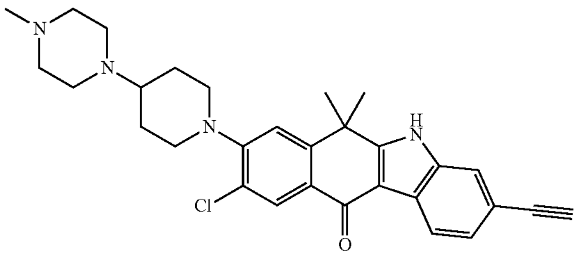
E23
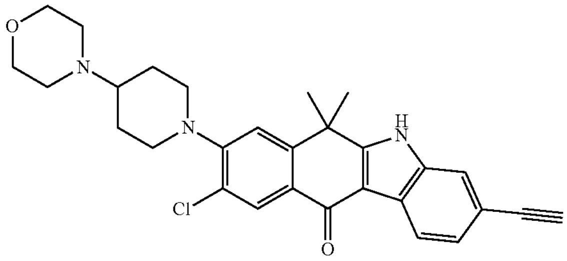
E24
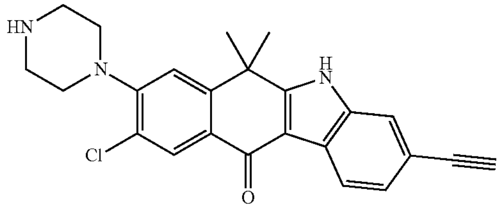
E25
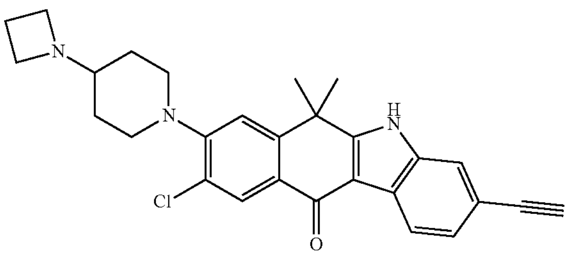
E26
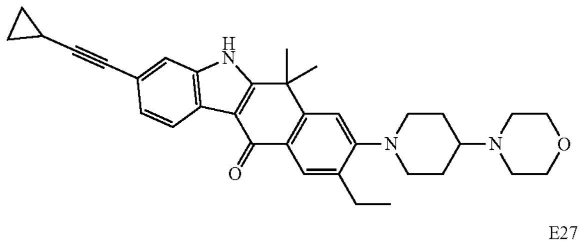
E27
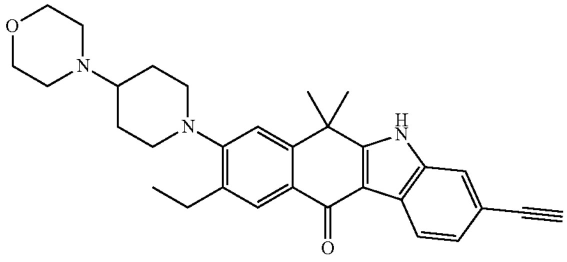

-continued

E28

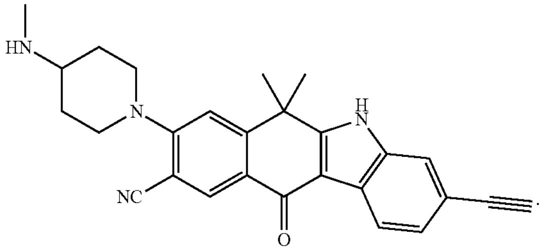

The second aspect of the present application provides a pharmaceutical composition, which comprises a therapeutically effective amount of the compound shown in formula (I) or a pharmaceutically acceptable salt thereof, and a medicinal carrier or excipient.

The third aspect of the present application provides use of the pharmaceutical composition in preparing a medicament for inhibiting ALK activity.

The fourth aspect of the present application provides use of the pharmaceutical composition for treating ALK-positive tumors or cancers.

The pharmaceutical composition according to the present application prepared from the compound of formula (I) or a pharmaceutically acceptable salt thereof and a medicinal carrier or excipient can be used to treat ALK-positive tumors and cancers, including but not limited to melanoma, neuroblastoma, glioblastoma, rhabdomyosarcoma, astrocytoma, Ewing's sarcoma, retinoblastoma, anaplastic large cell lymphoma (ALCL) inflammatory myofibroblastoma (IMT), diffuse large B-cell lymphoma (DLBCL), non-small cell lung cancer (NSCLC), renal medullary carcinoma (RMC), renal cell carcinoma (RCC), breast cancer, colon cancer, ovarian serous carcinoma (SOC), and esophageal squamous cell carcinoma (ESCC).

The compound provided in the present application is present in a form of a pharmaceutically acceptable salt. In terms of drug applications, the salt of the compound provided in the present application refers to non-toxic "pharmaceutically acceptable salt". The form of the pharmaceutically acceptable salt includes a pharmaceutically acceptable acid/anion salt or base/cation salt. A pharmaceutically acceptable acid/anion salt is generally present in a form of basic nitrogen subjected to protonation by inorganic acid or organic acid.

Typical organic or inorganic acid includes hydrochloric acid, hydrobromic acid, hydroiodic acid, perchloric acid, sulfuric acid, nitric acid, phosphoric acid, acetic acid, propionic acid, glycollic acid, lactic acid, succinic acid, maleic acid, fumaric acid, malic acid, tartaric acid, citric acid, benzoic acid, mandelic acid, methanesulfonic acid, hydroxyethyl sulfonic acid, benzenesulfonic acid, oxalic acid, pamoic acid, 2-naphthalene sulfonic acid, p-toluene sulfonic acid, cyclohexylsulfamic acid, salicylic acid, saccharin acid or trifluoroacetic acid. The pharmaceutically acceptable alkali/cation salt includes but is not limited to aluminum salt, calcium salt, chloroprocaine salt, choline, diethanolamine salt, ethylenediamine salt, lithium salt, magnesium salt, potassium salt, sodium salt, and zinc salt.

The fifth aspect of the present application provides a method for preparing the compound or a pharmaceutically acceptable salt thereof, comprising at least the following steps: adding a carbonate into a solution of a compound shown in formula (II) in methanol, and stirring the mixture to conduct a reaction; wherein, the compound shown in formula (II) is represented by the following formula:

Formula (II)

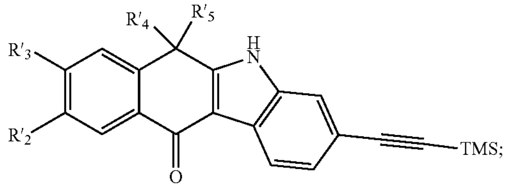

wherein, $R'_2$ is selected from ethyl, cyano, Cl, Br, and F; $R'_3$ is selected from

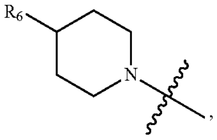

,

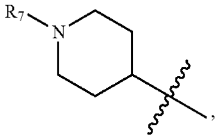

, and

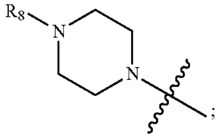

;

$R_6$, $R_7$ and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R_4$ and $R'_4$ represent the same group;

$R_5$ and $R'_5$ represent the same group.

The sixth aspect of the present application provides a method for preparing the compound or a pharmaceutically acceptable salt thereof, comprising at least the following steps: adding a compound shown in formula (III) and a carbonate into acetonitrile and methanol, and stirring the mixture to conduct a reaction;

wherein, the compound shown in formula (III) is represented by the following formula:

Formula (III)

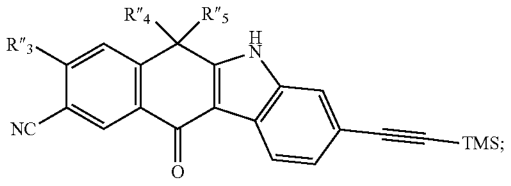

$R''_3$ is selected from

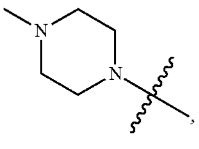

,

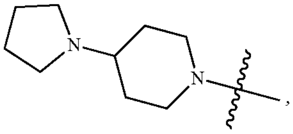

,

-continued

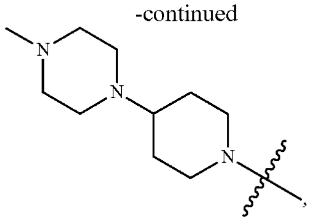

, and

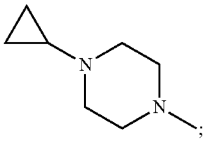

;

$R_4$ and $R''_4$ represent the same group;

$R_5$ and $R''_5$ represent the same group.

The seventh aspect of the present application provides a method for preparing the compound or a pharmaceutically acceptable salt thereof, comprising at least the following steps: adding tetrabutylammonium fluoride into a solution of a compound shown in formula (IV) in tetrahydrofuran, and stirring the mixture to conduct a reaction;

wherein the the compound shown in formula (IV) is represented by the following formula:

Formula (IV)

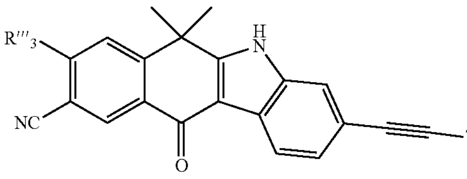

$R'''_3$ is selected from

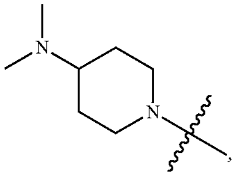

,

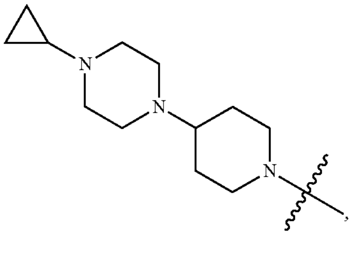

, and

-continued

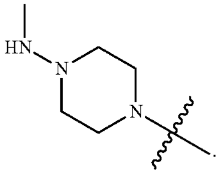

.

The eighth aspect of the present application provides a method for preparing the compound or a pharmaceutically acceptable salt thereof, comprising at least the following steps: adding tripotassium phosphate, 2-dicyclohexylphosphino-2,4,6-triisopropylbiphenyl and tris(dibenzylideneacetone) dipalladium into a solution of a compound shown in formula (V) and alkyl alkyne in acetonitrile, and stirring the mixture to conduct a reaction in an inert atmosphere; wherein, the compound shown in formula (V) is represented by the following formula:

Formula (V)

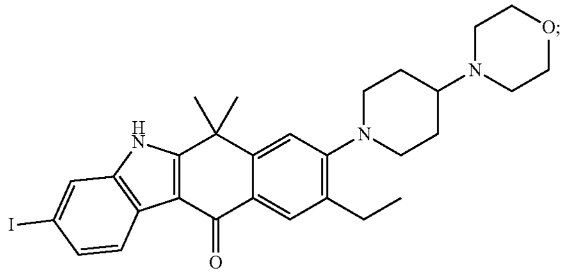

the alkyl alkyne is one selected from the group consisting of ethynyl cyclopropane, propyne, ethynyl cyclobutane, and butyne.

Next, the technical solution of the present application will be described in detail in combination with examples, but the present application is not limited to the scope of the examples. The experimental methods without specific conditions specified in the following examples shall be selected according to conventional methods and conditions, or according to the product manuals.

Reagents and raw materials used in the present application are all commercially available.

Example 1

9-ethyl-3-ethynyl-6,6-dimethyl-8-(4-morpholinopiperidin-1-yl)-5,6-dihydro-11H-benzo[b]carbazo 1-11-one (E1)

E1

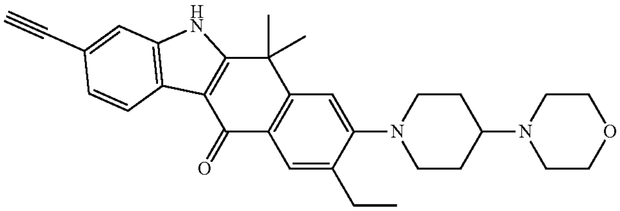

-continued
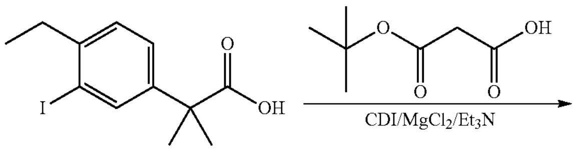
1-1
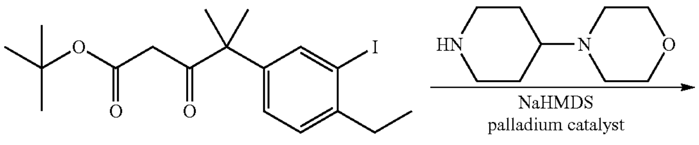
1-2
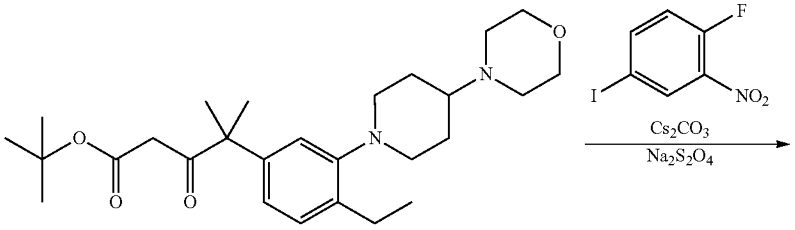
1-3
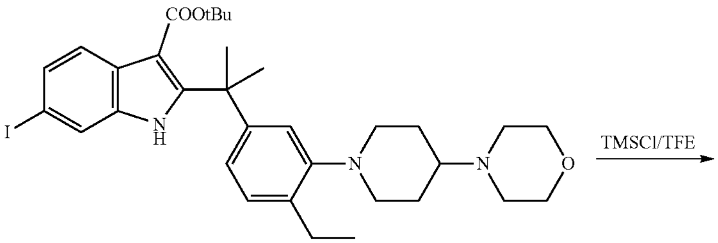
1-4
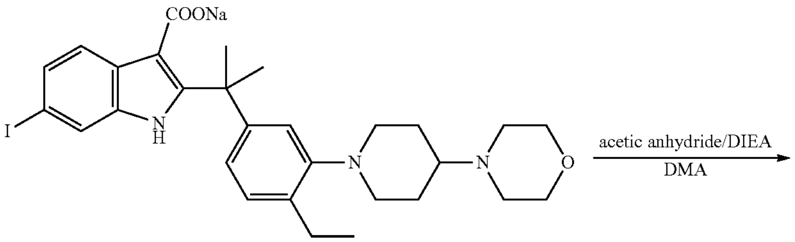
1-5
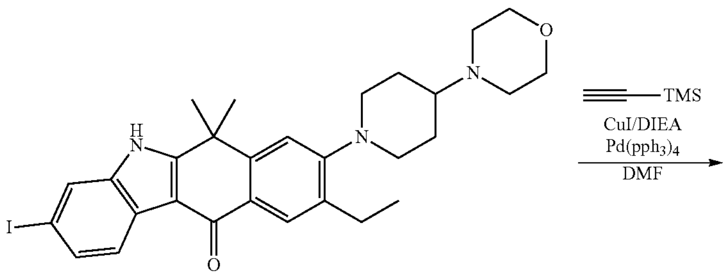
1-6

-continued

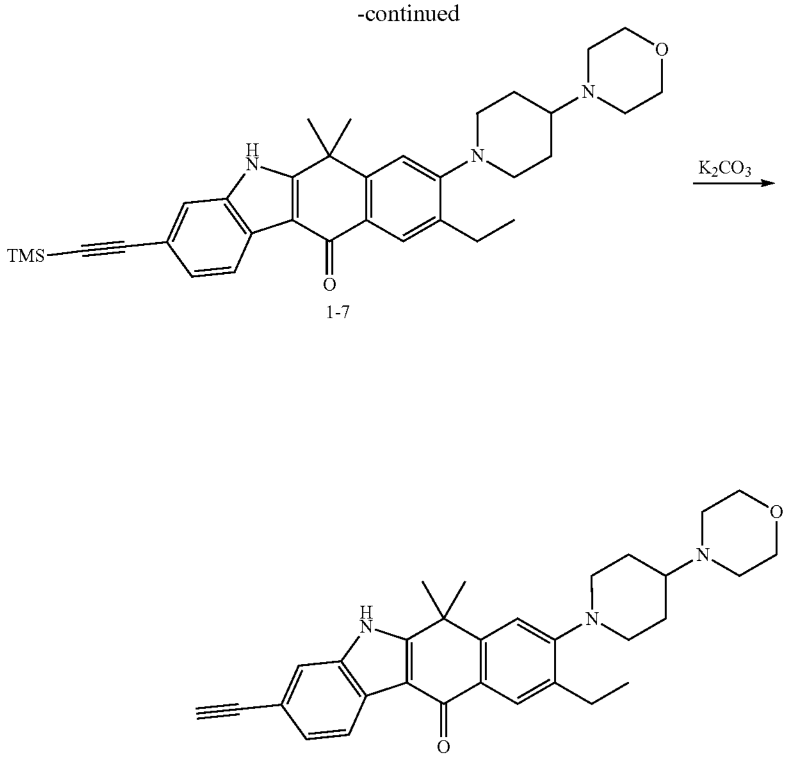

1-7

E1

Tert-butyl 4-(4-ethyl-3-iodophenyl)-4-methyl-3-oxopentanoate

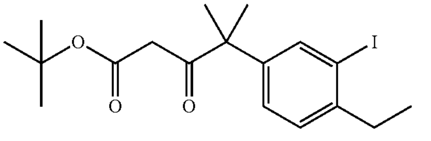 [SMILES: CCc1ccc(C(C)(C)C(=O)CC(=O)OC(C)(C)C)cc1I]

Triethylamine (52.6 mL, 378.4 mmol) and magnesium chloride (8.24 g, 86.6 mmol) were added into a solution of 3-(tertbutoxy)-3-oxopropionic acid (20.0 g, 124.8 mmol) in N,N-dimethylacetamide (100 mL). A reaction was conducted for 2 hours with stirring at room temperature. Carbonyldiimidazole (14.7 g, 90.6 mmol) was added into a solution of 2-(4-ethyl-3-iodophenyl)-2-methylpropionic acid (25.0 g, 78.6 mmol) in dichloroethane (100 mL) and stirred for 1 hour at room temperature. The prepared solution was dropwise added into the above solution, heated to 70° C. and then stirred for 5 hours. The completion of the reaction was monitored by LCMS. The reaction solution was diluted with ethyl acetate (500 mL) and water (500 mL), and then an organic phase was separated. The organic phase was washed with saturated brine, and then dried with anhydrous sodium sulfate. The dried organic phase was filtered, and the filtrate was concentrated at reduced pressure to obtain a crude product. The crude product was purified by silica gel column chromatography (petroleum ether:ethyl acetate=40:1) to obtain tert-butyl 4-(4-ethyl-3-iodophenyl)-4-methyl-3-oxopentanoate as colorless oil (28.7 g, with a yield of 87.8%). MS (ESI) m/z: 415.1 $(M-H)^-$ Tert-butyl 4-(4-ethyl-3-(4-morpholinopiperidin-1-yl)phenyl)-4-methyl-3-oxopentanoate

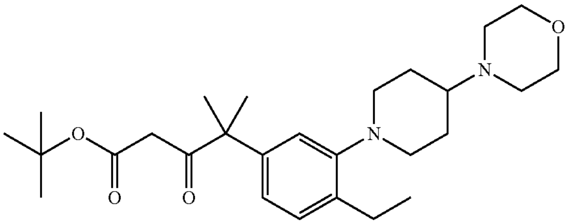 [SMILES: CCc1ccc(C(C)(C)C(=O)CC(=O)OC(C)(C)C)cc1N1CCC(N2CCOCC2)CC1]

1,3-bis-(2,6-diisopropylphenyl)-diazol-2-alkylene(allyl) palladium(II) chloride (2.0 g, 3.50 mmol) and sodium bis (trimethylsilyl)amide (144 mL, 288 mmol) were added into a solution of tert-butyl 4-(4-ethyl-3-iodophenyl)-4-methyl-3-oxopentanoate (20.0 g, 48.0 mmol) and 4-(piperidin-4-yl) morpholine (12.3 g, 72.2 mmol) in dichloroethane (400 mL). The above mixture was heated to 60° C. and stirred for 3 hours. The completion of the reaction was monitored by thin layer chromatography. The reaction solution was poured into a saturated aqueous solution of ammonium chloride, and extracted with ethyl acetate (2×200 mL). Organic phases were combined, washed with saturated brine and dried with anhydrous sodium sulfate. The dried organic phases were filtered, and the filtrate was concentrated at reduced pressure to obtain a crude product. The crude product was purified by silica gel column chromatography (petroleum ether:ethyl acetate=1:2) to obtain tert-butyl 4-(4-ethyl-3-(4-morpholinopiperidin-1-yl)phenyl)-4-methyl-3-oxopentanoate as a light brown oil (14.8 g, with a yield of 67.4%). MS (ESI) m/z: 459.3 $(M+H)^+$ Tert-butyl 2-(2-(2-(4-ethyl-3-(4-morpholinopiperidin-1-yl)phenyl)propan-2-yl)-6-iodo-1H-indole-3-carboxylate

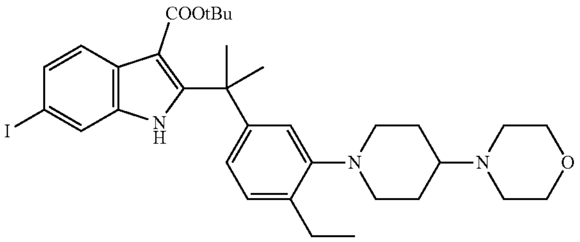

Cesium carbonate (21.3 g, 65.4 mmol) was added into a solution of tert-butyl 4-(4-ethyl-3-(4-morpholinopiperidin-1-yl)phenyl)-4-methyl-3-oxopentanoate (10.0 g, 21.8 mmol) and 1-fluoro-4-iodo-2-nitrobenzene (7.3 g, 27.3 mmol) in DMF (200 mL). The mixture was heated to 35° C. and allowed to react for 8 hours with stirring. The completion of the reaction was monitored by LCMS. The reaction solution was diluted with water (200 mL) and then extracted with ethyl acetate (2×200 mL). Organic phases were combined, washed with saturated brine and dried with anhydrous sodium sulfate. The dried organic phases were filtered and concentrated to obtain an intermediate. The intermediate was dissolved in tetrahydrofuran (60 mL) and water (30 mL), and sodium sulfite (20.0 g, 109 mmol) was added. The above mixture was stirred overnight at room temperature. The obtained mixture was diluted with water (300 mL) and filtered to obtain a residue, and the residue was dissolved in a mixed solution (v/v=10/1, 100 mL) of dichloromethane and methanol. P-methylbenzene sulfonic acid (3.7 g, 21.8 mmol) was added. The above solution was stirred for 1 hour at room temperature. The completion of the reaction was monitored by LCMS. The reaction solution was concentrated, diluted with water (200 mL) and then extracted with ethyl acetate (2×300 mL). Organic phases were combined, washed with saturated brine and dried with anhydrous sodium sulfate. The dried organic phases were filtered and concentrated to obtain a crude product, and the crude product was purified by silica gel column chromatography (petroleum ether:ethyl acetate=1:1) to obtain tert-butyl 2-(2-(2-(4-ethyl-3-(4-morpholinopiperidin-1-yl)phenyl)propan-2-yl)-6-iodo-1H-indole-3-carboxylate as a white solid (10.7 g, with a yield of 70.1%). MS (ESI) m/z: 658.4 $(M+H)^+$;

Sodium 2-(2-(2-(4-ethyl-3-(4-morpholinopiperidin-1-yl)phenyl)propan-2-yl)-6-iodo-1H-indole-3-carboxylate

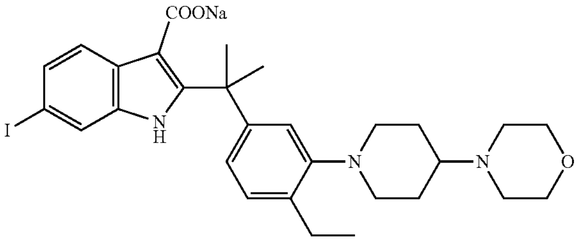

Trimethylchlorosilane (9.23 mL, 73.0 mmol) was added into a solution (120 mL) of tert-butyl 2-(2-(2-(4-ethyl-3-(4-morpholinopiperidin-1-yl)phenyl)propan-2-yl)-6-iodo-1H-indole-3-carboxylate (16.0 g, 24.3 mmol) in trifluoroethanol at 0° C. A reaction was conducted for 2 hours with stirring at 0° C. By LCMS monitoring, 70% of the product was a target compound. The reaction was quenched with a saturated aqueous solution of sodium carbonate (100 mL). The solution after quenching was extracted with ethyl acetate (2×200 mL). Organic phases were combined, washed with saturated brine and dried with anhydrous sodium sulfate. The dried organic phases were filtered, and the filtrate was concentrated at reduced pressure to obtain a crude product of sodium 2-(2-(2-(4-ethyl-3-(4-morpholinopiperidin-1-yl)phenyl)propan-2-yl)-6-iodo-1H-indole-3-carboxylate (15.4 g), which was a light yellow solid. MS (ESI) m/z: 602.2 $(M+H)^+$;

9-ethyl-3-iodo-6,6-dimethyl-8-(4-morpholinopiperidin-1-yl)-5,6-dihydro-11H-benzo[b]carbazol-11-one

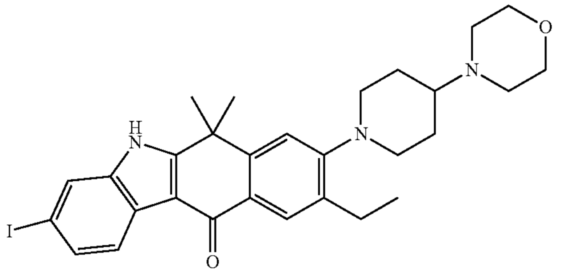 [SMILES: CCc1cc2c(cc1N1CCC(N3CCOCC3)CC1)C(C)(C)c1[nH]c3cc(I)ccc3c1C2=O]

Diisopropylethylamine (32 mL, 193.1 mmol) and acetic anhydride (7.2 mL, 76.4 mmol) were added into a solution of sodium 2-(2-(2-(4-ethyl-3-(4-morpholinopiperidin-1-yl)phenyl)propan-2-yl)-6-iodo-1H-indole-3-carboxylate (15.4 g, 24.7 mmol) in N, N-dimethylacetamide (240 mL). The above mixture was heated to 90° C. and stirred for 1 hour. The completion of the reaction was monitored by LCMS. The reaction solution was diluted with water (200 mL). The solution after dilution was extracted with ethyl acetate (3×200 mL). Organic phases were combined, washed with water (300 mL) and saturated brine (300 mL), and then dried with anhydrous sodium sulfate. The dried organic phases were filtered and concentrated to obtain a residue as a crude product. The crude product was purified by silica gel column chromatography (dichloromethane:methanol=30:1) to obtain 9-ethyl-3-iodo-6,6-dimethyl-8-(4-morpholinopiperidin-1-yl)-5,6-dihydro-11H-benzo[b]carbazol-11-one as a light brown solid (6.7 g, with a two-step yield of 47.5%). 1H NMR (400 MHz, $CDCl_3$): δ 12.23 (s, 1H), 8.02 (s, 1H), 7.99 (d, J=8.0 Hz, 1H), 7.83 (s, 1H), 7.52 (d, J=8.4 Hz, 1H), 7.32 (s, 1H), 3.60 (m, 4H), 3.21~3.19 (m, 2H), 2.78-2.67 (m, 4H), 2.55-2.45 (m, 4H), 2.31-2.29 (m, 1H), 1.92-1.89 (m, 2H), 1.72 (s, 6H), 1.63-1.58 (m, 2H), 1.27 (t, 3H).

9-ethyl-6,6-dimethyl-8-(4-morpholinopiperidin-1-yl)-3-((trimethylsilyl)ethynyl)-5,6-dihydro-11H-benzo[b]carbazol-11-one

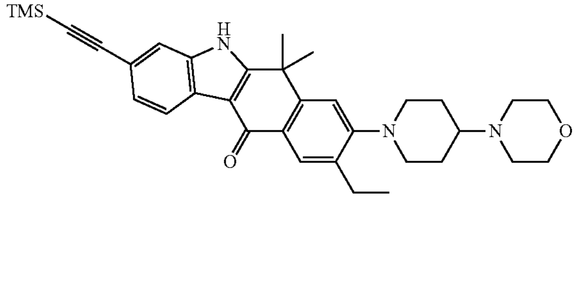 [SMILES: CCc1cc2c(cc1N1CCC(N3CCOCC3)CC1)C(C)(C)c1[nH]c3cc(C#C[Si](C)(C)C)ccc3c1C2=O]

Copper(I) iodide (32 mg, 0.17 mmol), diisopropylethylamine (44 mg, 0.37 mmol) and tetrakis(triphenylphosphin) palladium (9 mg) were added into a solution of 9-ethyl-3-iodo-6,6-dimethyl-8-(4-morpholinopiperidin-1-yl)-5,6-dihydro-11H-benzo[b]carbazol-11-one (98 mg, 0.17 mmol) and ethynyl trimethylsilane (1.67 g, 17.0 mmol) in DMF (10 mL). The mixture was stirred for 2 hours at 100° C. under the protection of argon. The completion of the reaction was monitored by LCMS. The reaction mixture was diluted with water and extracted with ethyl acetate (3×100 mL). Organic phases were combined, washed with water (100 mL) and saturated brine (100 mL) and dried with anhydrous sodium sulfate. The dried organic phases were filtered and concentrated to obtain a crude product of 9-ethyl-6,6-dimethyl-8-(4-morpholinopiperidin-1-yl)-3-((trimethylsilyl)ethynyl)-5,6-dihydro-11H-benzo[b]carbazol-11-one (300 mg). The crude product was directly used for the next step without further purification. MS (ESI) m/z: 552.3 $(M-H)^-$;

9-ethyl-3-ethynyl-6,6-dimethyl-8-(4-morpholinopiperidin-1-yl)-5,6-dihydro-11H-benzo[b]carbazo 1-11-one

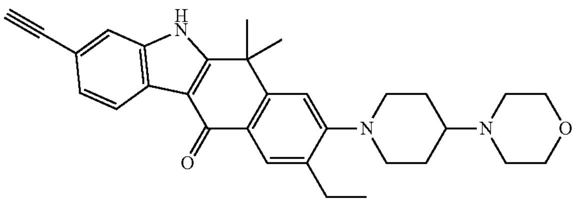 [SMILES: C#Cc1ccc2c3c([nH]c2c1)C(C)(C)c1cc(N2CCC(N4CCOCC4)CC2)c(CC)cc1C3=O]

Potassium carbonate (200 mg) was added into a solution of 9-ethyl-6,6-dimethyl-8-(4-morpholinopiperidin-1-yl)-3-((trimethylsilyl)ethynyl)-5,6-dihydro-11H-benzo[b]carbazol-11-one (300 mg) in methanol (30 mL). The above mixture was stirred overnight at room temperature. The completion of the reaction was monitored by LCMS. The reaction solution was diluted with water and extracted with ethyl acetate (3×50 mL). Organic phases were combined, washed with saturated brine (100 mL) and dried with anhydrous sodium sulfate. The dried organic phases were filtered and concentrated to obtain a residue. The obtained residue was purified by Prep-HPLC to obtain 9-ethyl-3-ethynyl-6,6-dimethyl-8-(4-morpholinopiperidin-1-yl)-5,6-dihydro-11H-benzo[b]carbazo 1-11-one as a white solid (8 mg, with a two-step yield of 9.9%). 1H NMR (400 MHz, $CDCl_3$): δ 8.70 (s, 1H), 8.40 (d, J=8.4 Hz, 1H), 8.28 (s, 1H), 7.58 (s, 1H), 7.46 (d, J=8.0 Hz, 1H), 7.15 (s, 1H), 3.79-3.79 (m, 4H), 3.32-3.29 (m, 2H), 3.08 (s, 1H), 2.79-2.66 (m, 8H), 2.40-2.39 (m, 1H), 2.03-2.00 (m, 2H), 1.76 (m, 8H), 1.33 (t, 3H).

Example 2

9-ethyl-3-ethynyl-6,6-dimethyl-8-(4-methylpiperazin-1-yl)-5,6-dihydro-11H-benzo[b]carbazol-11-one (E2)

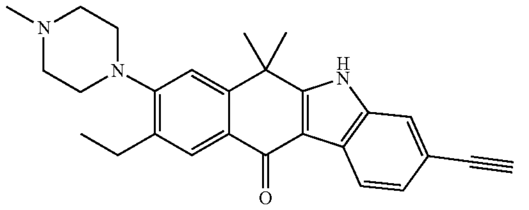

E2

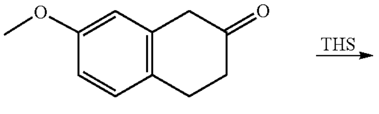

2-1

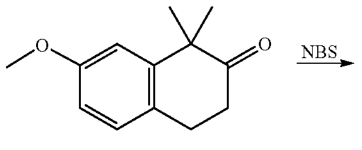

2-2

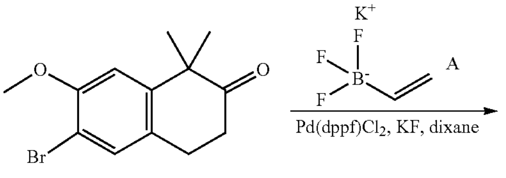

2-3

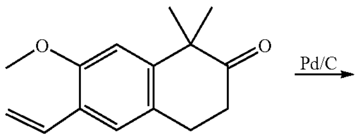

2-4

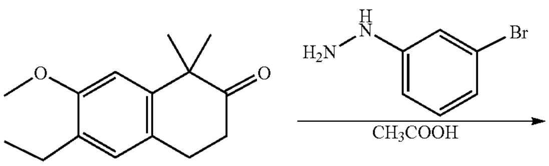

2-5

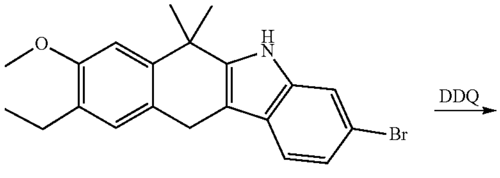

2-6

-continued

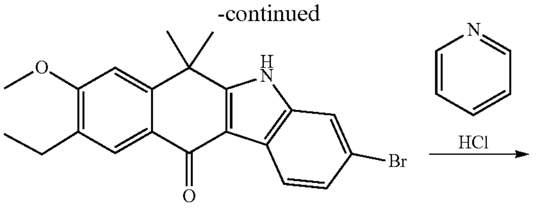

2-7

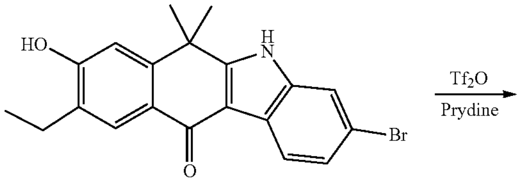

2-8

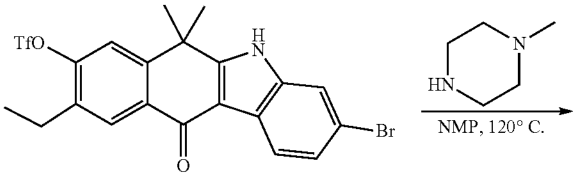

2-9

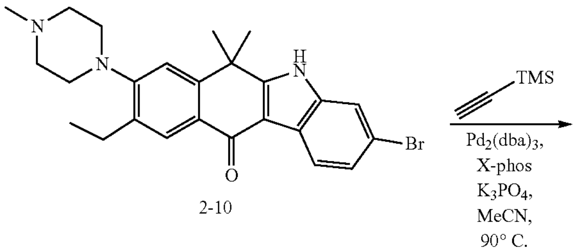

2-10

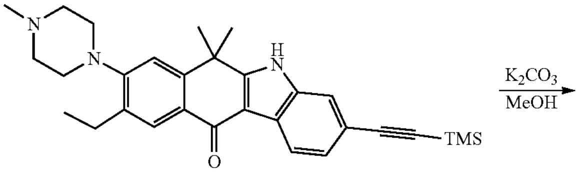

2-11

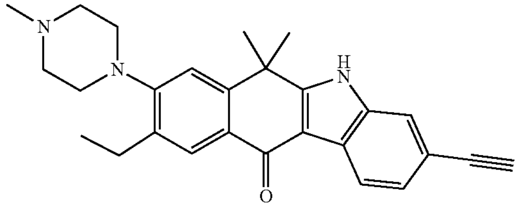

E2

7-methoxy-1,1-dimethyl-3,4-dihydronaphthalen-2 (1H)-one

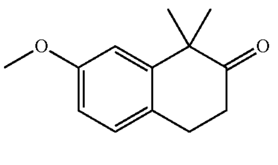

50% potassium hydroxide aqueous solution (400 mL) was dropwise added into a solution of 7-methoxy-3,4-dihydronaphthalen-2(1H)-one (200 g, 1136 mmol) in tetrahydrofuran (1 L) in an ice-water bath under the protection of nitrogen, and then iodomethane (403 g, 2840 mmol) was dropwise added. A reaction was conducted for 3 hours with stirring at room temperature. The completion of the reaction was monitored by LCMS. The reaction solution was diluted with water, and extracted with ethyl acetate. Organic phases were combined, washed with saturated brine, dried with anhydrous sodium sulfate and filtered. The filtrate was concentrated at reduced pressure to obtain a crude product of 7-methoxy-1,1-dimethyl-3,4-dihydronaphthalen-2(1H)-one (300 g, with a yield of 100%). 1H NMR (400 MHz, DMSO) δ 7.11 (t, J=7.3 Hz, 1H), 6.91 (d, J=2.5 Hz, 1H), 6.77 (dd, J=8.3, 2.6 Hz, 1H), 3.73 (d, J=11.7 Hz, 3H), 2.98 (t, J=6.8 Hz, 2H), 2.63-2.57 (m, 2H), 1.37-1.29 (m, 6H).

6-bromo-7-methoxy-1,1-dimethyl-3,4-dihydronaphthalen-2 (1H)-one

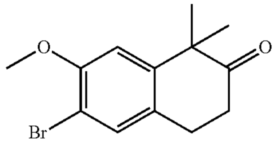 [SMILES: COc1cc2c(cc1Br)CCC(=O)C2(C)C]

N-bromosuccinimide (192 g, 1078 mmol) was added into a solution of 7-methoxy-1,1-dimethyl-3,4-dihydronaphthalen-2 (1H)-one (200 g, 980 mmol) in DMF (1500 mL).

A reaction was conducted for 3 hours with stirring at room temperature. The completion of the reaction was monitored by thin layer chromatography. The reaction solution was poured into ice water (1 L). The obtained solution was extracted with ethyl acetate (3×800 mL). Organic phases were combined, washed with saturated brine (100 mL), dried with anhydrous sodium sulfate, filtered and concentrated to obtain a crude product. The crude product was recrystallized to obtain 6-bromo-7-methoxy-1,1-dimethyl-3,4-dihydronaphthalen-2(1H)-one as a white solid (200 g, with a yield of 60.4%). 1H NMR (400 MHz, DMSO-$d_6$) δ 7.43 (s, 1H), 7.05 (s, 1H), 3.86 (s, 3H), 2.98 (t, J=6.9 Hz, 2H), 2.68-2.53 (m, 2H), 1.37 (s, 6H).

7-methoxy-1,1-dimethyl-6-vinyl-3,4-dihydronaphthalen-2(1H)-one

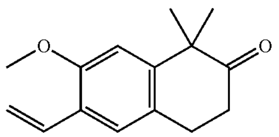 [SMILES: C=Cc1cc2c(cc1OC)C(C)(C)C(=O)CC2]

Potassium trifluoro(vinyl)borate (2.36 g, 17.6 mmol) and potassium fluoride (1.36 g, 23.40 mmol) were added into a solution of 6-bromo-7-methoxy-1,1-dimethyl-3,4-dihydronaphthalen-2(1H)-one (33.0 g, 11.7 mmol) in dioxane (50 mL). Vacuum degassing was performed by replacement with nitrogen for three times, followed by adding a [1,1'-bis (diphenylphosphino)ferrocene] palladium(II) dichloride dichloromethane complex (955 mg, 1.2 mmol). Vacuum degassing was performed by replacement with nitrogen for three times. The obtained solution was heated overnight at 100° C. The completion of the reaction was monitored by LCMS. The reaction solution was filtered, and the filter cake was washed with ethyl acetate. The filtrate and the washing solution were combined, and then the combined solution was concentrated at reduced pressure to dryness. The crude product was purified by silica gel column chromatography (petroleum ether:ethyl acetate=20:1-6:1) to obtain 7-methoxy-1,1-dimethyl-6-vinyl-3,4-dihydronaphthalen-2(1H)-one as an earthy yellow solid (2.54 g, with a yield of 94%).

6-ethyl-7-methoxy-11-dimethyl-3,4-dihydronaphthalen-2(1H)-one

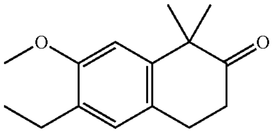 [SMILES: CCc1cc2c(cc1OC)C(C)(C)C(=O)CC2]

Palladium carbon (10%, 500 mg) was added into a solution of 7-methoxy-1,1-dimethyl-6-vinyl-3,4-dihydronaphthalen-2(1H)-one (2.54 g, 11.0 mmol) in ethyl acetate (50 mL). Vacuum degassing was performed by replacement with hydrogen for three times. A reaction was conducted overnight with stiring at room temperature. The reaction solution was filtered, and the filtrate was concentrated at reduced pressure to obtain 6-ethyl-7-methoxy-1,1-dimethyl-3,4-dihydronaphthalen-2(1H)-one as a light yellow solid (2.46 g, with a yield of 97%). MS(ESI) m/z: 233.2 $(M+H)^+$ 3-bromo-9-ethyl-8-methoxy-6,6-dimethyl-6,11-dihydro-5H-benzo[b]carbazole

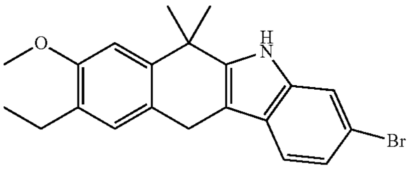 [SMILES: CCc1cc2c(cc1OC)C(C)(C)c1[nH]c3cc(Br)ccc3c1C2]

3-bromophenylhydrazine hydrochloride (2.20 g, 9.8 mmol) was added into a solution of 6-ethyl-7-dimethoxy-1,1-dimethyl-3,4-dihydronaphthalen-2(1H)-one (2.27 g, 9.8 mmol) in acetic acid (25 mL). The above mixed solution was heated to 125° C. and allowed to react for 6 hours with stirring, and the completion of the reaction was monitored by LCMS. The reaction solution was concentrated to dryness to obtain 3-bromo-9-ethyl-8-methoxy-6,6-dimethyl-6,11-dihydro-5H-benzo[b]carbazole (3.90 g, a crude product). MS (ESI) m/z: 384.0 $(M+H)^+$;

3-bromo-9-ethyl-8-methoxy-6,6-dimethyl-5,6-dihydro-11H-benzo[b]carbazol-11-one

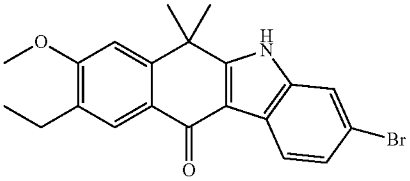 [SMILES: CCc1cc2c(cc1OC)C(C)(C)c1[nH]c3cc(Br)ccc3c1C2=O]

3-bromo-9-ethyl-8-methoxy-6,6-dimethyl-6,11-dihydro-5H-benzo[b]carbazole (3.76 g, 9.8 mmol) was dissolved into tetrahydrofuran (40 mL) and water (4 mL). The mixture was stirred for 10 minutes at room temperature. 2,3-dichloro-5,6-dicyano-1,4-benzoquinone (3.35 g, 14.8 mmol) was added. The mixture was stirred for 3 hour at room temperature. The completion of the reaction was monitored by LCMS. The reaction was quenched with water (100 mL) and then extracted with ethyl acetate (3×100 mL). Organic phases were combined, and then washed with sodium hydroxide (0.5M), brine (0.5M) and saturated brine in sequence. The washed organic phases were dried with anhydrous sodium sulfate, filtered and concentrated to dryness to obtain a crude product. The crude product was purified by silica gel column chromatography to obtain 3-bromo-9-ethyl-8-methoxy-6,6-dimethyl-5,6-dihydro-11H-benzo[b]carbazol-11-one as an earthy yellow solid (2.10 g, a crude product).

3-bromo-9-ethyl-8-hydroxy-6,6-dimethyl-5,6-dihydro-11H-benzo[b]carbazol-11-one

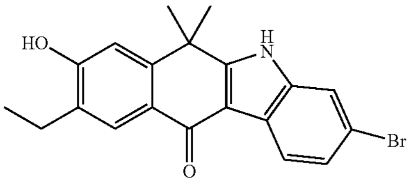 [SMILES: CCc1cc2c(cc1O)C(C)(C)c1[nH]c3cc(Br)ccc3c1C2=O]

3-bromo-9-ethyl-8-methoxy-6,6-dimethyl-5,6-dihydro-11H-benzo[b]carbazol-11-one (2.10 g, 5.3 mmol) and pyridine hydrochloride (30 g) were heated to 170° C. and allowed to react for 13 hours with stirring. The completion of the reaction was monitored by LCMS. The reaction solution was cooled to room temperature and then poured into ice water (100 mL). The mixture was extracted with ethyl acetate (3×100 mL). Organic phases were combined, washed with saturated brine, dried with anhydrous sodium sulfate and filtered, and then concentrated to dryness to obtain a crude product. The crude product was purified by silica gel column chromatography to obtain 3-bromo-9-ethyl-8-hydroxy-6,6-dimethyl-5,6-dihydro-11H-benzo[b]carbazol-11-one as a brown solid (1.32 g, with a yield of 65%). MS (ESI) m/z: 385.1 $(M+H)^+$;

3-bromo-9-ethyl-6,6-dimethyl-11-oxo-6,11-dihydro-5H-benzo[b]carbazol-8-yl trifluoromethanesulfonate

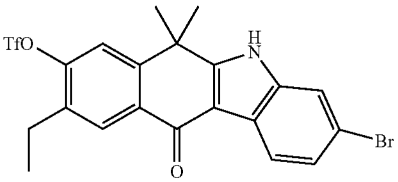 [SMILES: CCc1cc2c(cc1OS(=O)(=O)C(F)(F)F)C(C)(C)c1[nH]c3cc(Br)ccc3c1C2=O]

3-bromo-9-ethyl-8-hydroxy-6,6-dimethyl-5,6-dihydro-11H-benzo[b]carbazol-11-one (1.26 g, 3.3 mmol) was added into a pyridine (30 mL) solution at 0° C. Trifluoromethanesulfonic anhydride (2.7 g, 9.6 mmol) was dropwise added after stirring for 10 minutes at 0° C. A reaction was conducted for 1 hour with stirring at room temperature. The completion of the reaction was monitored by LCMS. The reaction was quenched with water (100 mL). The mixture was extracted with ethyl acetate (3×100 mL). Organic phases were combined, washed with saturated brine, dried with anhydrous sodium sulfate and filtered, and concentrated to dryness to obtain a crude product. The crude product was purified by silica gel column chromatography (ptroleum ether:toluene=8:1-2:1) to obtain 3-bromo-9-ethyl-6,6-dimethyl-11-oxo-6,11-dihydro-5H-benzo[b]carbazol-8-yl trifluoromethanesulfonate as a brown solid (816 mg, with a yield of 48%). MS (ESI) m/z: 528.0 $(M+H)^+$;

3-bromo-9-ethyl-6,6-dimethyl-8-(4-methylpiperazin-1-yl)-5,6-dihydro-11H-benzo[b]carbazol-11

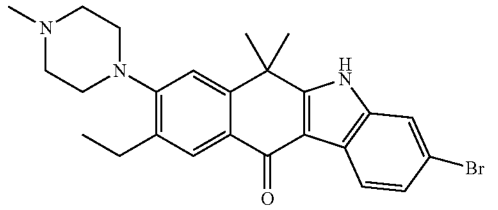 [SMILES: CCc1cc2c(cc1N1CCN(C)CC1)C(C)(C)c1[nH]c3cc(Br)ccc3c1C2=O]

1-methylpiperazine (2.33 g, 23.3 mmol) was dissolved into an N-methylpyrrolidone solution (6 mL). The mixture was stirred for 10 min at 150° C. 3-bromo-9-ethyl-6,6-dimethyl-11-oxo-6,11-dihydro-5H-benzo[b]carbazol-8-yl trifluoromethanesulfonate (600 mg, 1.16 mmol) was added. The above mixture was stirred for 6 hours at 150° C. The completion of the reaction was monitored by LCMS. The reaction solution was cooled to room temperature and then the reaction was quenched with water (30 mL). The reaction solution was filtered to obtain 3-bromo-9-ethyl-6,6-dimethyl-8-(4-methylpiperazin-1-yl)-5,6-dihydro-11H-benzo [b]carbazol-11-one as a brown solid (630 mg, a crude product). MS (ESI) m/z: 466.1 $(M+H)^+$; 9-ethyl-6,6-dimethyl-8-(4-methylpiperazin-1-yl)-3-((trimethylsilyl)ethynyl)-5,6-dihydro-11H-ben

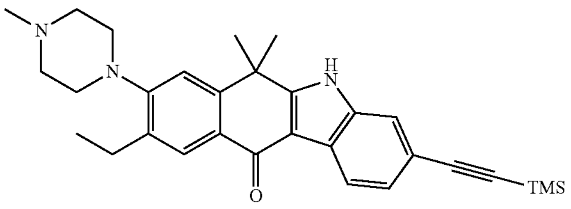 [SMILES: CCc1cc2c(cc1N1CCN(C)CC1)C(C)(C)c1[nH]c3cc(C#C[Si](C)(C)C)ccc3c1C2=O]

Ethynyltrimethylsilane (2.10 g, 21.50 mmol) and tripotassium phosphate (137 mg, 0.65 mmol) were added into a solution of 3-bromo-9-ethyl-6,6-dimethyl-8-(4-methylpiperazin-1-yl)-5,6-dihydro-11H-benzo[b]carbazol-11-one (200 mg, 0.43 mmol) in acetonitrile (10 mL). Air was replaced with nitrogen three times, and then tris(dibenzylideneacetone) dipalladium (79 mg, 0.09 mmol) and 2-dicyclohexylphosphino-2,4,6-triisopropylbiphenyl (82 mg, 0.17 mmol) were added. Air was replaced three times and then the mixture was heated to 90° C. and stirred overnight. The reaction solution was filtered and the filter cake was washed with a mixed solvent of dichloromethane and methanol (v/v=10/1, 50 mL). The filtrate was concentrated at reduced pressure to dryness to obtain a crude product. The crude product was purified by silica gel column chromatography (dichloromethane:methanol=100:1-30:1) to obtain 9-ethyl-6,6-dimethyl-8-(4-methylpiperazin-1-yl)-3-((trimethylsilyl)ethynyl)-5,6-dihydro-11H-ben zo[b]carbazol-11-one as a brown solid (100 mg, with a yield of 43%). MS (ESI) m/z: 484.3 $(M+H)^+$;

9-ethyl-3-ethynyl-6,6-dimethyl-8-(4-methylpiperazin-1-yl)-5,6-dihydro-11H-benzo[b]carbazol-11-one

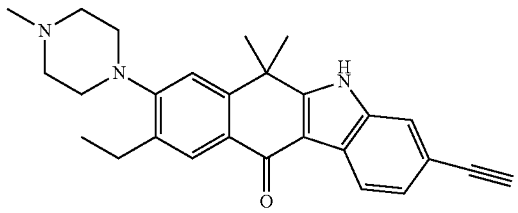 [SMILES: C#Cc1ccc2c3c([nH]c2c1)C(C)(C)c1cc(N2CCN(C)CC2)c(CC)cc1C3=O]

Potassium carbonate (143 mg, 1.01 mmol) was added into a solution of 9-ethyl-6,6-dimethyl-8-(4-methylpiperazin-1-yl)-3-((trimethylsilyl)ethynyl)-5,6-dihydro-11H-ben zo[b] carbazol-11-one (183 mg, 0.38 mmol) in methanol (10 mL). The above solution was stirred for 4 hour at room temperature. The completion of the reaction was monitored by LCMS. The reaction was quenched with water (30 mL), and then extracted with a mixed solvent of dichloromethane and methanol (v/v=10/1, 3×50 mL). Organic phases were combined, washed with saturated brine, dried with anhydrous sodium sulfate and filtered, and then concentrated to dryness to obtain a crude product. The crude product was purified by silica gel column chromatography (dichloromethane:methanol=100:1-20:1) to obtain 9-ethyl-3-ethynyl-6,6-dimethyl-8-(4-methylpiperazin-1-yl)-5,6-dihydro-11H-benzo[b]carbazol-11-one as a brown solid (57.67 mg, with a yield of 55%). 1H NMR (400 MHz, DMSO-$d_6$): δ 12.61 (s, 1H), 8.16 (d, J=8.0 Hz, 1H), 8.04 (s, 1H), 7.61 (s, 1H), 7.35 (s, 1H), 7.32 (d, J=8.0 Hz, 1H), 4.15 (s, 1H), 3.17 (d, J=4.8 Hz, 4H), 3.02 (s, 4H), 2.74-2.61 (m, 5H), 2.33 (s, 3H), 1.75 (s, 6H), 1.29-1.23 (m, 5H).

Example 3

3-ethynyl-6,6-dimethyl-8-(4-methylpiperazin-1-yl)-11-oxo-6,11-dihydro-5H-benzo[b]carbazole-9-carbonitrile (E3)

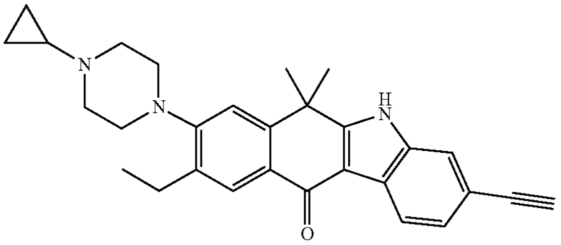

E3

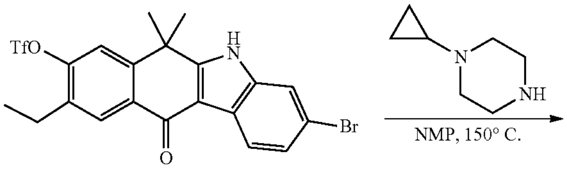

2-9

-continued

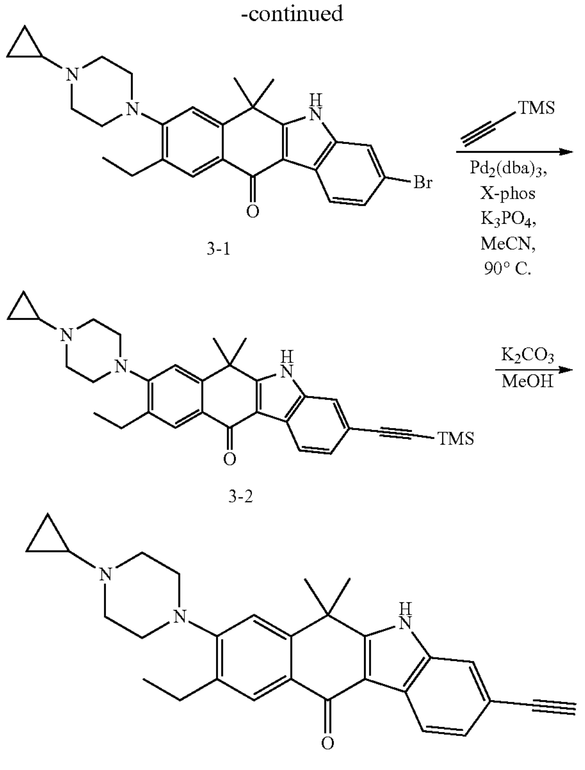

3-1

3-2

E3

3-bromo-8-(4-cyclopropylpiperazin-1-yl)-9-ethyl-6,6-dimethyl-5,6-dihydro-11H-benzo[b]carbazol-11-one

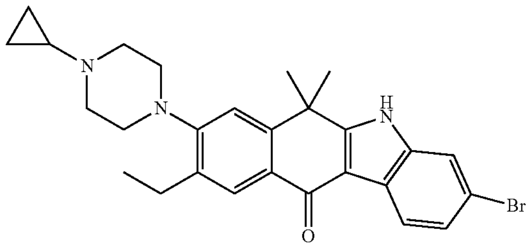 [SMILES: CCc1cc2c(cc1N1CCN(C3CC3)CC1)C(C)(C)c1[nH]c3cc(Br)ccc3c1C2=O]

1-cyclopropylpiperazine (2.5 g, 19.5 mmol) was dissolved into N-methylpyrrolidone (4 mL), then heated to 150° C. and stirred for 10 minutes. 3-bromo-9-ethyl-6,6-dimethyl-11-oxo-6,11-dihydro-5H-benzo[b]carbazole-8-yl trifluoromethanesulfonate (500 mg, 0.98 mmol) was added. The above mixture was stirred for 5 hours at 150° C. The completion of the reaction was monitored by LCMS. The reaction was quenched with water (30 mL) and then extracted with ethyl acetate (3×50 mL). Organic phases were combined, washed with saturated brine, dried with anhydrous sodium sulfate and filtered, and then concentrated to dryness to obtain a crude product. The crude product was purified by silica gel column chromatography (dichloromethane:methanol=100:1-30:1) to obtain 3-bromo-8-(4-cyclopropylpiperazin-1-yl)-9-ethyl-6,6-dimethyl-5,6-dihydro-11H-benzo[b]carbazol-11-one as a brown solid (280 mg, with a yield of 58%). MS(ESI) m/z: 492.1 $(M+H)^+$.

8-(4-cyclopropylpiperazin-1-yl)-9-ethyl-6,6-dimethyl-3-((trimethylsilyl)ethynyl)-5,6-dihydro-11H-benzo[b]carbazol-11-one

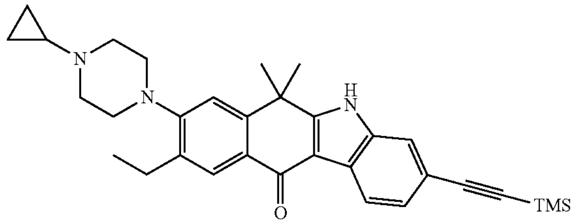 [SMILES: CCc1cc2c(cc1N1CCN(C3CC3)CC1)C(C)(C)c1[nH]c3cc(C#C[Si](C)(C)C)ccc3c1C2=O]

Ethynyltrimethylsilane (1.1 g, 11.24 mmol) and tripotassium phosphate (157 mg, 0.74 mmol) were added into a solution of 3-bromo-8-(4-cyclopropylpiperazin-1-yl)-9-ethyl-6,6-dimethyl-5,6-dihydro-11H-benzo[b]carbazol-11-one (180 mg, 0.37 mmol) in acetonitrile (10 mL). Vacuum degassing was performed by replacement with nitrogen for three times. Tris(dibenzylideneacetone) dipalladium (68 mg, 0.07 mmol) and 2-dicyclohexylphosphino-2,4,6-triisopropylbiphenyl (71 mg, 0.15 mmol) were added. Vacuum degassing was performed by replacement with nitrogen again for three times. The reaction solution was heated to 90° C. and stirred overnight. The obtained solution was filtered, and the filter cake was washed with a mixed solvent (v/v=10/1, 50 mL) of dichloromethane and methanol. The filtrate was concentrated at reduced pressure to dryness to obtain a crude product. The crude product was purified by silica gel column chromatography (dichloromethane:methanol 100:1-30:1) to obtain 8-(4-cyclopropylpiperazin-1-yl)-9-ethyl-6,6-dimethyl-3-((trimethylsilyl)ethynyl)-5,6-dihydro-11H-benzo[b]carbazol-11-one as a brown solid (40 mg, with a yield of 21%). MS (ESI) m/z: 510.2 $(M+H)^+$; 8-(4-cyclopropylpiperazin-1-yl)-9-ethyl-3-ethynyl-6,6-dimethyl-5,6-dihydro-11H-benzo[b]carbaz ol-11-one

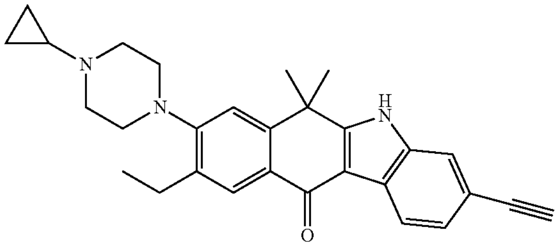 [SMILES: C#Cc1ccc2c3c([nH]c2c1)C(C)(C)c1cc(N2CCN(C4CC4)CC2)c(CC)cc1C3=O]

Potassium carbonate (54 mg, 0.39 mmol) was added into a solution of 8-(4-cyclopropylpiperazin-1-yl)-9-ethyl-6,6-dimethyl-3-((trimethylsilyl)ethynyl)-5,6-dihydro-11H-benzo[b]carbazol-11-one (40 mg, 0.08 mmol) in methanol (3 mL). The above solution was stirred for 3 hour at room temperature. The completion of the reaction was monitored by LCMS. The reaction was quenched with water (30 mL). The reaction solution was extracted with a mixed solvent of dichloromethane and methanol (v/v=10/1, 3×50 mL). Organic phases were combined, washed with saturated brine, dried with anhydrous sodium sulfate and filtered, and then concentrated to dryness to obtain a crude product. The crude product was purified by silica gel column chromatography (dichloromethane:methanol=100:1-20:1) to obtain 8-(4-cyclopropylpiperazin-1-yl)-9-ethyl-3-ethynyl-6,6-dimethyl-5,6-dihydro-11H-benzo[b]carbaz ol-11-one as a white solid (4.93 mg, with a yield of 14%). 1H NMR (400 MHz, DMSO-$d_6$): δ 12.35 (s, 1H), 8.15 (d, J=4.4 Hz, 1H), 8.05 (s, 1H), 7.60 (s, 1H), 7.35-7.31 (m, 2H), 4.11 (s, 1H), 3.39 (s, 2H), 2.98 (s, 4H), 2.79 (s, 2H), 2.76 (q, J=11.2 Hz, 3H), 2.55 (s, 1H), 1.73 (s, 6H), 1.30 (t, J=14.8 Hz, 3H), 0.53-0.39 (m, 3H).

Example 4

8-(4-(azetidin-1-yl)piperidin-1-yl)-9-ethyl-3-ethynyl-6,6-dimethyl-5,6-dihydro-11H-benzo[b]carb azol-11-one (E4)

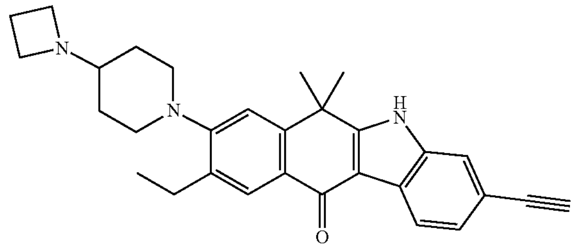

E4

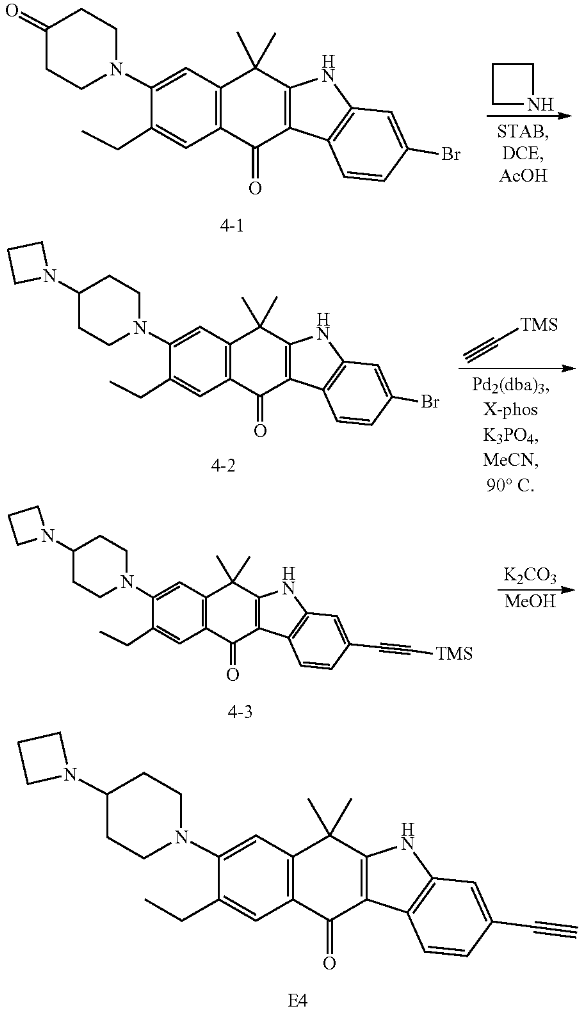

4-1

4-2

4-3

E4

8-(4-(azetidin-1-yl)piperidin-1-yl)-3-bromo-9-ethyl-6,6-dimethyl-5,6-dihydro-11H-benzo[b]carba zol-11-one

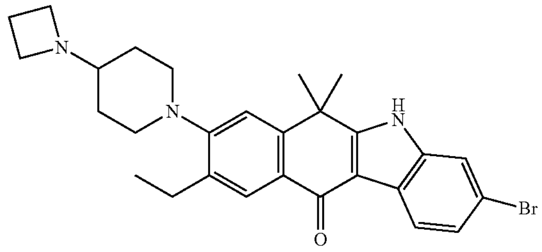 [SMILES: CCc1cc2c(cc1N1CCC(N3CCC3)CC1)C(C)(C)c1[nH]c3cc(Br)ccc3c1C2=O]

Acetic acid (5 drops) and azetidine (280 mg, 4.9 mmol) were added into a solution of 3-bromo-9-ethyl-6,6-dimethyl-8-(4-oxopiperidin-1-yl)-5,6-dihydro-11H-benzo[b]carba-zol-11-one (230 mg, 0.49 mmol) in dichloromethane (20 mL). A reaction was conducted for 1 hour with stirring at room temperature. Sodium triacetoxyborohydride (312 mg, 1.47 mmol) was added. The mixture was heated to 60° C. and allowed to react for 3 hours with stirring. The completion of the reaction was monitored by LCMS. The reaction was quenched with saturated ammonium chloride (30 mL). The solution after quenching was extracted with a mixed solvent (v/v=10/1, 3×50 mL) of dichloromethane and methanol. Organic phases were combined, washed with saturated brine, dried with anhydrous sodium sulfate and filtered, and then concentrated to dryness to obtain a crude product. The crude product was purified by silica gel column chromatography (dichloromethane:methanol=60:1-15:1) to obtain 8-(4-(azetidin-1-yl)piperidin-1-yl)-3-bromo-9-ethyl-6,6-dimethyl-5,6-dihydro-11H-benzo[b]carba zol-11-one as a yellow solid (290 mg, a crude product). MS (ESI) m/z: 506.1 $(M+H)^+$; 8-(4-(azetidin-1-yl)piperidin-1-yl)-9-ethyl-6,6-dimethyl-3-((trimethylsilyl)ethynyl)-5,6-dihydro-11H-benzo[b]carbazol-11-one

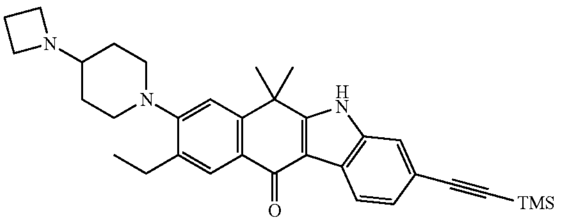 [SMILES: CCc1cc2c(cc1N1CCC(N3CCC3)CC1)C(C)(C)c1[nH]c3cc(C#C[Si](C)(C)C)ccc3c1C2=O]

Ethynyltrimethylsilane (1.34 g, 13.66 mmol) and tripotassium phosphate (193 mg, 0.91 mmol) were added into a solution of 8-(4-(azetidin-1-yl)piperidin-1-yl)-3-bromo-9-ethyl-6,6-dimethyl-5,6-dihydro-11H-benzo[b]carba zol-11-one (230 mg, 0.46 mmol) in acetonitrile (10 mL). The mixture was vacuum degassed using nitrogen for three times. Tris(dibenzylideneacetone) dipalladium (83 mg, 0.09 mmol) and 2-dicyclohexylphosphino-2,4,6-triisopropylbiphenyl (86 mg, 0.18 mmol) were added. The above mixture was degassed three times. The solution after degassing was heated to 90° C. and stirred overnight. The obtained solution was filtered, and the filter cake was washed with a mixed solution (v/v=10/1, 50 mL) of dichloromethane and methanol. The filtrate was concentrated at reduced pressure to dryness to obtain a crude product. The crude product was purified by silica gel column chromatography (dichloromethane:methanol=100:1-30:1) to obtain 8-(4-(azetidin-1-yl)piperidin-1-yl)-9-ethyl-6,6-dimethyl-3-((trimethylsilyl)ethynyl)-5,6-dihydro-11H-benzo[b]carbazol-11-one as a brown solid (200 mg, with a yield of 83%). MS (ESI) m/z: 524.3 (M+H)

8-(4-(azetidin-1-yl)piperidin-1-yl)-9-ethyl-3-ethynyl-6,6-dimethyl-5,6-dihydro-11H-benzo[b]carb azol-11-one

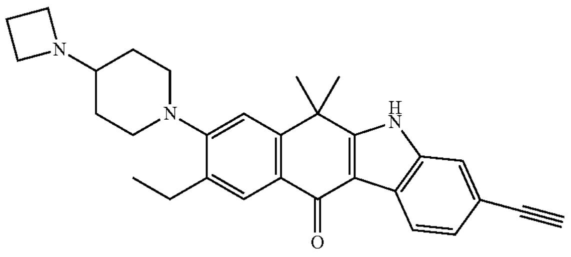 [SMILES: C#Cc1ccc2c3c([nH]c2c1)C(C)(C)c1cc(N2CCC(N4CCC4)CC2)c(CC)cc1C3=O]

Potassium carbonate (263 mg, 1.91 mmol) was added into a solution of 8-(4-(azetidin-1-yl)piperidin-1-yl)-9-ethyl-6,6-dimethyl-3-((trimethylsilyl)ethynyl)-5,6-dihydro-11H-benzo[b]carbazol-11-one (200 mg, 0.38 mmol) in methanol (30 mL). A reaction was conducted overnight with stirring at room temperature. The completion of the reaction was monitored by LCMS. The reaction was quenched with water (30 mL). The solution after quenching was extracted with a mixed solvent (v/v=10/1, 3×50 mL) of dichloromethane and methanol. Organic phases were combined, washed with saturated brine, dried with anhydrous sodium sulfate and filtered, and then concentrated to dryness to obtain a crude product. The crude product was purified by silica gel column chromatography (dichloromethane:methanol=100:1-20:1) to obtain 8-(4-(azetidin-1-yl)piperidin-1-yl)-9-ethyl-3-ethynyl-6,6-dimethyl-5,6-dihydro-11H-benzo[b]carb azol-11-one as a yellow solid (57.67 mg, with a yield of 33%). 1H NMR (400 MHz, DMSO-$d_6$): δ 12.35 (s, 1H), 8.16 (d, J=8.0 Hz, 1H), 8.03 (s, 1H), 7.59 (s, 1H), 7.33 (t, J=8.0 Hz, 2H), 4.13 (s, 1H), 3.34 (s, 2H), 3.16 (d, J=12.0 Hz, 2H), 2.77-2.65 (m, 5H), 2.01 (s, 2H), 1.81 (d, J=10.4 Hz, 2H), 1.73 (s, 6H), 1.41-1.15 (m, 7H).

Example 5

9-ethyl-3-ethynyl-6,6-dimethyl-8-(4-(pyrrolidin-1-yl)piperidin-1-yl)-5,6-dihydro-11H-benzo[b]carbazol-11-one (E5)

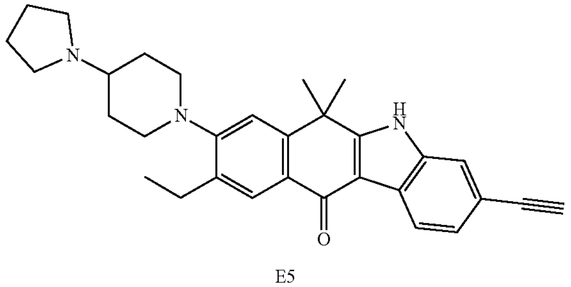

E5

-continued

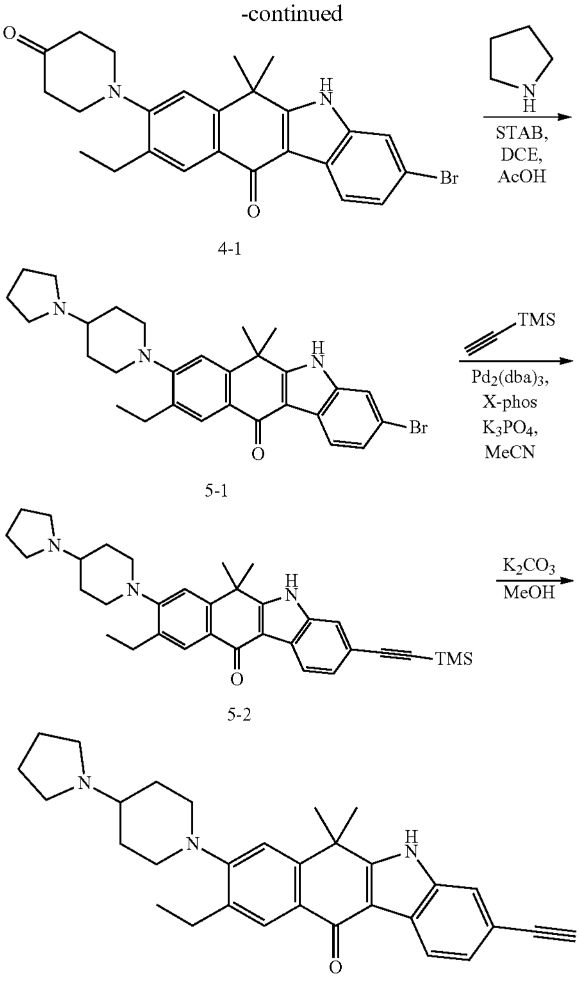

4-1

5-1

5-2

E5

3-bromo-9-ethyl-6,6-dimethyl-8-(4-(pyrrolidin-1-yl)piperidin-1-yl)-5,6-dihydro-11H-benzo[b]carbazol-11-one

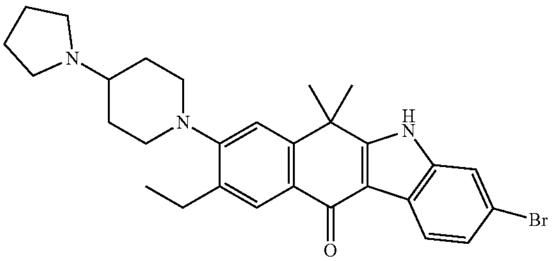 [SMILES: CCc1cc2c(cc1N1CCC(N3CCCC3)CC1)C(C)(C)c1[nH]c3cc(Br)ccc3c1C2=O]

Pyrrolidine (306 mg, 4.3 mmol) and acetic acid (5 drops) were added into a solution of 3-bromo-9-ethyl-6,6-dimethyl-8-(4-oxopiperidin-1-yl)-5,6-dihydro-11H-benzo[b]carbazol-11-one (200 mg, 0.43 mmol) in dichloroethane (20 mL). Sodium triacetoxyborohydride (273 mg, 1.29 mmol) was added after stirring for 1 hour at room temperature. The mixture was heated to 60° C. and allowed to react for 3 hours with stirring. The completion of the reaction was monitored by LCMS. The reaction was quenched with saturated ammonium chloride (30 mL). The solution after quenching was extracted with a mixed solvent (v/v=10/1, 3×50 mL) of dichloromethane and methanol. Organic phases were combined, washed with saturated brine, dried with anhydrous sodium sulfate and filtered, and then concentrated to dryness to obtain a crude product. The crude product was purified by silica gel column chromatography (dichloromethane:methanol=60:1-15:1) to obtain 3-bromo-9-ethyl-6,6-dimethyl-8-(4-(pyrrolidin-1-yl)piperidin-1-yl)-5,6-dihydro-11H-benzo[b]carbazol-11-one as a yellow solid (260 mg, a crude product). MS (ESI) m/z: 520.2 (M+H) 9-ethyl-6,6-dimethyl-8-(4-(pyrrolidin-1-yl)piperidin-1-yl)-3-((trimethylsilyl)ethynyl)-5,6-dihydro-11H-benzo[b]carbazol-11-one

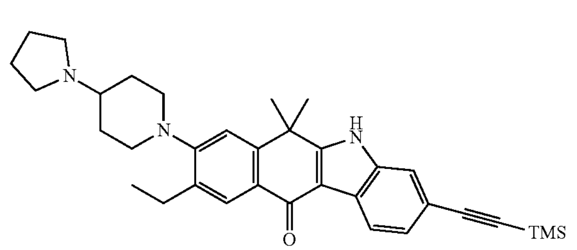 [SMILES: CCc1cc2c(cc1N1CCC(N3CCCC3)CC1)C(C)(C)c1[nH]c3cc(C#C[Si](C)(C)C)ccc3c1C2=O]

Ethynyltrimethylsilane (1200 mg, 12.48 mmol) and tripotassium phosphate (178 mg, 0.84 mmol) were added into a solution of 3-bromo-9-ethyl-6,6-dimethyl-8-(4-(pyrrolidin-1-yl)piperidin-1-yl)-5,6-dihydro-11H-benzo[b]carbazol-11-one (216 mg, 0.42 mmol) in acetonitrile (10 mL). The mixture was vacuum degassed with nitrogen for three times. Tris(dibenzylideneacetone) dipalladium (77 mg, 0.08 mmol) and 2-dicyclohexylphosphino-2,4,6-triisopropylbiphenyl (80 mg, 0.17 mmol) were added. The above mixture was degassed for three times again. The obtained mixture was heated to 90° C. and allowed to react overnight with stirring. The reaction solution was filtered, and the filter cake was washed with a mixed solvent (v/v=10/1, 50 mL) of dichloromethane and methanol. The filtrate was concentrated at reduced pressure to dryness to obtain a crude product. The crude product was purified by silica gel column chromatography (dichloromethane:methanol=100:1-30:1) to obtain 9-ethyl-6,6-dimethyl-8-(4-(pyrrolidin-1-yl)piperidin-1-yl)-3-((trimethylsilyl)ethynyl)-5,6-dihydro-11H-benzo[b]carbazol-11-one as a brown solid (216 mg, with a yield of 95%). MS (ESI) m/z: 538.3 $(M+H)^+$;

9-ethyl-3-ethynyl-6,6-dimethyl-8-(4-(pyrrolidin-1-yl)piperidin-1-yl)-5,6-dihydro-11H-benzo[b]carbazol-11-one

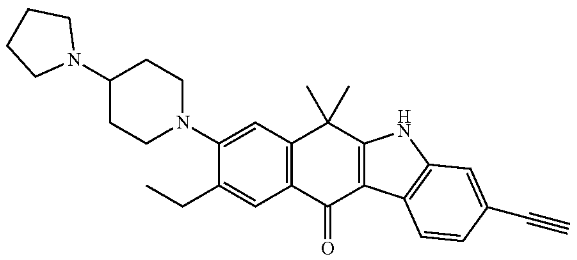 [SMILES: C#Cc1ccc2c3c([nH]c2c1)C(C)(C)c1cc(N2CCC(N4CCCC4)CC2)c(CC)cc1C3=O]

Potassium carbonate (352 mg, 1.91 mmol) was added into a solution of 9-ethyl-6,6-dimethyl-8-(4-(pyrrolidin-1-yl)piperidin-1-yl)-3-((trimethylsilyl)ethynyl)-5,6-dihydro-11H-benzo[b]carbazol-11-one (216 mg, 0.38 mmol) in methanol (30 mL). A reaction was conducted overnight with stirring at room temperature. The completion of the reaction was monitored by LCMS. The reaction was quenched with water (30 mL), and extracted with a mixed solvent (v/v=10/1, 3×50 mL) of dichloromethane and methanol. Organic phases were combined, washed with saturated brine, dried with anhydrous sodium sulfate and filtered, and then concentrated to dryness to obtain a crude product. The crude product was purified by silica gel column chromatography (dichloromethane:methanol=100:1-20:1) to obtain 9-ethyl-3-ethynyl-6,6-dimethyl-8-(4-(pyrrolidin-1-yl)piperidin-1-yl)-5,6-dihydro-11H-benzo[b]carbazol-11-one as a yellow solid (37.94 mg, with a yield of 33%). 1H NMR (400 MHz, DMSO-$d_6$): δ 12.41 (s, 1H), 8.16 (d, J=8.0 Hz, 1H), 8.04 (s, 1H), 7.60 (s, 1H), 7.34-7.31 (m, 2H), 4.12 (s, 1H), 3.25 (d, J=11.6 Hz, 3H), 3.18 (d, J=4.8 Hz, 1H), 2.78-2.70 (m, 6H), 2.11 (s, 2H), 1.86 (s, 6H), 1.74 (s, 6H), 1.33-1.23 (m, 4H).

Example 6

8-(4-(dimethylamino)piperidin-1-yl)-9-ethyl-3-ethynyl-6,6-dimethyl-5,6-dihydro-11H-benzo[b]carbazol-11-one (E6)

E6

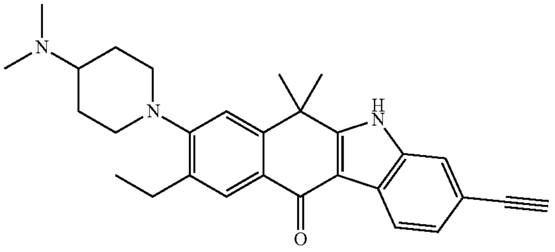

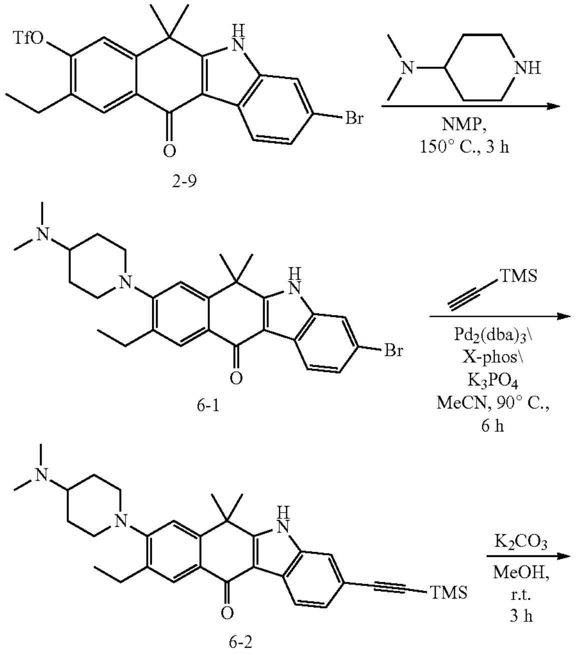

-continued

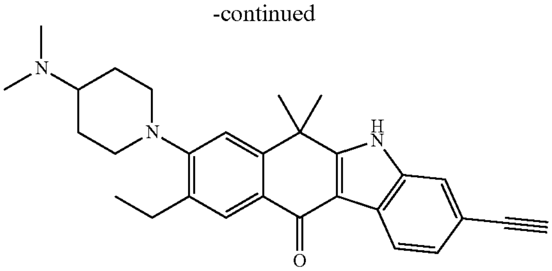

E6

3-bromo-8-(4-(dimethylamino)piperidin-1-yl)-9-ethyl-6,6-dimethyl-5,6-dihydro-11H-benzo[b]carbazol-11-one

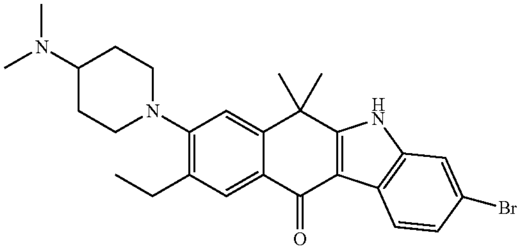 [SMILES: CCc1cc2c(cc1N1CCC(N(C)C)CC1)C(C)(C)c1[nH]c3cc(Br)ccc3c1C2=O]

N,N-dimethylpiperidin-4-amine (2.49 g, 19.37 mmol) was dissolved in N-methylpyrrolidone (30 mL) under the protection of nitrogen. The above mixed solution was heated to 150° C. and stirred for 5 min, and then 3-bromo-9-ethyl-6,6-dimethyl-11-oxo-6,11-dihydro-5H-benzo[b]carbazol-8-yl trifluoromethanesulfonate (500 mg, 0.97 mmol) was added. A reaction was conducted for 3 h with stirring at 150° C. The completion of the reaction was monitored by LCMS. The reaction solution was cooled to room temperature and then poured into water (100 mL). The obtained mixture was extracted with ethyl acetate (2x30 mL). Organic phases were combined, washed with saturated brine (30 mL), dried with anhydrous sodium sulfate and then filtered, and the filtrate was concentrated to dryness at reduced pressure to obtain a crude product. The crude product was purified by silica gel column chromatography (petroleum ether:ethyl acetate=3:1) to obtain 3-bromo-8-(4-(dimethylamino)piperidin-1-yl)-9-ethyl-6,6-dimethyl-5,6-dihydro-11H-benzo[b]carbazol-11-one as a white solid (210 mg, with a yield of 43.8%). MS (ESI) m/z: 496.0 $(M+H)^+$; 9-ethyl-6,6-dimethyl-8-(4-(methylamino)piperidin-1-yl)-3-((trimethylsilyl)ethynyl)-5,6-dihydro-11H-benzo[b]carbazol-11-one

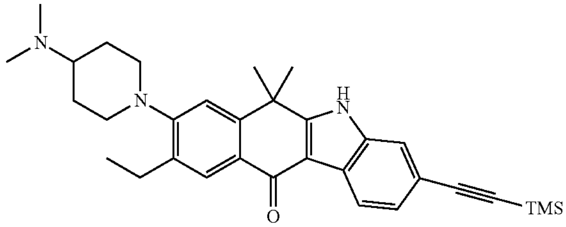 [SMILES: CCc1cc2c(cc1N1CCC(N(C)C)CC1)C(C)(C)c1[nH]c3cc(C#C[Si](C)(C)C)ccc3c1C2=O]

Tris(dibenzylideneacetone) dipalladium (44 mg, 0.05 mmol) and 2-dicyclohexylphosphino-2,4,6-triisopropylbiphenyl (46 mg, 0.10 mmol) and tripotassium phosphate (203 mg, 0.95 mmol) were added into a solution of 3-bromo-8-(4-(dimethylamino)piperidin-1-yl)-9-ethyl-6,6-dimethyl-5,6-dihydro-11H-benzo[b]carbazol-11-one (118 mg, 0.24 mmol) and ethynyltrimethylsilane (235 mg, 2.39 mmol) in acetonitrile (18 mL). The mixture was heated to 90° C. and allowed to react for 6 hours with stirring. The completion of the reaction was monitored by LCMS. The reaction solution was filtered, and the filter cake was washed with dichloromethane and methanol. The filtrate was concentrated to dryness at reduced pressure to obtain a crude product, and the crude product was purified by silica gel column chromatography (dichloromethane:methanol=10:1) to obtain 9-ethyl-6,6-dimethyl-8-(4-(methylamino)piperidin-1-yl)-3-(trimethylsilyl)ethynyl)-5,6-dihydro-11H-benzo[b]carbazol-11-one as a yellow solid (75 mg, with a yield of 61.4%). MS (ESI) m/z: 512.4 $(M+H)^+$;

8-(4-(dimethylamino)piperidin-1-yl)-9-ethyl-3-ethynyl-6,6-dimethyl-5,6-dihydro-11H-benzo[b]carbazol-11-one

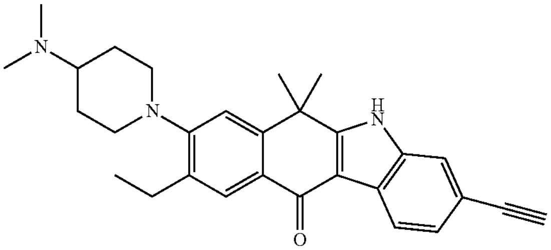 [SMILES: C#Cc1ccc2c3c([nH]c2c1)C(C)(C)c1cc(N2CCC(N(C)C)CC2)c(CC)cc1C3=O]

Potassium carbonate (102 mg, 0.73 mmol) was added into a solution of 9-ethyl-6,6-dimethyl-8-(4-(methylamino)piperidin-1-yl)-3-((trimethylsilyl)ethynyl)-5,6-dihydro-11H-benzo[b]carbazol-11-one (75 mg, 0.15 mmol) in methanol (10 mL). A reaction was conducted for 3 hours with stirring at room temperature. The completion of the reaction was monitored by LCMS. The reaction solution was poured into ice water (120 mL) and then extracted with ethyl acetate (2x30 mL). Organic phases were combined, washed with saturated brine (30 mL), dried with anhydrous sodium sulfate, filtered and concentrated to obtain a crude product. The crude product was purified by silica gel column chromatography (dichloromethane:methanol=10:1) to obtain 8-(4-(dimethylamino)piperidin-1-yl)-9-ethyl-3-ethynyl-6,6-dimethyl-5,6-dihydro-11H-benzo[b]carbazol-11-one as a yellow solid (12 mg, 0.03 mmol, with a yield of 18.6%). 1H NMR (400 MHz, DMSO-$d_6$): δ 12.83 (s, 1H), 8.14 (d, J=8.0 Hz, 1H), 8.04 (s, 1H), 7.63 (s, 1H), 7.35 (m, 1H), 7.31 (dd, J=16.0, 8.0 Hz, 1H), 4.11 (s, 1H), 3.23 (m, 6H), 2.79 (t, J=10.9 Hz, 4H), 2.71 (dd, J=15.0, 7.6 Hz, 4H), 2.10-2.01 (m, 4H), 2.00-1.94 (m, 2H), 1.75 (s, 6H), 1.34-1.25 (m, 3H).

Example 7

9-ethyl-3-(3-hydroxyprop-1-yn-1-yl)-6,6-dimethyl-8-(piperazin-1-yl)-5H-benzo[b]carbazol-11(6H)-one (E7)

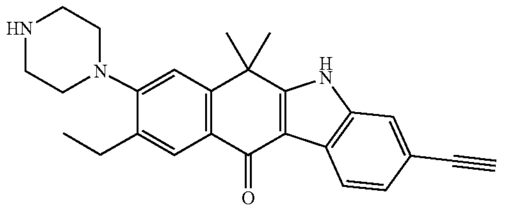

E-7

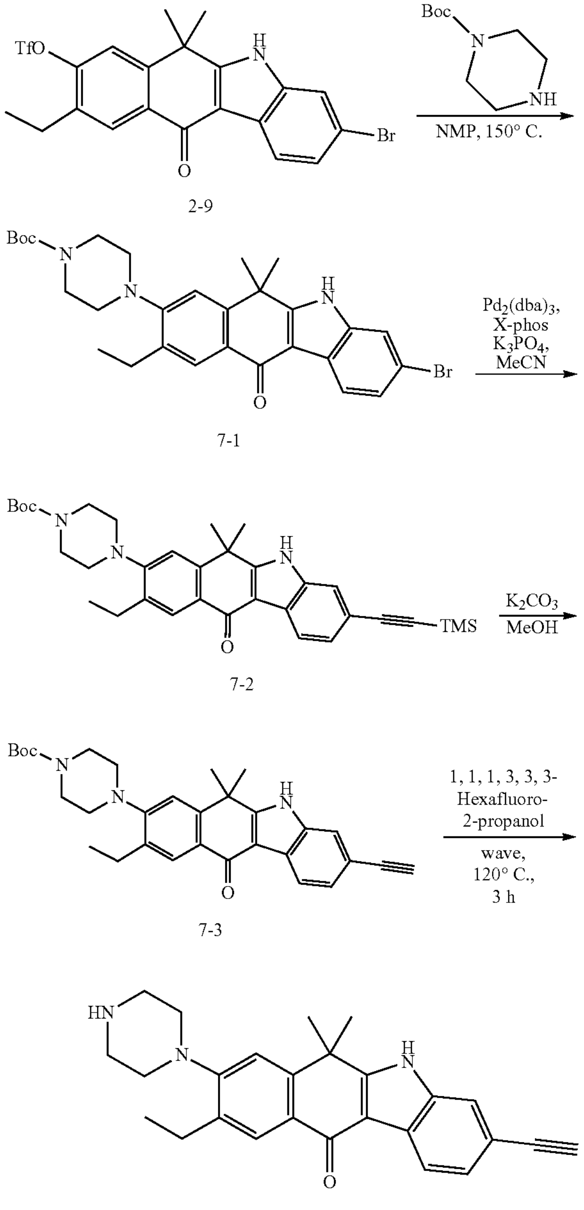

2-9

7-1

7-2

7-3

E-7

Tert-butyl 4-(3-bromo-9-ethyl-6,6-dimethyl-11-oxo-6,11-dihydro-5H-benzo[b]carbazol-8-yl)piperazine-1-car boxylate

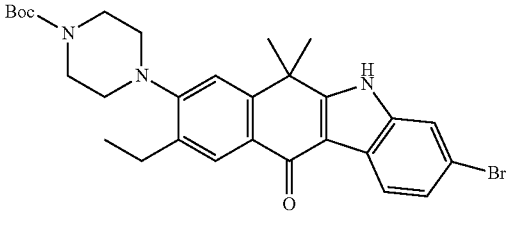 [SMILES: CCc1cc2c(cc1N1CCN(C(=O)OC(C)(C)C)CC1)C(C)(C)c1[nH]c3cc(Br)ccc3c1C2=O]

Tert-butyl piperazine-1-carboxylate (3.6 g, 19.4 mmol) was added into a solution of 3-bromo-9-ethyl-6,6-dimethyl-11-oxo-6,11-dihydro-5H-benzo[b]carbazol-8-yl trifluoromethanesulfonate (1 g, 1.94 mmol) in N-methylpyrrolidone (5 mL). The mixture was stirred overnight at 150° C. The reaction solution was cooled to room temperature and then poured into ice water (30 mL) and extracted with ethyl acetate (3x20 mL). Organic phases were combined, washed with saturated brine, dried with anhydrous sodium sulfate, filtered and concentrated to obtain a crude product. The crude product was purified by silica gel column chromatography (petroleum ether:ethyl acetate=2:1) to obtain tert-butyl 4-(3-bromo-9-ethyl-6,6-dimethyl-11-oxo-6,11-dihydro-5H-benzo[b]carbazol-8-yl)piperazine-1-car boxylate as a yellow solid (280 mg, with a yield of 26.8%). MS (ESI) m/z: 552.1 $(M+H)^+$; Tert-butyl

4-(9-ethyl-6,6-dimethyl-11-oxo-3-((trimethylsilyl) ethynyl)-6,11-dihydro-5H-benzo[b]carbazol-8-yl) piperazine-1-carboxylate

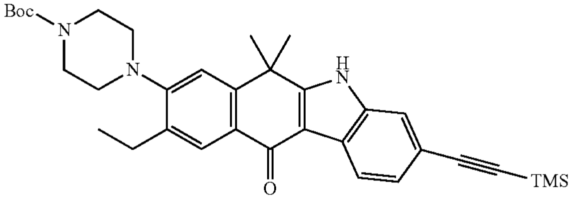 [SMILES: CCc1cc2c(cc1N1CCN(C(=O)OC(C)(C)C)CC1)C(C)(C)c1[nH]c3cc(C#C[Si](C)(C)C)ccc3c1C2=O]

Tris(dibenzylideneacetone) dipalladium (45 mg, 0.05 mmol), 2-dicyclohexylphosphino-2,4,6-triisopropylbiphenyl (47 mg, 0.1 mmol), tripotassium phosphate (318 mg, 1.5 mmol) and ethynyltrimethylsilane (490 mg, 5 mmol) were added into a solution of tert-butyl 4-(3-bromo-9-ethyl-6,6-dimethyl-11-oxo-6,11-dihydro-5H-benzo[b]carbazol-8-yl) piperazine-1-carboxylate (280 mg, 0.51 mmol) in acetonitrile (5 mL). The mixture was heated to 90° C. and allowed to react for 3 h with stirring under the protection of argon. The completion of the reaction was monitored by LCMS. The reaction solution was diluted with water and extracted with ethyl acetate (2x30 mL). Organic phases were combined, washed with saturated brine (30 mL), dried with anhydrous sodium sulfate, filtered and concentrated to obtain a crude product.

The crude product was purified by silica gel column chromatography (dichloromethane:ethyl acetate=0-50%) to obtain tert-butyl 4-(9-ethyl-6,6-dimethyl-11-oxo-3-((trimethylsilyl)ethynyl)-6,11-dihydro-5H-benzo[b]carbazol-8-yl) piperazine-1-carboxylate as a yellow solid (120 mg, with a yield of 64%). MS (ESI) m/z: 470.1 (M+H) Tert-butyl 4-(9-ethyl-3-ethynyl-6,6-dimethyl-11-oxo-6,11-dihydro-5H-benzo[b]carbazol-8-yl)piperazine-1-carboxylate

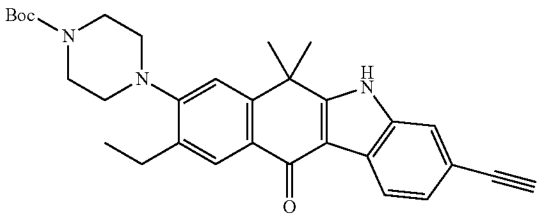 [SMILES: C#Cc1ccc2c3c([nH]c2c1)C(C)(C)c1cc(N2CCN(C(=O)OC(C)(C)C)CC2)c(CC)cc1C3=O]

Potassium carbonate (318 mg, 1.5 mmol) was added into a solution of tertbutyl 4-(9-ethyl-6,6-dimethyl-11-oxo-3-((trimethylsilyl)ethynyl)-6,11-dihydro-5H-benzo[b]carbazol-8-yl) piperazine-1-carboxylate (180 mg, 0.32 mmol) in methanol (5 mL). A reaction was conducted for 2 hours with stirring at 25° C. The completion of the reaction was monitored by LCMS. The reaction mixture was diluted with water and extracted with ethyl acetate (2×30 mL). Organic phases were combined, washed with saturated brine (30 mL), dried with anhydrous sodium sulfate, filtered and concentrated to obtain a crude product. The crude product was purified by silica gel column chromatography (petroleum ether:ethyl acetate=2:1) to obtain tert-butyl 4-(9-ethyl-3-ethynyl-6,6-dimethyl-11-oxo-6,11-dihydro-5H-benzo[b]carbazol-8-yl)piperazine-1-carboxylate (100 mg, with a yield of 89%) as a yellow solid. MS (ESI) m/z: 498.1 $(M+H)^+$; 9-ethyl-3-ethynyl-6,6-dimethyl-8-(piperazin-1-yl)-5H-benzo[b]carbazol-11(6H)-one

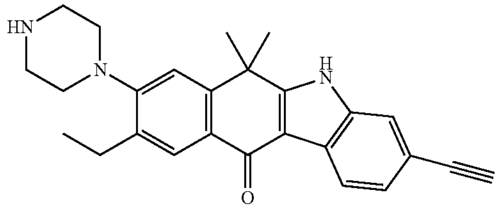 [SMILES: C#Cc1ccc2c3c([nH]c2c1)C(C)(C)c1cc(N2CCNCC2)c(CC)cc1C3=O]

Tert-butyl 4-(9-ethyl-3-ethynyl-6,6-dimethyl-11-oxo-6,11-dihydro-5H-benzo[b]carbazol-8-yl)piperazine-1-carboxylate (100 mg, 0.20 mmol) was added into 1,1,1,3,3,3-hexafluoro-2-propanol (5 mL). The above materials reacted for 1 hour at 120° C. under the condition of microwave. The reaction solution was concentrated at reduced pressure to obtain a crude product. The crude product was purified by Prep-HPLC to obtain 9-ethyl-3-ethynyl-6,6-dimethyl-8-(piperazin-1-yl)-5H benzo[b]carbazol-11(6H)-one as a yellow solid (4 mg, with a yield of 6%). 1H NMR (400 MHz, CD3OD) δ 8.22-8.20 (m, 2H), 7.59 (s, 1H), 7.41-7.38 (d, J=12 Hz, 1H), 7.36-7.33 (m, 2H), 4.95 (s, 1H), 3.47-3.42 (m, 6H), 3.29-3.23 (m, 2H), 2.83-2.79 (m, 2H), 1.79 (s, 6H), 1.37-1.33 (m, 3H).

Example 8

9-ethyl-3-ethynyl-6,6-dimethyl-8-(piperidin-4-yl)-5,6-dihydro-11H-benzo[b]carbazol-11-one (E8)

E8

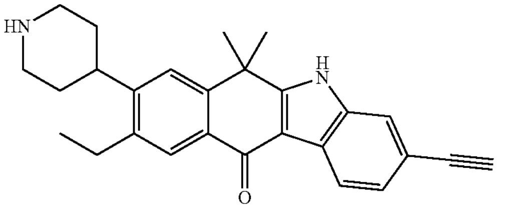

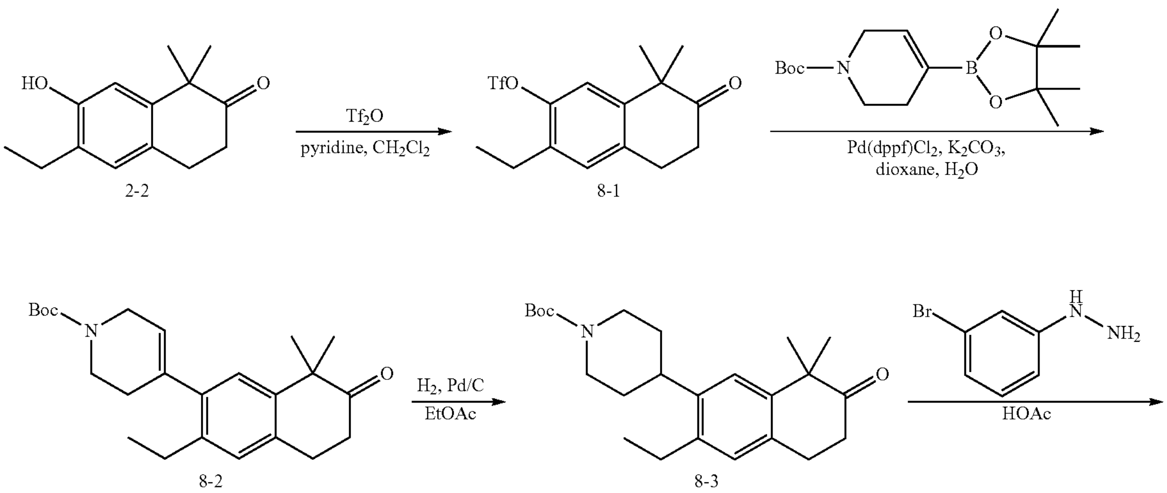

-continued

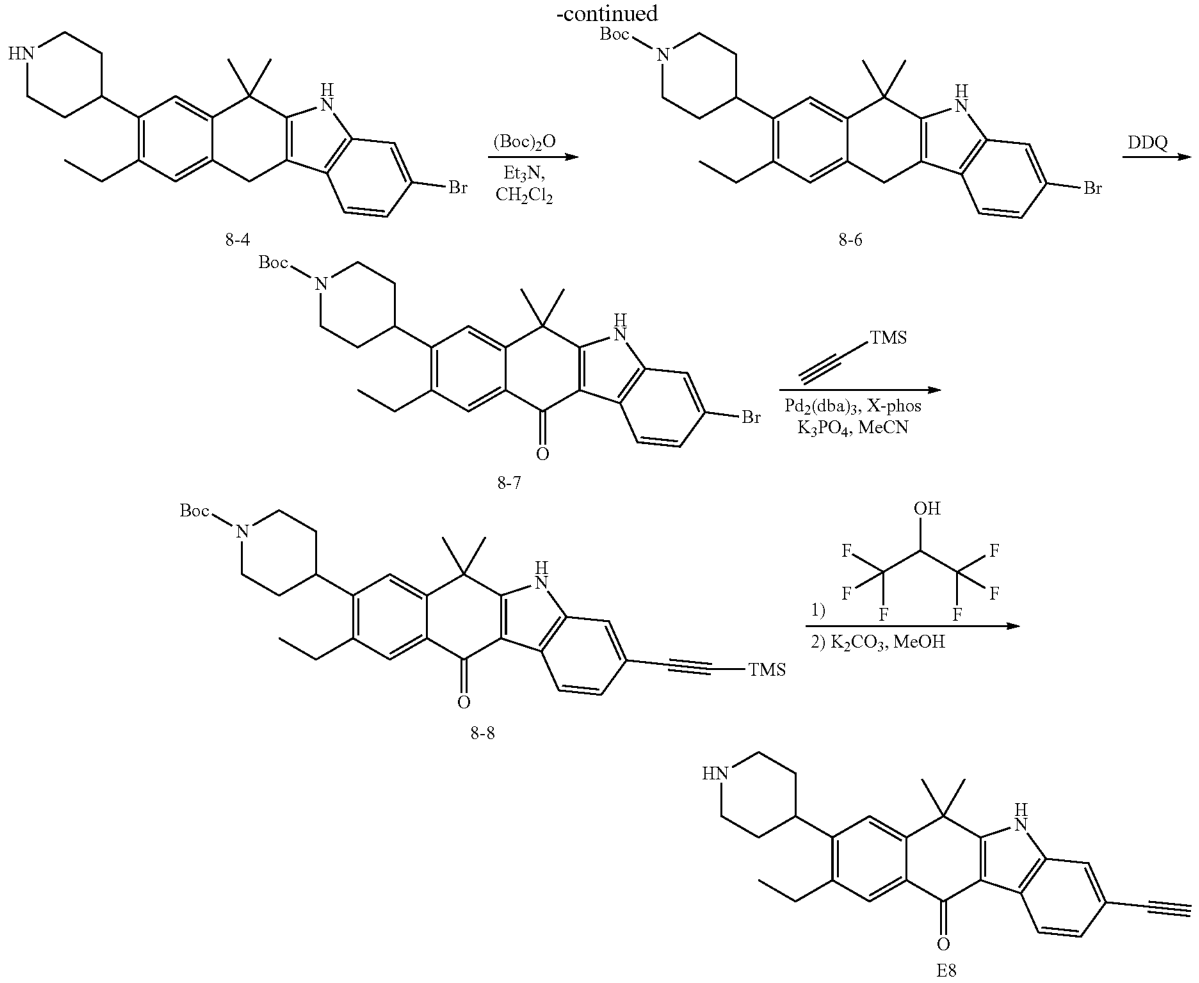

3-ethyl-8,8-dimethyl-7-oxo-5,6,7,8-tetrahydronaphthalen-2-yl trifluoromethanesulfonate

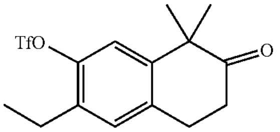 [SMILES: CCc1cc2c(cc1OS(=O)(=O)C(F)(F)F)C(C)(C)C(=O)CC2]

Pyridine (11.60 g, 146.59 mmol) was added into a solution of 6-ethyl-7-hydroxy-1,1-dimethyl-3,4-dihydronaphthalen-2 (1H)-one (3.2 g, 14.66 mmol) in dichloromethane (50 mL). Trifluoromethanesulfonic anhydride (20.68 g, 73.30 mmol) was dropwise added under the protection of argon at 0° C. A reaction was conducted for 4 hours with stirring at room temperature. The reaction was quenched with water. The obtained mixture was washed with saturated brine (3×100 mL), dried with anhydrous sodium sulfate and concentrated to obtain a crude product. The crude product was purified by silica gel chromatography (petroleum ether: ethyl acetate=20:1) to obtain 3-ethyl-8,8-dimethyl-7-oxo-5,6,7,8-tetrahydronaphthalen-2-yl trifluoromethanesulfonate as a yellow solid (3.6 g, with a yield of 70%). 1H NMR (400 MHz, $CDCl_3$): δ 7.16 (s, 1H), 7.14 (s, 1H), 3.10 (t, J=6.8 Hz, 2H), 2.75~2.67 (m, 4H), 1.42 (s, 6H), 1.27 (t, J=7.6 Hz, 3H).

Tert-butyl 4-(3-ethyl-8,8-dimethyl-7-oxo-5,6,7,8-tetrahydronaphthalen-2-yl)-3,6-dihydropyridine-1 (2H)-carboxylate

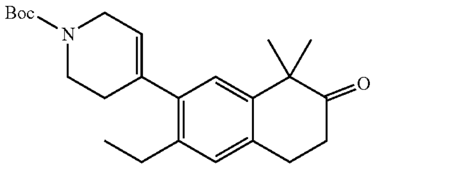 [SMILES: CCc1cc2c(cc1C1=CCN(C(=O)OC(C)(C)C)CC1)C(C)(C)C(=O)CC2]

4-(4,4,5,5-tetramethyl-1,3,2-dioxaborolan-2-yl)-3,6-dihydropyridine-1(2H)-carboxylate (6.35 g, 20.55 mmol), a [1,1'-bis(diphenylphosphino)ferrocene]palladium(II) dichloride dichloromethane complex (752 mg, 1.03 mmol) and potassium carbonate (4.26 g, 30.83 mmol) were added into a suspension of 3-ethyl-8,8-dimethyl-7-oxo-5,6,7,8-tetrahydronaphthalen-2-yl trifluoromethanesulfonate (3.6 g, 10.28 mmol) in dioxane (40 mL) and water (4 mL). The obtained mixture was degassed with argon three times. The mixture was heated and refluxed to conduct a reaction overnight. Ethyl acetate (50 mL) was added after the reaction was completed, and the obtained suspension was filtered. The filtrate was concentrated at reduced pressure to obtain a crude product, and the crude product was purified by silica gel chromatography (petroleum ether:ethyl acetate=15:1) to obtain tert-butyl 4-(3-ethyl-8,8-dimethyl-7-oxo-5,6,7,8-tetrahydronaphthalen-2-yl)-3,6-dihydropyridine-1(2H)-carb oxylate as a light yellow solid (4.8 g, with a yield of 100%). 1H NMR (400 MHz, $CDCl_3$): δ 7.02 (s, 1H), 7.00 (s, 1H), 5.55 (s, 1H), 4.03 (s, 2H), 3.63 (t, J=5.2 Hz, 2H), 3.07 (t, J=6.4 Hz, 2H), 2.68 (t, J=7.6 Hz, 2H), 2.61 (q, J=7.2 Hz, 2H), 2.34 (s, 2H), 1.51 (s, 9H), 1.42 (s, 6H), 1.20 (t, J=7.6 Hz, 3H).

Tert-butyl 4-(3-ethyl-8,8-dimethyl-7-oxo-5,6,7,8-tetrahydronaphthalen-2-yl)piperidine-1-carboxylate

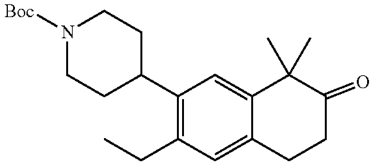 [SMILES: CCc1cc2c(cc1C1CCN(C(=O)OC(C)(C)C)CC1)C(C)(C)C(=O)CC2]

Palladium carbon (10%, 500 mg) was added into a solution of tert-butyl 4-(3-ethyl-8,8-dimethyl-7-oxo-5,6,7,8-tetrahydronaphthalen-2-yl)-3,6-dihydropyridine-1(2H)-carb oxylate (4.8 g, 12.52 mmol) in ethyl acetate (50 mL). The obtained mixture was degassed with hydrogen three times. The reaction solution was stirred overnight at room temperature. After the reaction was completed, the reaction solution was filtered, and the filtrate was concentrated at reduced pressure to obtain tert-butyl 4-(3-ethyl-8,8-dimethyl-7-oxo-5,6,7,8-tetrahydronaphthalen-2-yl)piperidine-1-carboxylate as a light yellow solid (4.7 g, with a yield of 97%). MS (ESI) m/z: 286.2 (M−100+H); 3-bromo-9-ethyl-6,6-dimethyl-8-(piperidin-4-yl)-6,11-dihydro-5H-benzo[b]carbazole

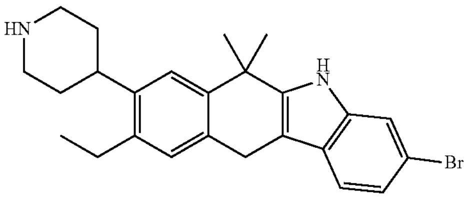 [SMILES: CCc1cc2c(cc1C1CCNCC1)C(C)(C)c1[nH]c3cc(Br)ccc3c1C2]

(3-bromophenyl) hydrazine (7.32 g, 39.16 mmol) was added into a solution of tert-butyl 4-(3-ethyl-8,8-dimethyl-7-oxo-5,6,7,8-tetrahydronaphthalen-2-yl)piperidine-1-carboxylate (14.0 g, 39.16 mmol) in acetic acid (150 mL). The mixture was stirred for 6 h at 125° C. The reaction solution was concentrated, the residue was poured into water, and the pH was adjusted to 9 with saturated sodium bicarbonate solution. The obtained solution was filtered, and the filter cake was washed with water and a solvent (petroleum ether:ethyl acetate=10:1) to obtain 3-bromo-9-ethyl-6,6-dimethyl-8-(piperidin-4-yl)-6,11-dihydro-5H-benzo[b]carbazole as a yellow solid (11.2 g, with a yield of 70%). MS (ESI) m/z: 437.4 $(M+1)^+$;

Tert-butyl 4-(3-bromo-9-ethyl-6,6-dimethyl-6,11-dihydro-5H-benzo[b]carbazol-8-yl)piperidine-1-carboxylate

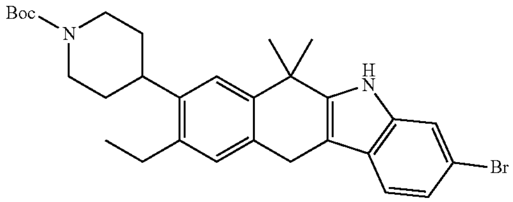 [SMILES: CCc1cc2c(cc1C1CCN(C(=O)OC(C)(C)C)CC1)C(C)(C)c1[nH]c3cc(Br)ccc3c1C2]

Di-tertbutyl dicarbonate (6.71 g, 30.73 mmol) was added into a solution of 3-bromo-9-ethyl-6,6-dimethyl-8-(piperidin-4-yl)-6,11-dihydro-5H-benzo[b]carbazole (11.2 g, 25.61 mmol) and triethylamine (5.18 g, 51.21 mmol) in dichloromethane (120 mL). A reaction was conducted for 3 hours with stirring at room temperature. The reaction solution was concentrated at reduced pressure to obtain tert-butyl 4-(3-bromo-9-ethyl-6,6-dimethyl-6,11-dihydro-5H-benzo[b]carbazol-8-yl)piperidine-1-carboxylat e (14.5 g, a crude product). The crude product was used for next step without further purification.

Tert-butyl 4-(3-bromo-9-ethyl-6,6-dimethyl-11-oxo-6,11-dihydro-5H-benzo[b]carbazol-8-yl)piperidine-1-car boxylate

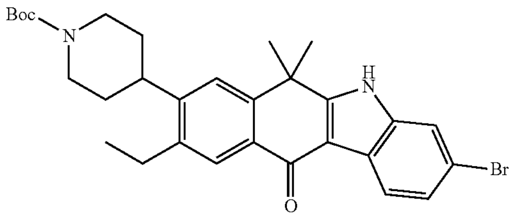 [SMILES: CCc1cc2c(cc1C1CCN(C(=O)OC(C)(C)C)CC1)C(C)(C)c1[nH]c3cc(Br)ccc3c1C2=O]

Tert-butyl 4-(3-bromo-9-ethyl-6,6-dimethyl-6,11-dihydro-5H-benzo[b]carbazol-8-yl)piperidine-1-carboxylate (14.5 g, 26.98 mmol) and 2,3-dichloro-5,6-dicyano-1,4-benzoquinone (6.12 g, 26.98 mmol) were added into tetrahydrofuran (150 mL) and water (15 mL). The above solution was stirred for 2 hour at room temperature. The reaction solution was concentrated at reduced pressure to remove most of the tetrahydrofuran solvent. Ethyl acetate (150 mL) was added, and the obtained mixed solution was washed with saturated brine (3×150 mL), dried with anhydrous sodium sulfate and concentrated to obtain a crude product. The crude product was purified by silica gel chromatography (dichloromethane:methanol=20:1) to obtain tert-butyl 4-(3-bromo-9-ethyl-6,6-dimethyl-11-oxo-6,11-dihydro-5H-benzo[b]carbazol-8-yl)piperidine-1-car boxylate as a yellow solid (3.6 g, with a two-step yield of 25%). 1H NMR (400 MHz, $CDCl_3$): δ 9.61 (s, 1H), 8.32 (d, J=8.4 Hz, 1H), 8.23 (s, 1H), 7.62 (d, J=1.6 Hz, 1H), 7.43-7.41 (m, 2H), 4.35-4.33 (m, 2H), 3.06-2.99 (m, 1H), 2.89 (t, J=11.6 Hz, 2H), 2.82 (q, J=7.2 Hz, 2H), 1.84-1.78 (m, 8H), 1.71-1.66 (m, 2H), 1.54 (s, 9H), 1.28 (t, J=7.6 Hz, 3H).

4-(9-ethyl-6,6-dimethyl-11-oxo-3-((trimethylsilyl)ethynyl)-6,11-dihydro-5H-benzo[b]carbazol-8-yl)piperidine-1-carboxylate

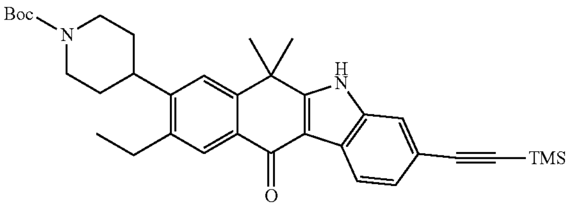 [SMILES: CCc1cc2c(cc1C1CCN(C(=O)OC(C)(C)C)CC1)C(C)(C)c1[nH]c3cc(C#C[Si](C)(C)C)ccc3c1C2=O]

2-dicyclohexylphosphino-2,4,6-triisopropylbiphenyl (35 mg, 0.07 mmol) and tris(dibenzylideneacetone) dipalladium (33 mg, 0.04 mmol) were added into a solution of tert-butyl 4-(3-bromo-9-ethyl-6,6-dimethyl-11-oxo-6,11-dihydro-5H-benzo[b]carbazol-8-yl)piperidine-1-car boxylate (200 mg, 0.36 mmol), ethynyltrimethylsilane (356 mg, 3.63 mmol) and potassium carbonate (154 mg, 0.74 mmol) in acetonitrile (8 mL). The obtained mixture was degassed with argon three times. The mixture was stirred overnight at 90° C. A mixed solvent (v/v=10/1, 30 mL) of dichloromethane and methanol was added followed by filtration. The filtrate was concentrated at reduced pressure to obtain a crude product, and the crude product was purified by silica gel chromatography (dichloromethane:methanol=10:1) to obtain 4-(9-ethyl-6,6-dimethyl-11-oxo-3-((trimethylsilyl)ethynyl)-6,11-dihydro-5H-benzo[b]carbazol-8-yl) piperidine-1-carboxylate as a yellow solid (130 mg, with a yield of 63%). MS (ESI) m/z:569.2 $(M+H)^+$;

9-ethyl-3-ethynyl-6,6-dimethyl-8-(piperidin-4-yl)-5,6-dihydro-11H-benzo[b]carbazol-11-one

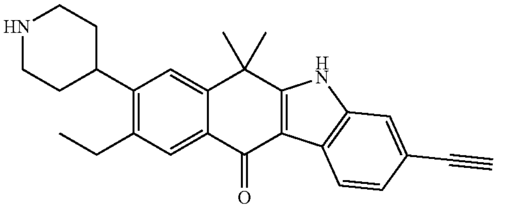 [SMILES: C#Cc1ccc2c3c([nH]c2c1)C(C)(C)c1cc(C2CCNCC2)c(CC)cc1C3=O]

4-(9-ethyl-6,6-dimethyl-11-oxo-3-((trimethylsilyl)ethynyl)-6,11-dihydro-5H-benzo[b]carbazol-8-yl) piperidine-1-carboxylate (130 mg, 0.23 mmol) was added into 1,1,1,3,3,3-hexafluoro-2-propanol (10 mL). The mixture was stirred for 2 days in a sealing tube at 100° C. The reaction solution was concentrated at reduced pressure, and the obtained residue was diluted with methanol (5 mL). Potassium carbonate (64 mg, 0.46 mmol) was added, and the mixture was stirred for 5 hours at room temperature. The reaction solution was concentrated to obtain a crude product, and the crude product was purified by Prep-TLC (dichloromethane: methanol=10:1) to obtain 9-ethyl-3-ethynyl-6,6-dimethyl-8-(piperidin-4-yl)-5,6-dihydro-11H-benzo[b]carbazol-11-one as a white solid (30.62 mg, with a yield of 34%). 1H NMR (400 MHz, DMSO-$d_6$): δ 12.50 (s, 1H), 8.17 (d, J=8.4 Hz, 1H), 8.01 (s, 1H), 7.62 (s, 1H), 7.61 (s, 1H), 7.34 (dd, J=8.0, 1.2 Hz, 1H), 4.12 (s, 1H), 3.36-3.20 (m, 2H), 3.22-3.15 (m, 1H), 3.07-3.02 (m, 2H), 2.82 (q, J=7.6 Hz, 2H), 2.09-2.01 (m, 2H), 1.85-1.82 (m, 2H), 1.75 (s, 6H), 1.24 (t, J=7.6 Hz, 3H).

Example 9

9-ethyl-3-ethynyl-6,6-dimethyl-8-(1-methylpiperidin-4-yl)-5,6-dihydro-11H-benzo[b]carbazol-11-one (E9)

E9

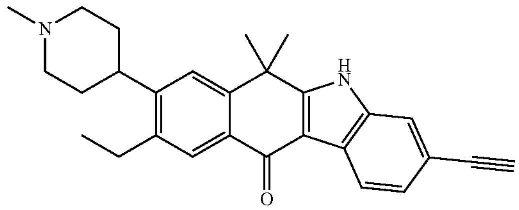

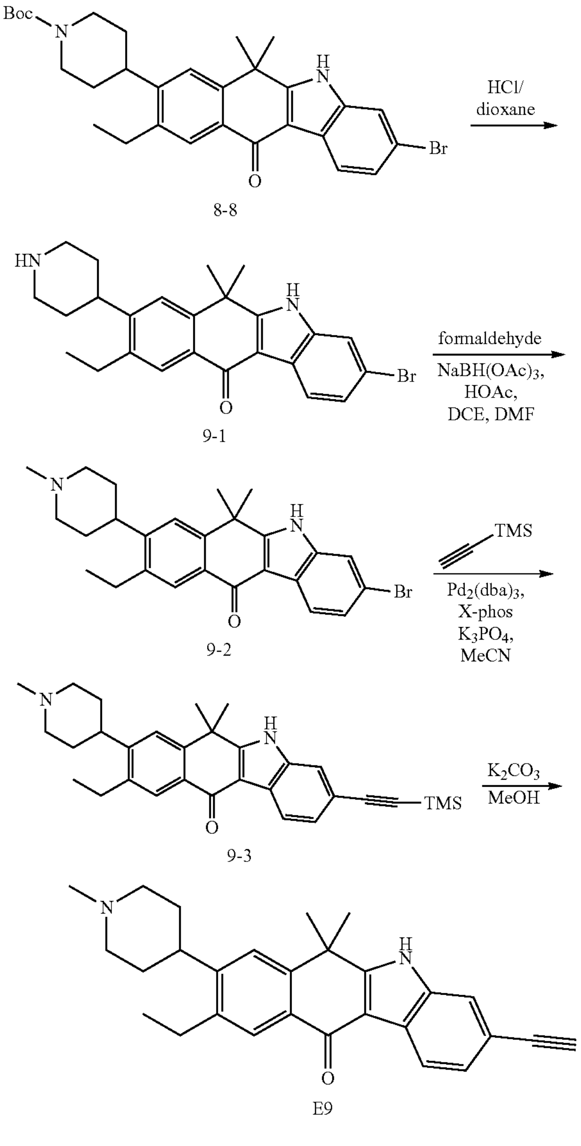

8-8

9-1

9-2

9-3

E9

3-bromo-9-ethyl-6,6-dimethyl-8-(piperidin-4-yl)-5,6-dihydro-11H-benzo[b]carbazol-11-one

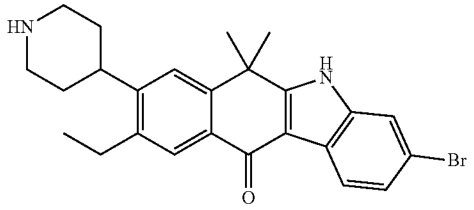 [SMILES: CCc1cc2c(cc1C1CCNCC1)C(C)(C)c1[nH]c3cc(Br)ccc3c1C2=O]

A hydrogen chloride dioxane solution (4N, 15 mL) was added into a solution of tert-butyl 4-(3-bromo-9-ethyl-6,6-dimethyl-11-oxo-6,11-dihydro-5H-benzo[b]carbazol-8-yl) piperidine-1-car boxylate (2.0 g, 3.63 mmol) in dioxane (15 mL). A reaction was conducted overnight with stirring at room temperature. The reaction solution was concentrated at reduced pressure to obtain a crude product of hydrochloride (1.8 g). The crude product was dissolved into water (30 mL), and alkalized with a 1N sodium hydroxide aqueous solution until pH 9 and then filtered to obtain 3-bromo-9-ethyl-6,6-dimethyl-8-(piperidin-4-yl)-5,6-dihydro-11H-benzo[b]carbazol-11-one as a yellow solid (1.46 g, with a yield of 89%). MS (ESI) m/z: 453.1 $(M+H)^+$;

3-bromo-9-ethyl-6,6-dimethyl-8-(1-methylpiperidin-4-yl)-5,6-dihydro-11H-benzo[b]carbazol-11-0

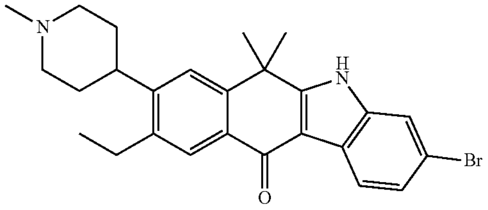 [SMILES: CCc1cc2c(cc1C1CCN(C)CC1)C(C)(C)c1[nH]c3cc(Br)ccc3c1C2=O]

37% aqueous solution of formaldehyde (1 mL), anhydrous magnesium sulfate (1.0 g) and acetic acid (53 mg, 0.89 mmol) were added into a solution of 3-bromo-9-ethyl-6,6-dimethyl-8-(piperidin-4-yl)-5,6-dihydro-11H-benzo[b]carbazol-11-one (400 mg, 0.89) in dichloroethane (4 mL) and DMF (4 mL). A reaction was conducted for 3 hours with stirring at room temperature. Sodium triacetoxyborohydride (376 mg, 1.76 mmol) was added. The mixture was heated to 60° C. and allowed to react for 2 hours with stirring. The reaction solution was concentrated at reduced pressure, and the residue was diluted with ethyl acetate (30 mL), washed with water (3×50 mL), dried with anhydrous sodium sulfate and concentrated to obtain a crude product. The crude product was washed with petroleum ether:ethyl acetate=10:1 to obtain 3-bromo-9-ethyl-6,6-dimethyl-8-(1-methylpiperidin-4-yl)-5,6-dihydro-11H-benzo[b]carbazol-11-one as a yellow solid (310 mg, with a yield of 75%). MS (ESI) m/z: 467.1 $(M+H)^+$;

9-ethyl-6,6-dimethyl-8-(1-methylpiperidin-4-yl)-3-((trimethylsilyl)ethynyl)-5,6-dihydro-11H-benz o[b]carbazol-11-one

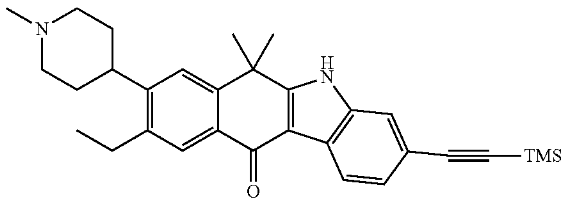 [SMILES: CCc1cc2c(cc1C1CCN(C)CC1)C(C)(C)c1[nH]c3cc(C#C[Si](C)(C)C)ccc3c1C2=O]

2-dicyclohexylphosphion-2,4,6-triisopropylbiphenyl (41 mg, 0.09 mmol) and tris(dibenzylideneacetone) dipalladium (39 mg, 0.04 mmol) were added into a solution of 3-bromo-9-ethyl-6,6-dimethyl-8-(1-methylpiperidin-4-yl)-5,6-dihydro-11H-benzo[b]carbazol-11-one (200 mg, 0.43 mmol), tripotassium phosphate (183 mg, 0.86 mmol) and ethynyltrimethylsilane (422 mg, 4.30 mmol) in acetonitrile (8 mL). The obtained mixture was degassed with argon three times. The obtained solution was heated to 90° C. and stirred overnight. The reaction solution was diluted with a mixed solvent of dichloromethane and methanol (v/v=10/1, 30 mL) and filtered. The filtrate was concentrated at reduced pressure to obtain a crude product, and the crude product was purified by silica gel chromatography (dichloromethane: methanol=10:1) to obtain 9-ethyl-6,6-dimethyl-8-(1-methylpiperidin-4-yl)-3-((trimethylsilyl)ethynyl)-5,6-dihydro-11H-benz o[b]carbazol-11-one as a yellow solid (120 mg, with a yield of 58%). MS (ESI) m/z: 483.2 $(M+H)^+$;

9-ethyl-3-ethynyl-6,6-dimethyl-8-(1-methylpiperidin-4-yl)-5,6-dihydro-11H-benzo[b]carbazol-11-one

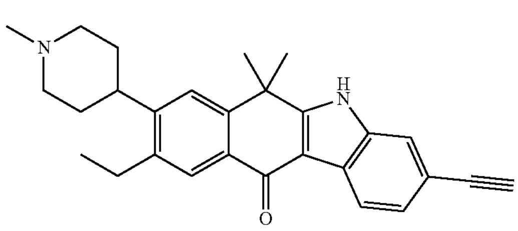 [SMILES: C#Cc1ccc2c3c([nH]c2c1)C(C)(C)c1cc(C2CCN(C)CC2)c(CC)cc1C3=O]

9-ethyl-6,6-dimethyl-8-(1-methylpiperidin-4-yl)-3-((trimethylsilyl)ethynyl)-5,6-dihydro-11H-benz o[b]carbazol-11-one (120 mg, 0.25 mmol) and potassium carbonate (69 mg, 0.50 mmol) were added into a methanol solution (5 mL) and stirred overnight. After a reaction was completed, the reaction solution was concentrated to obtain a crude product, and the crude product was purified by Prep-TLC (dichloromethane:methanol=10:1) and Prep-HPLC (0.1% ammonia bicarbonate/water/acetonitrile) to obtain 9-ethyl-3-ethynyl-6,6-dimethyl-8-(1-methylpiperidin-4-yl)-5,6-dihydro-11H-benzo[b]carbazol-11-one as a white solid (17.73 mg, with a yield of 17%). 1H NMR (400 MHz, DMSO-$d_6$): δ 12.44 (s, 1H), 8.17 (d, J=8.0 Hz, 1H), 8.00 (s, 1H), 7.66 (s, 1H), 7.60 (s, 1H), 7.34 (dd, J=8.0, 1.2 Hz, 1H), 4.12 (s, 1H), 3.20-3.13 (m, 2H), 2.96-2.94 (m, 1H), 2.80 (q, J=7.6 Hz, 2H), 2.51-2.49 (m, 5H), 2.05-2.02 (m, 2H), 1.80-1.75 (m, 8H), 1.25 (t, J=7.6 Hz, 3H).

Example 10

8-(1-cyclopropylpiperidin-4-yl)-9-ethyl-3-ethynyl-6,6-dimethyl-5,6-dihydro-11H-benzo[b]carbazo 1-11-one (E10)

E10

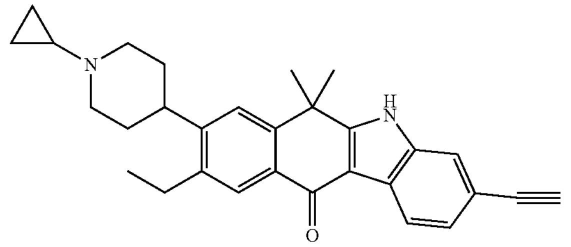

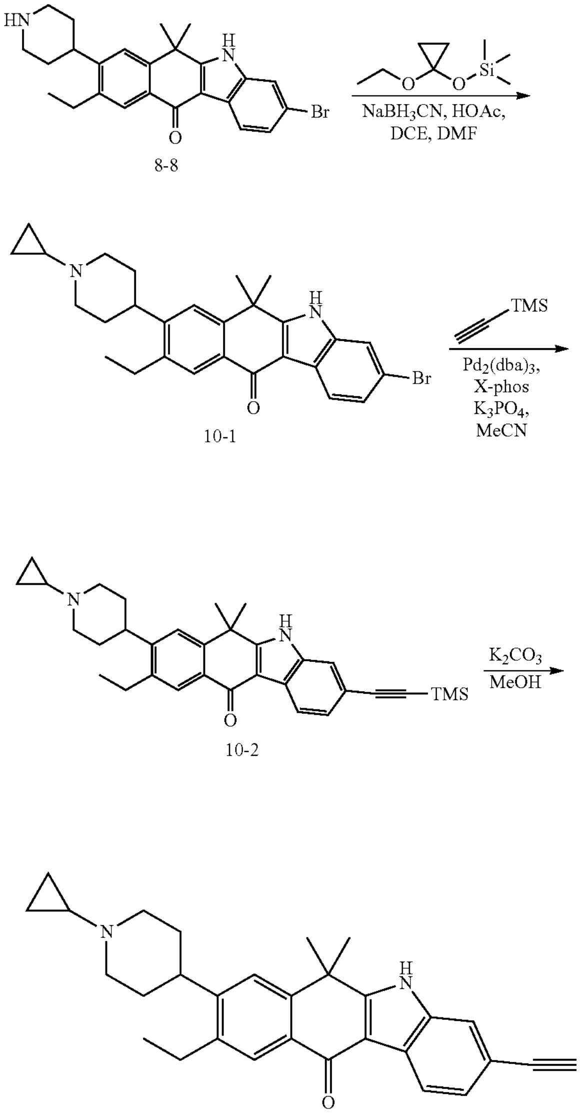

8-8

10-1

10-2

E10

3-bromo-8-(1-cyclopropylpiperidin-4-yl)-9-ethyl-6,6-dimethyl-5,6-dihydro-11H-benzo[b]carbazol

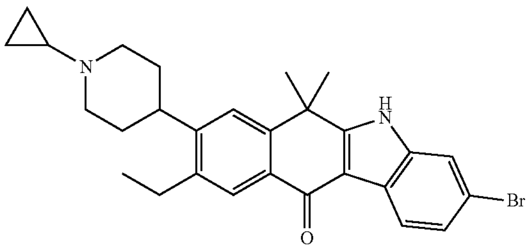 [SMILES: CCc1cc2c(cc1C1CCN(C3CC3)CC1)C(C)(C)c1[nH]c3cc(Br)ccc3c1C2=O]

Acetic acid (86 mg, 1.44 mmol) was added into a solution of 3-bromo-9-ethyl-6,6-dimethyl-8-(piperidin-4-yl)-5,6-dihydro-11H-benzo[b]carbazol-11-one (650 mg, 1.44 mmol) and (1-ethoxycyclopropoxy)trimethylsilane (1.0 g, 5.74 mmol) in 1,2-dichloroethane (5 mL) and N, N-dimethylformamide (8 mL). Sodium cyanoborohydride (181 mg, 2.88 mmol) was added therein after stirring for 6 hours at room temperature. The mixture was stirred overnight at 60° C. The obtained reaction solution was diluted with ethyl acetate (30 mL), washed with saturated brine (3×50 mL), dried with anhydrous sodium sulfate and filtered, and the filtrate was concentrated at reduced pressure to obtain a crude product. The crude product was purified by silica gel chromatography (dichloromethane:methanol=10:1) to obtain 3-bromo-8-(1-cyclopropylpiperidin-4-yl)-9-ethyl-6,6-dimethyl-5,6-dihydro-11H-benzo[b]carbazol-11-one as a yellow solid (240 mg, with a yield of 34%). MS (ESI) m/z: 493.2 $(M+H)^+$;

8-(1-cyclopropylpiperidin-4-yl)-9-ethyl-6,6-dimethyl-3-((trimethylsilyl)ethynyl)-5,6-dihydro-11H-benzo[b]carbazol-11-one

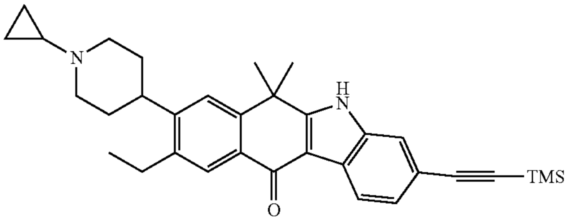 [SMILES: CCc1cc2c(cc1C1CCN(C3CC3)CC1)C(C)(C)c1[nH]c3cc(C#C[Si](C)(C)C)ccc3c1C2=O]

2-dicyclohexylphosphino-2,4,6-triisopropylbiphenyl (21 mg, 0.06 mmol) and tris(dibenzylideneacetone) dipalladium (26 mg, 0.03 mmol) were added into a solution of 3-bromo-8-(1-cyclopropylpiperidin-4-yl)-9-ethyl-6,6-dimethyl-5,6-dihydro-11H-benzo[b]carbazol-11-one (140 mg, 0.28 mmol), ethynyltrimethylsilane (280 mg, 2.85 mmol) and tripotassium phosphate (121 mg, 0.57 mmol) in acetonitrile (5 mL). The obtained mixture was degassed with argon three times. The mixture was heated to 90° C. and stirred overnight. The obtained reaction solution was diluted with a mixed solvent of dichloromethane and methanol (v/v=10/1, 30 mL) and filtered. The filtrate was concentrated to dryness at reduced pressure to obtain a crude product, and the crude product was purified by silica gel chromatography (dichloromethane:methanol=10:1) to obtain 8-(1-cyclopropylpiperidin-4-yl)-9-ethyl-6,6-dimethyl-3-((trimethylsilyl)ethynyl)-5,6-dihydro-11H-benzo[b]carbazol-11-one as a yellow solid (55 mg, with a yield of 38%). MS (ESI) m/z: 509.6 $(M+H)^+$;

8-(1-cyclopropylpiperidin-4-yl)-9-ethyl-3-ethynyl-6,6-dimethyl-5,6-dihydro-11H-benzo[b]carbazo 1-11-one

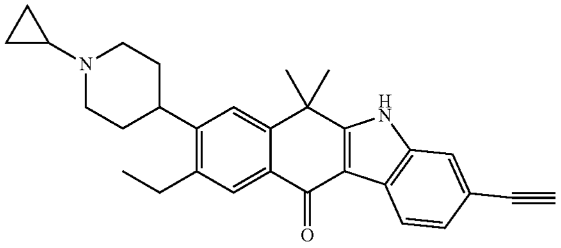 [SMILES: C#Cc1ccc2c3c([nH]c2c1)C(C)(C)c1cc(C2CCN(C4CC4)CC2)c(CC)cc1C3=O]

8-(1-cyclopropylpiperidin-4-yl)-9-ethyl-6,6-dimethyl-3-((trimethylsilyl)ethynyl)-5,6-dihydro-11H-benzo[b]carbazol-11-one (55 mg, 0.11 mmol) and potassium carbonate (30 mg, 0.22 mmol) were added into methanol (3 mL). The above materials were stirred overnight at room temperature. The reaction solution was concentrated to dryness at reduced pressure to obtain a crude product, and the crude product was purified by Prep-TLC (dichloromethane:methanol=10:1) and then Prep-HPLC (0.1% ammonia bicarbonate/water/acetonitrile) to obtain 8-(1-cyclopropylpiperidin-4-yl)-9-ethyl-3-ethynyl-6,6-dimethyl-5,6-dihydro-11H-benzo[b]carbazo 1-11-one as a white solid (4.38 mg, with a yield of 9.2%). 1H NMR (400 MHz, DMSO-$d_6$): δ 12.31 (s, 1H), 8.17 (d, J=8.0 Hz, 1H), 7.97 (s, 1H), 7.65 (s, 1H), 7.59 (s, 1H), 7.33 (d, J=8.0 Hz, 1H), 4.12 (s, 1H), 3.10 (d, J=11.2 Hz, 2H), 2.86-2.67 (m, 3H), 2.35-2.29 (m, 2H), 1.84-1.66 (m, 11H), 1.22 (t, J=7.6 Hz, 3H), 0.48-0.45 (m, 2H), 0.35-0.31 (m, 2H).

Example 11

8-(4-(4-cyclopropylpiperazin-1-yl)piperidin-1-yl)-9-ethyl-3-ethynyl-6,6-dimethyl-5,6-dihydro-11H-benzo[b]carbazol-11-one (E11)

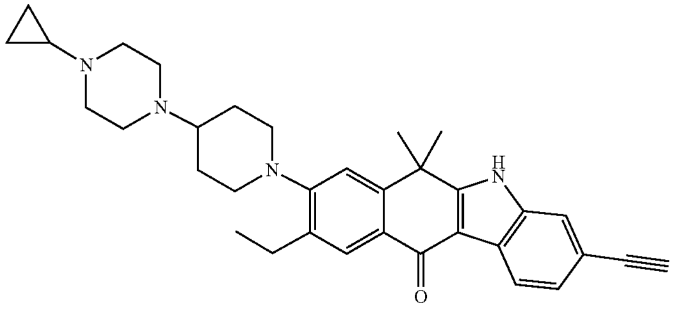

E11

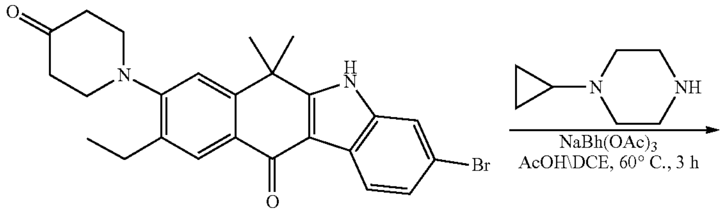

11-1

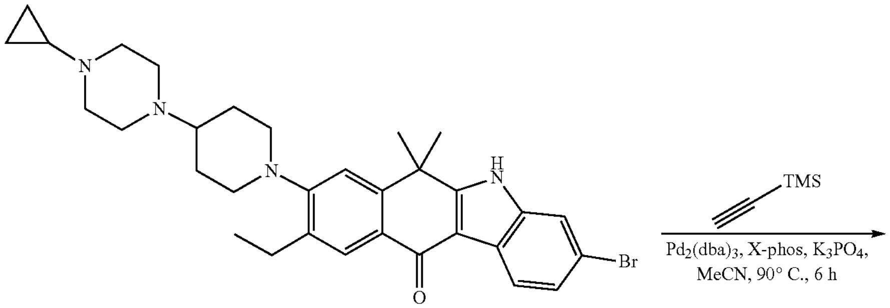

11-2

-continued

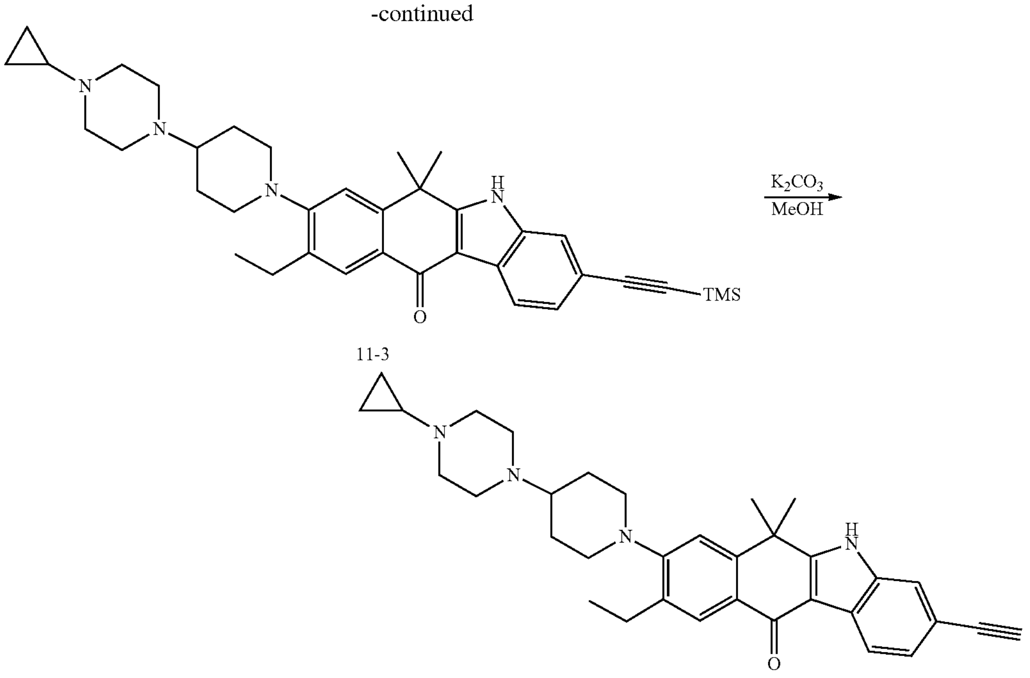

11-3

E11

Tert-butyl 3-bromo-8-(4-(4-cyclopropylpiperazin-1-yl)piperidin-1-yl)-9-ethyl-6,6-dimethyl-5,6-dihydro-11H-benzo[b]carbazol-11-one

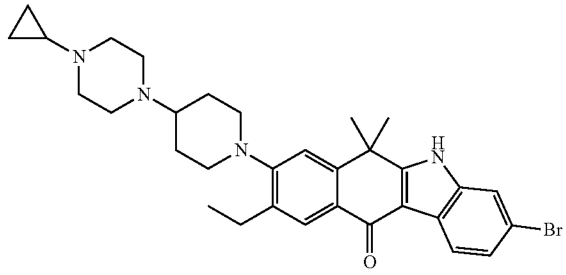 [SMILES: CCc1cc2c(cc1N1CCC(N3CCN(C4CC4)CC3)CC1)C(C)(C)c1[nH]c3cc(Br)ccc3c1C2=O]

Acetic acid (26 mg, 0.43 mmol) was added into a solution of 3-bromo-9-ethyl-6,6-dimethyl-8-(4-oxopiperidin-1-yl)-5,6-dihydro-11H-benzo[b]carbazol-11-one (200 mg, 0.43 mmol) and 1-cyclopropylpiperazine (543 mg, 4.30 mmol) in 1,2-dichloroethane (30 mL). The above materials were stirred for 1 h at room temperature. Then, sodium triacetoxyborohydride (212 mg, 1.29 mmol) was added. The mixture was heated to 60° C. and allowed to react for 3 hours with stiring. The completion of the reaction was monitored by LCMS. The reaction solution was cooled to room temperature and then poured into ice water (200 mL). The above mixed solution was extracted with dichloromethane (2×40 mL). Organic phases were combined, washed with saturated brine (40 mL), dried with anhydrous sodium sulfate, filtered and concentrated at reduced pressure to obtain a crude product. The crude product was purified by silica gel column chromatography (dichloromethane:methanol=20:1) to obtain tert-butyl 3-bromo-8-(4-(4-cyclopropylpiperazin-1-yl)piperidin-1-yl)-9-ethyl-6,6-dimethyl-5,6-dihydro-11H-benzo[b]carbazol-11-one as a yellow solid (153 mg, with a yield of 61.8%). MS (ESI) m/z: 575.2 $(M+H)^+$;

8-(4-(4-cyclopropylpiperazin-1-yl)piperidin-1-yl)-9-ethyl-6,6-dimethyl-3-((trimethylsilyl)ethynyl)-5,6-dihydro-11H-benzo[b]carbazol-11-one

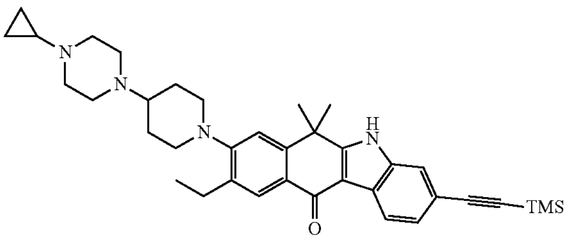 [SMILES: CCc1cc2c(cc1N1CCC(N3CCN(C4CC4)CC3)CC1)C(C)(C)c1[nH]c3cc(C#C[Si](C)(C)C)ccc3c1C2=O]

2-dicyclohexylphosphino-2,4,6-triisopropylbiphenyl (51 mg, 0.11 mmol) and tris(dibenzylideneacetone) dipalladium (49 mg, 0.05 mmol) were added into a solution of tert-butyl 3-bromo-8-(4-(4-cyclopropylpiperazin-1-yl)piperidin-1-yl)-9-ethyl-6,6-dimethyl-5,6-dihydro-11H-benzo[b]carbazol-11-one (153 mg, 0.26 mmol), ethynyltrimethylsilane (522 mg, 5.32 mmol) and tripotassium phosphate (141 mg, 0.66 mmol) in acetonitrile (15 mL). The mixture was heated to 90° C. and allowed to react for 6 hours with stiring. The completion of the reaction was monitored by LCMS. The reaction solution was filtered, and then the filter cake was washed with dichloromethane and methanol. The filtrate was concentrated to obtain a crude product, and the crude product was purified by silica gel column chromatography (dichloromethane:methanol=20:1) to obtain 8-(4-(4-cyclopropylpiperazin-1-yl)piperidin-1-yl)-9-ethyl-6,6-dimethyl-3-((trimethylsilyl)ethynyl)-5,6-dihydro-11H-benzo[b]carbazol-11-one as a yellow solid (40 mg, with a yield of 25.4%). MS (ESI) m/z: 593.5 $(M+H)^+$;

8-(4-(4-cyclopropylpiperazin-1-yl)piperidin-1-yl)-9-ethyl-3-ethynyl-6,6-dimethyl-5,6-dihydro-11H-benzo[b]carbazol-11-one

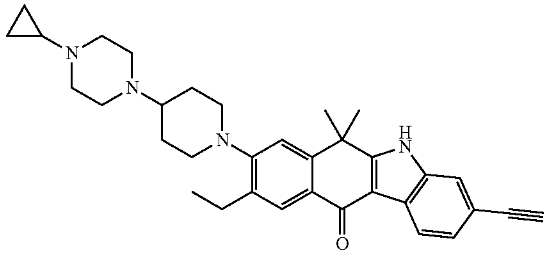 [SMILES: C#Cc1ccc2c3c([nH]c2c1)C(C)(C)c1cc(N2CCC(N4CCN(C5CC5)CC4)CC2)c(CC)cc1C3=O]

Potassium carbonate (48 mg, 0.35 mmol) was added into a solution of 8-(4-(4-cyclopropylpiperazin-1-yl)piperidin-1-yl)-9-ethyl-6,6-dimethyl-3-((trimethylsilyl)ethynyl)-5,6-dihydro-11H-benzo[b]carbazol-11-one (40 mg, 0.07 mmol) in methanol (10 mL). A reaction was conducted for 3 h with stirring at room temperature. The completion of the reaction was monitored by LCMS. The reaction solution was poured into ice water (100 mL) and extracted with ethyl acetate (2×30 mL). Organic phases were combined, washed with saturated brine (40 mL), dried with anhydrous sodium sulfate, filtered and concentrated at reduced pressure to obtain a crude product. The crude product was purified by silica gel column chromatography (dichloromethane:methanol=20:1) to obtain 8-(4-(4-cyclopropylpiperazin-1-yl)piperidin-1-yl)-9-ethyl-3-ethynyl-6,6-dimethyl-5,6-dihydro-11H-benzo[b]carbazol-11-one as a yellow solid (14 mg, with a yield of 39.8%). 1H NMR (400 MHz, DMSO-$d_6$) δ 12.29 (s, 1H), 8.15 (d, J=8.1 Hz, 1H), 8.03 (s, 1H), 7.58 (s, 1H), 7.31 (dd, J=7.3, 2.1 Hz, 2H), 4.11 (s, 1H), 3.20 (d, J=11.4 Hz, 2H), 2.72 (dt, J=15.0, 9.5 Hz, 5H), 2.65-2.52 (m, 4H), 2.47-2.21 (m, 4H), 1.88 (d, J=10.3 Hz, 2H), 1.72 (s, 6H), 1.69-1.51 (m, 3H), 1.27 (t, J=7.5 Hz, 3H), 0.40 (d, J=4.5 Hz, 2H), 0.28 (s, 2H).

Example 12

3-ethynyl-6,6-dimethyl-8-(4-morpholinopiperidin-1-yl)-11-oxo-6,11-dihydro-5H-benzo[b]carbazole-9-carbonitrile (E12)

E12

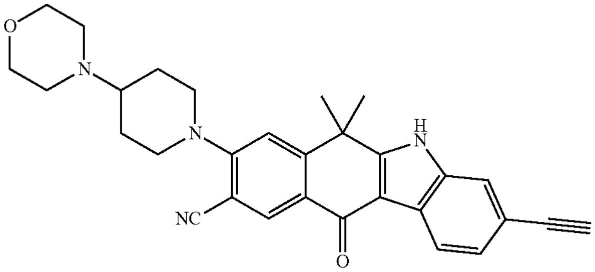

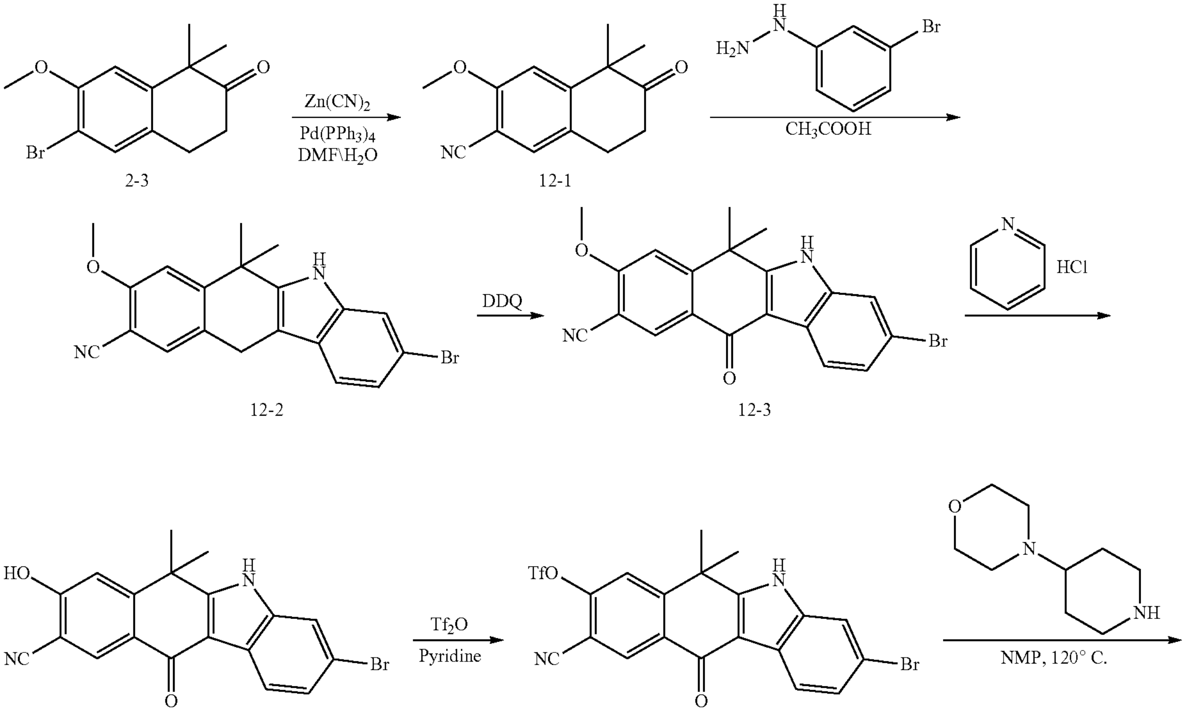

2-3
12-1
12-2
12-3
12-4
12-5

-continued

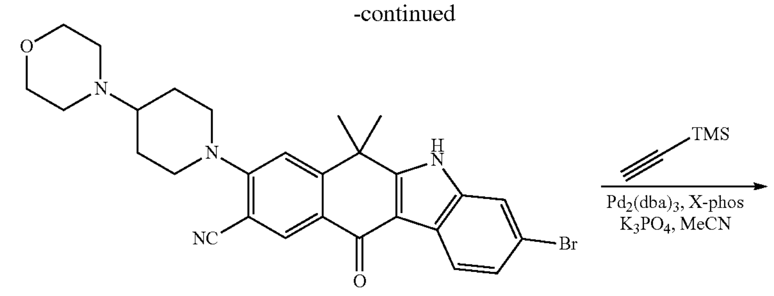

12-6

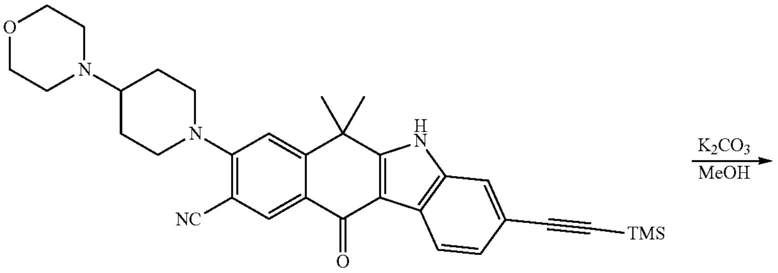

12-7

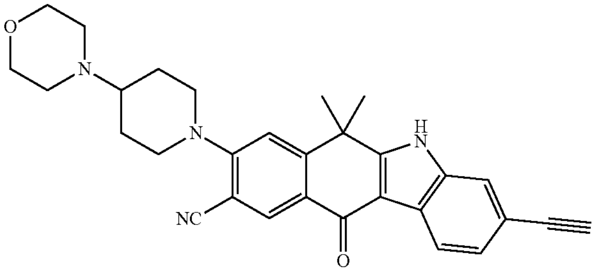

E12

3-methoxy-5,5-dimethyl-6-oxo-5,6,7,8-tetrahydronaphthalene-2-carbonitrile

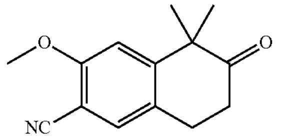 [SMILES: COc1cc2c(cc1C#N)CCC(=O)C2(C)C]

Tetra(triphenylphosphine) palladium (41 g, 35.5 mmol) was added into a solution of 6-bromo-7-methoxy-1,1-dimethyl-3,4-dihydronaphthalen-2(1H)-one (100 g, 355 mmol), zinc cyanide (84 g, 710 mmol) in DMF (1 L) and water (50 mL). Air was replaced with nitrogen three times. The mixture was heated to 120° C. and allowed to react overnight with stirring. The reaction solution was diluted with ethyl acetate and filtered. The filtrate was washed with water, dried with anhydrous sodium sulfate and concentrated at reduced pressure to obtain 3-methoxy-5,5-dimethyl-6-oxo-5,6,7,8-tetrahydronaphthalene-2-carbonitrile as a white solid (49.4 g, with a yield of 61.8%).

1H NMR (400 MHz, DMSO-$d_6$) δ 7.60 (s, 1H), 7.18 (s, 1H), 3.94 (s, 3H), 3.07-2.92 (m, 2H), 2.60 (dd, J=13.6, 6.9 Hz, 2H), 1.39 (s, 6H).

3-bromo-8-methoxy-6,6-dimethyl-6,11-dihydro-5H-benzo[b]carbazole-9-carbonitrile

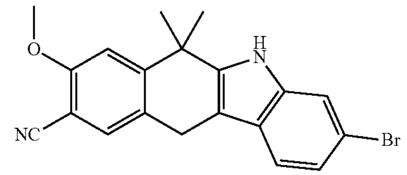 [SMILES: COc1cc2c(cc1C#N)Cc1c([nH]c3cc(Br)ccc13)C2(C)C]

3-methoxy-5,5-dimethyl-6-oxo-5,6,7,8-tetrahydronaphthalene-2-carbonitrile (60 g, 262 mmol) and 3-bromophenylhydrazine hydrochloride (60 g, 288 mmol) was added into acetic acid (1.2 L). The mixture was heated to 125° C. and allowed to react for 6 hours under the protection of nitrogen.

The reaction solution was diluted with water (1.2 L) and stirred to precipitate out a light red solid.

A crude product (100 g, with a yield of 100%) was obtained by filtration. The crude product was directly used for next step.

3-bromo-8-methoxy-6,6-dimethyl-11-oxo-6,11-dihydro-5H-benzo[b]carbazole-9-carbonitrile

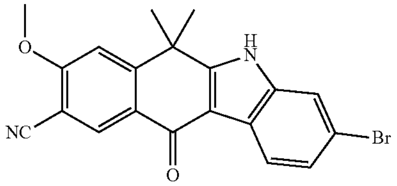 [SMILES: COc1cc2c(cc1C#N)C(=O)c1c([nH]c3cc(Br)ccc13)C2(C)C]

2,3-dichloro-5,6-dicyano-1,4-benzoquinone (100 g, 440 mmol) was added into a solution of 3-bromo-8-methoxy-6,6-dimethyl-6,11-dihydro-5H-benzo[b]carbazole-9-carbonitrile (150 g, 394 mmol) in tetrahydrofuran (1.5 L) and water (150 mL). A reaction was conducted for 2 hours with stirring at room temperature. A saturated sodium bicarbonate aqueous solution (500 mL) was added. The obtained solution was extracted with ethyl acetate (2×500 mL), and organic phases were combined, dried with anhydrous sodium sulfate, filtered and concentrated to obtain 3-bromo-8-methoxy-6,6-dimethyl-11-oxo-6,11-dihydro-5H-benzo[b]carbazole-9-carbonitrile (74 g, with a yield of 48.2%). The crude product was directly used for next step.

3-bromo-8-hydroxy-6,6-dimethyl-11-oxo-6,11-dihydro-5H-benzo[b]carbazole-9-carbonitrile

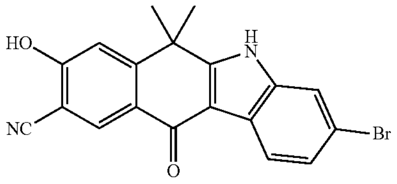 [SMILES: CC1(C)c2cc(O)c(C#N)cc2C(=O)c2c1[nH]c1cc(Br)ccc21]

3-bromo-8-methoxy-6,6-dimethyl-11-oxo-6,11-dihydro-5H-benzo[b]carbazole-9-carbonitrile (150 g, 380 mmol) and pyridine hydrochloride (750 g, 6466 mmol) were heated to 170° C. to react for 16 h. The reaction solution was diluted with ice water (800 mL) and extracted with ethyl acetate (3×500 mL). Organic phases were combined, dried with anhydrous sodium sulfate and filtered. The filtrate was concentrated to obtain 3-bromo-8-hydroxy-6,6-dimethyl-11-oxo-6,11-dihydro-5H-benzo[b]carbazole-9-carbonitrile as an off-white solid (145 g, with a yield of 100%).

1H NMR (400 MHz, DMSO-$d_6$) δ 13.22 (s, 1H), 12.24 (s, 1H), 8.32 (s, 1H), 8.08 (d, J=8.3 Hz, 1H), 7.72 (d, J=1.2 Hz, 1H), 7.60 (s, 1H), 7.38 (dd, J=8.3, 1.3 Hz, 1H), 1.75 (s, 6H).

3-bromo-9-cyano-6,6-dimethyl-11-oxo-6,11-dihydro-5H-benzo[b]carbazol-8-yl trifluoromethanesulfonate

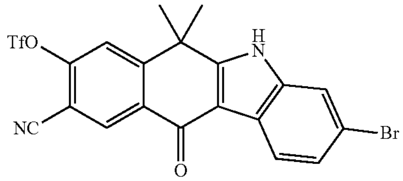

Trifluoromethanesulfonic anhydride (111 g, 395 mmol) was dropwise added into a solution of 3-bromo-8-hydroxy-6,6-dimethyl-11-oxo-6,11-dihydro-5H-benzo[b]carbazole-9-carbonitrile (150 g, 395 mmol) and pyridine (125 g, 1580 mmol) in dichloromethane (1 L) in an ice-water bath. A reaction was conducted for 3 hours with stirring at room temperature. The reaction was quenched with ice water, washed with water, dried with anhydrous sodium sulfate, filtered and concentrated at reduced pressure to obtain a crude product. The crude product was purified by silica gel column chromatography (petroleum ether:ethyl acetate=2:1) to obtain 3-bromo-9-cyano-6,6-dimethyl-11-oxo-6,11-dihydro-5H-benzo[b]carbazol-8-yl trifluoromethanesulfonate as a light yellow solid (88 g, with a yield of 43.5%). 1H NMR (400 MHz, DMSO-$d_6$) δ 12.66 (s, 1H), 8.73 (s, 1H), 8.41 (d, J=13.0 Hz, 1H), 8.10 (d, J=8.4 Hz, 1H), 7.73 (d, J=1.5 Hz, 1H), 7.44 (dt, J=16.6, 8.3 Hz, 1H), 1.82 (s, 6H).

3-bromo-6,6-dimethyl-8-(4-morpholinopiperidin-1-yl)-11-oxo-6,11-dihydro-5H-benzo[b]carbazole-9-carbonitrile

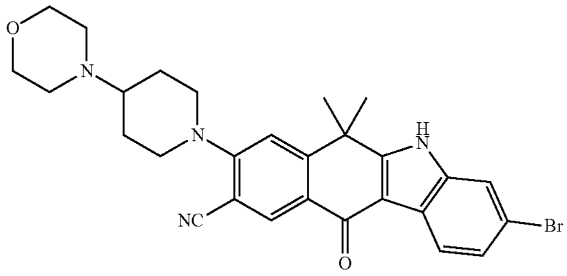 [SMILES: CC1(C)c2cc(N3CCC(N4CCOCC4)CC3)c(C#N)cc2C(=O)c2c1[nH]c1cc(Br)ccc21]

3-bromo-9-cyano-6,6-dimethyl-11-oxo-6,11-dihydro-5H-benzo[b]carbazol-8-yl trifluoromethanesulfonate (250 mg, 0.49 mmol) and 4-(piperidin-4-yl) morpholine (1.66 g, 9.74 mmol) were added into N-methylpyrrolidone (5 mL). The mixture was heated to 120° C. and stirred for 4 hours under the protection of argon. The obtained reaction solution was diluted with ethyl acetate (30 mL), washed with saturated brine (3×50 mL), dried with anhydrous sodium sulfate, filtered and concentrated at reduced pressure to obtain a crude product. The crude product was purified by silica gel column chromatography (dichloromethane:methanol=10:1) to obtain 3-bromo-6,6-dimethyl-8-(4-morpholinopiperidin-1-yl)-11-oxo-6,11-dihydro-5H-benzo[b]carbazole-9-carbonitrile as a yellow solid (220 mg, with a yield of 85%). MS (ESI) m/z: 533.0 $(M+H)^+$; 6,6-dimethyl-8-(4-morpholinopiperidin-1-yl)-11-oxo-3-((trimethylsilyl)ethynyl)-6,11-dihydro-5H-benzo[b]carbazole-9-carbonitrile

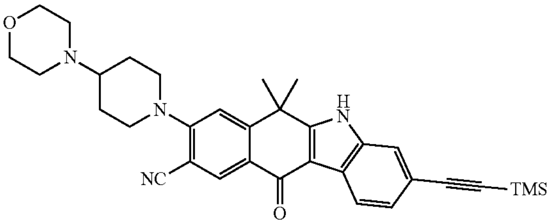 [SMILES: CC1(C)c2cc(N3CCC(N4CCOCC4)CC3)c(C#N)cc2C(=O)c2c1[nH]c1cc(C#C[Si](C)(C)C)ccc21]

3-bromo-6,6-dimethyl-8-(4-morpholinopiperidin-1-yl)-11-oxo-6,11-dihydro-5H-benzo[b]carbazole-9-carbonitrile (200 mg, 0.39 mmol), tripotassium phosphate (123 mg, 0.58 mmol) and ethynyltrimethylsilane (378 mg, 3.85 mmol) were added into acetonitrile (10 mL). Air was replaced with argon three times and then tris(dibenzylideneacetone) dipalladium (35 mg, 0.04 mmol) and 2-dicyclohexylphosphino-2,4,6-triisopropylbiphenyl (37 mg, 0.08 mmol) were added. Air was replaced with argon three times again. The solution was heated to 90° C. and stirred overnight. The reaction solution was diluted with a mixed solvent of dichloromethane and methanol (v/v=10/1, 30 mL) and filtered. The filtrate was concentrated to dryness at reduced pressure to obtain a crude product, and then the crude product was purified by silica gel column chromatography (dichloromethane:methanol=10:1) to obtain 6,6-dimethyl-8-(4-morpholinopiperidin-1-yl)-11-oxo-3-((trimethylsilyl)ethynyl)-6,11-dihydro-5H-benzo[b]carbazole-9-carbonitrile as a light yellow solid (200 mg, with a yield of 97%). MS (ESI) m/z: 551.2 $(M+1)^+$.

3-ethynyl-6,6-dimethyl-8-(4-morpholinopiperidin-1-yl)-11-oxo-6,11-dihydro-5H-benzo[b]carbazole-9-carbonitrile

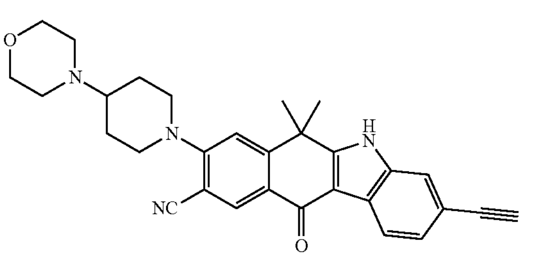 [SMILES: C#Cc1ccc2c3c([nH]c2c1)C(C)(C)c1cc(N2CCC(N4CCOCC4)CC2)c(C#N)cc1C3=O]

Potassium carbonate (139 mg, 1.01 mmol) was added into a solution of 6,6-dimethyl-8-(4-morpholinopiperidin-1-yl)-11-oxo-3-((trimethylsilyl)ethynyl)-6,11-dihydro-5H-benzo[b]carbazole-9-carbonitrile (180 mg, 0.34 mmol) in methanol (10 mL). The above mixture was stirred overnight at room temperature. The methanol solvent was removed by concentration at reduced pressure. The residue was diluted with dichloromethane (30 mL) and filtered. The filtrate was concentrated at reduced pressure to obtain a crude product, and the crude product was purified by Prep-TLC (dichloromethane:methanol=15:1) to obtain 3-ethynyl-6,6-dimethyl-8-(4-morpholinopiperidin-1-yl)-11-oxo-6,11-dihydro-5H-benzo[b]carbazole-9-carbonitrile as a light yellow solid (25 mg, with a yield of 16%). 1H NMR (400 MHz, DMSO-$d_6$): δ 12.55 (s, 1H), 8.33 (s, 1H), 8.15 (d, J=8.0 Hz, 1H), 7.61 (s, 1H), 7.34 (dd, J=8.0, 1.2 Hz, 1H), 4.14 (s, 1H), 3.84 (d, J=12.4 Hz, 2H), 3.60 (t, J=4.0 Hz, 4H), 3.33-3.26 (m, 4H), 3.01 (t, J=11.6 Hz, 2H), 2.50-2.40 (m, 1H), 1.97 (d, J=11.6 Hz, 2H), 1.78 (s, 6H), 1.64-1.55 (m, 2H).

Example 13

3-ethynyl-6,6-dimethyl-8-(4-methylpiperazin-1-yl)-11-oxo-6,11-dihydro-5H-benzo[b]carbazole-9-carbonitrile (E13)

E13

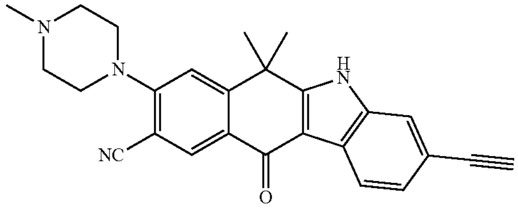

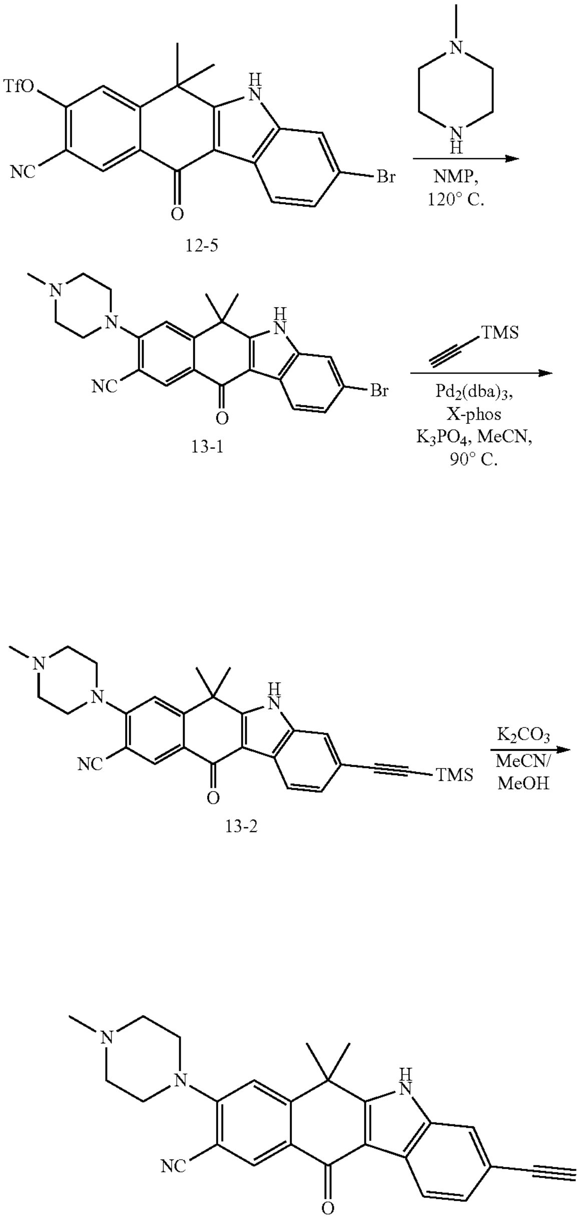

12-5

13-1

13-2

E13

3-bromo-6,6-dimethyl-8-(4-methylpiperazin-1-yl)-11-oxo-6,11-dihydro-5H-benzo[b]carbazole-9-carbonitrile

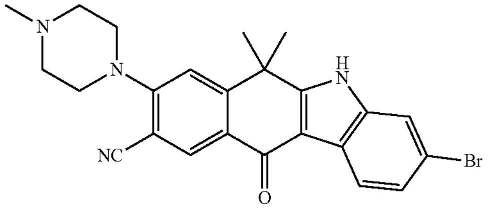 [SMILES: CN1CCN(c2cc3c(cc2C#N)C(=O)c2c([nH]c4cc(Br)ccc24)C3(C)C)CC1]

3-bromo-9-cyano-6,6-dimethyl-11-oxo-6,11-dihydro-5H-benzo[b]carbazol-8-yl trifluoromethanesulfonate (500 mg, 0.98 mmol) and 1-methylpiperazine (1.95 g, 19.5 mmol) were added into an N-methylpyrrolidone (4 mL) solution at 120° C. The mixture was heated to 120° C. and allowed to react for 5 hours with stirring. The completion of the reaction was monitored by LCMS. The reaction solution was cooled to room temperature and then quenched with water (30 mL) and extracted with ethyl acetate (3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-30:1) to obtain 3-bromo-6,6-dimethyl-8-(4-methylpiperazin-1-yl)-11-oxo-6,11-dihydro-5H-benzo[b]carbazole-9-carbonitrile as a brown solid (357 mg, with a yield of 78%). MS (ESI) m/z:463.0 $(M+H)^+$. 6,6-dimethyl-8-(4-methylpiperazin-1-yl)-11-oxo-3-((trimethylsilyl)ethynyl)-6,11-dihydro-5H-benz o[b]carbazole-9-carbonitrile

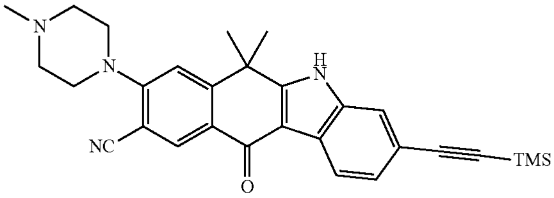 [SMILES: CN1CCN(c2cc3c(cc2C#N)C(=O)c2c([nH]c4cc(C#C[Si](C)(C)C)ccc24)C3(C)C)CC1]

3-bromo-6,6-dimethyl-8-(4-methylpiperazin-1-yl)-11-oxo-6,11-dihydro-5H-benzo[b]carbazole-9-carbonitrile (200 mg, 0.43 mmol), ethynyltrimethylsilane (850 mg, 6.39 mmol) and tripotassium phosphate (183 mg, 0.86 mmol) were dissolved in acetonitrile (10 mL). Air in the mixture was replaced with nitrogen three times. Tris(dibenzylideneacetone) dipalladium (79 mg, 0.09 mmol) and 2-dicyclohexylphosphino-2,4,6-triisopropylbiphenyl (82 mg, 0.17 mmol) were added. Air in the mixture was replaced with nitrogen three times again. The obtained solution was heated to 90° C. and stirred overnight. The heated solution was filtered, and the filter cake was washed with a mixed solvent of dichloromethane and methanol (v/v=10/1, 50 mL). The filtrate was concentrated at reduced pressure to dryness to obtain a crude product. The crude product was purified by silica gel column chromatography (dichloromethane:methanol=100:1-30:1) to obtain 6,6-dimethyl-8-(4-methylpiperazin-1-yl)-11-oxo-3-((trimethylsilyl)ethynyl)-6,11-dihydro-5H-benz o[b]carbazole-9-carbonitrile as a brown solid (183 mg, with a yield of 88%). MS (ESI) m/z: 481.2 $(M+H)^+$.

3-ethynyl-6,6-dimethyl-8-(4-methylpiperazin-1-yl)-11-oxo-6,11-dihydro-5H-benzo[b]carbazole-9-carbonitrile

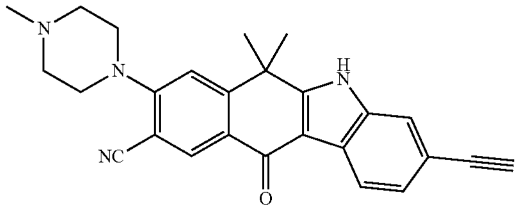 [SMILES: C#Cc1ccc2c3c([nH]c2c1)C(C)(C)c1cc(N2CCN(C)CC2)c(C#N)cc1C3=O]

6,6-dimethyl-8-(4-methylpiperazin-1-yl)-11-oxo-3-((trimethylsilyl)ethynyl)-6,11-dihydro-5H-benz o[b]carbazole-9-carbonitrile (183 mg, 0.38 mmol) and potassium carbonate (263 mg, 1.91 mmol) were added into a mixed solution of acetonitrile (20 mL) and methanol (3 mL). The above mixture was stirred overnight at room temperature. The completion of the reaction was monitored by LCMS. The reaction was quenched with water (30 mL). The reaction solution was extracted with a mixed solvent of dichloromethane and methanol (v/v=10/1, 3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-20:1) to obtain 3-ethynyl-6,6-dimethyl-8-(4-methylpiperazin-1-yl)-11-oxo-6,11-dihydro-5H-benzo[b]carbazole-9-carbonitrile as a yellow solid (86.21 mg, with a yield of 55%). 1H NMR (400 MHz, DMSO-$d_6$): δ 12.44 (s, 1H), 8.35 (s, 1H), 8.15 (d, J=8.0 Hz, 1H), 7.60 (s, 1H), 7.42 (s, 1H), 7.35 (q, J=4.6 Hz, 1H), 4.14 (s, 2H), 3.41 (t, J=8.8 Hz, 4H), 2.55 (s, 4H), 2.28 (s, 3H), 1.78 (s, 6H).

Example 14

3-ethynyl-6,6-dimethyl-11-oxo-8-(4-(pyrrolidin-1-yl)piperidin-1-yl)-6,11-dihydro-5H-benzo[b]carbazole-9-carbonitrile (E14)

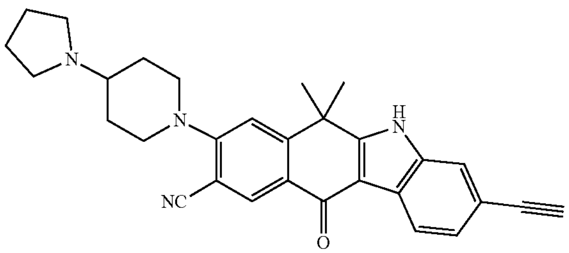

E14

-continued

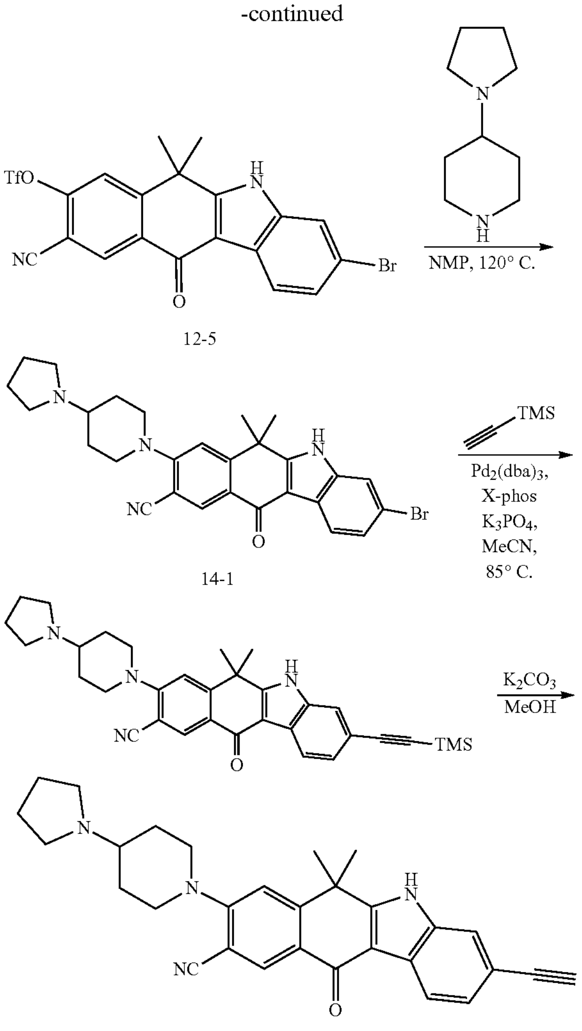

12-5

14-1

E14

3-bromo-6,6-dimethyl-11-oxo-8-(4-(pyrrolidin-1-yl) piperidin-1-yl)-6,11-dihydro-5H-benzo[b]carb azole-9-carbonitrile

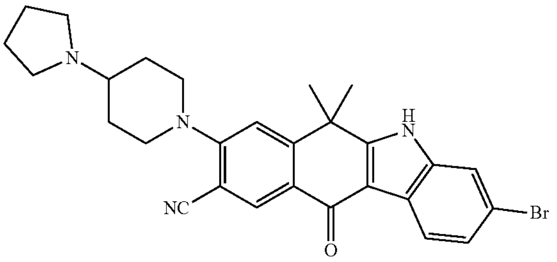 [SMILES: CC1(C)c2cc(N3CCC(N4CCCC4)CC3)c(C#N)cc2C(=O)c2c1[nH]c1cc(Br)ccc21]

3-bromo-9-cyano-6,6-dimethyl-11-oxo-6,11-dihydro-5H-benzo[b]carbazol-8-yl trifluoromethanesulfonate (500 mg, 0.98 mmol) and 4-(pyrrolidin-1-yl)piperidine (3.0 g, 19.5 mmol) were dissolved in N-methylpyrrolidone (4 mL). A reaction was conducted for 5 hours with stirring at 120° C. under the protection of nitrogen. The completion of the reaction was monitored by LCMS. The reaction was quenched with water (30 mL) and extracted with ethyl acetate (3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-20:1) to obtain 3-bromo-6,6-dimethyl-11-oxo-8-(4-(pyrrolidin-1-yl)piperidin-1-yl)-6,11-dihydro-5H-benzo[b]carb azole-9-carbonitrile as a white solid (165 mg, with a yield of 33%). MS (ESI) m/z: 517.1 (M+H) 6,6-dimethyl-11-oxo-8-(4-(pyrrolidin-1-yl)piperidin-1-yl)-3-((trimethylsilyl)ethynyl)-6,11-dihydro-5H-benzo[b]carbazole-9-carbonitrile

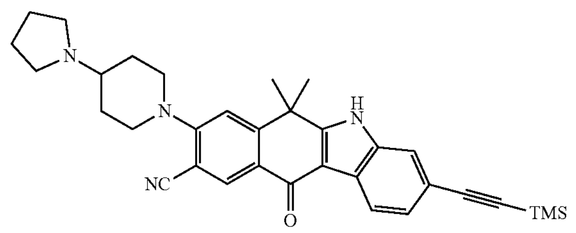 [SMILES: CC1(C)c2cc(N3CCC(N4CCCC4)CC3)c(C#N)cc2C(=O)c2c1[nH]c1cc(C#C[Si](C)(C)C)ccc21]

3-bromo-6,6-dimethyl-11-oxo-8-(4-(pyrrolidin-1-yl)piperidin-1-yl)-6,11-dihydro-5H-benzo[b]carb azole-9-carbonitrile (165 mg, 0.32 mmol), ethynyltrimethylsilane (628 mg, 6.39 mmol) and tripotassium phosphate (204 mg, 0.96 mmol) were dissolved in acetonitrile (10 mL). Air was replaced with nitrogen three times, and then tris(dibenzylideneacetone) dipalladium (59 mg, 0.06 mmol) and 2-dicyclohexylphosphino-2,4,6-triisopropylbiphenyl (61 mg, 0.13 mmol) were added. Air was replaced with nitrogen three times again. The mixture was heated to 85° C. and allowed to react for 10 hours with stirring. The reaction solution was filtered, and the filter cake was washed with a mixed solvent of dichloromethane and methanol (v/v=10/1, 50 mL). The filtrate was concentrated to dryness at reduced pressure to obtain a crude product, and the crude product was purified by silica gel column chromatography (dichloromethane:methanol=100:1-30:1) to obtain 6,6-dimethyl-11-oxo-8-(4-(pyrrolidin-1-yl)piperidin-1-yl)-3-((trimethylsilyl)ethynyl)-6,11-dihydro-5H-benzo[b]carbazole-9-carbonitrile as a brown solid (110 mg, with a yield of 66%). MS (ESI) m/z: 535.3 $(M+H)^+$.

3-ethynyl-6,6-dimethyl-11-oxo-8-(4-(pyrrolidin-1-yl)piperidin-1-yl)-6,11-dihydro-5H-benzo[b]carbazole-9-carbonitrile

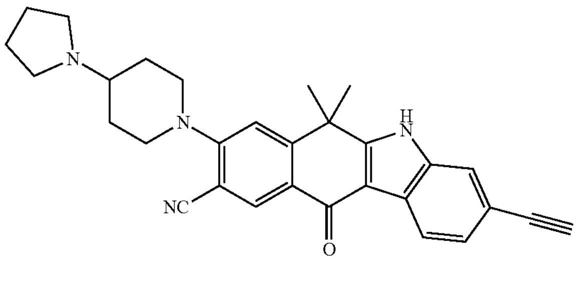 [SMILES: C#Cc1ccc2c3c([nH]c2c1)C(C)(C)c1cc(N2CCC(N4CCCC4)CC2)c(C#N)cc1C3=O]

6,6-dimethyl-11-oxo-8-(4-(pyrrolidin-1-yl)piperidin-1-yl)-3-((trimethylsilyl)ethynyl)-6,11-dihydro-5H-benzo[b] carbazole-9-carbonitrile (110 mg, 0.21 mmol) and potassium carbonate (138 mg, 1.03 mmol) were added into acetonitrile (15 mL) and methanol (5 mL). The above mixture was stirred overnight at room temperature. The completion of the reaction was monitored by LCMS.

The reaction was quenched with water (30 mL). The reaction solution was extracted with a mixed solvent of dichloromethane and methanol (v/v=10/1, 3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-20:1) to obtain 3-ethynyl-6,6-dimethyl-11-oxo-8-(4-(pyrrolidin-1-yl)piperidin-1-yl)-6,11-dihydro-5H-benzo[b]carbazole-9-carbonitrile as a light yellow solid (53.61 mg, with a yield of 17%). 1H NMR (400 MHz, DMSO-$d_6$): δ 12.60 (s, 1H), 8.34 (s, 1H), 8.15 (d, J=8.0 Hz, 1H), 7.62 (s, 1H), 7.42 (s, 1H), 7.29 (q, J=4.6 Hz, 1H), 4.22 (s, 1H), 3.83 (d, J=11.2 Hz, 2H), 3.08 (t, J=11.4 Hz, 3H), 2.10 (s, 2H), 1.91 (s, 2H), 1.79 (s, 6H), 1.35-1.23 (m, 8H).

Example 15

8-(4-(dimethylamino)piperidin-1-yl)-3-ethynyl-6,6-dimethyl-11-oxo-6,11-dihydro-5H-benzo[b]carbazole-9-carbonitrile (E15)

E15

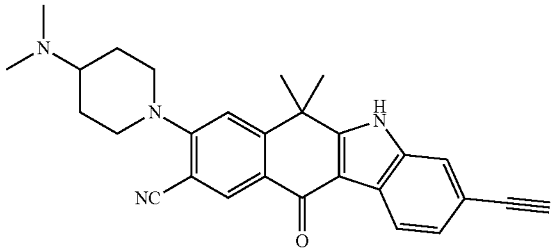

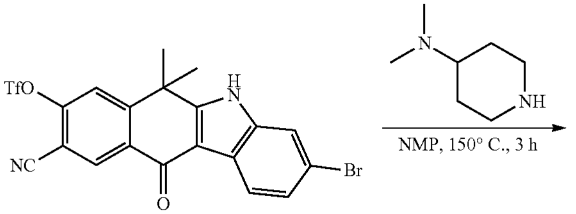

12-5

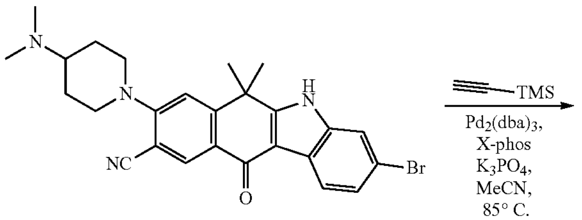

15-1

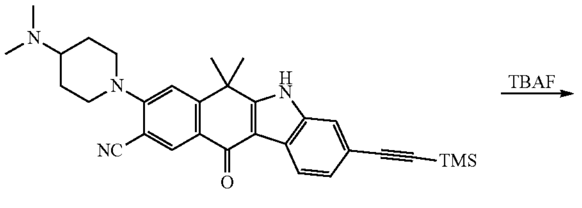

15-2

-continued

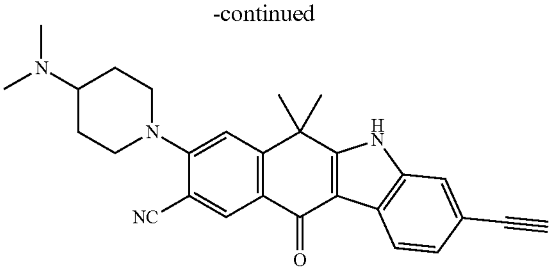

E15

3-bromo-8-(4-(dimethylamino)piperidin-1-yl)-6,6-dimethyl-11-oxo-6,11-dihydro-5H-benzo[b]carbazole-9-carbonitrile

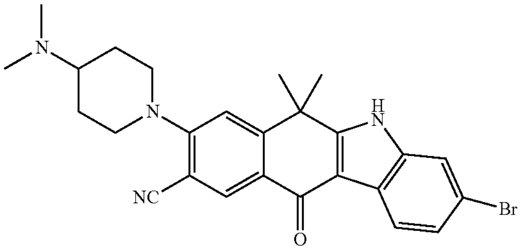 [SMILES: CN(C)C1CCN(c2cc3c(cc2C#N)C(=O)c2c([nH]c4cc(Br)ccc24)C3(C)C)CC1]

N,N-dimethylpiperidin-4-amine (148.2 g, 1160 mmol) was added into to N-methylpyrrolidone (800 mL), heated to 120° C. and stirred for 5 minutes. 3-bromo-9-cyano-6,6-dimethyl-11-oxo-6,11-dihydro-5H-benzo[b]carbazol-8-yl trifluoromethanesulfonate (88 g, 232 mmol) was added. A reaction was conducted for 5 hours with stirring at 120° C. under the protection of nitrogen. The completion of the reaction was monitored by LCMS. The reaction solution was cooled to room temperature and poured into methanol (8.0 L). The obtained solution was stirred and filtered to obtain 3-bromo-8-(4-(dimethylamino)piperidin-1-yl)-6,6-dimethyl-11-oxo-6,11-dihydro-5H-benzo[b]carbazole-9-carbonitrile as a yellow solid (61 g, 124.5 mmol, with a yield of 72.4%). 1H NMR (400 MHz, DMSO-$d_6$) δ 12.43 (s, 1H), 8.33 (s, 1H), 8.09 (d, J=8.4 Hz, 1H), 7.68 (d, J=1.5 Hz, 1H), 7.39 (dd, J=7.2, 2.5 Hz, 2H), 4.10 (q, J=5.1 Hz, 1H), 3.81 (d, J=12.3 Hz, 2H), 3.01 (t, J=11.5 Hz, 2H), 2.23 (s, 6H), 1.92 (d, J=10.8 Hz, 2H), 1.77 (s, 6H), 1.58 (dd, J=20.5, 11.0 Hz, 2H).

8-(4-(dimethylamino)piperidin-1-yl)-6,6-dimethyl-11-oxo-3-((trimethylsilyl)ethynyl)-6,11-dihydro-5H-benzo[b]carbazole-9-carbonitrile

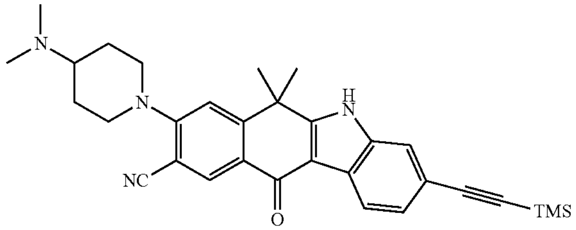 [SMILES: CN(C)C1CCN(c2cc3c(cc2C#N)C(=O)c2c([nH]c4cc(C#C[Si](C)(C)C)ccc24)C3(C)C)CC1]

Tris(dibenzylideneacetone) dipalladium (918 mg, 1.02 mmol), 2-dicyclohexylphosphino-2,4,6-triisopropylbiphenyl (946 mg, 8.16 mmol) and tripotassium phosphate (26 g, 122.4 mol) were added into a solution of 3-bromo-8-(4-(dimethylamino)piperidin-1-yl)-6,6-dimethyl-11-oxo-6,11-dihydro-5H-benzo[b]carbazole-9-carbonitrile (10 g, 20.4 mmol) and ethynyltrimethylsilane (20 g, 204 mmol) in acetonitrile (150 mL). The mixture was heated to 90° C. and allowed to react for 6 hours with stirring under the protection of nitrogen. The completion of the reaction was monitored by LCMS. The reaction solution was cooled to room temperature. The cooled reaction solution was filtered, and the filter cake was washed with dichloromethane and methanol. The filtrate was concentrated at reduced pressure to obtain a crude product, and the crude product was purified by silica gel column chromatography (dichloromethane:methanol=10:1) to obtain 8-(4-(dimethylamino)piperidin-1-yl)-6,6-dimethyl-11-oxo-3-((trimethylsilyl)ethynyl)-6,11-dihydro-5H-benzo[b]carbazole-9-carbonitrile as a yellow solid (43 g, with a yield of 68.04%).

8-(4-(dimethylamino)piperidin-1-yl)-3-ethynyl-6,6-dimethyl-11-oxo-6,11-dihydro-5H-benzo[b]carbazole-9-carbonitrile

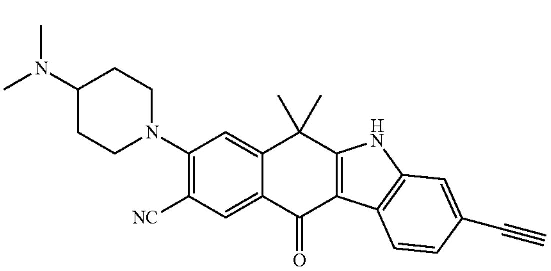 [SMILES: C#Cc1ccc2c3c([nH]c2c1)C(C)(C)c1cc(N2CCC(N(C)C)CC2)c(C#N)cc1C3=O]

Tetrabutyl ammonium fluoride (22.1 g, 84.6 mmol) was added into a solution of 8-(4-(dimethylamino)piperidin-1-yl)-6,6-dimethyl-11-oxo-3-((trimethylsilyl)ethynyl)-6,11-dihydro-5H-benzo[b]carbazole-9-carbonitrile (43 g, 84.6 mmol) in tetrahydrofuran (200 mL). The above solution was stirred for 2 hour at room temperature. The completion of the reaction was monitored by LCMS. The reaction solution was poured into ice water (150 mL) and extracted with ethyl acetate (2×300 mL). Organic phases were combined, washed with saturated brine (400 mL), dried with anhydrous sodium sulfate and filtered, and the filtrate was concentrated at reduced pressure to obtain a crude product. The crude product was purified by silica gel column chromatography (dichloromethane:methanol=10:1) to obtain 8-(4-(dimethylamino)piperidin-1-yl)-3-ethynyl-6,6-dimethyl-11-oxo-6,11-dihydro-5H-benzo[b]carbazole-9-carbonitrile as a light yellow solid (20.062 g, with a yield of 54.4%). 1H NMR (400 MHz, DMSO-$d_6$) δ 12.43 (s, 1H), 8.33 (s, 1H), 8.16-8.10 (m, 1H), 7.60 (s, 1H), 7.39 (s, 1H), 7.33 (dd, J=8.1, 1.3 Hz, 1H), 4.13 (s, 1H), 3.80 (d, J=12.5 Hz, 2H), 3.00 (t, J=11.3 Hz, 2H), 2.35-2.25 (m, 1H), 2.22 (s, 6H), 1.91 (d, J=11.0 Hz, 2H), 1.77 (s, 6H), 1.64-1.51 (m, 2H).

Example 16

3-ethynyl-6,6-dimethyl-8-(4-(4-methylpiperazin-1-yl)piperidin-1-yl)-11-oxo-6,11-dihydro-5H-ben zo[b]carbazole-9-carbonitrile (E16)

E16

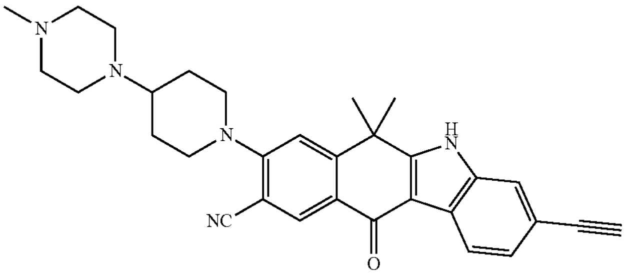

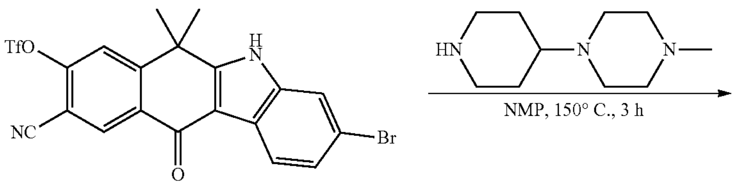

12-5

-continued

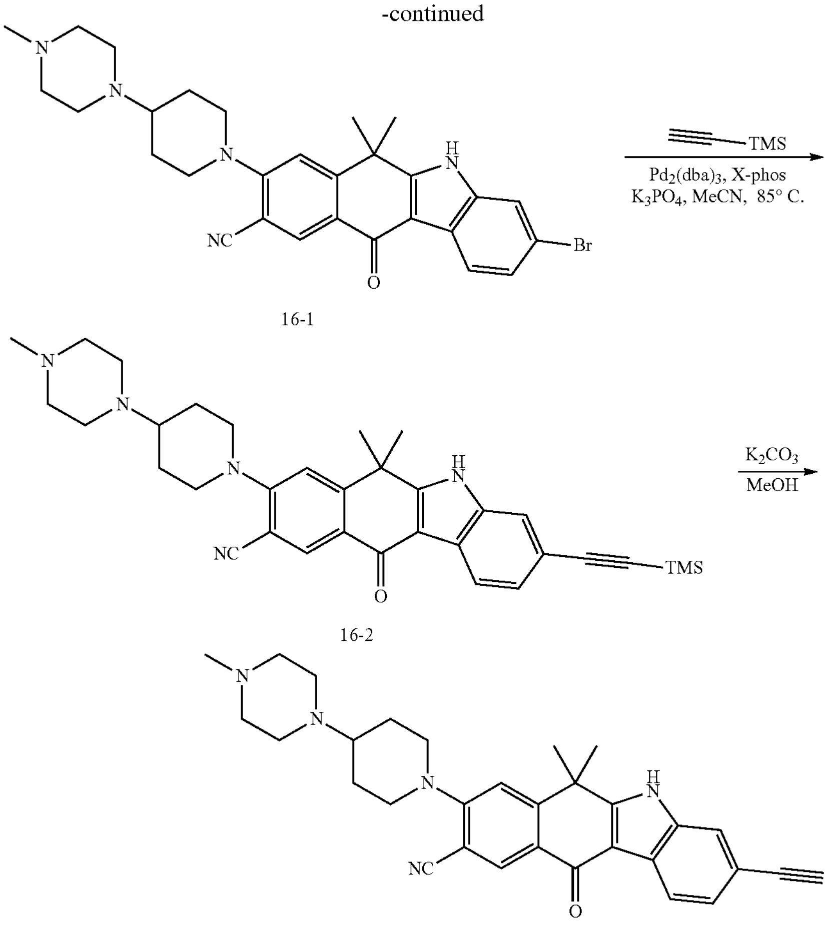

E16

3-bromo-6,6-dimethyl-8-(4-(4-methylpiperazin-1-yl)piperidin-1-yl)-6,11-dihydro-5H-benzo[b]carbazole-9-carbonitrile

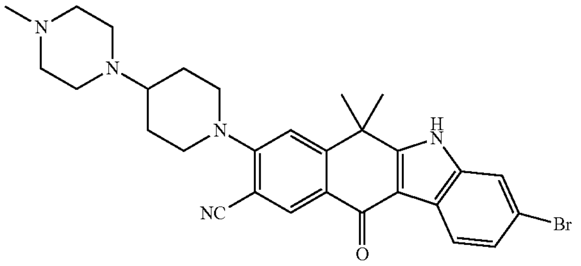 [SMILES: CN1CCN(C2CCN(c3cc4c(cc3C#N)C(=O)c3c([nH]c5cc(Br)ccc35)C4(C)C)CC2)CC1]

1-methyl-4-(piperidin-4-yl)piperazine (1.79 g, 9.7 mmol) was added into a solution of 3-bromo-9-cyano-6,6-dimethyl-11-oxo-6,11-dihydro-5H-benzo[b]carbazol-8-yl trifluoromethanesulfonate (500 mg, 0.97 mmol) in N-methylpyrrolidone (6 mL). The mixture was heated to 150° C. and allowed to react for 3 hours with stirring. The reaction solution was cooled to room temperature, quenched with ice water (30 mL) and extracted with a mixed solvent of dichloromethane and methanol (v/v=10/1, 3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-30:1) to obtain 3-bromo-6,6-dimethyl-8-(4-(4-methylpiperazin-1-yl)piperidin-1-yl)-6,11-dihydro-5H-benzo[b]carbazole-9-carbonitrile as a white solid (273 mg, with a yield of 53%). MS (ESI) m/z: 532, 534 $(M+H)^+$.

6,6-dimethyl-8-(4-(4-methylpiperazin-1-yl)piperidin-1-yl)-11-oxo-3-((trimethylsilyl)ethynyl)-6,11-dihydro-5H-benzo[b]carbazole-9-carbonitrile

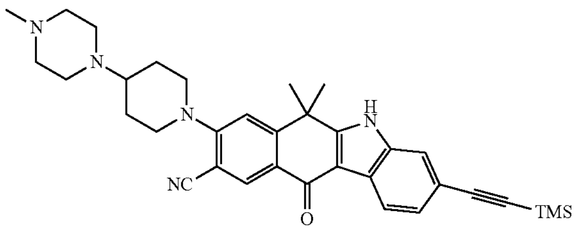 [SMILES: CN1CCN(C2CCN(c3cc4c(cc3C#N)C(=O)c3c([nH]c5cc(C#C[Si](C)(C)C)ccc35)C4(C)C)CC2)CC1]

3-bromo-6,6-dimethyl-8-(4-(4-methylpiperazin-1-yl)piperidin-1-yl)-6,11-dihydro-5H-benzo[b]carbazole-9-carbonitrile (273 mg, 0.48 mmol), ethynyltrimethylsilane (946 mg, 9.63 mmol) and tripotassium phosphate (307 mg, 1.44 mmol) were dissolved in acetonitrile (30 mL). Air was replaced with nitrogen three times. Tris(dibenzylideneacetone) dipalladium (88 mg, 0.096 mmol) and 2-dicyclohexylphosphino-2,4,6-triisopropylbiphenyl (92 mg, 0.19 mmol) were added. Air was replaced with nitrogen three times again. The mixture was heated to 90° C. and allowed to react for 6 hours with stirring. The reaction solution was cooled to room temperature and then diluted with water (100 mL). The obtained solution was filtered, and the filter cake was washed with a mixed solvent of dichloromethane and methanol (v/v=10/1, 50 mL). The filtrate was extracted with dichloromethane and methanol (10:1, 3×50 mL). Organic phases were separated, washed with saturated brine (30 mL) and concentrated to dryness to obtain a crude product. The crude product was purified by silica gel column chromatography (dichloromethane:methanol=100:1-30:1) to obtain 6,6-dimethyl-8-(4-(4-methylpiperazin-1-yl)piperidin-1-yl)-11-oxo-3-((trimethylsilyl)ethynyl)-6,11-dihydro-5H-benzo[b]carbazole-9-carbonitrile as a yellow solid (90 mg, with a yield of 32%). MS (ESI) m/z:564 $(M+H)^+$.

3-ethynyl-6,6-dimethyl-8-(4-(4-methylpiperazin-1-yl)piperidin-1-yl)-11-oxo-6,11-dihydro-5H-ben zo[b]carbazole-9-carbonitrile

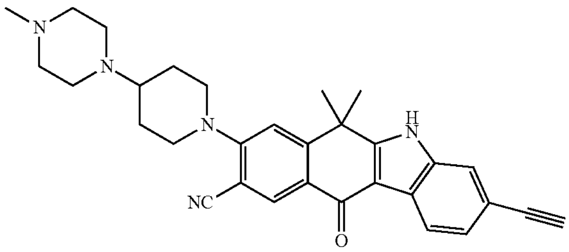 [SMILES: C#Cc1ccc2c3c([nH]c2c1)C(C)(C)c1cc(N2CCC(N4CCN(C)CC4)CC2)c(C#N)cc1C3=O]

6,6-dimethyl-8-(4-(4-methylpiperazin-1-yl)piperidin-1-yl)-11-oxo-3-((trimethylsilyl)ethynyl)-6,11-dihydro-5H-benzo[b]carbazole-9-carbonitrile (90 mg, 0.17 mmol) and potassium carbonate (110 mg, 0.84 mmol) were added into acetonitrile (10 mL) and methanol (10 mL). A reaction was conducted for 2 hours with stirring at room temperature. The reaction solution was concentrated to dryness at reduced pressure to obtain a crude product, and the crude product was purified by silica gel column chromatography (dichloromethane:methanol=10:1) to obtain 3-ethynyl-6,6-dimethyl-8-(4-(4-methylpiperazin-1-yl)piperidin-1-yl)-11-oxo-6,11-dihydro-5H-ben zo[b]carbazole-9-carbonitrile as a white solid (29.85 mg, with a yield of 38%). 1H NMR (400 MHz, DMSO-$d_6$) δ12.43 (s, 1H), 8.33 (s, 1H), 8.14 (d, J=8.0 Hz, 1H), 7.60 (s, 1H), 7.34 (t, J=2.4 Hz, 1H), 7.32 (s, 2H), 4.12 (s, 1H), 3.80 (d, J=12.0 Hz, 2H), 3.01 (m, 2H), 2.98 (t, J=11.7 Hz, 2H), 2.66 (m, 4H), 2.49 (m, 2H), 2.05 (m, 2H), 2.17 (s, 3H), 1.78 (s, 6H), 1.27 (m, 2H).

Example 17

8-(4-cyclopropylpiperazin-1-yl)-3-ethynyl-6,6-dimethyl-11-oxo-6,11-dihydro-5H-benzo[b]carbaz ole-9-carbonitrile (E17)

E17

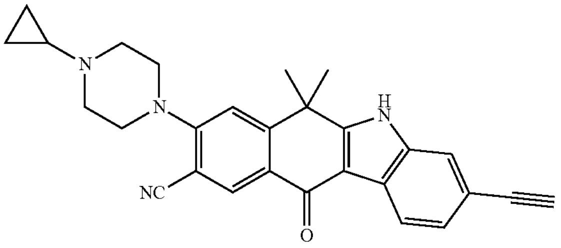

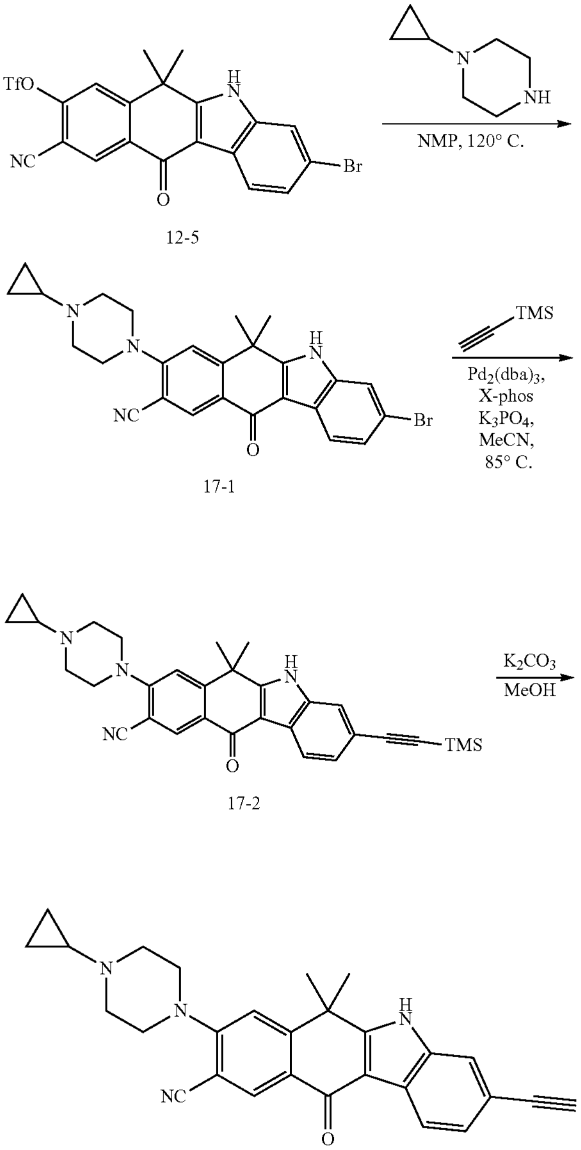

12-5

17-1

17-2

E17

3-bromo-8-(4-cyclopropylpiperazin-1-yl)-6,6-dimethyl-11-oxo-6,11-dihydro-5H-benzo[b]carbazole-9-carbonitrile

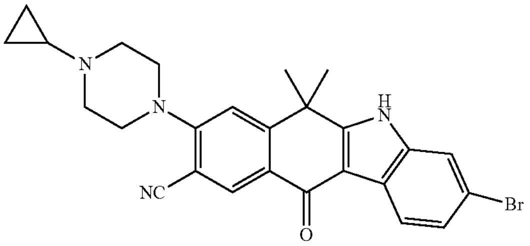 [SMILES: CC1(C)c2cc(N3CCN(C4CC4)CC3)c(C#N)cc2C(=O)c2c1[nH]c1cc(Br)ccc21]

1-cyclopropylpiperazine (2.5 g, 19.5 mmol) and 3-bromo-9-cyano-6,6-dimethyl-11-oxo-6,11-dihydro-5H-benzo[b]carbazol-8-yl trifluoromethanesulfonate (500 mg, 0.98 mmol) were added into N-methylpyrrolidone (10 mL). The mixture was stirred for 5 hours at 120° C. The completion of the reaction was monitored by LCMS. The reaction was quenched with water (30 mL) and extracted with a mixed solvent of dichloromethane and methanol (v/v=10/1, 3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-30:1) to obtain 3-bromo-8-(4-cyclopropylpiperazin-1-yl)-6,6-dimethyl-11-oxo-6,11-dihydro-5H-benzo[b]carbazole-9-carbonitrile as a white solid (329 mg, with a yield of 69%). MS (ESI) m/z: 489.1 $(M+H)^+$. 8-(4-cyclopropylpiperazin-1-yl)-6,6-dimethyl-11-oxo-3-((trimethylsilyl)ethynyl)-6,11-dihydro-5H-benzo[b]carbazole-9-carbonitrile

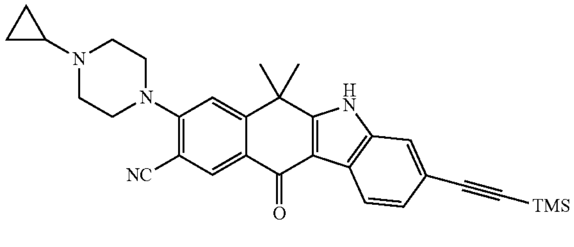 [SMILES: CC1(C)c2cc(N3CCN(C4CC4)CC3)c(C#N)cc2C(=O)c2c1[nH]c1cc(C#C[Si](C)(C)C)ccc21]

3-bromo-8-(4-cyclopropylpiperazin-1-yl)-6,6-dimethyl-11-oxo-6,11-dihydro-5H-benzo[b]carbazole-9-carbonitrile (329 mg, 0.67 mmol), ethynyltrimethylsilane (1324 mg, 13.48 mmol) and tripotassium phosphate (284 mg, 1.34 mmol) were dissolved in acetonitrile (10 mL). After the mixture was vacuum degassed with nitrogen for three times, tris(dibenzylideneacetone) dipalladium (123 mg, 0.13 mmol) and 2-dicyclohexylphosphino-2,4,6-triisopropylbiphenyl (128 mg, 0.27 mmol) were added. The mixture was degassed with nitrogen for three times again. The above mixture was heated to 85° C. and stirred for 10 hours. The obtained solution was filtered, and the filter cake was washed with a mixed solvent of dichloromethane and methanol (v/v=10/1, 50 mL). The filtrate was washed with saturated brine (30 mL), dried with anhydrous sodium sulfate and filtered, and the filtrate was concentrated to dryness at reduced pressure to obtain a crude product. The crude product was purified by silica gel column chromatography (dichloromethane:methanol=100:1-30:1) to obtain 8-(4-cyclopropylpiperazin-1-yl)-6,6-dimethyl-11-oxo-3-((trimethylsilyl)ethynyl)-6,11-dihydro-5H-benzo[b]carbazole-9-carbonitrile as a brown solid (426 mg). MS (ESI) m/z: 507.1 $(M+H)^+$.

8-(4-cyclopropylpiperazin-1-yl)-3-ethynyl-6,6-dimethyl-11-oxo-6,11-dihydro-5H-benzo[b]carbaz ole-9-carbonitrile

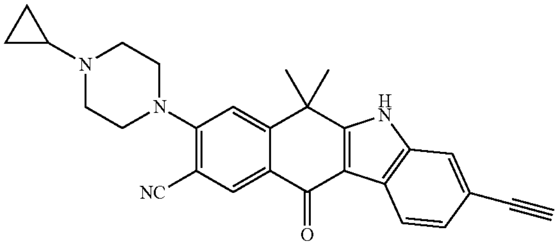 [SMILES: C#Cc1ccc2c3c([nH]c2c1)C(C)(C)c1cc(N2CCN(C4CC4)CC2)c(C#N)cc1C3=O]

8-(4-cyclopropylpiperazin-1-yl)-6,6-dimethyl-11-oxo-3-((trimethylsilyl)ethynyl)-6,11-dihydro-5H-benzo[b]carbazole-9-carbonitrile (426 mg, 0.84 mmol) and potassium carbonate (464 mg, 3.36 mmol) were added into acetonitrile (15 mL) and methanol (5 mL). A reaction was conducted for 6 hours with stirring at room temperature. The completion of the reaction was monitored by LCMS.

The reaction was quenched with water (30 mL) and extracted with a mixed solvent of dichloromethane and methanol (v/v=10/1, 3×50 mL). Organic phases were combined, washed with saturated brine, dried with anhydrous sodium sulfate and filtered, and the filtrate was concentrated to dryness at reduced pressure to obtain a crude product. The crude product was purified by silica gel column chromatography (dichloromethane:methanol=100:1-30:1) to obtain 8-(4-cyclopropylpiperazin-1-yl)-3-ethynyl-6,6-dimethyl-11-oxo-6,11-dihydro-5H-benzo[b]carbaz ole-9-carbonitrile as a light yellow solid (48 mg, with a yield of 17%). 1H NMR (400 MHz, DMSO-$d_6$): δ 12.45 (s, 1H), 8.35 (s, 1H), 8.15 (d, J=8.4 Hz, 1H), 7.61 (s, 1H), 7.41 (s, 1H), 7.35 (d, J=8.0 Hz, 1H), 4.14 (s, 1H), 2.76 (s, 4H), 2.70 (s, 2H), 2.20 (t, J=8.0 Hz, 1H), 1.94-1.86 (m, 2H), 1.78 (s, 6H), 0.48 (s, 2H), 0.38 (s, 2H).

Example 18
8-(4-(4-cyclopropylpiperazin-1-yl)piperidin-1-yl)-3-ethynyl-6,6-dimethyl-11-oxo-6,11-dihydro-5H-benzo[b]carbazole-9-carbonitrile (E18)
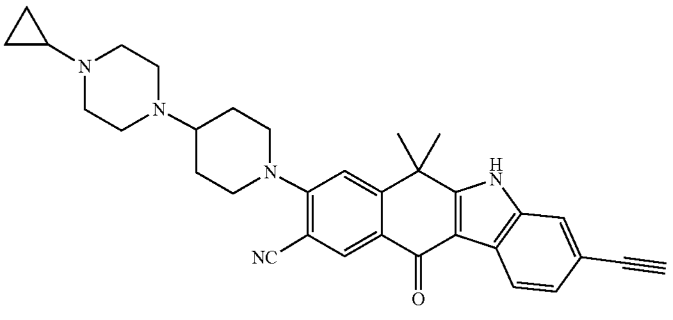
E18
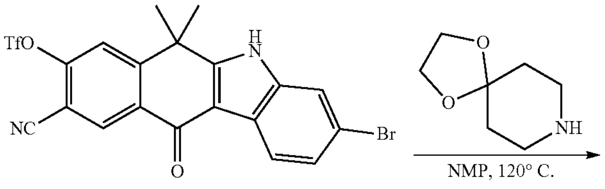
12-5
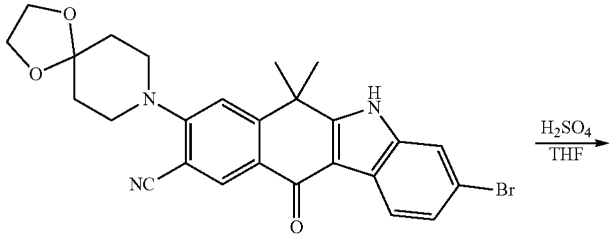
18-1
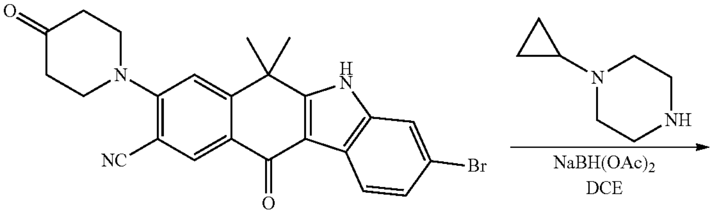
18-2
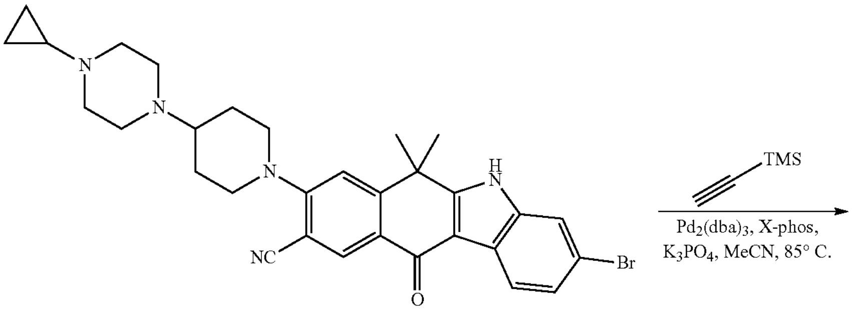
18-3

-continued

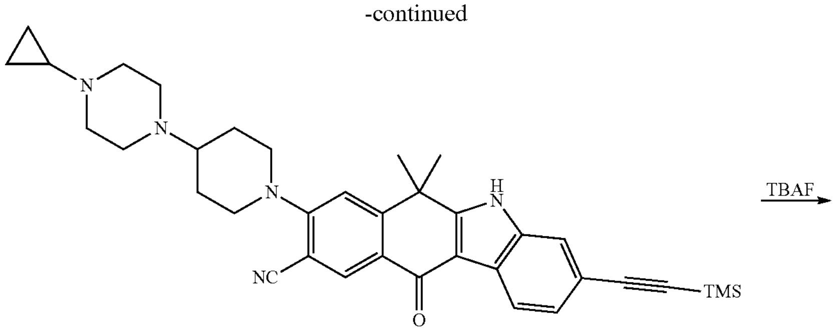

18-4

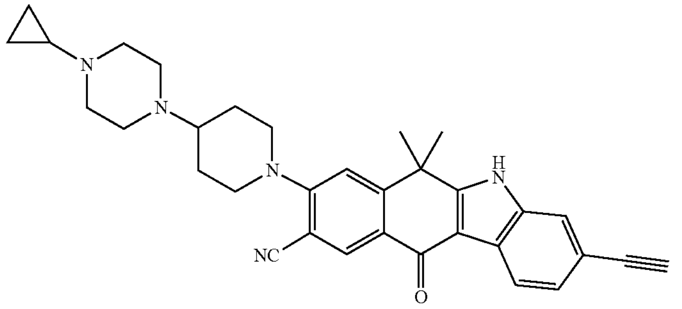

E18

3-bromo-6,6-dimethyl-11-oxo-8-(1,4-dioxa-8-azaspiro[4.5]decan-8-yl)-6,11-dihydro-5H-benzo[b]carbazole-9-carbonitrile

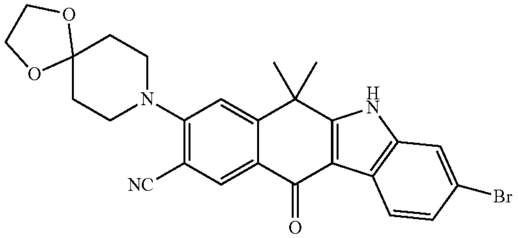 [SMILES: CC1(C)c2cc(N3CCC4(CC3)OCCO4)c(C#N)cc2C(=O)c2c1[nH]c1cc(Br)ccc21]

1,4-dioxa-8-azaspiro[4.5]decane (1.7 g, 11.70 mmol) was added into a solution of 3-bromo-9-cyano-6,6-dimethyl-1-oxo-6,11-dihydro-5H-benzo[b]carbazol-8-yl trifluoromethanesulfonate (1.2 g, 2.34 mmol) in N-methylpyrrolidone (10 mL). The mixture was heated to 140° C. and allowed to react overnight with stirring. The completion of the reaction was monitored by LCMS. The reaction solution was diluted with ethyl acetate (200 mL) and water (200 mL). Organic phases were separated, washed with saturated brine (2×200 mL), dried with anhydrous sodium sulfate and filtered. The filtrate was concentrated to dryness at reduced pressure to obtain a crude product, and the crude product was purified by silica gel column chromatography (petroleum ether:ethyl acetate=5:1) to obtain 3-bromo-6,6-dimethyl-11-oxo-8-(1,4-dioxa-8-azaspiro[4.5]decan-8-yl)-6,11-dihydro-5H-benzo[b]carbazole-9-carbonitrile as a yellow solid (350 mg, with a yield of 29.70%).

3-bromo-6,6-dimethyl-11-oxo-8-(4-oxopiperidin-1-yl)-6,11-dihydro-5H-benzo[b]carbazole-9-carb onitrilec

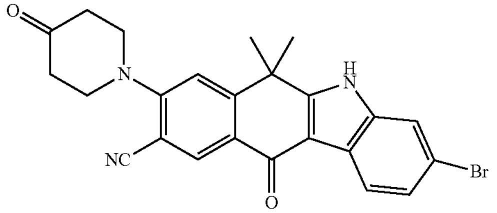 [SMILES: CC1(C)c2cc(N3CCC(=O)CC3)c(C#N)cc2C(=O)c2c1[nH]c1cc(Br)ccc21]

An aqueous solution of sulfuric acid (10%, 5 mL) was added into a solution of 3-bromo-6,6-dimethyl-11-oxo-8-(1,4-dioxa-8-azaspiro[4.5]decan-8-yl)-6,11-dihydro-5H-benzo[b]carbazole-9-carbonitrile (350 mg, 0.69 mmol) in tetrahydrofuiran (10 mL). The mixture was heated to 50° C. and allowed to react overnight with stirring. The completion of the reaction was monitored by LCMS. The reaction solution was diluted with ethyl acetate (200 mL) and water (200 mL). The organic phase was washed with saturated brine (2×200 mL) and dried with anhydrous sodium sulfate. The organic phase was filtered and concentrated at reduced pressure to obtain a crude product. The crude product was purified by silica gel column chromatography (petroleum ether:ethyl acetate=1:1) to obtain 3-bromo-6,6-dimethyl-11-oxo-8-(4-oxopiperidin-1-yl)-6,11-dihydro-5H-benzo[b]carbazole-9-carb onitrile as a yellow solid (250 mg, with a yield of 78.6%).

3-bromo-8-(4-(4-cyclopropylpiperazin-1-yl)piperidin-1-yl)-6,6-dimethyl-11-oxo-6,11-dihydro-5H-benzo[b]carbazole-9-carbonitrile

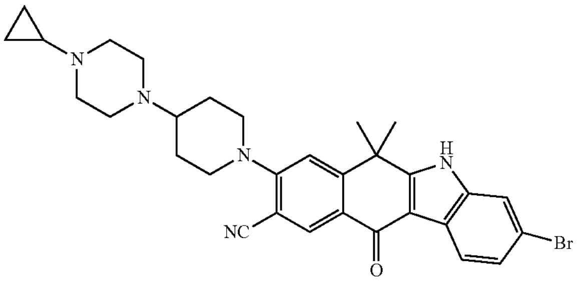 [SMILES: CC1(C)c2cc(N3CCC(N4CCN(C5CC5)CC4)CC3)c(C#N)cc2C(=O)c2c1[nH]c1cc(Br)ccc21]

1-cyclopropylpiperazine (204 mg, 1.62 mmol) was added into a solution of 3-bromo-6,6-dimethyl-11-oxo-8-(4-oxopiperidin-1-yl)-6,11-dihydro-5H-benzo[b]carbazole-9-carb onitrile (250 mg, 0.54 mmol) in 1,2-dichloroethane (10 mL). The above materials were stirred for 2 hours at room temperature and then sodium triacetoxyborohydride (420 mg, 2 mmol) was added. The above mixture was stirred overnight at room temperature. The completion of the reaction was monitored by LCMS. The reaction mixture was diluted with ethyl acetate (200 mL) and water (200 mL). The organic phase was washed with saturated brine (2×200 mL), dried with anhydrous sodium sulfate and filtered, and the filtrate was concentrated at reduced pressure to obtain a crude product. The crude product was purified by silica gel column chromatography (dichloromethane:methanol=10:1) to obtain 3-bromo-8-(4-(4-cyclopropylpiperazin-1-yl)piperidin-1-yl)-6,6-dimethyl-11-oxo-6,11-dihydro-5H-benzo [b]carbazole-9-carbonitrile as a yellow solid (220 mg, with a yield of 71.4%).

8-(4-(4-cyclopropylpiperazin-1-yl)piperidin-1-yl)-6,6-dimethyl-11-oxo-3-((trimethylsilyl)ethynyl)-6,11-dihydro-5H-benzo[b]carbazole-9-carbonitrile

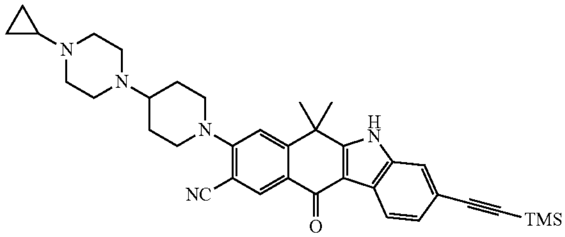 [SMILES: CC1(C)c2cc(N3CCC(N4CCN(C5CC5)CC4)CC3)c(C#N)cc2C(=O)c2c1[nH]c1cc(C#C[Si](C)(C)C)ccc21]

Tris(dibenzylideneacetone) dipalladium (37 mg, 0.04 mmol) and 2-dicyclohexylphosphino-2,4,6-triisopropylbiphenyl (38 mg, 0.08 mmol) were added into a solution of 3-bromo-8-(4-(4-cyclopropylpiperazin-1-yl)piperidin-1-yl)-6,6-dimethyl-11-oxo-6,11-dihydro-5H-benzo[b]carbazole-9-carbonitrile (220 mg, 0.39 mmol), ethynyltrimethylsilane (172 mg, 1.76 mmol) and tripotassium phosphate (250 mg, 1.2 mmol) in acetonitrile (10 mL). Air was replaced with nitrogen three times. The solution was heated to 70° C. and stirred overnight. The completion of the reaction was monitored by LCMS. The reaction mixture was diluted with dichloromethane (200 mL) and water (200 mL). The organic phase was washed with saturated brine (2×200 mL) and dried with anhydrous sodium sulfate. The organic phase was filtered, and the filtrate was concentrated at reduced pressure to obtain a crude product. The crude product was purified by silica gel column chromatography (dichloromethane:methanol=10:1) to obtain 8-(4-(4-cyclopropylpiperazin-1-yl)piperidin-1-yl)-6,6-dimethyl-11-oxo-3-((trimethylsilyl)ethynyl)-6,11-dihydro-5H-benzo[b]carbazole-9-carbonitrile as a brown solid (90 mg, with a yield of 39.1%).

8-(4-(4-cyclopropylpiperazin-1-yl)piperidin-1-yl)-3-ethynyl-6,6-dimethyl-11-oxo-6,11-dihydro-5H-benzo[b]carbazole-9-carbonitrile

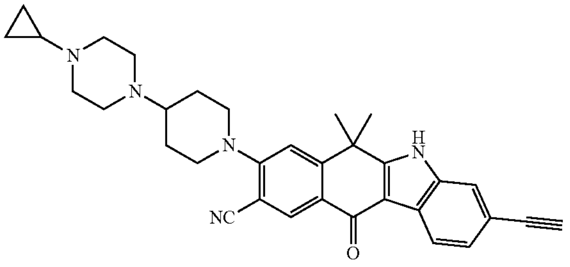 [SMILES: C#Cc1ccc2c3c([nH]c2c1)C(C)(C)c1cc(N2CCC(N4CCN(C5CC5)CC4)CC2)c(C#N)cc1C3=O]

A tetrahydrofuran solution of tetrabutyl ammonium fluoride (1M, 1 mL) was added into a solution of 8-(4-(4-cyclopropylpiperazin-1-yl)piperidin-1-yl)-6,6-dimethyl-11-oxo-3-((trimethylsilyl)ethynyl)-6,11-dihydro-5H-benzo[b] carbazole-9-carbonitrile (220 mg, 0.39 mmol) in tetrahydrofuran (10 mL). The mixture was stirred overnight at room temperature under the protection of nitrogen. The completion of the reaction was monitored by LCMS. The reaction solution was diluted with dichloromethane (200 mL) and water (200 mL) The organic phase was washed with saturated brine (2×200 mL) and dried with anhydrous sodium sulfate. The organic phase was filtered, the filtrate was concentrated at reduced pressure to obtain a crude product, and the crude product was purified by silica gel column chromatography (dichloromethane:methanol=10:1) to obtain 8-(4-(4-cyclopropylpiperazin-1-yl)piperidin-1-yl)-3-ethynyl-6,6-dimethyl-11-oxo-6,11-dihydro-5H-benzo[b] carbazole-9-carbonitrile as a light yellow solid (10.03 mg, with a yield of 5.0%). 1H NMR (400 MHz, DMSO-$d_6$) δ 8.61 (s, 2H), 8.36 (d, J=8.1 Hz, 1H), 7.58 (s, 1H), 7.47 (d, J=8.1 Hz, 1H), 7.06 (s, 1H), 3.89 (d, J=12.0 Hz, 2H), 3.10 (s, 1H), 2.98 (t, J=11.7 Hz, 2H), 2.66 (d, J=23.6 Hz, 7H), 2.49 (s, 1H), 2.05 (s, 1H), 2.00 (s, 2H), 1.78 (s, 6H), 1.61 (s, 1H), 1.27 (d, J=9.9 Hz, 2H), 0.44 (d, J=11.4 Hz, 3H).

Example 19

9-chloro-3-ethynyl-6,6-dimethyl-8-(4-methylpiperazin-1-yl)-5,6-dihydro-11H-benzo[b]carbazol-11-one (E19)

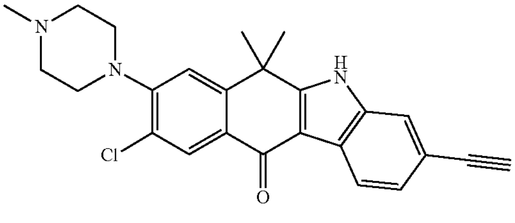

E19

-continued

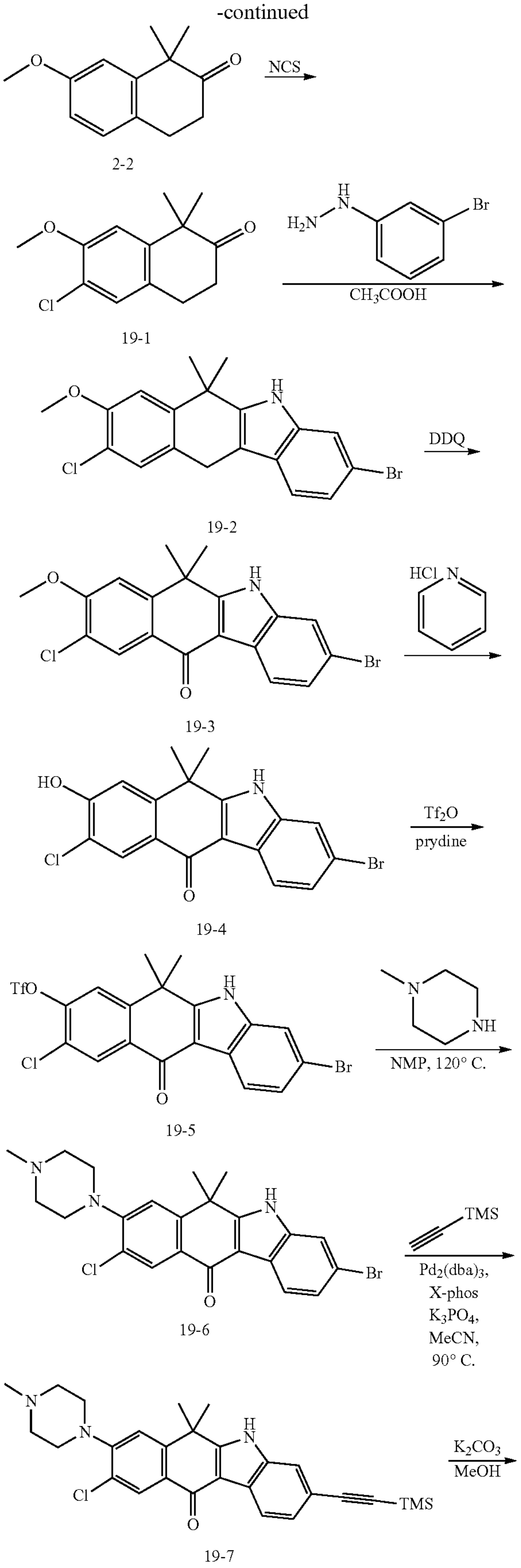

2-2

19-1

19-2

19-3

19-4

19-5

19-6

19-7

-continued

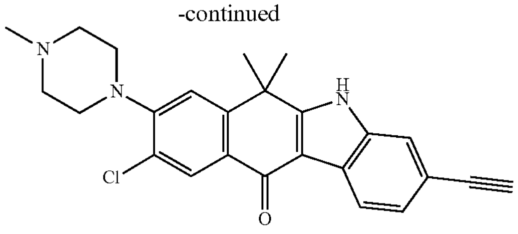

E19

6-chloro-7-methoxy-1,1-dimethyl-3,4-dihydronaphthalen-2(1H)-one

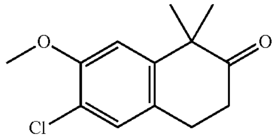 [SMILES: COc1cc2c(cc1Cl)CCC(=O)C2(C)C]

N-chlorosuccinimide (15.8 g, 118 mmol) was added into a solution of 7-methoxy-1,1-dimethyl-3,4-dihydronaphthalen-2 (1H)-one (22 g, 108 mmol) in acetonitrile (500 mL). The above mixture was heated to 80° C. and stirred for 1 hour. The reaction solution was cooled to room temperature and then poured into water (1000 mL), and then extracted with ethyl acetate (2×300 mL). Organic phases were combined and concentrated at reduced pressure to obtain a crude product, and the crude product was purified by silica gel column chromatography (petroleum ether:ethyl acetate=5:1) to obtain 6-chloro-7-methoxy-1,1-dimethyl-3,4-dihydronaphthalen-2(1H)-one as a yellow oil (21 g, with a yield of 81%). 1H NMR (400 MHz, DMSO-$d_6$) δ 7.11 (d, J=8.3 Hz, 1H), 6.92 (d, J=2.6 Hz, 1H), 6.77 (dd, J=8.3, 2.6 Hz, 1H), 3.75 (s, 3H), 3.01-2.94 (m, 2H), 2.59 (dd, J=7.5, 6.2 Hz, 2H), 1.34 (s, 6H).

3-bromo-9-chloro-8-methoxy-6,6-dimethyl-6,11-dihydro-5H-benzo[b]carbazole

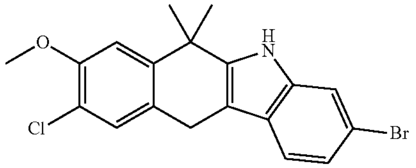 [SMILES: COc1cc2c(cc1Cl)Cc1c([nH]c3cc(Br)ccc13)C2(C)C]

6-chloro-7-methoxy-1,1-dimethyl-3,4-dihydronaphthalen-2(1H)-one (23.9 g, 100 mmol) and (3-bromophenyl) hydrazine hydrochloride (22.4 g, 100 mmol) were dissolved in acetic acid (400 mL). The above mixture was heated to 120° C. and stirred for 8 hours. The obtained solution was cooled to room temperature and filtered. The filter cake was washed with water to obtain 3-bromo-9-chloro-8-methoxy-6,6-dimethyl-6,11-dihydro-5H-benzo[b]carbazole as a brown solid (25 g, with a yield of 64.2%). 1H NMR (400 MHz, DMSO-$d_6$) δ 11.64 (s, 1H), 7.80 (d, J=0.7 Hz, 1H), 7.62 (d, J=8.1 Hz, 1H), 7.39 (s, 1H), 7.35 (dd, J=8.1, 1.4 Hz, 1H), 7.30 (s, 1H), 4.02 (s, 2H), 3.92 (s, 3H), 1.70 (s, 6H).

3-bromo-9-chloro-8-methoxy-6,6-dimethyl-5,6-dihydro-11H-benzo[b]carbazol-11-one

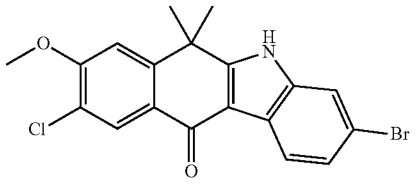 [SMILES: COc1cc2c(cc1Cl)C(=O)c1c([nH]c3cc(Br)ccc13)C2(C)C]

3-bromo-9-chloro-8-methoxy-6,6-dimethyl-6,11-dihydro-5H-benzo[b]carbazole (500 mg, 1.28 mmol) and 2,3-dichloro-5,6-dicyano-1,4-benzoquinone (467 mg, 2.06 mmol) were dissolved in tetrahydrofuran (9 mL) and water (1 mL). The above materials were stirred at 25° C. to react for 1 hour. The reaction solution was poured into water (100 mL) and extracted with ethyl acetate (3×20 mL). Organic phases were combined, washed with saturated brine, dried with anhydrous sodium sulfate, filtered and concentrated at reduced pressure to obtain a crude product. The crude product was purified by silica gel column chromatography (dichloromethane:methanol=10:1) to obtain 3-bromo-9-chloro-8-methoxy-6,6-dimethyl-5,6-dihydro-11H-benzo[b]carbazol-11-one as a red solid (300 mg, with a yield of 58%). 1H NMR (400 MHz, DMSO-$d_6$) δ 12.80 (s, 1H), 8.31 (d, J=8.1 Hz, 1H), 8.13 (s, 1H), 8.03 (s, 1H), 7.62 (dd, J=8.1, 1.2 Hz, 1H), 7.53 (s, 1H), 4.05 (s, 3H), 1.82 (s, 6H).

3-bromo-9-chloro-8-hydroxy-6,6-dimethyl-5,6-dihydro-11H-benzo[b]carbazol-11-one

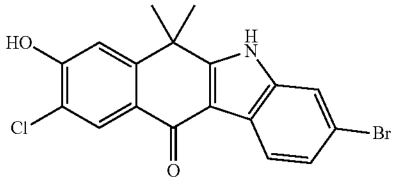

3-bromo-9-chloro-8-methoxy-6,6-dimethyl-5,6-dihydro-11H-benzo[b]carbazol-11-one (5 g, 12.3 mmol) and pyridine hydrochloride (28.6 g, 247 mmol) were added into a reaction flask. The mixture was heated to 170° C. and allowed to react for 13 hours with stirring. The completion of the reaction was monitored by LCMS. The reaction was quenched with ice water (500 mL). The reaction solution was extracted with ethyl acetate (3×150 mL), and organic phases were combined, washed with saturated brine (2×100 mL) and dried with anhydrous sodium sulfate. The obtained product was filtered, and the filtrate was concentrated to dryness at reduced pressure to obtain 3-bromo-9-chloro-8-hydroxy-6,6-dimethyl-5,6-dihydro-11H-benzo[b]carbazol-11-one as a brown solid (4.1 g, a crude product). 1H NMR (400 MHz, DMSO-$d_6$) δ 12.78 (s, 1H), 11.08 (s, 1H), 8.31 (d, J=8.1 Hz, 1H), 8.09 (s, 1H), 8.01 (s, 1H), 7.61 (dd, J=8.1, 1.2 Hz, 1H), 7.31 (s, 1H), 1.73 (s, 6H).

3-bromo-9-chloro-6,6-dimethyl-11-oxo-6,11-dihydro-5H-benzo[b]carbazol-8-yl trifluoromethanesulfonate

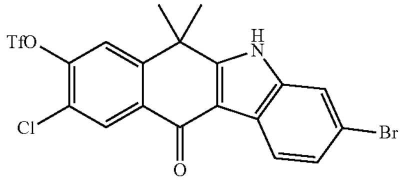 [SMILES: CC1(C)c2cc(OS(=O)(=O)C(F)(F)F)c(Cl)cc2C(=O)c2c1[nH]c1cc(Br)ccc21]

3-bromo-9-chloro-8-hydroxy-6,6-dimethyl-5,6-dihydro-11H-benzo[b]carbazol-11-one (810 mg, 2.0 mmol), triethylamine (606 mg, 6.0 mmol) and N, N-dimethylpyridine (24 mg, 0.2 mmol) were dissolved in dichloromethane (20 mL). The mixture was stirred for 10 minitues at 0° C.

Trifluoromethanesulfonic anhydride (846 mg, 3.0 mmol) was dropwise added. The above mixture was stirred for 2 hours at 0° C. The reaction solution was quenched with water (50 mL), extracted with ethyl acetate (3×30 mL), and washed with saturated brine (30 mL). The obtained solution was concentrated at reduced pressure to obtain a crude product, and the crude product was purified by silica gel column chromatography (dichloromethane:methanol=20:1) to obtain 3-bromo-9-chloro-6,6-dimethyl-11-oxo-6,11-dihydro-5H-benzo[b]carbazol-8-yl trifluoromethanesulfonate as a yellow oil (650 mg, with a yield of 62.5%). 1H NMR (400 MHz, DMSO-$d_6$) δ 12.98 (s, 1H), 8.38 (s, 1H), 8.31 (d, J=8.1 Hz, 1H), 8.25 (s, 1H), 8.07 (s, 1H), 7.67 (dd, J=8.1, 1.2 Hz, 1H), 1.81 (s, 6H).

3-bromo-9-chloro-6,6-dimethyl-8-(4-methylpiperazin-1-yl)-5,6-dihydro-11H-benzo[b]carbazol-11-one

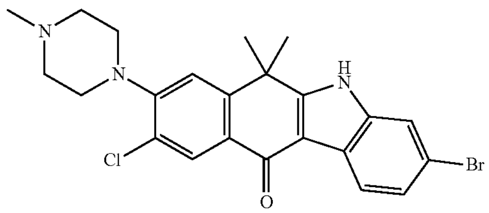 [SMILES: CN1CCN(c2cc3c(cc2Cl)C(=O)c2c([nH]c4cc(Br)ccc24)C3(C)C)CC1]

3-bromo-9-chloro-6,6-dimethyl-11-oxo-6,11-dihydro-5H-benzo[b]carbazol-8-yl trifluoromethanesulfonate (240 mg, 0.46 mmol) and 1-methylpiperazine (69 mg, 0.69 mmol) were added into N-methylpyrrolidone (5 mL). The above mixture was heated to 120° C. and stirred for 2 hours. The completion of the reaction was monitored by LCMS. The reaction solution was poured into ice water (150 mL) and extracted with ethyl acetate (3×50 mL). Organic phases were combined, washed with saturated brine and dried with anhydrous sodium sulfate. The obtained product was filtered, and the filtrate was concentrated at reduced pressure to obtain a crude product. The crude product was purified by Prep-TLC to obtain 3-bromo-9-chloro-6,6-dimethyl-8-(4-methylpiperazin-1-yl)-5,6-dihydro-11H-benzo[b]carbazol-11-one as a brown oil (165 mg, with a yield of 76%). MS (ESI) m/z: 472.1 $(M+H)^+$.

9-chloro-6,6-dimethyl-8-(4-methylpiperazin-1-yl)-3-((trimethylsilyl)ethynyl)-5,6-dihydro-11H-benzo[b]carbazol-11-one

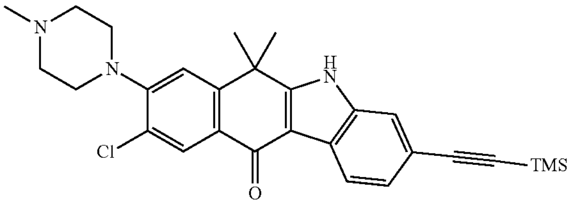 [SMILES: CN1CCN(c2cc3c(cc2Cl)C(=O)c2c([nH]c4cc(C#C[Si](C)(C)C)ccc24)C3(C)C)CC1]

Tris(dibenzylideneacetone) dipalladium (16 mg, 0.018 mmol) and 2-dicyclohexylphosphino-2,4,6-triisopropylbiphenyl (9 mg, 0.018 mmol) were added into a solution of 3-bromo-9-chloro-6,6-dimethyl-8-(4-methylpiperazin-1-yl)-5,6-dihydro-11H-benzo[b]carbazol-11-one (100 mg, 0.18 mmol), ethynyltrimethylsilane (176 mg, 1.8 mmol) and tripotassium phosphate (114 mg, 0.54 mmol) in acetonitrile (5 mL). The mixture was heated to 80° C. and stirred for 18 hours under the protection of nitrogen. The reaction solution was cooled and concentrated to obtain a crude product. The crude product was purified by silica gel column chromatography to obtain 9-chloro-6,6-dimethyl-8-(4-methylpiperazin-1-yl)-3-((trimethylsilyl)ethynyl)-5,6-dihydro-11H-benzo[b]carbazol-11-one as a yellow oil (84 mg, with a yield of 81%). MS (ESI) m/z: 490.2 $(M+H)^+$.

9-chloro-3-ethynyl-6,6-dimethyl-8-(4-methylpiperazin-1-yl)-5,6-dihydro-11H-benzo[b]carbazol-11-one

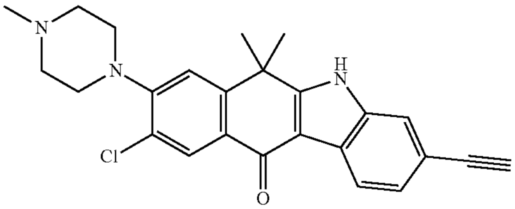 [SMILES: C#Cc1ccc2c3c([nH]c2c1)C(C)(C)c1cc(N2CCN(C)CC2)c(Cl)cc1C3=O]

9-chloro-6,6-dimethyl-8-(4-methylpiperazin-1-yl)-3-((trimethylsilyl)ethynyl)-5,6-dihydro-11H-benzo[b]carbazol-11-one (84 mg, 0.17 mmol) and potassium carbonate (235 mg, 1.7 mmol) were added into methanol (5 mL). The mixture was heated to 30° C. and stirred for 2 hours under the protection of nitrogen. The reaction solution was filtered, and the filtrate was concentrated to obtain a crude product. The crude product was purified by Prep-HPLC to obtain 9-chloro-3-ethynyl-6,6-dimethyl-8-(4-methylpiperazin-1-yl)-5,6-dihydro-11H-benzo[b]carbazol-11-one as a white solid (23.55 mg, with a yield of 32%). 1H NMR (400 MHz, DMSO-$d_6$) δ 8.14 (d, J=8.1 Hz, 1H), 8.08 (s, 1H), 7.61 (s, 1H), 7.43 (s, 1H), 7.33 (dd, J=8.1, 1.3 Hz, 1H), 4.12 (s, 1H), 3.17 (s, 4H), 2.51 (s, 4H), 2.26 (s, 3H), 1.76 (s, 6H).

Example 20

9-chloro-8-(4-cyclopropylpiperazin-1-yl)-3-ethynyl-6,6-dimethyl-5,6-dihydro-11H-benzo[b]carba zol-11-one (E20)

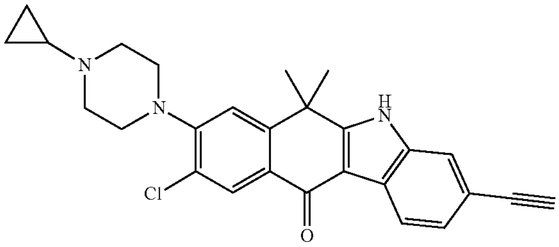

E20

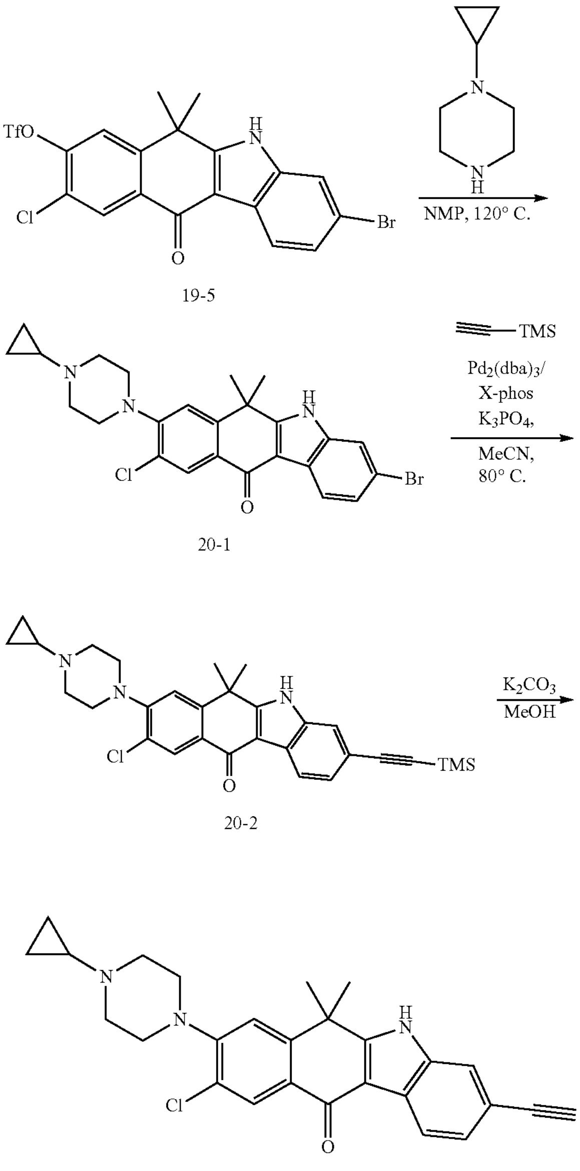

E20

3-bromo-9-chloro-8-(4-cyclopropylpiperazin-1-yl)-6,6-dimethyl-5,6-dihydro-11H-benzo[b]carbaz ol-11-one

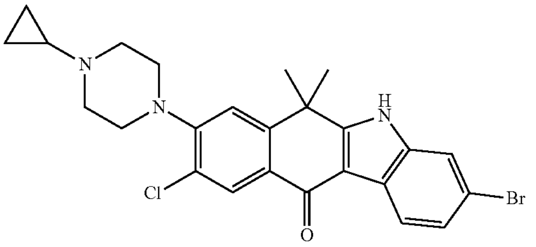 [SMILES: CC1(C)c2cc(N3CCN(C4CC4)CC3)c(Cl)cc2C(=O)c2c1[nH]c1cc(Br)ccc21]

3-bromo-9-chloro-6,6-dimethyl-11-oxo-6,11-dihydro-5H-benzo[b]carbazol-8-yl trifluoromethanesulfonate (300 mg, 0.57 mmol) and 1-cyclopropylpiperazine (1.44 g, 11.4 mmol) were added into N-methylpyrrolidone (3 mL). The above mixture was heated to 120° C. and stirred for 16 hours. The reaction solution was cooled to room temperature. The cooled reaction solution was filtered, and the filtrate was concentrated to dryness at reduced pressure to obtain a crude product. The crude product was purified by silica gel column chromatography (dichloromethane:methanol=20:1) to obtain 3-bromo-9-chloro-8-(4-cyclopropylpiperazin-1-yl)-6,6-dimethyl-5,6-dihydro-11H-benzo[b]carbaz ol-11-one as a yellow solid (90 mg, with a yield of 31%). MS (ESI) m/z: 498.1 $(M+H)^+$. 9-chloro-8-(4-cyclopropylpiperazin-1-yl)-6,6-dimethyl-3-((trimethylsilyl)ethynyl)-5,6-dihydro-11H-benzo[b]carbazol-11-one

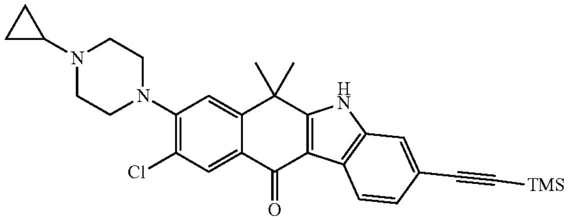 [SMILES: CC1(C)c2cc(N3CCN(C4CC4)CC3)c(Cl)cc2C(=O)c2c1[nH]c1cc(C#C[Si](C)(C)C)ccc21]

Tris(dibenzylideneacetone) dipalladium (16 mg, 0.018 mmol) and 2-dicyclohexylphosphino-2,4,6-triisopropylbiphenyl (9 mg, 0.018 mmol) were added into a solution of 3-bromo-9-chloro-8-(4-cyclopropylpiperazin-1-yl)-6,6-dimethyl-5,6-dihydro-11H-benzo[b]carbaz ol-11-one (75 mg, 0.15 mmol), ethynyltrimethylsilane (294 mg, 3 mmol) and tripotassium phosphate (95.4 mg, 0.45 mmol) in acetonitrile (8.0 mL). The mixture was heated to 80° C. and stirred for 18 hours under the protection of nitrogen. The reaction solution was cooled and concentrated to obtain a crude product. The crude product was purified by silica gel column chromatography (dichloromethane:methanol=20:1) to obtain 9-chloro-8-(4-cyclopropylpiperazin-1-yl)-6,6-dimethyl-3-((trimethylsilyl)ethynyl)-5,6-dihydro-11H-benzo[b] carbazol-11-one as a yellow solid (37 mg, with a yield of 47%). MS (ESI) m/z: 516.2 $(M+H)^+$.

9-chloro-8-(4-cyclopropylpiperazin-1-yl)-3-ethynyl-6,6-dimethyl-5,6-dihydro-11H-benzo[b]carba zol-11-one

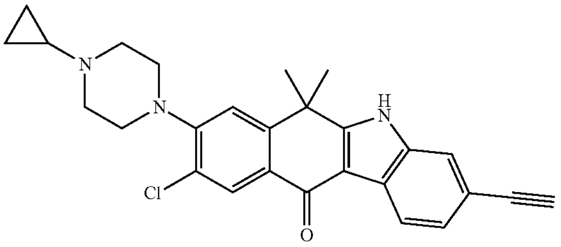 [SMILES: C#Cc1ccc2c3c([nH]c2c1)C(C)(C)c1cc(N2CCN(C4CC4)CC2)c(Cl)cc1C3=O]

9-chloro-8-(4-cyclopropylpiperazin-1-yl)-6,6-dimethyl-3-((trimethylsilyl)ethynyl)-5,6-dihydro-11H-benzo[b]carbazol-11-one (37 mg, 0.07 mmol) and potassium carbonate (60 mg, 0.43 mmol) were added into methanol (20 mL). The mixture was heated to 30° C. and stirred for 2 hours under the protection of nitrogen. The reaction solution was filtered, and the filtrate was concentrated at reduced pressure to obtain a crude product. The crude product was purified by Prep-HPLC to obtain 9-chloro-8-(4-cyclopropylpiperazin-1-yl)-3-ethynyl-6,6-dimethyl-5,6-dihydro-11H-benzo[b]carba zol-11-one as a white solid (7 mg, with a yield of 22%). 1H NMR (400 MHz, DMSO-$d_6$) δ 8.13 (d, J=8.4 Hz, 1H), 8.08 (s, 1H), 7.60 (s, 1H), 7.42 (s, 1H), 7.28 (dd, J=1.2, 6.8 Hz, 1H), 4.11 (s, 1H), 3.12 (br, 4H), 2.74 (br, 4H), 1.74 (s, 6H). 0.46 (br, 2H), 0.35 (br, 2H).

Example 21

9-chloro-8-(4-(dimethylamino)piperidin-1-yl)-3-ethynyl-6,6-dimethyl-5,6-dihydro-11H-benzo[b]c arbazol-11-one (E21)

E21

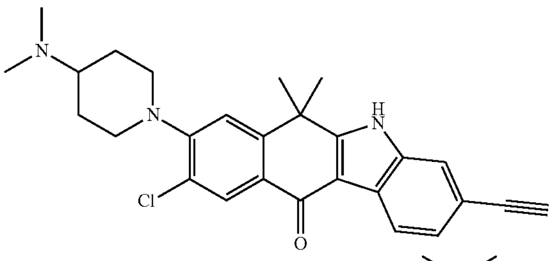

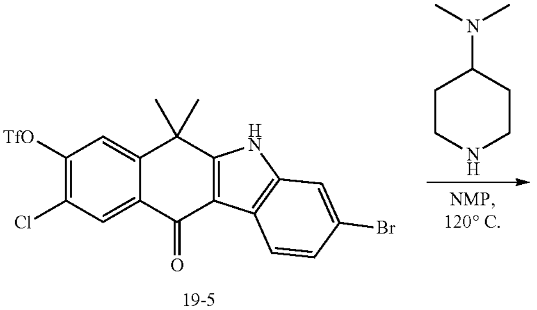

19-5

-continued

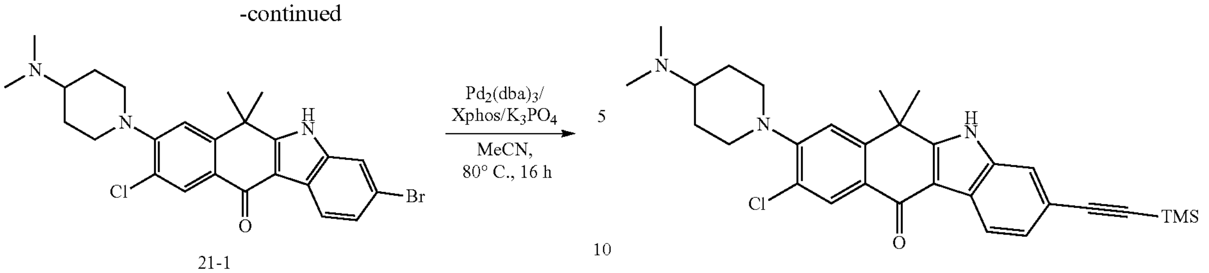

21-1

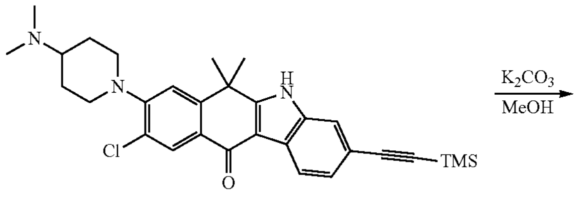

21-2

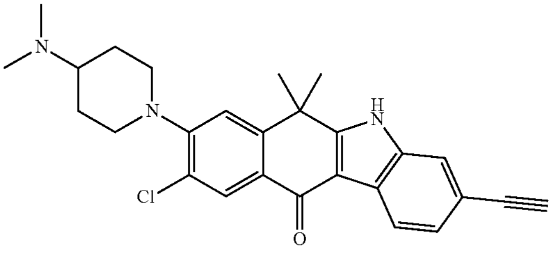

E21

3-bromo-9-chloro-8-(4-(dimethylamino)piperidin-1-yl)-6,6-dimethyl-5,6-dihydro-11H-benzo[b]carbazol-11-one

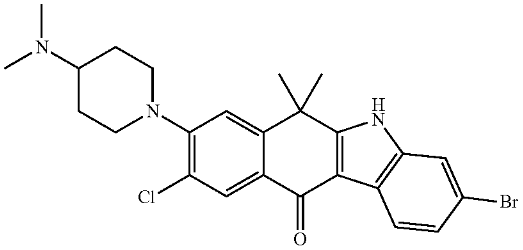 [SMILES: CN(C)C1CCN(c2cc3c(cc2Cl)C(=O)c2c([nH]c4cc(Br)ccc24)C3(C)C)CC1]

3-bromo-9-chloro-6,6-dimethyl-11-oxo-6,11-dihydro-5H-benzo-[b]carbazol-8-yl trifluoromethanesulfonate (500 mg, 0.96 mmol) and N,N-dimethylpiperidin-4-amine (2.4 g, 19.2 mmol) were added into N-methylpyrrolidone (5 mL). The above mixture was heated to 120° C. and stirred for 16 hours. The obtained solution was cooled to room temperature and then purified by Prep-HPLC (acetonitrile/water/0.1% trifluoroacetic acid) to obtain 3-bromo-9-chloro-8-(4-(dimethylamino)piperidin-1-yl)-6,6-dimethyl-5,6-dihydro-11H-benzo[b]carbazol-11-one as a brown solid (200 mg, with a yield of 42%). MS (ESI) m/z: 500.1 $(M+1)^+$.

9-chloro-8-(4-(dimethylamino)piperidin-1-yl)-6,6-dimethyl-3-((trimethylsilyl)ethynyl)-5,6-dihydro-11H-benzo[b]carbazol-11-one Tris(dibenzylideneacetone) dipalladium (36.6 mg, 0.04 mmol) and 2-dicyclohexylphosphino-2,4,6-triisopropylbiphenyl (38.08 mg, 0.08 mmol) were added into a solution of 3-bromo-9-chloro-8-(4-(dimethylamino)piperidin-1-yl)-6,6-dimethyl-5,6-dihydro-11H-benzo[b]carbazol-11-one (100 mg, 0.2 mmol), ethynyltrimethylsilane (392 mg, 4 mmol) and tripotassium phosphate (127.2 mg, 0.6 mmol) in acetonitrile (8.0 mL). The mixture was heated to 80° C. and stirred for 18 hours under the protection of nitrogen. The reaction solution was cooled and concentrated to obtain a crude product. The crude product was purified by silica gel column chromatography (dichloromethane:methanol=10:1) to obtain 9-chloro-8-(4-(dimethylamino)piperidin-1-yl)-6,6-dimethyl-3-((trimethylsilyl)ethynyl)-5,6-dihydro-11H-benzo[b]carbazol-11-one as a brown solid (47 mg, with a yield of 45%). MS (ESI) m/z:518.2 $(M+1)^+$.

9-chloro-8-(4-(dimethylamino)piperidin-1-yl)-3-ethynyl-6,6-dimethyl-5,6-dihydro-11H-benzo[b]carbazol-11-one

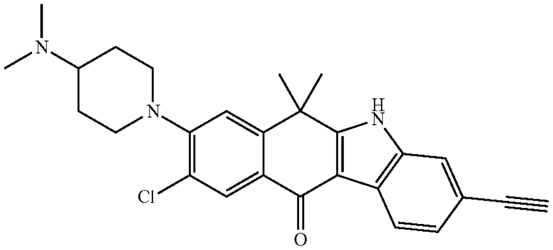 [SMILES: C#Cc1ccc2c3c([nH]c2c1)C(C)(C)c1cc(N2CCC(N(C)C)CC2)c(Cl)cc1C3=O]

9-chloro-8-(4-(dimethylamino)piperidin-1-yl)-6,6-dimethyl-3-((trimethylsilyl)ethynyl)-5,6-dihydro-11H-benzo[b]carbazol-11-one (47 mg, 0.09 mmol) and potassium carbonate (125 mg, 0.9 mmol) were added into methanol (5 mL). The above solution was stirred for 2 hour at room temperature. The obtained solution was filtered, and the filtrate was concentrated at reduced pressure to remove the methanol solvent to obtain a crude product, and the crude product was purified by Prep-HPLC to obtain 9-chloro-8-(4-(dimethylamino)piperidin-1-yl)-3-ethynyl-6,6-dimethyl-5,6-dihydro-11H-benzo[b]carbazol-11-one as a white solid (12.3 mg, with a yield of 30%). 1H NMR (400 MHz, DMSO-$d_6$) δ 12.46 (s, 1H), 8.23 (s, 1H), 8.14 (d, J=8.4 Hz, 1H), 8.08 (s, 1H), 7.61 (s, 1H), 7.42 (s, 1H), 7.33 (dd, J=1.2, 6.8 Hz, 1H), 4.13 (s, 1H), 2.81 (t, J=12.0 Hz, 2H), 2.45-2.40 (m, 1H), 2.30 (s, 6H), 1.94-1.91 (m, 2H), 1.75 (s, 6H). 1.65-1.60 (m, 2H).

Example 22
9-chloro-3-ethynyl-6,6-dimethyl-8-(4-(4-methylpiperazin-1-yl)piperidin-1-yl)-5,6-dihydro-11H-benzo[b]carbazol-11-one (E22)
E22
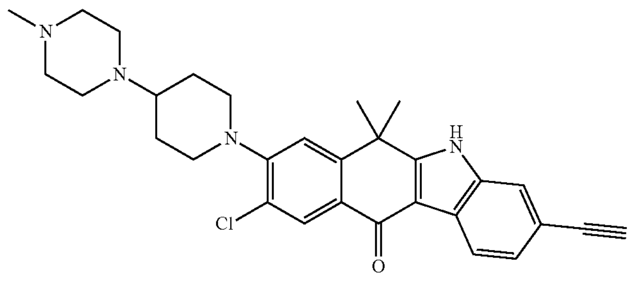
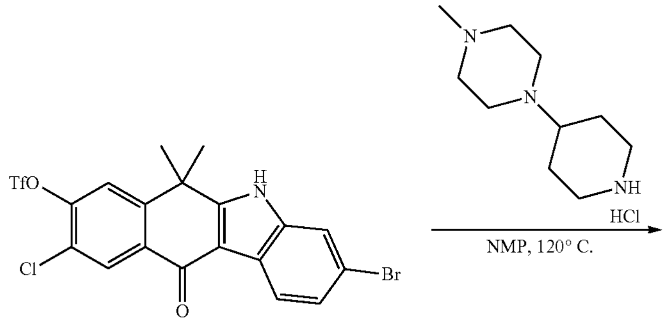
19-6
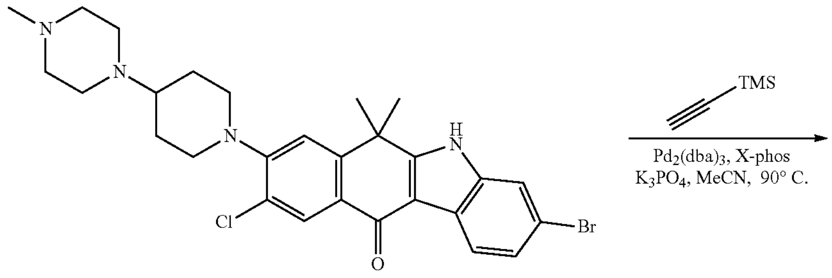
22-1
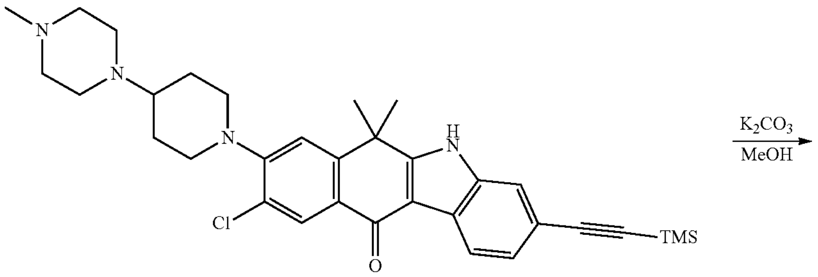
22-2

-continued

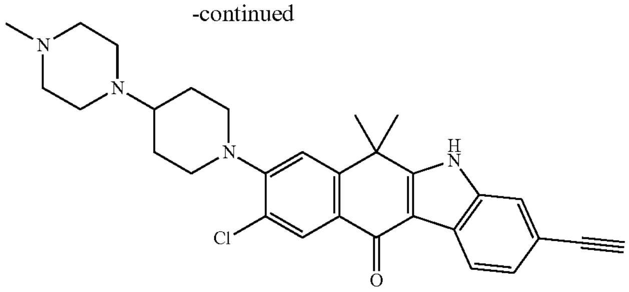

E22

3-bromo-9-chloro-6,6-dimethyl-8-(4-(4-methylpiperazin-1-yl)piperidin-1-yl)-,6-dihydro-11H-benzo[b]carbazol-11-one

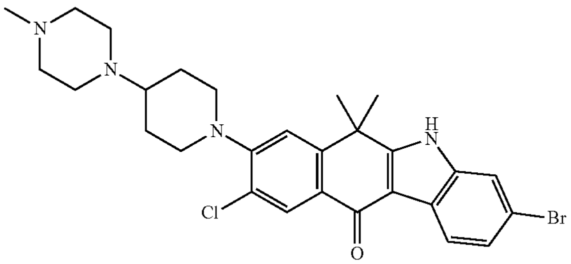 [SMILES: CN1CCN(C2CCN(c3cc4c(cc3Cl)C(=O)c3c([nH]c5cc(Br)ccc35)C4(C)C)CC2)CC1]

3-bromo-9-chloro-6,6-dimethyl-11-oxo-6,11-dihydro-5H-benzo[b]carbazol-8-yl trifluoromethanesulfonate (1.2 g, 2.3 mmol), 1-(1-methylpiperidin-4-yl)piperazine hydrochloride (504 mg, 22.9 mmol) and sodium bicarbonate (2.4 g, 22.9 mmol) were added into N-methylpyrrolidone (20 mL). The above mixture was heated to 120° C. and stirred for 3 hours. The reaction solution was cooled to room temperature and poured into water (100 mL), and then extracted with ethyl acetate (3×20 mL). Organic phases were combined, washed with saturated brine, dried with anhydrous sodium sulfate and filtered, and concentrated at reduced pressure to obtain a crude product. The crude product was purified by silica gel column chromatography (dichloromethane:methanol=10:1) to obtain 3-bromo-9-chloro-6,6-dimethyl-8-(4-(4-methylpiperazin-1-yl)piperidin-1-yl)-5,6-dihydro-11H-benzo[b]carbazol-11-one as a brown oil (205 mg, with a yield of 17%). MS (ESI) m/z: 555.1 $(M+H)^+$.

9-chloro-6,6-dimethyl-8-(4-(4-methylpiperazin-1-yl)piperidin-1-yl)-3-((trimethylsilyl)ethynyl)-5,6-dihydro-11H-benzo[b]carbazol-11-one

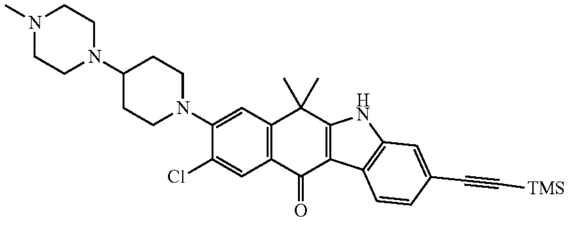 [SMILES: CN1CCN(C2CCN(c3cc4c(cc3Cl)C(=O)c3c([nH]c5cc(C#C[Si](C)(C)C)ccc35)C4(C)C)CC2)CC1]

Tris(dibenzylideneacetone) dipalladium (16 mg, 0.018 mmol) and 2-dicyclohexylphosphino-2,4,6-triisopropylbiphenyl (9 mg, 0.018 mmol) were added into a solution of 3-bromo-9-chloro-6,6-dimethyl-8-(4-(4-methylpiperazin-1-yl)piperidin-1-yl)-5,6-dihydro-11H-benzo[b]carbazol-11-one (100 mg, 0.18 mmol), ethynyltrimethylsilane (176 mg, 1.8 mmol) and tripotassium phosphate (114 mg, 0.54 mmol) in acetonitrile (5 mL). The mixture was heated to 80° C. and stirred for 18 hours under the protection of nitrogen. The reaction solution was filtered. The filter cake was washed with dichloromethane, and the filtrate was concentrated at reduced pressure to obtain a crude product. The crude product was purified by silica gel column chromatography (dichloromethane:methanol=10:1) to obtain 9-chloro-6,6-dimethyl-8-(4-(4-methylpiperazin-1-yl)piperidin-1-yl)-3-((trimethylsilyl)ethynyl)-5,6-dihydro-11H-benzo[b]carbazol-11-one as a yellow oil (65 mg, with a yield of 63%). MS (ESI) m/z: 573.3 $(M+H)^+$.

9-chloro-3-ethynyl-6,6-dimethyl-8-(4-(4-methylpiperazin-1-yl)piperidin-1-yl)-5,6-dihydro-11H-benzo[b]carbazol-11-one

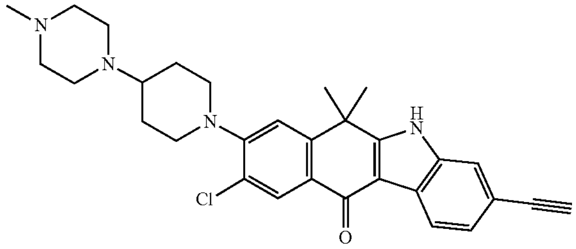 [SMILES: C#Cc1ccc2c3c([nH]c2c1)C(C)(C)c1cc(N2CCC(N4CCN(C)CC4)CC2)c(Cl)cc1C3=O]

9-chloro-6,6-dimethyl-8-(4-(4-methylpiperazin-1-yl)piperidin-1-yl)-3-((trimethylsilyl)ethynyl)-5,6-dihydro-11H-benzo[b]carbazol-11-one (65 mg, 0.11 mmol) and potassium carbonate (152 mg, 1.1 mmol) were added into methanol (5 mL). A reaction was conducted for 2 hours with stirring at 30° C. under the protection of nitrogen. The reaction solution was filtered, and the filtrate was concentrated at reduced pressure to obtain a crude product. The crude product was purified by Prep-HPLC to obtain 9-chloro-3-ethynyl-6,6-dimethyl-8-(4-(4-methylpiperazin-1-yl)piperidin-1-yl)-5,6-dihydro-11H-benzo[b]carbazol-11-one as a white solid (8.17 mg, with a yield of 15%). 1H NMR (400 MHz, DMSO-$d_6$) δ 8.14 (d, J=8.0 Hz, 1H), 8.08 (s, 1H), 7.60 (s, 1H), 7.41 (s, 1H), 7.32 (d, J=8.6 Hz, 1H), 4.10 (s, 1H), 3.50 (s, 4H), 2.85-2.65 (m, 4H), 2.33 (s, 4H), 2.15 (s, 3H), 1.90 (d, J=11.6 Hz, 2H), 1.75 (s, 6H), 1.60 (d, J=12.4 Hz, 3H).

Example 23

9-chloro-3-ethynyl-6,6-dimethyl-8-(4-morpholinopiperidin-1-yl)-5,6-dihydro-11H-benzo[b]carbaz ol-11-one (E23)

E23

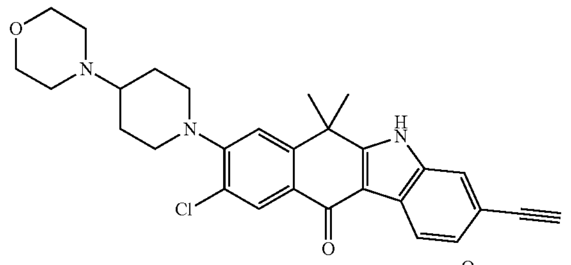

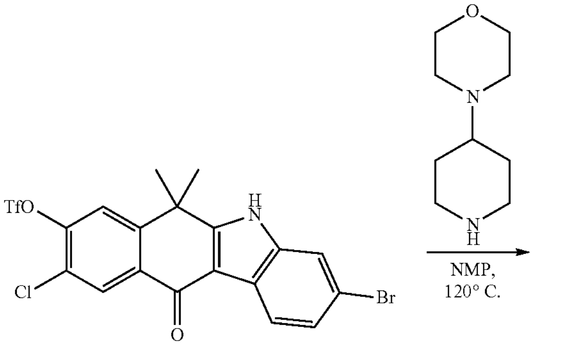

22-6

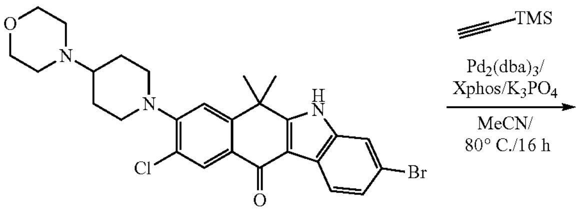

23-1

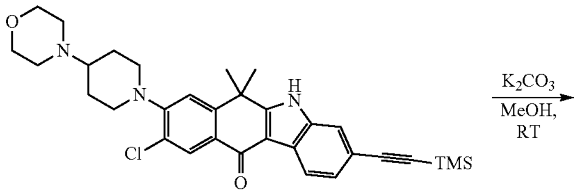

23-2

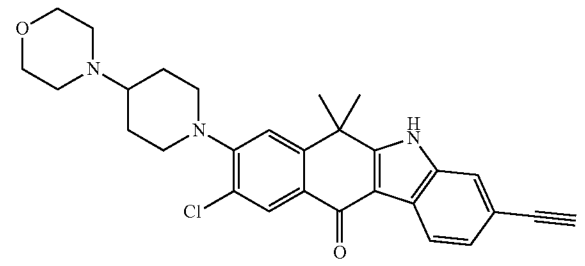

E23

3-bromo-9-chloro-6,6-dimethyl-8-(4-morpholinopiperidin-1-yl)-5,6-dihydro-11H-benzo[b]carbaz ol-11-one

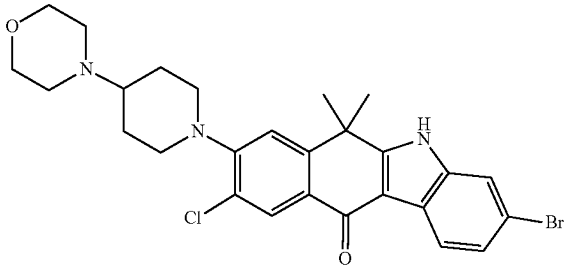 [SMILES: CC1(C)c2cc(N3CCC(N4CCOCC4)CC3)c(Cl)cc2C(=O)c2c1[nH]c1cc(Br)ccc21]

3-bromo-9-chloro-6,6-dimethyl-11-oxo-6,11-dihydro-5H-benzo[b]carbazol-8-yl trifluoromethanesulfonate (300 mg, 0.57 mmol) and 4-(piperidin-4-yl) morpholine (1.94 g, 11.4 mmol) were added into N-methypyrrolidone (3 mL). The above mixture was heated to 120° C. and stirred for 16 hours. The reaction solution was cooled to room temperature, and purified by C18 chromatography to obtain 3-bromo-9-chloro-6,6-dimethyl-8-(4-morpholinopiperidin-1-yl)-5,6-dihydro-11H-benzo[b]carbazol-11-one as a yellow solid (100 mg, with a yield of 32%). MS (ESI) m/z: 542.1 $(M+H)^+$.

9-chloro-6,6-dimethyl-8-(4-morpholinopiperidin-1-yl)-3-((trimethylsilyl)ethynyl)-5,6-dihydro-11H-benzo[b]carbazol-11-one

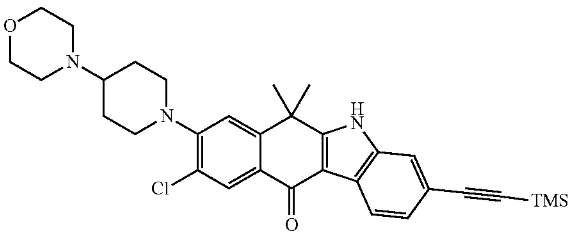 [SMILES: CC1(C)c2cc(N3CCC(N4CCOCC4)CC3)c(Cl)cc2C(=O)c2c1[nH]c1cc(C#C[Si](C)(C)C)ccc21]

Tris(dibenzylideneacetone) dipalladium (32.9 mg, 0.036 mmol) and 2-dicyclohexylphosphino-2,4,6-triisopropylbiphenyl (34.3 mg, 0.072 mmL) were added into a solution of 3-bromo-9-chloro-6,6-dimethyl-8-(4-morpholinopiperidin-1-yl)-5,6-dihydro-11H-benzo[b]carbaz ol-11-one (100 mg, 0.18 mmol), ethynyltrimethylsilane (353 mg, 3.6 mmol) and tripotassium phosphate (127.2 mg, 0.6 mmol) in acetonitrile (8.0 mL). The mixture was stirred for 18 hours at 80° C. under the protection of nitrogen. The reaction solution was filtered, and the filter cake was washed with dichloromethane. The filtrate was concentrated at reduced pressure to obtain a crude product. The crude product was purified by silica gel column chromatography (dichloromethane:methanol=10:1) to obtain 9-chloro-6,6-dimethyl-8-(4-morpholinopiperidin-1-yl)-3-((trimethylsilyl)ethynyl)-5,6-dihydro-11H-benzo[b]carbazol-11-one as a brown solid (40 mg, with a yield of 39%). MS (ESI) m/z: 560.2 $(M+H)^+$.

9-chloro-8-(4-cyclopropylpiperazin-1-yl)-3-(3-hydroxyprop-1-yn-1-yl)-6,6-dimethyl-5,6-dihydro-11H-benzo[b]carbazol-11-one

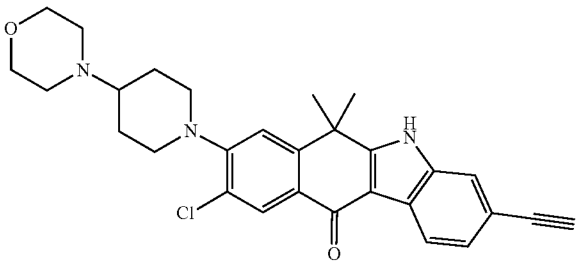 [SMILES: C#Cc1ccc2c3c([nH]c2c1)C(C)(C)c1cc(N2CCC(N4CCOCC4)CC2)c(Cl)cc1C3=O]

9-chloro-6,6-dimethyl-8-(4-morpholinopiperidin-1-yl)-3-((trimethylsilyl)ethynyl)-5,6-dihydro-11H-benzo[b]carbazol-11-one (40 mg, 0.07 mmol) and potassium carbonate (60 mg, 0.43 mmol) were added into methanol (20 mL). The above solution was stirred for 2 hour at room temperature. The reaction solution was filtered, and the filtrate was concentrated to dryness at reduced pressure to obtain a crude product. The crude product was purified by Prep-HPLC to obtain 9-chloro-8-(4-cyclopropylpiperazin-1-yl)-3-(3-hydroxyprop-1-yn-1-yl)-6,6-dimethyl-5,6-dihydro-11H-benzo[b]carbazol-11-one as a white solid (4.0 mg, with a yield of 11%). 1H NMR (400 MHz, DMSO-$d_6$) δ 12.45 (s, 1H), 8.31 (s, 1H), 8.13 (d, J=7.6 Hz, 1H), 8.08 (s, 1H), 7.60 (s, 1H), 7.42 (s, 1H), 7.32 (dd, J=1.2, 6.8 Hz, 1H), 4.13 (s, 1H), 3.60-3.40 (m, 7H), 2.84-2.78 (m, 2H), 2.38-2.32 (m, 2H), 1.94-1.91 (m, 2H), 1.77 (s, 6H). 1.62-1.52 (m, 2H).

Example 24

9-chloro-3-ethynyl-6,6-dimethyl-8-(piperazin-1-yl)-5,6-dihydro-11H-benzo[b]carbazol-11-one (E24)

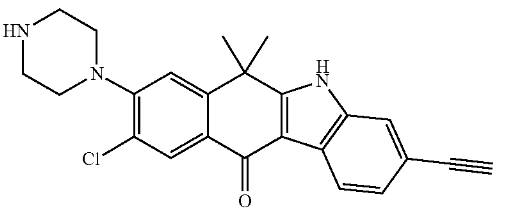

E24

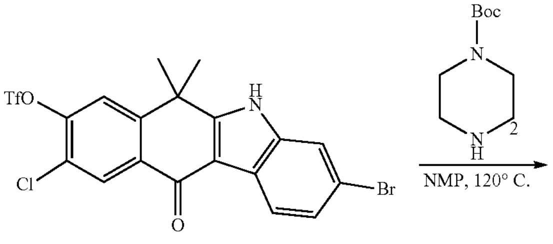

19-6

-continued

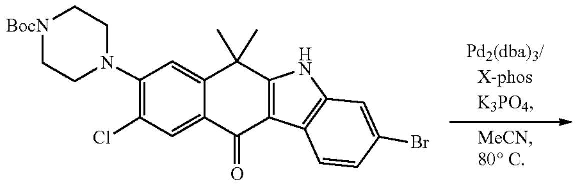

24-1

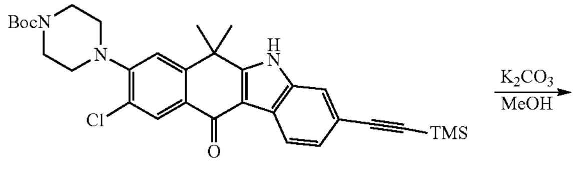

24-2

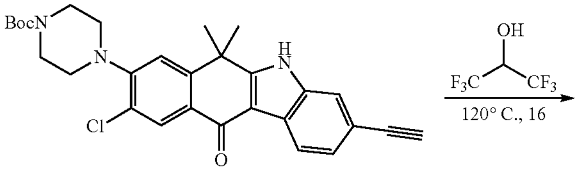

24-3

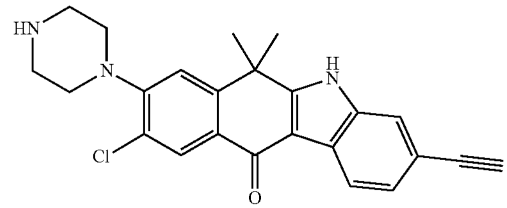

E24

Tert-butyl 4-(3-bromo-9-chloro-6,6-dimethyl-11-oxo-6,11-dihydro-5H-benzo[b]carbazol-8-yl) piperazine-1-carboxylate

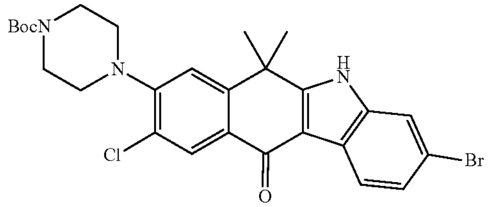 [SMILES: CC(C)(C)OC(=O)N1CCN(c2cc3c(cc2Cl)C(=O)c2c([nH]c4cc(Br)ccc24)C3(C)C)CC1]

3-bromo-9-chloro-6,6-dimethyl-11-oxo-6,11-dihydro-5H-benzo[b]carbazol-8-yl trifluoromethanesulfonate (500 mg, 0.96 mmol) and tert-butyl piperazine-1-carboxylate (3.56 g, 19 mmol) were added into N-methylpyrrolidone (5 mL). The above mixture was heated to 120° C. and stirred for 16 hours. The reaction solution was cooled to room temperature and then purified by Prep-HPLC to obtain tert-butyl 4-(3-bromo-9-chloro-6,6-dimethyl-11-oxo-6,11-dihydro-5H-benzo[b]carbazol-8-yl)piperazine-1-carboxylate as a white solid (200 mg, with a yield of 37%). MS (ESI) m/z: 558.1 $(M+H)^+$.

Tert-butyl 4-(9-chloro-6,6-dimethyl-11-oxo-3-((trimethylsilyl)ethynyl)-6,11-dihydro-5H-benzo[b]carbazol-8-yl) piperazine-1-carboxylate

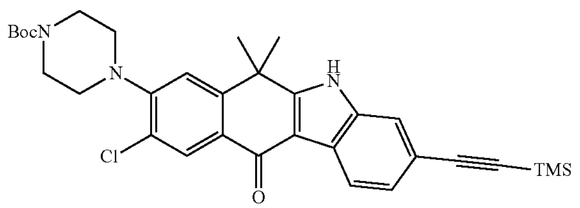 [SMILES: CC(C)(C)OC(=O)N1CCN(c2cc3c(cc2Cl)C(=O)c2c([nH]c4cc(C#C[Si](C)(C)C)ccc24)C3(C)C)CC1]

Tris(dibenzylideneacetone) dipalladium (27.5 mg, 0.03 mmol) and 2-dicyclohexylphosphino-2,4,6-triisopropylbiphenyl (28.6 mg, 0.06 mmL) were added into a solution of tert-butyl 4-(3-bromo-9-chloro-6,6-dimethyl-11-oxo-6,11-dihydro-5H-benzo[b]carbazol-8-yl)piperazine-1-carboxylate (100 mg, 0.18 mmol), ethynyltrimethylsilane (352.8 mg, 3.6 mmol) and tripotassium phosphate (95.4 mg, 0.45 mmol) in acetonitrile (8.0 mL). The mixture was stirred for 18 hours at 80° C. under the protection of nitrogen. The reaction solution was filtered. The filter cake was washed with dichloromethane, and the filtrate was concentrated at reduced pressure to obtain a crude product. The crude product was purified by silica gel column chromatography (dichloromethane:methanol=10:1) to obtain tert-butyl 4-(9-chloro-6,6-dimethyl-11-oxo-3-((trimethylsilyl)ethynyl)-6,11-dihydro-5H-benzo[b]carbazol-8-yl)piperazine-1-carboxylate as a yellow solid (70 mg, with a yield of 68%). MS (ESI) m/z: 576.2 $(M+1)^+$.

Tert-butyl 4-(9-chloro-3-ethynyl-6,6-dimethyl-11-oxo-6,11-dihydro-5H-benzo[b]carbazol-8-yl) piperazine-1-carboxylate

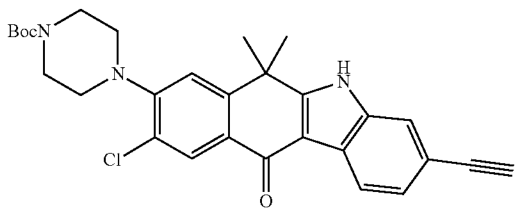 [SMILES: C#Cc1ccc2c3c([nH]c2c1)C(C)(C)c1cc(N2CCN(C(=O)OC(C)(C)C)CC2)c(Cl)cc1C3=O]

Tert-butyl 4-(9-chloro-6,6-dimethyl-11-oxo-3-((trimethylsilyl)ethynyl)-6,11-dihydro-5H-benzo[b]carbazol-8-yl) piperazine-1-carboxylate (70 mg, 0.07 mmol) and potassium carbonate (60 mg, 0.43 mmol) were added into methanol (20 mL). The above solution was stirred for 2 hour at room temperature. The reaction solution was filtered, and the filtrate was concentrated to dryness at reduced pressure to obtain a crude product. The crude product was purified by Prep-HPLC to obtain tert-butyl 4-(9-chloro-3-ethynyl-6,6-dimethyl-11-oxo-6,11-dihydro-5H-benzo[b]carbazol-8-yl) piperazine-1-carboxylate as a white solid (30 mg, with a yield of 41%). MS (ESI) m/z: 504.2 $(M+H)^+$.

9-chloro-3-ethynyl-6,6-dimethyl-8-(piperazin-1-yl)-5,6-dihydro-11H-benzo[b]carbazol-11-one

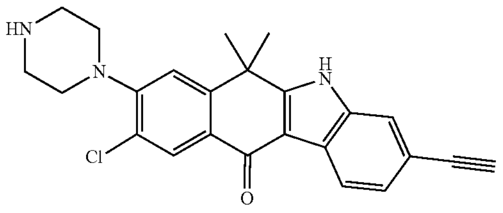 [SMILES: C#Cc1ccc2c3c([nH]c2c1)C(C)(C)c1cc(N2CCNCC2)c(Cl)cc1C3=O]

Tert-butyl 4-(9-chloro-3-ethynyl-6,6-dimethyl-11-oxo-6,11-dihydro-5H-benzo[b]carbazol-8-yl) piperazine-1-carboxylate (30 mg, 0.059 mmol) was added into 1,1,1,3,3,3-hexafluoropropan 2-ol (2.0 mL). The above mixture was heated to 120° C. and stirred for 16 hours. The reaction solution was concentrated to remove the solvent to obtain a crude product, and the crude product was purified by Prep-HPLC (acetonitrile/water/0.1% formic acid) to obtain 9-chloro-3-ethynyl-6,6-dimethyl-8-(piperazin-1-yl)-5,6-dihydro-11H-benzo[b]carbazol-11-one as a white solid (7.1 mg, with a yield of 29%). 1H NMR (400 MHz, DMSO-$d_6$) δ 12.48 (s, 1H), 8.28 (s, 1H), 8.14 (d, J=7.6 Hz, 1H), 8.08 (s, 1H), 7.60 (s, 1H), 7.41 (s, 1H), 7.32 (dd, J=1.2, 6.8 Hz, 1H), 4.13 (s, 1H), 3.10 (br, 4H), 2.90 (br, 4H), 1.76 (s, 6H).

Example 25

8-(4-(azetidin-1-yl)piperidin-1-yl)-9-chloro-3-ethynyl-6,6-dimethyl-5,6-dihydro-11H-benzo[b]carbazol-11-one (E25)

E25

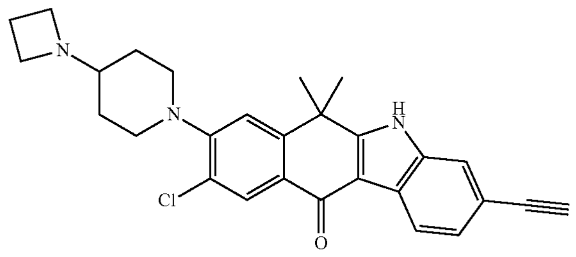

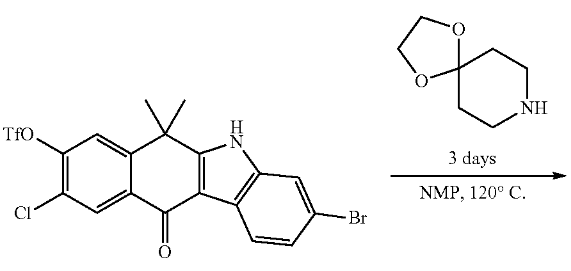

19-6

-continued

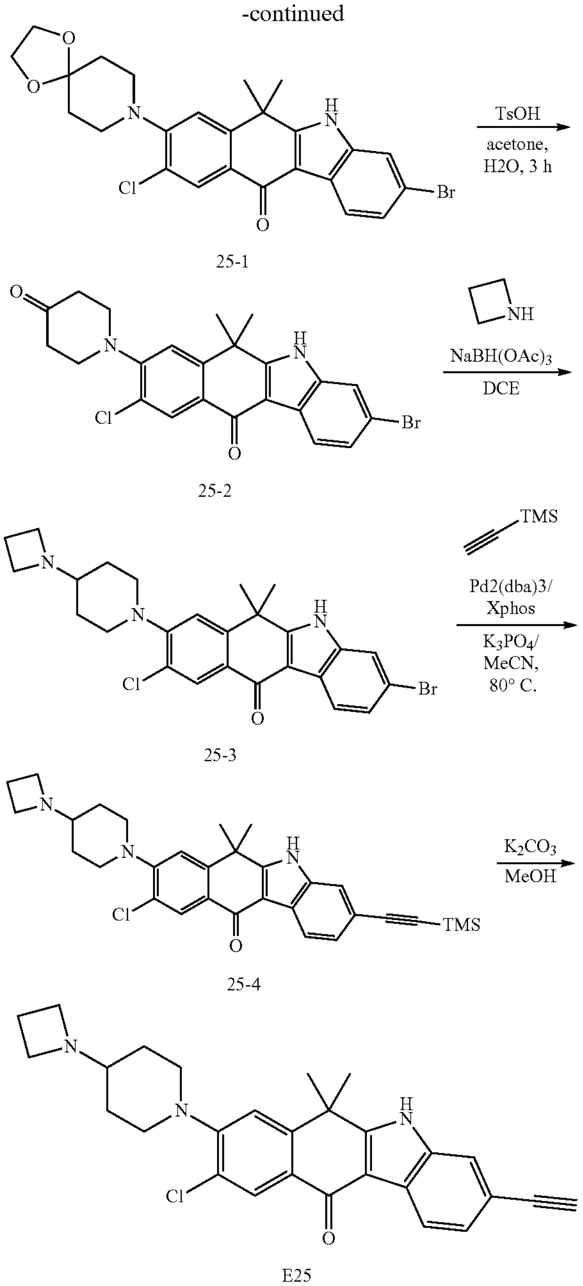

25-1

25-2

25-3

25-4

E25

3-bromo-9-chloro-6,6-dimethyl-8-(1,4-dioxa-8-azaspiro[4.5]decan-8-yl)-5,6-dihydro-11H-benzo[b]carbazol-11-one

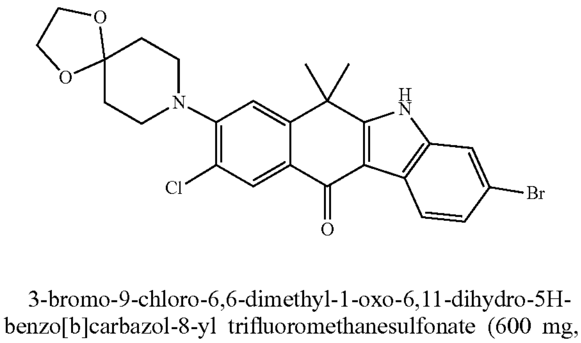

3-bromo-9-chloro-6,6-dimethyl-1-oxo-6,11-dihydro-5H-benzo[b]carbazol-8-yl trifluoromethanesulfonate (600 mg, 1.15 mmol) and 1,4-dioxa-8-azaspiro[4.5]decane (3.3 g, 23 mmol) were dissolved in N-methylpyrrolidone (5 mL). The mixture was heated to 120° C. and stirred for 3 days. The reaction solution was cooled to room temperature to obtain a crude product, and the crude product was purified by Prep-HPLC to obtain 3-bromo-9-chloro-6,6-dimethyl-8-(1,4-dioxa-8-azaspiro[4.5]decan-8-yl)-5,6-dihydro-11H-benzo[b]carbazol-11-one as a white solid (200 mg, with a yield of 34%). MS (ESI) N/z: 515.1 $(M+H)^+$. 3-bromo-9-chloro-6,6-dimethyl-8-(4-oxopiperidin-1-yl)-5,6-dihydro-11H-benzo[b]carbazol-11-one

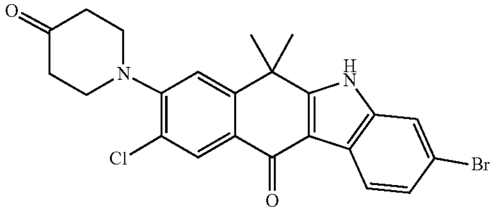 [SMILES: CC1(C)c2cc(N3CCC(=O)CC3)c(Cl)cc2C(=O)c2c1[nH]c1cc(Br)ccc21]

4-methyl benzenesulfonic acid (133 mg, 0.78 mmol) and water (3 mL) were added into a solution of 3-bromo-9-chloro-6,6-dimethyl-8-(1,4-dioxa-8-azaspiro[4.5]decan-8-yl)-5,6-dihydro-11H-benzo[b]carbazol-11-one (200 mg, 0.39 mmol) in acetone (20 mL). The above materials were heated, refluxed and stirred to react for 3 hours. The reaction solution was cooled to room temperature and then concentrated at reduced pressure to remove the solvent. The residue was dissolved with ethyl acetate (25 mL), washed with a saturated aqueous solution of sodium bicarbonate (2×10 mL), and dried with anhydrous sodium sulfate. The obtained product was filtered, and the filtrate was concentrated to dryness at reduced pressure to obtain 3-bromo-9-chloro-6,6-dimethyl-8-(4-oxopiperidin-1-yl)-5,6-dihydro-11H-benzo[b]carbazol-11-on e as a white solid (130 mg, with a yield of 31%). MS (ESI) m/z: 471.1 $(M+H)^+$. 8-(4-(azetidin-1-yl)piperidin-1-yl)-3-bromo-9-chloro-6,6-dimethyl-5,6-dihydro-11H-benzo[b]carb azol-11-one

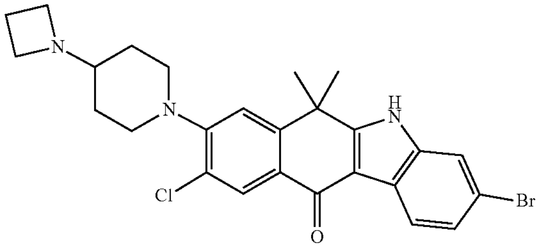 [SMILES: CC1(C)c2cc(N3CCC(N4CCC4)CC3)c(Cl)cc2C(=O)c2c1[nH]c1cc(Br)ccc21]

Acetic acid (5 drops) was added into a solution of 3-bromo-9-chloro-6,6-dimethyl-8-(4-oxopiperidin-1-yl)-5,6-dihydro-11H-benzo[b]carbazol-11-on e (130 mg, 0.27 mmol), azetidine (47 mg, 0.81 mmol) and anhydrous magnesium sulfate (50 mg, 0.42 mmoL) in 1,2-dichloroethane (5 mL). The above solution was stirred for 2 hour at room temperature. Sodium triacetoxyborohydride (114.5 mg, 0.54 mmol) was added. The above mixture was heated to 50° C. and stirred for 2 hours. The reaction solution was cooled to room temperature and then quenched with methanol. The solvent was removed by concentration at reduced pressure to obtain a crude product, and the crude product was purified by Prep-HPLC to obtain 8-(4-(azetidin-1-yl)piperidin-1-yl)-3-bromo-9-chloro-6,6-dimethyl-5,6-dihydro-11H-benzo[b]

carbazol-11-one as a yellow solid (100 mg, with a yield of 71%). MS (ESI) m/z: 512.1 $(M+H)^+$.

8-(4-(azetidin-1-yl)piperidin-1-yl)-9-chloro-6,6-dimethyl-3-((trimethylsilyl)ethynyl)-5,6-dihydro-11H-benzo[b]carbazol-11-one

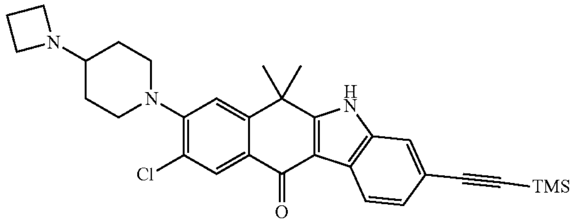 [SMILES: CC1(C)c2cc(N3CCC(N4CCC4)CC3)c(Cl)cc2C(=O)c2c1[nH]c1cc(C#C[Si](C)(C)C)ccc21]

Tris(dibenzylideneacetone) dipalladium (18 mg, 0.02 mmol) and 2-dicyclohexylphosphino-2,4,6-triisopropylbiphenyl (19 mg, 0.04 mmL) were added into a solution of 8-(4-(azetidin-1-yl)piperidin-1-yl)-3-bromo-9-chloro-6,6-dimethyl-5,6-dihydro-11H-benzo[b]carb azol-11-one (50 mg, 0.10 mmol), ethynyltrimethylsilane (196 mg, 2 mmol) and tripotassium phosphate (42.4 mg, 0.2 mmol) in acetonitrile (5 mL). The mixture was stirred for 18 hours at 80° C. under the protection of nitrogen. The reaction solution was filtered, the filter cake was washed with dichloromethane, and the filtrate was concentrated to dryness at reduced pressure to obtain a crude product. The crude product was purified by silica gel column chromatography (dichloromethane:methanol=10:1) to obtain 8-(4-(azetidin-1-yl)piperidin-1-yl)-9-chloro-6,6-dimethyl-3-((trimethylsilyl)ethynyl)-5,6-dihydro-11H-benzo[b]carbazol-11-one as a brown solid (40 mg, with a yield of 77%). MS (ESI) m/z: 530.3 $(M+H)^+$.

9-chloro-8-(4-cyclopropylpiperazin-1-yl)-3-(3-hydroxyprop-1-yn-1-yl)-6,6-dimethyl-5,6-dihydro-11H-benzo[b]carbazol-11-one

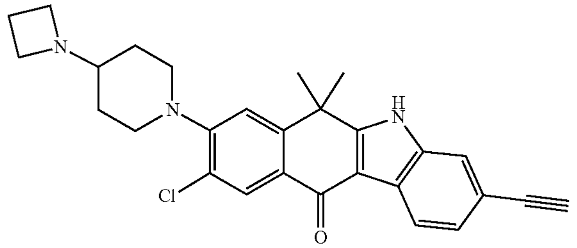 [SMILES: C#Cc1ccc2c3c([nH]c2c1)C(C)(C)c1cc(N2CCC(N4CCC4)CC2)c(Cl)cc1C3=O]

8-(4-(azetidin-1-yl)piperidin-1-yl)-9-chloro-6,6-dimethyl-3-((trimethylsilyl)ethynyl)-5,6-dihydro-11H-benzo[b]carbazol-11-one (40 mg, 0.075 mmol) and potassium carbonate (60 mg, 0.43 mmol) were dissolved in methanol (20 mL), and stirred for 2 hours at room temperature. The reaction solution was filtered, and the filtrate was concentrated to dryness at reduced pressure to obtain a crude product. The crude product was purified by Prep-HPLC to obtain 9-chloro-8-(4-cyclopropylpiperazin-1-yl)-3-(3-hydroxyprop-1-yn-1-yl)-6,6-dimethyl-5,6-dihydro-11H-benzo[b]carbazol-11-one as a brown solid (9.2 mg, with a yield of 27%). 1H NMR (400 MHz, DMSO-$d_6$) δ 12.47 (s, 1H), 10.21 (s, 1H), 8.13 (d, J=8.0 Hz, 1H), 8.10 (s, 1H), 7.61 (s, 1H), 7.44 (s, 1H), 7.33 (dd, J=1.6, 6.4 Hz, 1H), 4.21-4.01 (m, 5H), 3.59-3.50 (m, 2H), 2.83 (t, J=14.0 Hz, 2H), 2.40-2.32 (m 1H), 2.21-2.02 (m, 2H), 1.75 (s, 6H), 1.60-1.48 (m, 2H).

Example 26

3-(cyclopropylethynyl)-9-ethyl-6,6-dimethyl-8-(4-morpholinopiperidin-1-yl)-5,6-dihydro-11H-benzo[b]carbazol-11-one (E26)

E26

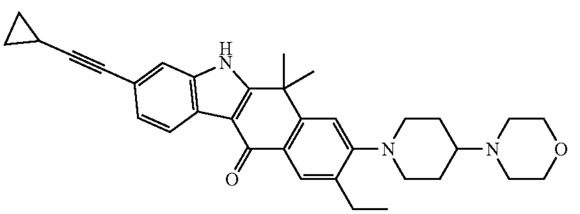

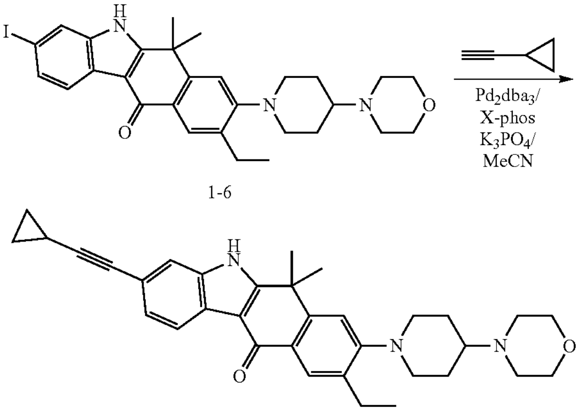

1-6

E26

3-(cyclopropylethynyl)-9-ethyl-6,6-dimethyl-8-(4-morpholinopiperidin-1-yl)-5,6-dihydro-11H-benzo[b]carbazol-11-one

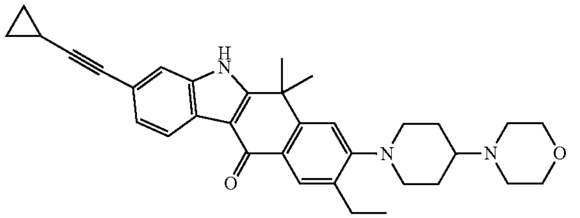 [SMILES: CCc1cc2c(cc1N1CCC(N3CCOCC3)CC1)C(C)(C)c1[nH]c3cc(C#CC4CC4)ccc3c1C2=O]

Tripotassium phosphate (42 mg, 0.20 mmol), 2-dicyclohexylphosphino-2,4,6-triisopropylbiphenyl (20 mg, 0.04 mmol) and tris(dibenzylideneacetone) dipalladium (20 mg, 0.02 mmol) were added into a solution of 9-ethyl-3-iodo-6,6-dimethyl-8-(4-morpholinopiperidin-1-yl)-5,6-dihydro-11H-benzo[b]carbazol-11-one (98 mg, 0.17 mmol) and ethynyl cyclopropane (2.0 mL, 70% toluene dissolved) in acetonitrile (10 mL). The mixture was stirred for 1 hour at 90° C. under the protection of argon, and the completion of the reaction was monitored by LCMS. The reaction solution was diluted with water, and extracted with ethyl acetate (2×100 mL). Organic phases were combined, washed with water (100 mL), washed with saturated brine (100 mL), dried with anhydrous sodium sulfate and filtered. The filtrate was concentrated to dryness at reduced pressure to obtain a crude product. The crude product was purified by Prep-HPLC to obtain 3-(cyclopropylethynyl)-9-ethyl-6,6-dimethyl-8-(4-morpholinopiperidin-1-yl)-5,6-dihydro-11H-benzo[b]carbazol-11-one as a grey white solid (22 mg, with a yield of 27.5%). 1H NMR (400 MHz, DMSO-$d_6$): δ 12.28 (s, 1H), 8.09 (d, J=8.4 Hz, 1H), 8.02 (s, 1H), 7.46 (s, 1H), 7.32 (s, 1H), 7.20 (d, J=8.0 Hz, 1H), 3.61-3.60 (m, 4H), 3.22-3.19 (m, 2H), 2.78-2.64 (m, 6H), 2.56-2.50 (m, 2H), 2.33-2.31 (m, 1H), 1.93-1.90 (m, 2H), 1.71 (s, 6H), 1.64-1.60 (m, 3H), 1.27 (t, J=6.0 Hz, 3H), 0.90-0.88 (m, 2H), 0.76-0.75 (m, 1H).

Example 27

9-ethyl-6,6-dimethyl-8-(4-morpholinopiperidin-1-yl)-3-(prop-1-yn-1-yl)-5,6-dihydro-11H-benzo[b]carbazol-11-one (E27)

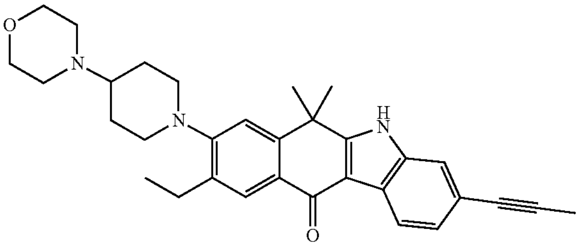

E27

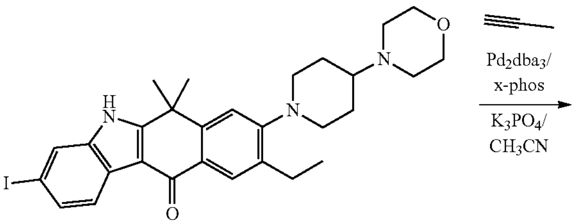

1-6

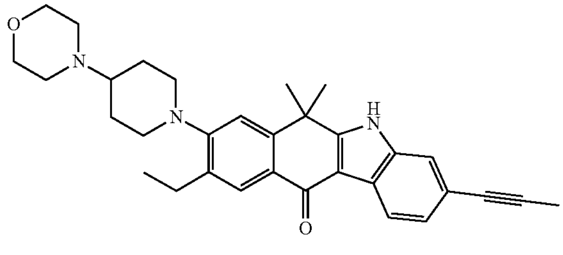

E27

9-ethyl-6,6-dimethyl-8-(4-morpholinopiperidin-1-yl)-3-(prop-1-yn-1-yl)-5,6-dihydro-11H-benzo[b]carbazol-11-one

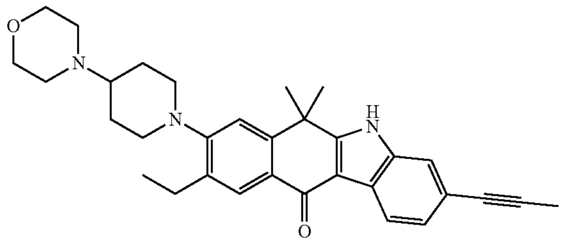 [SMILES: CC#Cc1ccc2c3c([nH]c2c1)C(C)(C)c1cc(N2CCC(N4CCOCC4)CC2)c(CC)cc1C3=O]

Tripotassium phosphate (20 mg, 0.10 mmol), 2-dicyclohexylphosphino-2,4,6-triisopropylbiphenyl (10 mg, 0.02 mmol) and tris(dibenzylideneacetone) dipalladium (10 mg, 0.01 mmol) were added into a solution of 9-ethyl-3-iodo-6,6-dimethyl-8-(4-morpholinopiperidin-1-yl)-5,6-dihydro-11H-benzo[b]carbazol-11-one (50 mg, 0.08 mmol) and prop-1-yne (3 mL, 4% DMF) in acetonitrile (10 mL). A reaction was conducted for 1 hour with stirring at 60° C. under the protection of argon, and the completion of the reaction was monitored by LCMS. The reaction solution was diluted with water, and extracted with ethyl acetate (2×50 mL). Organic phases were combined, washed with water (50 mL), washed with saturated brine (50 mL), and dried with anhydrous sodium sulfate and filtered.

The filtrate was concentrated to dryness at reduced pressure to obtain a crude product. The crude product was purified by Prep-HPLC to obtain 9-ethyl-6,6-dimethyl-8-(4-morpholinopiperidin-1-yl)-3-(prop-1-yn-1-yl)-5,6-dihydro-11H-benzo[b]carbazol-11-one as a grey white solid (8.0 mg, with a yield of 18.8%). 1H NMR (400 MHz, DMSO-$d_6$): δ 12.22 (s, 1H), 8.11 (d, J=8.4 Hz, 1H), 8.03 (s, 1H), 7.48 (s, 1H), 7.32 (s, 1H), 7.23 (d, J=6.8 Hz, 1H), 3.65-3.60 (m, 4H), 3.24-3.19 (m, 2H), 2.79-2.76 (m, 4H), 2.73-2.69 (m, 4H), 2.35-2.32 (m, 1H), 2.07 (s, 1H), 1.92-1.90 (m, 2H), 1.72 (s, 6H), 1.61-1.56 (m, 2H), 1.27 (t, J=6.0 Hz, 3H).

Example 28

3-ethynyl-6,6-dimethyl-8-(4-(methylamino)piperidin-1-yl)-11-oxo-6,11-dihydro-5H-benzo[b]carbazole-9-carbonitrile (E28)

E28

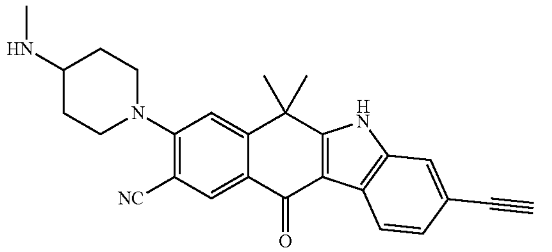

-continued

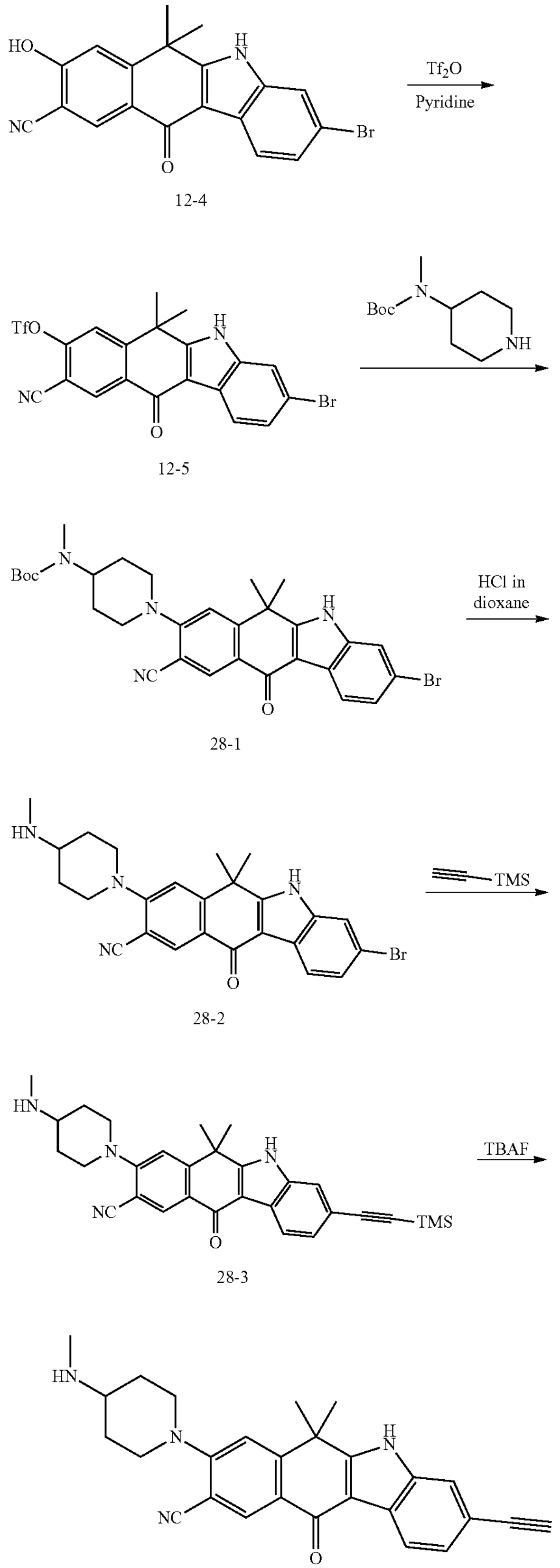

3-bromo-9-cyano-6,6-dimethyl-11-oxo-6,11-dihydro-5H-benzo[b]carbazol-8-yl trifluoromethanesulfonate

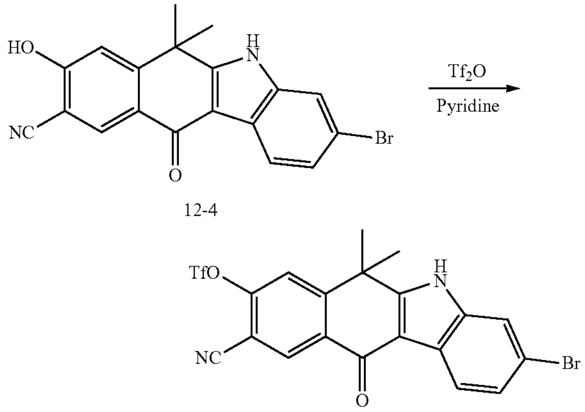

12-4

12-5

3-bromo-8-hydroxy-6,6-dimethyl-11-oxo-6,11-dihydro-5H-benzo[b]carbazole-9-carbonitrile (15 g, 39.5 mmol) and pyridine (12.5 g, 158 mmol) were added into dichloromethane (200 mL), cooled to 0-10 degrees, then trifluoromethanesulfonic anhydride (44.6 g, 158 mmol) was dropwise added, and a reaction was performed at room temperature for 3 hours. The reactants were completely extracted with dichloromethane and water. The extracted product was subjected to concentration and rotary drying by a column (petroleum ether:ethyl acetate=2:1) to obtain 3-bromo-9-cyano-6,6-dimethyl-11-oxo-6,11-dihydro-5H-benzo[b]carbazol-8-yl trifluoromethanesulfonate as a light yellow solid (9.0 g, 17.5 mmol, with a yield of 44.4%). 1H NMR (400 MHz, DMSO-$d_6$) δ 12.66 (s, 1H), 8.73 (s, 1H), 8.41 (d, J=13.0 Hz, 1H), 8.10 (d, J=8.4 Hz, 1H), 7.73 (d, J=1.5 Hz, 1H), 7.44 (dt, J=16.6, 8.3 Hz, 1H), 1.82 (s, 6H). Tert-butyl (1-(3-bromo-9-cyano-6,6-dimethyl-11-oxo-6,11-dihydro-5H-benzo[b]carbazol-8-yl) piperidin-4-yl)methyl carbamate

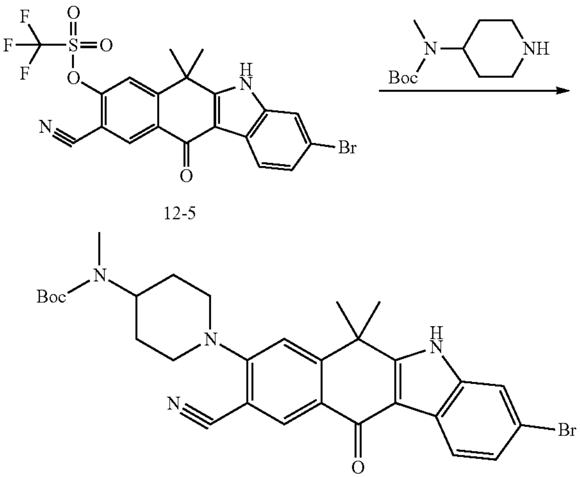

12-5

28-1

Tert-butyl methylpiperidine carbamate (18.7 g, 87.5 mmol) was stirred in an N-methylpyrrolidone solution (50 mL) at room temperature. Then, 3-bromo-9-cyano-6,6-dimethyl-11-oxo-6,11-dihydro-5H-benzo[b]carbazol-8-yl trifluoromethanesulfonate (9.0 g, 17.5 mmol) was added at 120° C., and the resulting mixture was stirred at 120° C. for 5 h in a nitrogen atmosphere. The completion of the reaction was monitored by LCMS. The reaction solution was cooled to room temperature and poured into water (500 mL), and filtered and washed with MeOH. After drying, tert-butyl (1-(3-bromo-9-cyano-6,6-dimethyl-11-oxo-6,11-dihydro-5H-benzo[b]carbazol-8-yl)piperidin-4-yl)methyl carbamate (8.2 g, 14.2 mmol, with a yield of 81.2%) was obtained as a yellow solid.

3-bromo-6,6-dimethyl-8-(4-(methylamino) piperidin-1-yl)-11-oxo-6,11-dihydro-5H-benzo[b]carba zole-9-carbonitrile

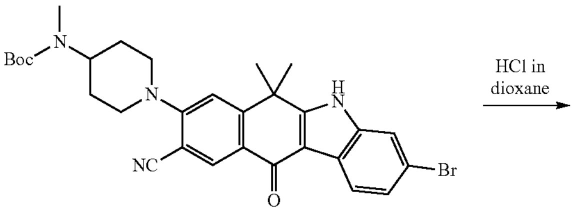

28-1

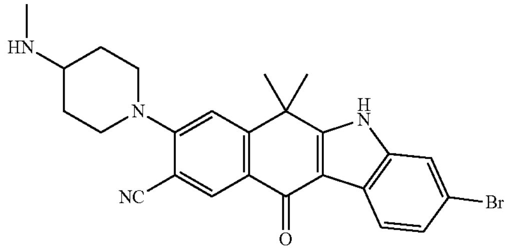

28-2

Tert-butyl (1-(3-bromo-9-cyano-6,6-dimethyl-11-oxo-6,11-dihydro-5H-benzo[b]carbazol-8-yl)piperidin-4-yl)methyl carbamate (8.2 g, 14.2 mmol) was added into a solution of dioxane hydrochloric acid (4M, 250 mL). The obtained mixture was stirred for 16 hours at room temperature and then concentrated until dry to obtain 3-bromo-6,6-dimethyl-8-(4-(methylamino)piperidin-1-yl)-11-oxo-6,11-dihydro-5H-benzo[b] carba zole-9-carbonitrile as a yellow solid (8.2 g, 17.2 mmol, with a yield of 100%).

6,6-dimethyl-8-(4-(methylamino)piperidin-1-yl)-11-oxo-3-((trimethylsilyl)ethynyl)-6,11-dihydro-5H-benzo[b]carbazole-9-carbonitrile

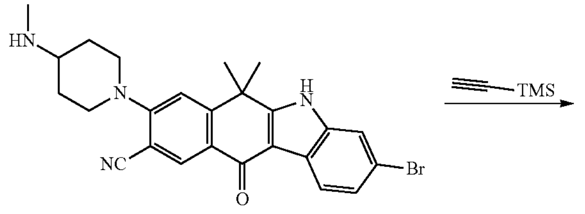

28-2

-continued

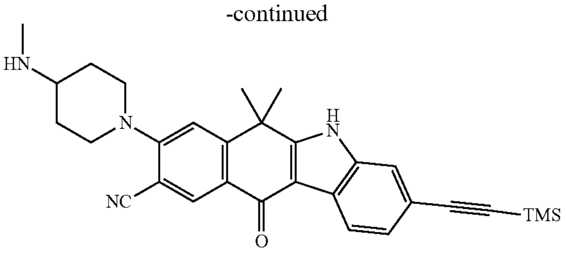

28-3

Ethynyltrimethylsilane (16.9 g, 172 mmol) was added into a solution of 3-bromo-6,6-dimethyl-8-(4-(methylamino)piperidin-1-yl)-11-oxo-6,11-dihydro-5H-benzo[b] carba zole-9-carbonitrile (8.2 g, 17.2 mmol) in acetonitrile (250 mL) and DMF (50 mL), and then $Pd_2(dba)_3$ (1.58 mg, 1.72 mmol), X-phos (1.64 g, 3.44 mmol), and tripotassium phosphate (21.9 g, 103.2 mol) were added in a nitrogen atmosphere. The obtained mixture was heated and stirred for 16 h at 90° C. After the completion of the reaction was monitored by LCMS, the reactant was filtered, washed with a mixture of dichloromethane and methanol. The solution was concentrated and purified by a column (methanol in dichloromethane:0-25%) to obtain 6,6-dimethyl-8-(4-(methylamino)piperidin-1-yl)-11-oxo-3-((trimethylsilyl) ethynyl)-6,11-dihydro-5H-benzo[b]carbazole-9-carbonitrile as a yellow solid (7.1 g, 14.4 mmol, with a yield of 83.7%).

3-ethynyl-6,6-dimethyl-8-(4-(methylamino)piperidin-1-yl)-11-oxo-6,11-dihydro-5H-benzo[b]carb azole-9-carbonitrile

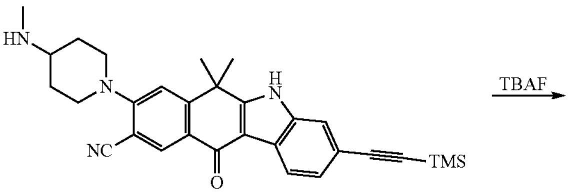

28-3

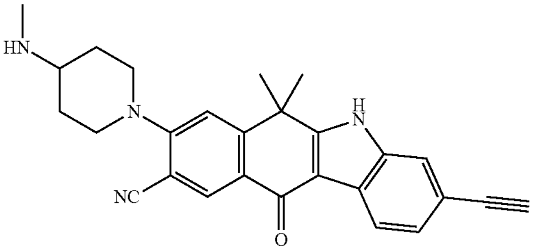

E28

6,6-dimethyl-8-(4-(methylamino)piperidin-1-yl)-11-oxo-3-((trimethylsilyl)ethynyl)-6,11-dihydro-5H-benzo[b]carbazole-9-carbonitrile (7.1 g, 14.4 mmol) was added into a tetrabutyl ammonium fluoride solution of tetrahydrofuran (1M, 144 mL, 14.4 mmol), and stirred at room temperature for 2 h. The completion of the reaction was monitored by LCMS. The reaction solution was poured into ice water (150 mL) and extracted with ethyl acetate (300 mL×2). Organic phases were combined, washed with saturated brine (300 mL), dried with anhydrous sodium sulfate, filtered, and concentrated to obtain a residue. The residue was purified by column (a dichloromethane solution of methanol: 0-25%) to obtain a crude product. The crude product was purified by preparative HPLC ($NH_3$, $H_2O$) to obtain 3-ethynyl-6,6-dimethyl-8-(4-(methylamino)piperidin-1-yl)-11-oxo-6,11-dihydro-5H-benzo[b]carb azole-9-carbonitrile as a light yellow solid (2.0 g, 4.73 mmol, with a yield of 32.8%). HPLC:254 nm:98.76%, 214 nm:99.00%. 1H NMR (400 MHz, DMSO) δ 12.33 (s, 1H), 8.33 (s, 1H), 8.14 (d, J=8.1 Hz, 1H), 7.60 (s, 1H), 7.39 (s, 1H), 7.33 (dd, J=8.1, 1.3 Hz, 1H), 4.13 (s, 1H), 3.72 (d, J=12.6 Hz, 2H), 3.07 (t, J=10.6 Hz, 2H), 2.54 (s, 1H), 2.32 (s, 3H), 1.97 (d, J=10.6 Hz, 2H), 1.77 (s, 6H), 1.44 (dd, J=20.0, 9.6 Hz, 2H).

Biological Assessments

1. ALK Kinase Inhibition Test

The inhibitory activity of the compound in the present application on ALK kinase will be determined through in vitro tests, which can be represented by IC50 value. The half-maximal inhibitory concentration IC50 of a compound (the concentration of a compound required to inhibit the activity of an enzyme at a certain concentration by 50%) is measured and calculated by mixing different compounds to be tested with a certain amount of kinase and a specific substrate to perform a reaction.

The specific experimental process was as follows: a test compound was formulated into a 10 mM mother solution with DMSO, stored at −20° C. after sub-packaging; the mother solution was thawed before use, diluted to 1 mM with DMSO, and then diluted with 1× kinase buffer (containing 50 mM 4-hydroxyethyl piperazine ethanesulfonic acid pH 7.0, 0.02% $NaN_3$, 0.01% BSA, 0.1 mM ortho-vanadate, 5 mM $MgCl_2$, 1 mM DTT, 37.5 nM supplementary enzyme buffer) by 40 times. 4 μL of the diluted solution of the test compound and 2 μL of 0.4 ng/well ALK kinase solution (Thermo Scientific) were added into reaction wells in turn, incubated for 10 min at room temperature, then 4 μL of 0.7 μM biotin-labeled tyrosine kinase substrate and 5 μM ATP solution were added to start the kinase reaction. After the reaction, 5 μL of 43.75 nM streptavidin-labeled XL665 was added, the materials were evenly mixed and then 5 μL of 0.04 nM europium-labeled tyrosine kinase antibody detection solution was imeddiately added. After reacting at room temperature for 1 hour, a fluorescence signal was detected using a SpectraMax i3× instrument (excited at 320 nm, emitted at 665 nm, 615 nm). Finally, the inhibitory rate of the test compound on ALK kinase activity was calculated according to the following equation:

Emission coefficient($ER$)=665 nm emission light signal/615 nm emission light signal Inhibition rate $\%=(ERv-ERs)/(ERv-ERb)\times 100\%$ ERs: ER of a sample processing group ERv: ER of a solvent control group ERb: ER of a blank group Software Graphpad Prism 6 was used to fit an IC50 curve and calculate an IC50 value. The calculation results are shown in Table 1.

From the data in Table 1, it can be seen that the compound provided in the present application has a significant inhibitory effect on ALK kinase activity.

Where, kinase buffer is represented by Kinase Buffer;

4-hydroxyethyl piperazine ethanesulfonic acid is represented by HEPES; Ortho-vanadate is represented by ortho-vanadate;

Supplement enzyme buffer is represented by SEB;

Biotin-labeled tyrosine kinase substrate is represented by TK-biotin substrate; Streptavidin-labeled XL665 is represented by Streptavidin-XL665;

Europium-labeled tyrosine kinase antibody is represented by TK antibody europium cryptate; 2. ALK gene fusion cell proliferation inhibition test The inhibitory activity of the compound according to the present application on proliferation of human anaplastic large cell lymphoma cell Karpas 299 with high expression of ALK gene fusion will be determined through in vitro experiments, which can be represented by IC50 value.

The specific experimental process was as follows: human anaplastic large cell lymphoma cell Karpas 299 in logarithmic growth phase was collected, adjusted to an appropriate concentration, and the appropriate concentration of cells were inoculated into a a 96-well culture plate, and 100 μL of cell suspension was added into to each well.

The 96-well culture plate was placed in a 5% carbon dioxide incubator at 37° C. to be cultured overnight. A test compound was formulated into a 10 mM storage solution with DMSO, and the 10 mM storage solution was gradually diluted with DMSO at a dilution ration of 1:4 to obtain 9 concentration gradients of solutions of the test compound. The test compound was diluted with culture medium to 5 times the set final concentration of corresponding action, and the diluted solution of the test compound was added at 25 μL/well to corresponding cell wells according to the set compound layout, and then incubated in a 5% carbon dioxide incubator at 37° C. for 72 hours. After 72 hours, 10 μL of CCK-8 was added into a cell culture medium, and the culture solution was sucked from adherent cells, then a freshly prepared CCK-8 detection solution was added and the cells were incubated in a 37° C. incubator for 1-4 hours. The absorbance at 450 nm wavelength on the SpectraMax i3× Microplate Reader was measured after gently shaking, with the absorbance at 650 nm as a reference. Finally, the inhibitory rate of the test compound on the proliferation of human anaplastic large cell lymphoma cell Karpas 299 was calculated according to the following equation:

$$\text{Cell proliferation inhibition rate } \% = [(Av-As)/(As-Ab)]\times 100\%$$

As: absorbance of sample treated cells (sample treatment group) (cells+CCK-8+to-be-tested compound)

Av: absorbance of solvent treated cells (solvent control group) (cells+CCK-8+DMSO)

Ab: absorbance ofcell-free blank control (blank group) (culture medium+CCK-8+DMSO) Software Graphpad Prism 6 was used to fit an IC50 curve and calculate an IC50 value. The calculation results were shown in Table 1.

From the data in Table 1, it can be seen that the compound provided in the present application has significant proliferation inhibitory activity on human anaplastic large cell lyinphoma cell Karpas 299.

TABLE 1
Test results of biological assessments
| Patent ID | Structure | MW | $IC_{50}$ value ALK (nM) | IC50 value Karpas 299 (nM) |
|---|---|---|---|---|
| Control group | 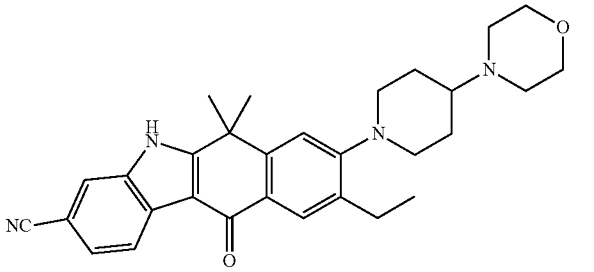 [SMILES: CCc1cc2c(cc1N1CCC(N3CCOCC3)CC1)C(C)(C)c1[nH]c3cc(C#N)ccc3c1C2=O] | 482.63 | 60.24 | 205.78 |
| E1 | 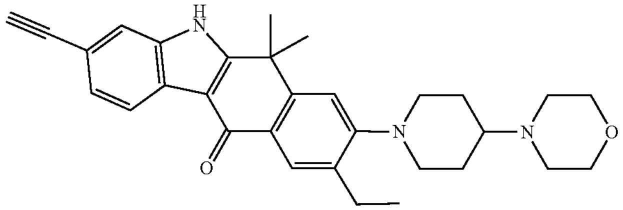 [SMILES: C#Cc1ccc2c3c([nH]c2c1)C(C)(C)c1cc(N2CCC(N4CCOCC4)CC2)c(CC)cc1C3=O] | 481.6 | 5.089 | 7.343 |
| E2 | 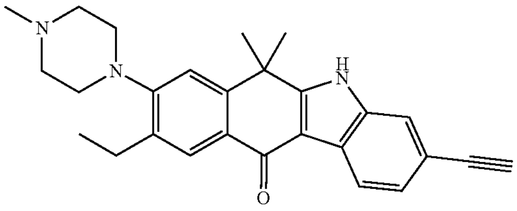 [SMILES: C#Cc1ccc2c3c([nH]c2c1)C(C)(C)c1cc(N2CCN(C)CC2)c(CC)cc1C3=O] | 411.55 | 7.385 | 18.123 |
| E12 | 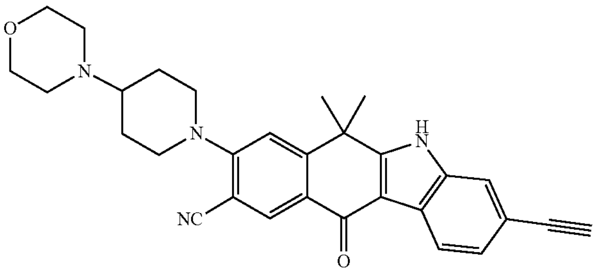 | 478.6 | 6.78 | 8.713 |
| E3 | 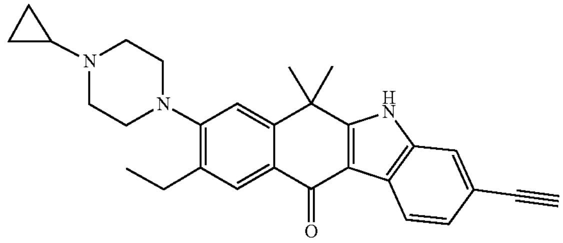 [SMILES: C#Cc1ccc2c3c([nH]c2c1)C(C)(C)c1cc(N2CCN(C4CC4)CC2)c(CC)cc1C3=O] | 483.61 | 37.85 | 144.1 |
| E4 | 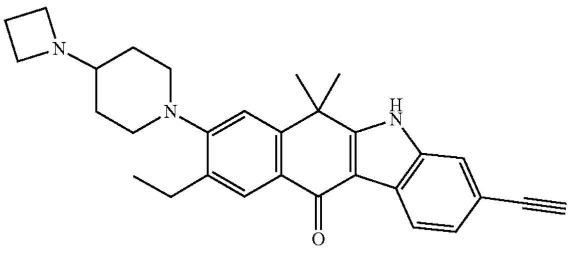 [SMILES: C#Cc1ccc2c3c([nH]c2c1)C(C)(C)c1cc(N2CCC(N4CCC4)CC2)c(CC)cc1C3=O] | 451.61 | 6.349 | 32.64 |

TABLE 1-continued
Test results of biological assessments
| Patent ID | Structure | MW | $IC_{50}$ value ALK (nM) | IC50 value Karpas 299 (nM) |
|---|---|---|---|---|
| E5 | 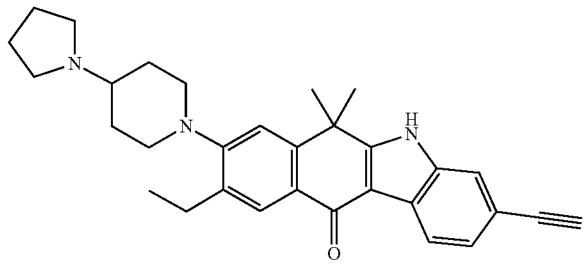 [SMILES: C#Cc1ccc2c3c([nH]c2c1)C(C)(C)c1cc(N2CCC(N4CCCC4)CC2)c(CC)cc1C3=O] | 465.64 | 13.77 | 24.92 |
| E6 | 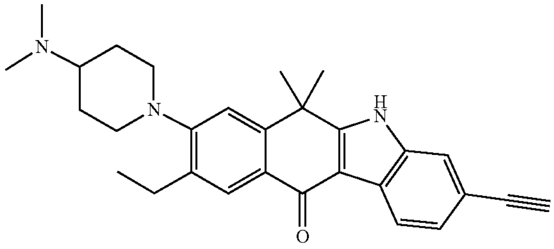 [SMILES: C#Cc1ccc2c3c([nH]c2c1)C(C)(C)c1cc(N2CCC(N(C)C)CC2)c(CC)cc1C3=O] | 439.6 | 20.99 | 107.2 |
| E7 | 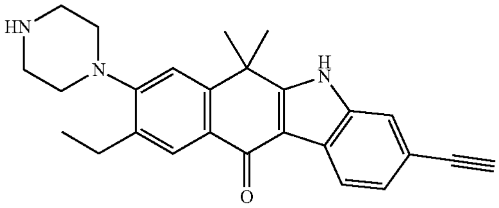 [SMILES: C#Cc1ccc2c3c([nH]c2c1)C(C)(C)c1cc(N2CCNCC2)c(CC)cc1C3=O] | 397.41 | 7.413 | 40.26 |
| E8 | 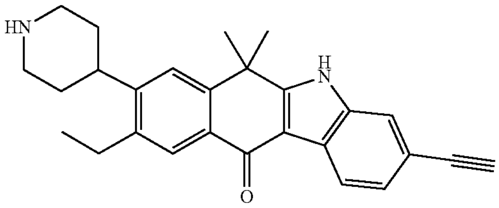 [SMILES: C#Cc1ccc2c3c([nH]c2c1)C(C)(C)c1cc(C2CCNCC2)c(CC)cc1C3=O] | 396.53 | 6.596 | 109 |
| E9 | 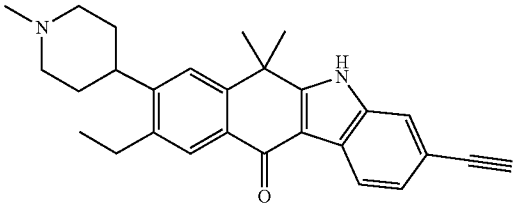 [SMILES: C#Cc1ccc2c3c([nH]c2c1)C(C)(C)c1cc(C2CCN(C)CC2)c(CC)cc1C3=O] | 410.56 | 8.106 | 54.21 |
| E13 | 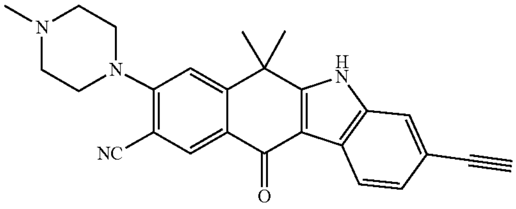 [SMILES: C#Cc1ccc2c3c([nH]c2c1)C(C)(C)c1cc(N2CCN(C)CC2)c(C#N)cc1C3=O] | 408.51 | 5.76 | 7.523 |

TABLE 1-continued
| Test results of biological assessments | | | | |
|---|---|---|---|---|
| Patent ID | Structure | MW | $IC_{50}$ value ALK (nM) | IC50 value Karpas 299 (nM) |
| E14 | 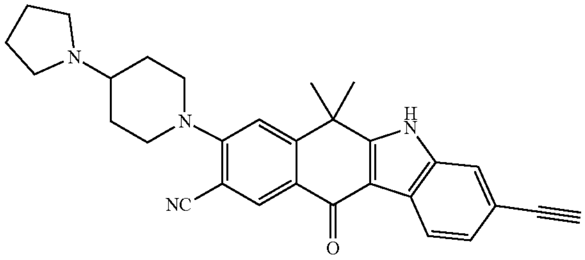 [SMILES: C#Cc1ccc2c3c([nH]c2c1)C(C)(C)c1cc(N2CCC(N4CCCC4)CC2)c(C#N)cc1C3=O] | 462.6 | 6.506 | 11.42 |
| E15 | 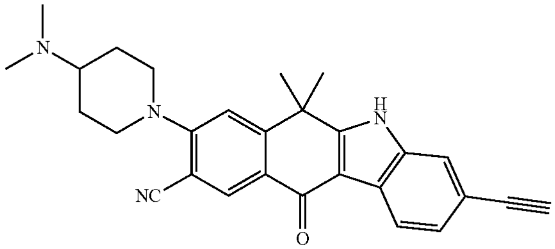 [SMILES: C#Cc1ccc2c3c([nH]c2c1)C(C)(C)c1cc(N2CCC(N(C)C)CC2)c(C#N)cc1C3=O] | 436.56 | 4.622 | 8.294 |
| E19 | 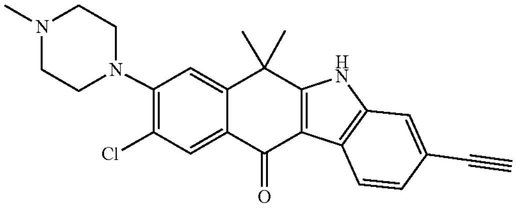 [SMILES: C#Cc1ccc2c3c([nH]c2c1)C(C)(C)c1cc(N2CCN(C)CC2)c(Cl)cc1C3=O] | 417.94 | 3.732 | 11.66 |
| E20 | 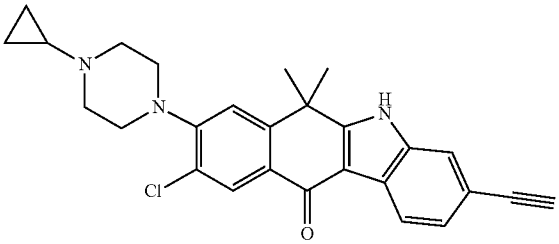 | 443.98 | 40.11 | 55.88 |
| E21 | 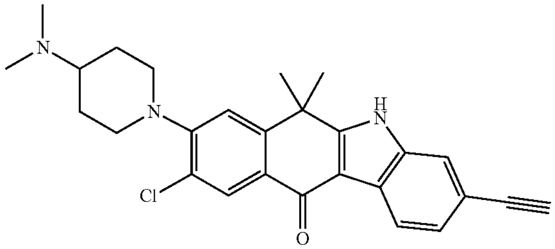 [SMILES: C#Cc1ccc2c3c([nH]c2c1)C(C)(C)c1cc(N2CCC(N(C)C)CC2)c(Cl)cc1C3=O] | 492.02 | 12.74 | 10.45 |

TABLE 1-continued
| Test results of biological assessments | | | | |
|---|---|---|---|---|
| Patent ID | Structure | MW | $IC_{50}$ value ALK (nM) | IC50 value Karpas 299 (nM) |
| E22 | 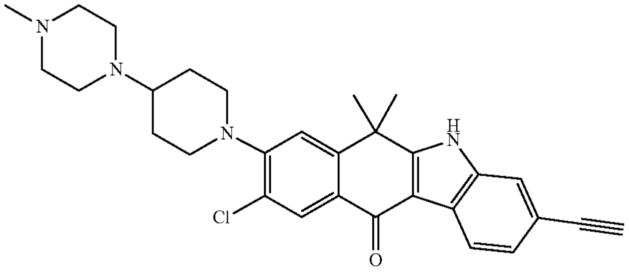 [SMILES: C#Cc1ccc2c3c([nH]c2c1)C(C)(C)c1cc(N2CCC(N4CCN(C)CC4)CC2)c(Cl)cc1C3=O] | 501.07 | 13.54 | 4.669 |
| E16 | 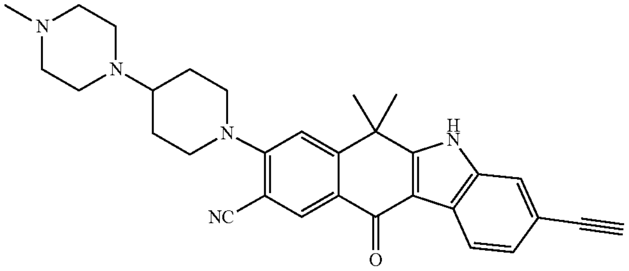 [SMILES: C#Cc1ccc2c3c([nH]c2c1)C(C)(C)c1cc(N2CCC(N4CCN(C)CC4)CC2)c(C#N)cc1C3=O] | 491.64 | 5.699 | 3.265 |
| E10 | 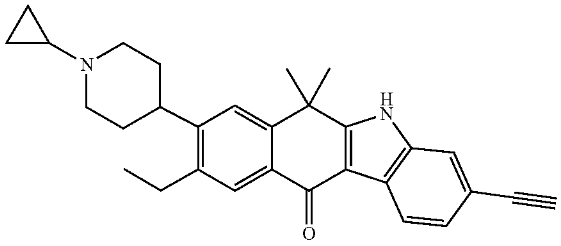 [SMILES: C#Cc1ccc2c3c([nH]c2c1)C(C)(C)c1cc(C2CCN(C4CC4)CC2)c(CC)cc1C3=O] | 436.6 | 20.48 | 208.5 |
| E11 | 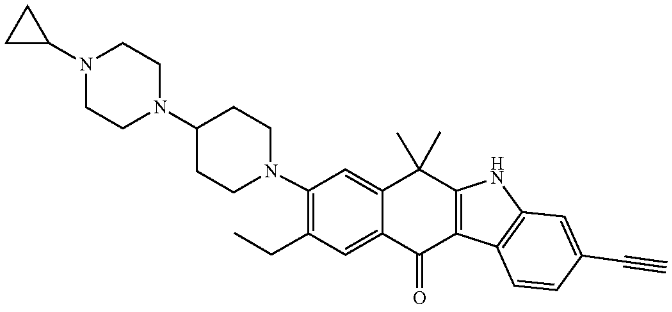 [SMILES: C#Cc1ccc2c3c([nH]c2c1)C(C)(C)c1cc(N2CCC(N4CCN(C5CC5)CC4)CC2)c(CC)cc1C3=O] | 520.72 | 59.04 | 186.3 |
| E17 | 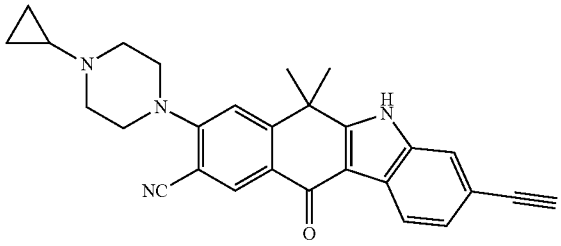 [SMILES: C#Cc1ccc2c3c([nH]c2c1)C(C)(C)c1cc(N2CCN(C4CC4)CC2)c(C#N)cc1C3=O] | 434.54 | 49.03 | 33.18 |

TABLE 1-continued
Test results of biological assessments
| Patent ID | Structure | MW | $IC_{50}$ value ALK (nM) | IC50 value Karpas 299 (nM) |
|---|---|---|---|---|
| E23 | 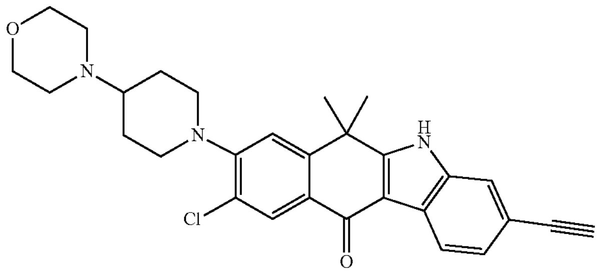 [SMILES: C#Cc1ccc2c3c([nH]c2c1)C(C)(C)c1cc(N2CCC(N4CCOCC4)CC2)c(Cl)cc1C3=O] | 534.05 | 2.611 | 22.23 |
| E24 | 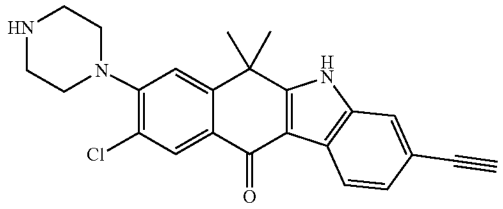 [SMILES: C#Cc1ccc2c3c([nH]c2c1)C(C)(C)c1cc(N2CCNCC2)c(Cl)cc1C3=O] | 449.94 | 3.293 | 18.17 |
| E25 | 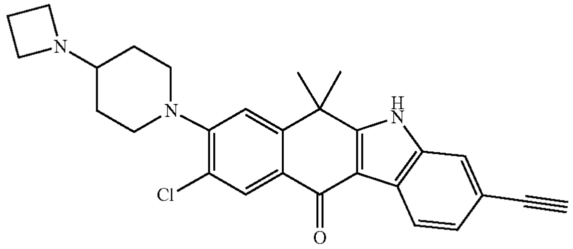 [SMILES: C#Cc1ccc2c3c([nH]c2c1)C(C)(C)c1cc(N2CCC(N4CCC4)CC2)c(Cl)cc1C3=O] | 504.03 | 49.85 | 52.99 |
| E18 | 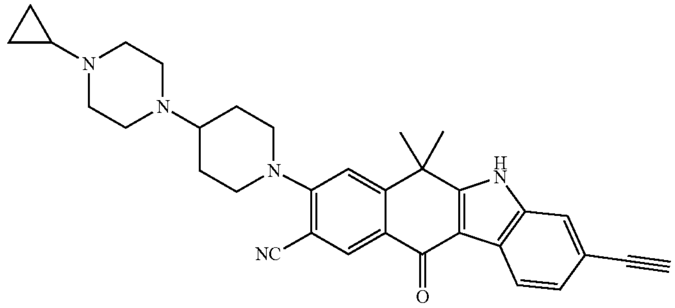 [SMILES: C#Cc1ccc2c3c([nH]c2c1)C(C)(C)c1cc(N2CCC(N4CCN(C5CC5)CC4)CC2)c(C#N)cc1C3=O] | 517.68 | 10.331 | 1.714 |
| E26 | 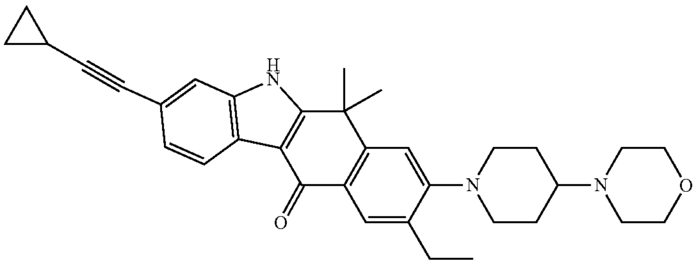 [SMILES: CCc1cc2c(cc1N1CCC(N3CCOCC3)CC1)C(C)(C)c1[nH]c3cc(C#CC4CC4)ccc3c1C2=O] | 521.7 | 38.4 | 20.564 |

TABLE 1-continued

| Test results of biological assessments | | | | |
|---|---|---|---|---|
| Patent ID | Structure | MW | $IC_{50}$ value ALK (nM) | IC50 value Karpas 299 (nM) |
| E27 | 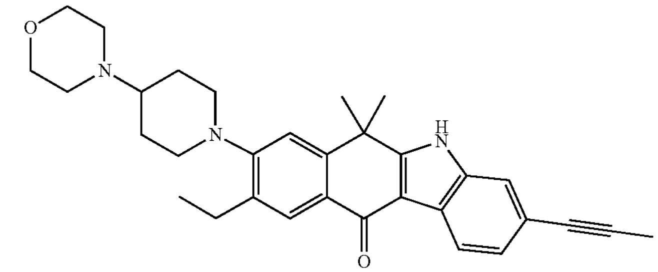 [SMILES: CC#Cc1ccc2c3c([nH]c2c1)C(C)(C)c1cc(N2CCC(N4CCOCC4)CC2)c(CC)cc1C3=O] | 495.7 | 10.23 | 109.5 |
| E28 | 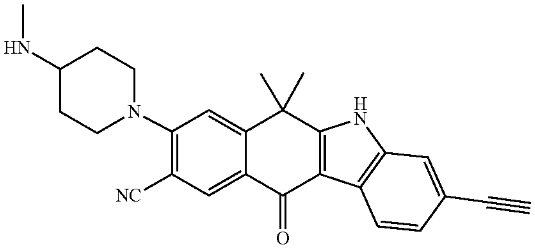 [SMILES: C#Cc1ccc2c3c([nH]c2c1)C(C)(C)c1cc(N2CCC(NC)CC2)c(C#N)cc1C3=O] | 422.53 | 2.623 | 5 |

The above examples are preferred embodiments of the present invention, but the embodiments of the present application are not limited by the above examples. Other any changes, modifications, substitutions, combinations and simplifications made without departing from the spirit and principle of the present application are all equivalent replacement modes and included within the protection scope of the present application.

INDUSTRIAL APPLICATION

The present application provides compounds with ALK inhibitory activity and preparation method and use thereof. The compounds with ALK inhibitory activity provided by the present application are ALK inhibitors for treating diseases responsive to the inhibition of ALK kinase, can be used for treating ALK-positive diseases, such as tumors and cancers, and have broad application prospects.

The invention claimed is:

1. A compound shown in formula (I) or a pharmaceutically acceptable salt thereof:

Formula (I)

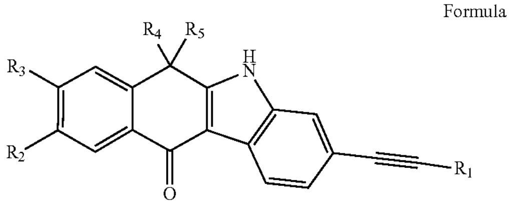

wherein, $R_1$ is selected from hydrogen, substituted or unsubstituted C1-C4 alkyl, C3-C6 cycloalkyl, substituted or unsubstituted aryl or heterocyclic aryl, and halogen;

$R_2$ is selected from hydrogen, substituted or unsubstituted C1-C4 alkyl, cyano, and halogen; the substituent of C1-C4 alkyl is selected from C3-C6 cycloalkyl, halogen, and cyano;

$R_3$ is selected from heterocyclic aryl, aryl, and substituted or unsubstituted 5-7 membered heterocycle, wherein the 5-7 membered heterocycle contains 1-3 heteroatoms that are each independently selected from N, P, O, and S;

$R_4$ and $R_5$ are each independently selected from hydrogen, substituted or unsubstituted saturated C1-C4 alkyl, and substituted or unsubstituted unsaturated C1-C4 alkyl.

2. The compound or a pharmaceutically acceptable salt thereof according to claim 1, wherein, $R_1$ is selected from hydrogen, substituted or unsubstituted C1-C4 alkyl, C3-C6 cycloalkyl;

$R_2$ is selected from hydrogen, unsubstituted C1-C4 alkyl, cyano, and halogen;

$R_3$ is selected from substituted or unsubstituted 5-7 membered heterocycle, wherein the 5-7 membered heterocycle contains 1-3 heteroatoms that are each independently selected from N, P, O, and S;

$R_4$ and $R_5$ are each independently selected from hydrogen, and unsubstituted saturated C1-C4 alkyl.

3. The compound or a pharmaceutically acceptable salt thereof according to claim 2, wherein,

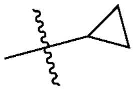 , 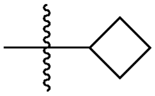 , and 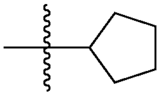 ;

$R_1$ is selected from hydrogen, methyl, ethyl, propyl, $R_2$ is selected from methyl, ethyl, propyl, cyano, Cl, Br, and F;

$R_3$ is selected from substituted or unsubstituted 6-membered heterocycle, wherein the 6-membered heterocycle contains 1-3 heteroatoms of N;

$R_4$ and $R_5$ are each independently selected from hydrogen, methyl, ethyl, and propyl.

4. The compound or a pharmaceutically acceptable salt thereof according to claim 3, wherein, $R_1$ is selected from hydrogen, methyl, and

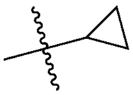

;

$R_2$ is selected from methyl, ethyl, cyano, Cl, Br and F;

$R_3$ is selected from

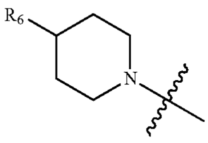

,

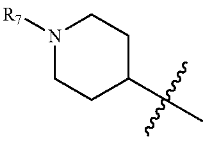

, and

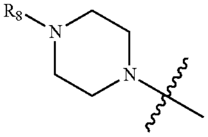

;

$R_6$, $R_7$, and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R_4$ and $R_5$ are each independently selected from methyl.

5. The compound or a pharmaceutically acceptable salt thereof according to claim 4, wherein, $R_6$, $R_7$, and $R_8$ are each independently selected from hydrogen, methyl, ethyl, cyano, dimethylamino, diethylamido,

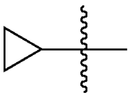

,

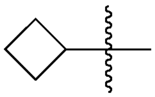

,

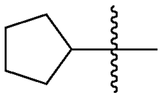

,

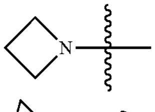

,

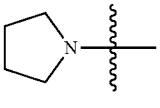

,

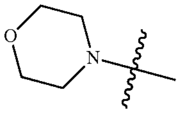

,

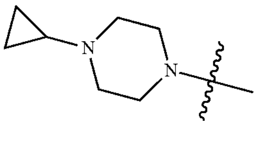

,

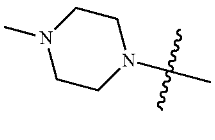

and

-continued

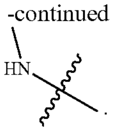

.

6. The compound or a pharmaceutically acceptable salt thereof according to claim 1, wherein, $R_1$ is selected from hydrogen and

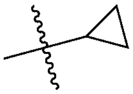

;

$R_2$ is selected from ethyl, cyano, and Cl;

$R_3$ is selected from

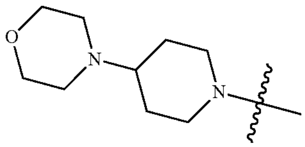

,

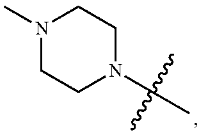

,

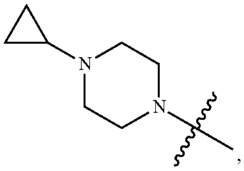

,

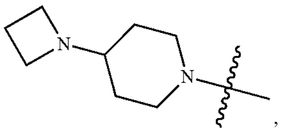

,

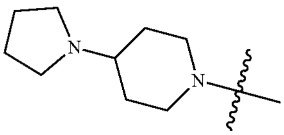

,

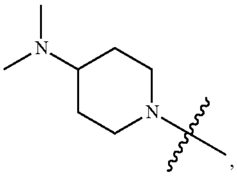

,

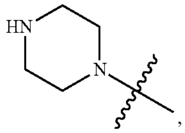

,

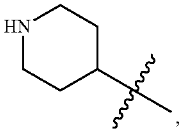

,

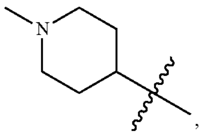

,

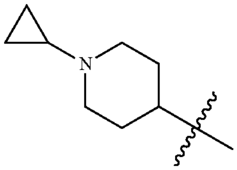

,

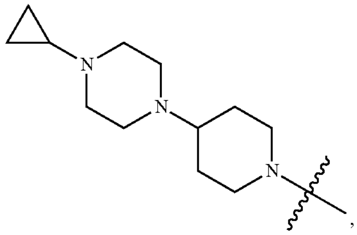

,

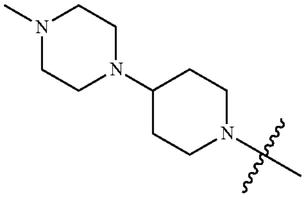

, and

-continued
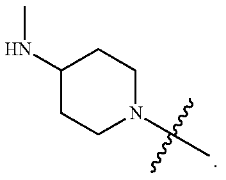
7. The compound or a pharmaceutically acceptable salt thereof according to claim 1, wherein, the compound shown in formula (I) is selected from:
E1
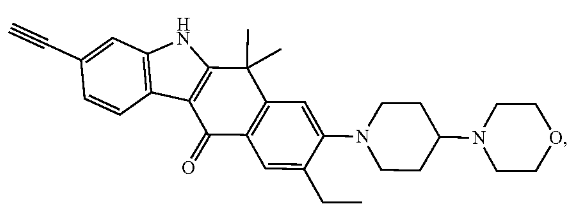
E2
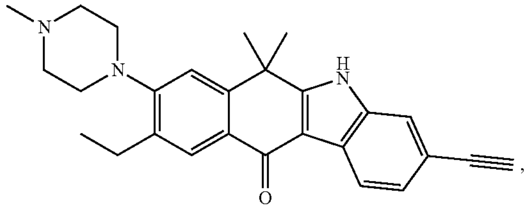
E3
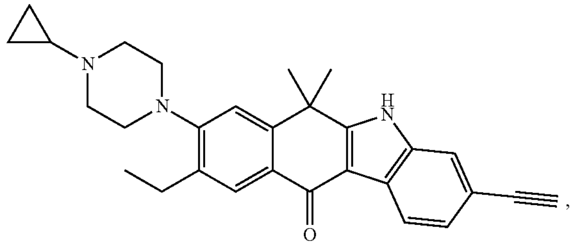
E4
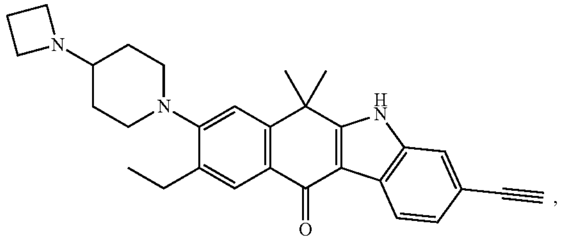
E5
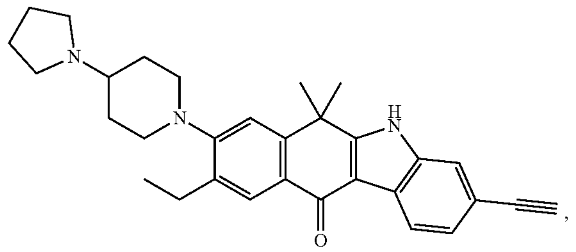
-continued
E6
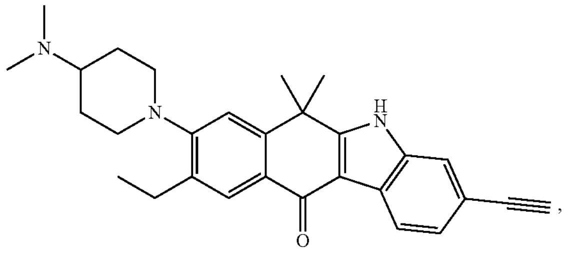
E7
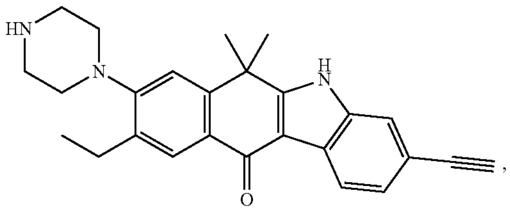
E8
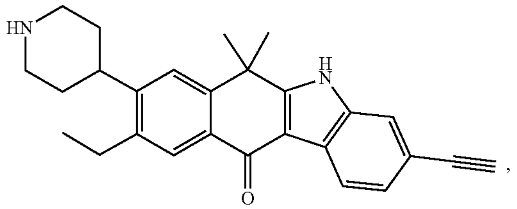
E9
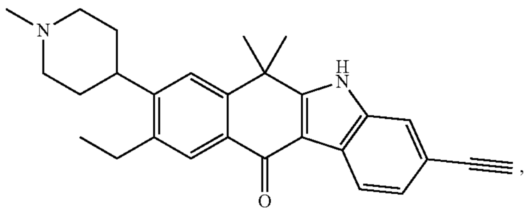
E10
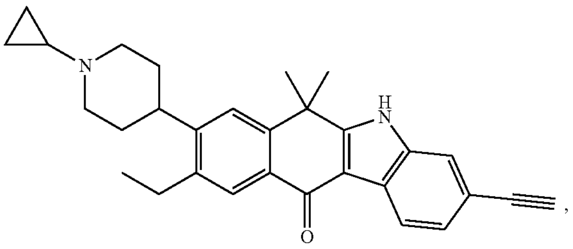
E11
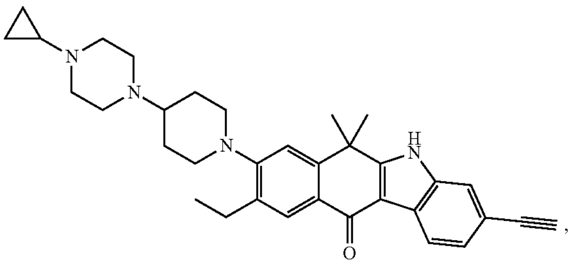

E12
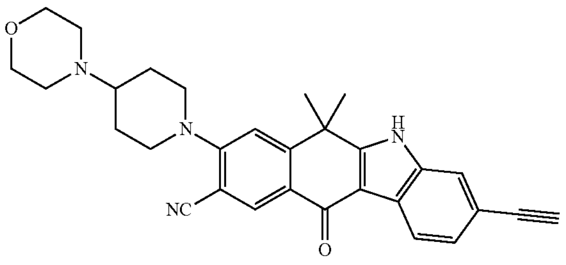,
E13
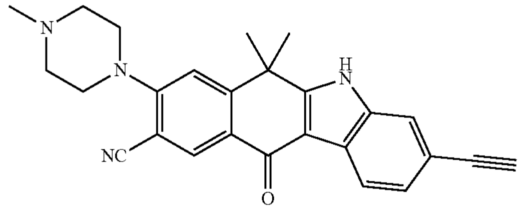,
E14
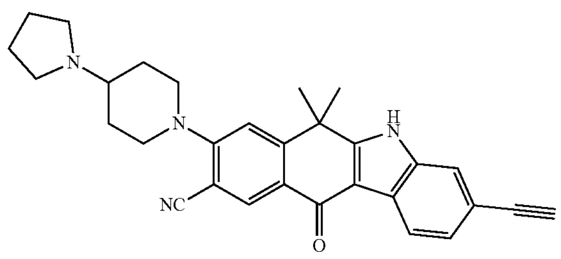,
E15
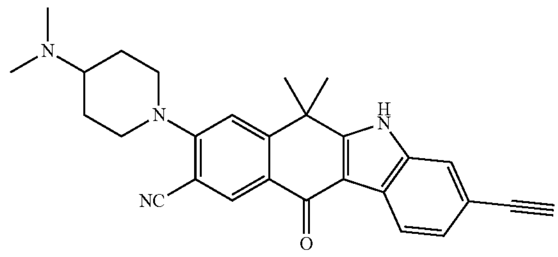,
E16
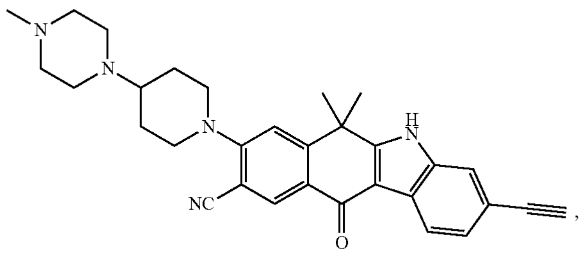,
E17
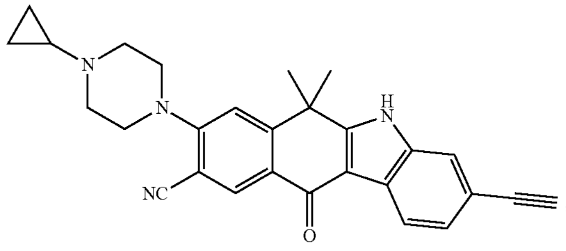,
E18
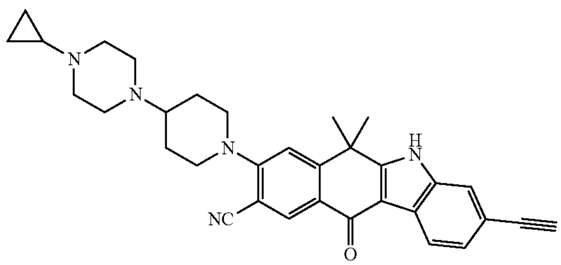,
E19
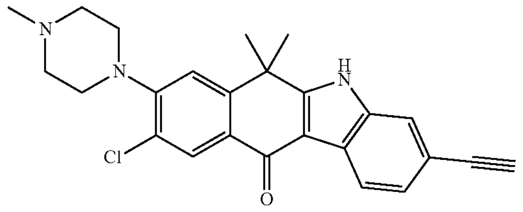,
E20
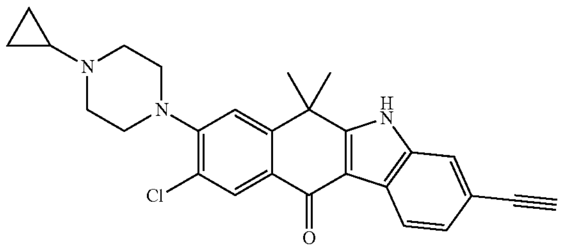,
E21
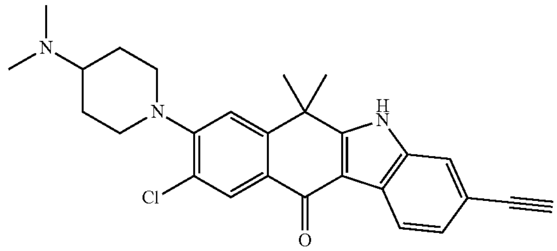,
E22
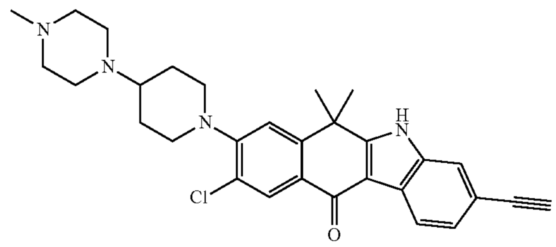,
E23
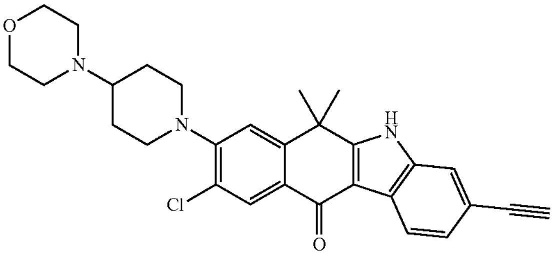, -continued

E24

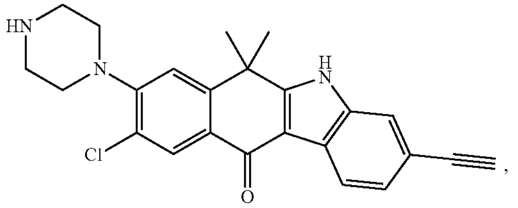

E25

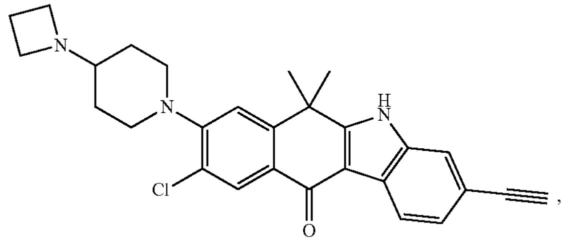

E26

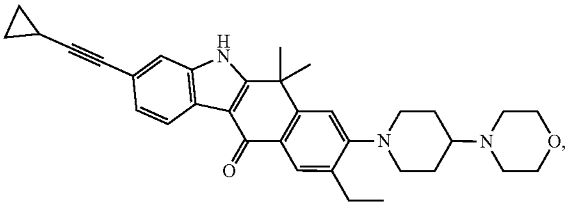

E27

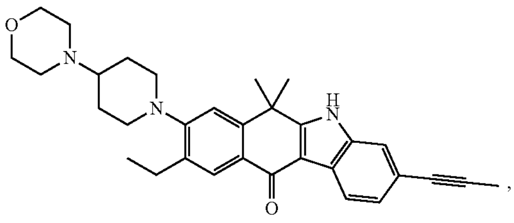

, and

E28

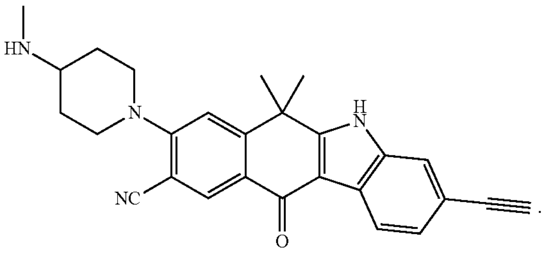

8. A method for preparing the compound or a pharmaceutically acceptable salt thereof according to claim 7, comprising at least the following steps: adding a carbonate into a solution of a compound of formula (II) in methanol, and stirring the mixture to conduct a reaction; wherein the compound of formula (II) is represented by the following formula:

Formula (II)

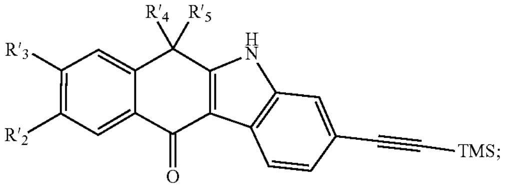

wherein, $R'_2$ is selected from ethyl, cyano, Cl, Br, and F; $R'_3$ is selected from

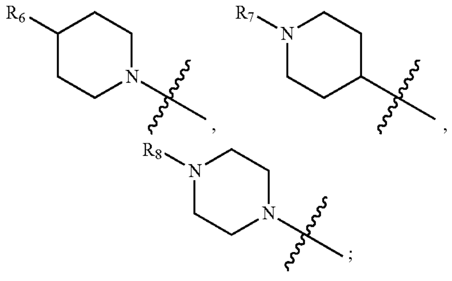

$R_6$, $R_7$, and $R_8$ are each independently selected from hydrogen, substituted or unsubstituted C1-C4 alkyl, substituted or unsubstituted C3-C6 cycloalkyl, substituted or unsubstituted 4-7 membered heterocycle, cyano, halogen, and nitrogen-containing alkyl; the 4-7 membered heterocycle contains 1-3 heteroatoms that are each independently selected from N, P, O, and S;

$R'_4$ represents hydrogen or unsubstituted saturated C1-C4 alkyl;

$R'_5$ represents hydrogen or unsubstituted saturated C1-C4 alkyl.

9. A method for preparing the compound or a pharmaceutically acceptable salt thereof according to claim 7, comprising at least the following steps: adding a compound of formula (III) and a carbonate into acetonitrile and methanol, and stirring the mixture to conduct a reaction, wherein the compound of formula (III) is represented by the following formula:

Formula (III)

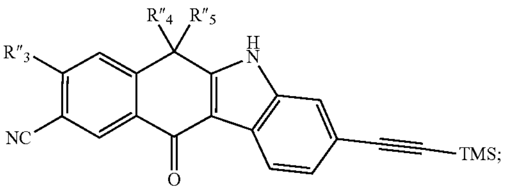

$R''_3$ is selected from

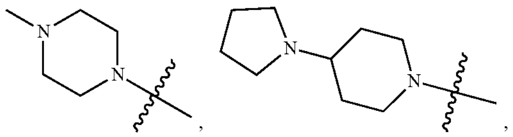

-continued

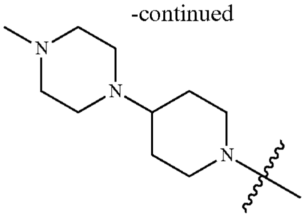

, and

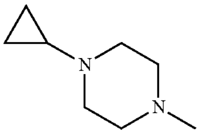

;

$R_4$ and $R''_4$ represent the same group;

$R_5$ and $R''_5$ represent the same group.

10. A method for preparing the compound or a pharmaceutically acceptable salt thereof according to claim 7, comprising at least the following steps: adding tetrabutylammonium fluoride into a solution of a compound of formula (IV) in tetrahydrofuran, and stirring the mixture to conduct a reaction, wherein the the compound of formula (IV) is represented by the following formula:

Formula (IV)

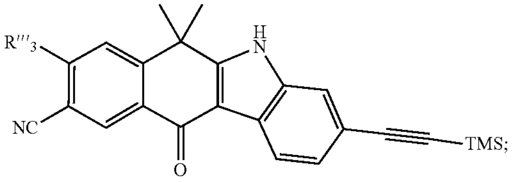

$R'''_3$ is selected from

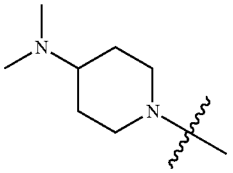

,

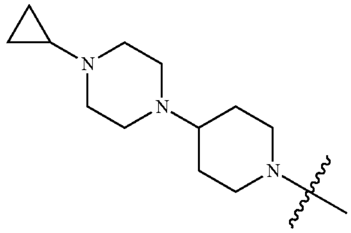

, and

-continued

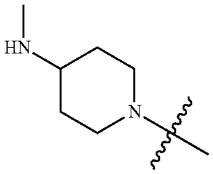

.

11. A method for preparing the compound or a pharmaceutically acceptable salt thereof according to claim 7, comprising at least the following steps: adding tripotassium phosphate, 2-dicyclohexylphosphino-2,4,6-triisopropylbiphenyl, and tris(dibenzylideneacetone) dipalladium into a solution of a compound of formula (V) and alkyl an alkyne in acetonitrile, and stirring the mixture to conduct a reaction in an inert atmosphere; wherein the compound of formula formula (V) is represented by the following formula:

Formula (V)

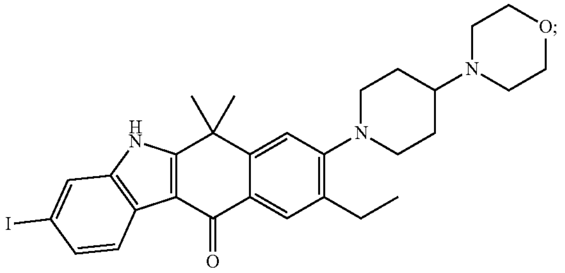

the alkyl alkyne is one selected from the group consisting of ethynyl cyclopropane, propyne, ethynyl cyclobutane, and butyne.

12. A pharmaceutical composition, comprising a therapeutically effective amount of the compound or a pharmaceutically acceptable salt thereof according to claim 1, and a medicinal carrier or excipient.

13. A method for inhibiting ALK activity in a subject in need thereof, which comprises a step of administrating a therapeutically effective amount of the pharmaceutical composition according to claim 12 to the subject.

14. A method for treating ALK-positive tumors or cancers in a subject in need thereof, which comprises a step of administrating a therapeutically effective amount of the pharmaceutical composition according to claim 12 to the subject.

* * * * *